US009113649B2

(12) United States Patent
Yu et al.

(10) Patent No.: US 9,113,649 B2
(45) Date of Patent: Aug. 25, 2015

(54) FOOD ADDITIVE COMPRISING AN AMIDASE FOR DETOXIFYING OCHRATOXIN

(75) Inventors: Shukun Yu, Gunnar Hejdemans Gata (SE); Charlotte Horsmans Poulsen, Langdalsvej (DK); Soren Dalsgaard, Logten (DK); Huaming Wang, Fremont, CA (US); Igor Nikolaev, Offemweg (NL)

(73) Assignee: DuPont Nutrition Biosciences ApS, Copenhagen (DK)

( * ) Notice: Subject to any disclaimer, the term of this patent is extended or adjusted under 35 U.S.C. 154(b) by 0 days.

(21) Appl. No.: 13/820,971

(22) PCT Filed: Sep. 6, 2011

(86) PCT No.: PCT/IB2011/053901

§ 371 (c)(1), (2), (4) Date: Mar. 5, 2013

(87) PCT Pub. No.: WO2012/032472

PCT Pub. Date: Mar. 15, 2012

(65) Prior Publication Data

US 2013/0216654 A1 Aug. 22, 2013

Related U.S. Application Data

(60) Provisional application No. 61/380,280, filed on Sep. 6, 2010.

(30) Foreign Application Priority Data

Sep. 17, 2010 (EP) .................................... 10177410

(51) Int. Cl.

| | |
|---|---|
| *A23L 1/03* | (2006.01) |
| *C12N 9/80* | (2006.01) |
| *A23K 1/165* | (2006.01) |
| *A23L 1/015* | (2006.01) |
| *A23K 1/00* | (2006.01) |

(52) U.S. Cl.

CPC ................ *A23L 1/034* (2013.01); *A23K 1/006* (2013.01); *A23K 1/1653* (2013.01); *A23L 1/0153* (2013.01); *C12N 9/80* (2013.01); *C12Y 305/01004* (2013.01)

(58) Field of Classification Search

None

See application file for complete search history.

(56) References Cited

U.S. PATENT DOCUMENTS

2004/0208956 A1 * 10/2004 Schatzmayr et al. ........... 426/49

FOREIGN PATENT DOCUMENTS

WO WO 2007/062936 * 6/2007 ............ C12N 15/80

OTHER PUBLICATIONS

Abrunhosa et al., "Isolation and purification of an enzyme hydrolyzing ochratoxin A from *Aspergillus niger*", Biotechnol Lett (2007) 29:1909-1914.*

Stander et al.. "Screening of Commercial Hydrolases for the Degradation of Ochratoxin A", J. Agric. Food Chem. 2000, 48(11), 5736-5739.*

UniProt Q0PW44—Lipase A sequence from *A. niger*—Retrived from < http://www.uniprot.org/uniprot/Q0PW44 > on Apr. 2, 2014.*

Dobritzsch et al., "Structural and functional characterization of ochratoxinase, a novel mycotoxin degrading enzyme", Biochemical Journal Immediate Publication. Published on Jun. 20, 2014 as manuscript BJ20140382.*

* cited by examiner

*Primary Examiner* — Suzanne M Noakes

(74) *Attorney, Agent, or Firm* — Shook, Hardy & Bacon L.L.P.

(57) ABSTRACT

The present invention relates to amidase enzymes and a feed or food additive comprising the amidase enzyme capable of degrading ochratoxin.

29 Claims, 62 Drawing Sheets

Note: one of the component in Band B and C is an unknown
A niger protein which has similarity to bacterial amidase Extracellular protein Transgenic *Aspergillus niger*.
Best strain are 3, 4, 7, 11, 13, 14, worst 2, 9 12, which are close to wt)

```
1    MVRRIASATP MVQSPMSPLG TTYCVRPNPV SLNLQRRPLV IASTDEAKVT
51   IIYAGLLIPG DGEPLRNAAL VISDKIIAFV GSEADIPKKY LRSTQSTHRV
101  PVLMPGLWDC HMHFGGDDDY YNDYTSGLAT HPASSGARLA RGCW EALQNG
151  YTSYRDLAGY GCEVAKAIND GTIVGPNVYS SGAALSQTAG HGDIFALPAG
201  EVLGSYGVMN PRPGYWGAGP LCIADGVEEV RRAVRLQIRR GAKVIKVMAS
251  GGVMSRDDNP NFAQFSPEEL KVIVEEAARQ NRIVSAHVHG KAGIMAAIKA
301  GCKSLEHVSY ADEEVWELMK EKGILYVATR SVIEIFLASN GEGLVKESWA
351  KLQALADSHL KAYQGAIKAG VTIALGTDTA PGGPTALELQ FAVERGGMTP
401  LEAIKAATAN APLSVGPQAP LTGQLREGYE ADVIALEENP LEDIKVFQEP
451  KAVTHVWKGG KLFKGPGIGP WGEDARNPFL
```

FIG. 18A

```
MVRRIASATPMVQSPMSPLGTTYCVRPNPVSLNLQRRPLVIASTDEAKVTIIYAGLLIPGDGE
PLRNAALVISDKIIAFVGSEADIPKKYLRSTQSTHRVPVLMPGLWDCHMHFGGDDDYYNDYTS
GLATHPASSGARLARGCWEALQNGYTSYRDLAGYGCEVAKAINDGTIVGPNVYSSGAALSQTA
GHGDIFALPAGEVLGSYGVMNPRPGYWGAGPLCIADGVEEVRRAVRLQIRRGAKVIKVMASGG
VMSRDDNPNFAQFSPEELKVIVEEAARQNRIVSAHVHGKAGIMAAIKAGCKSLEHVSYADEEV
WELMKEKGILYVATRSVIEIFLASNGEGLVKESWAKLQALADSHLKAYQGAIKAGVTIALGTD
TAPGGPTALELQFAVERGGMTPLEAIKAATANAPLSVGPQAPLTGQLREGYEADVIALEENPL
EDIKVFQEPKAVTHVWKGGKLFKGPGIGPWGEDARNPFLHHHHHH
```

FIG. 18B

```
1                                                   20
MetValArgArgIleAlaSerAlaThrProMetValGlnSerProMetSerProLeuGly
21                                                  40
ThrThrTyrCysValArgProAsnProValSerLeuAsnLeuGlnArgArgProLeuVal
41                                                  60
IleAlaSerThrAspGluAlaLysValThrIleIleTyrAlaGlyLeuLeuIleProGly
61                                                  80
AspGlyGluProLeuArgAsnAlaAlaLeuValIleSerAspLysIleIleAlaPheVal
81                                                  100
GlySerGluAlaAspIleProLysLysTyrLeuArgSerThrGlnSerThrHisArgVal
101           Motif 1 (104-113)                     120
ProValLeuMetProGlyLeuTrpAspCysHisMetHisPheGlyGlyAspAspAspTyr
121                                                 140
TyrAsnAspTyrThrSerGlyLeuAlaThrHisProAlaSerSerGlyAlaArgLeuAla
141                    Motif 2 (150-152)            160
ArgGlyCysTrpGluAlaLeuGlnAsnGlyTyrThrSerTyrArgAspLeuAlaGlyTyr
161                            Motif 3 (171-176)    180
GlyCysGluValAlaLysAlaIleAsnAspGlyThrIleValGlyProAsnValTyrSer
181                   Motif 4  (190-193)            200
SerGlyAlaAlaLeuSerGlnThrAlaGlyHisGlyAspIlePheAlaLeuProAlaGly
201                                                 220
GluValLeuGlySerTyrGlyValMetAsnProArgProGlyTyrTrpGlyAlaGlyPro
221                                                 240
LeuCysIleAlaAspGlyValGluGluValArgArgAlaValArgLeuGlnIleArgArg
241   Motif  5 (241-252)                            260
GlyAlaLysValIleLysValMetAlaSerGlyGlyValMetSerArgAspAspAsnPro
261                                                 280
AsnPheAlaGlnPheSerProGluGluLeuLysValIleValGluGluAlaAlaArgGln
281        Motif 6 (284-293)                        300
AsnArgIleValSerAlaHisValHisGlyLysAlaGlyIleMetAlaAlaIleLysAla
301                  Motif 7 (307-314)              320
GlyCysLysSerLeuGluHisValSerTyrAlaAspGluGluValTrpGluLeuMetLys
321                                                 340
GluLysGlyIleLeuTyrValAlaThrArgSerValIleGluIlePheLeuAlaSerAsn
341                                                 360
GlyGluGlyLeuValLysGluSerTrpAlaLysLeuGlnAlaLeuAlaAspSerHisLeu
361             Motif  8 (366-378)                  380
LysAlaTyrGlnGlyAlaIleLysAlaGlyValThrIleAlaLeuGlyThrAspThrAla
381                                                 400
ProGlyGlyProThrAlaLeuGluLeuGlnPheAlaValGluArgGlyGlyMetThrPro
401                                                 420
LeuGluAlaIleLysAlaAlaThrAlaAsnAlaProLeuSerValGlyProGlnAlaPro
421                                                 440
LeuThrGlyGlnLeuArgGluGlyTyrGluAlaAspValIleAlaLeuGluGluAsnPro
441   Motif  9(439-444)                             460
LeuGluAspIleLysValPheGlnGluProLysAlaValThrHisValTrpLysGlyGly
461                                                 480
LysLeuPheLysGlyProGlyIleGlyProTrpGlyGluAspAlaArgAsnProPheLeu
```

FIG. 19

FIG. 20
A
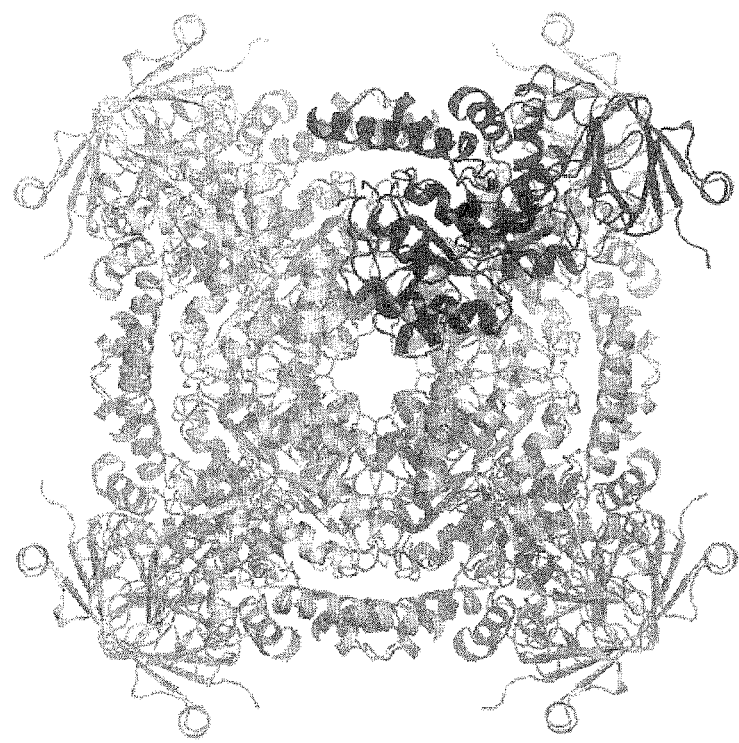
B

The coordinates of amidase 2 (am7).

```
ATOM    1   N    ASP A  45   -55.262  78.964 -22.746  1.00 59.73    N
ATOM    2   CA   ASP A  45   -55.515  77.490 -22.729  1.00 58.64    C
ATOM    3   CB   ASP A  45   -54.961  76.817  24.001  1.00 59.81    C
ATOM    4   CG   ASP A  45   -53.542  77.266 -24.344  1.00 60.51    C
ATOM    5   OD1  ASP A  45   -52.677  77.314 -23.441  1.00 59.27    O
ATOM    6   OD2  ASP A  45   -53.292  77.569 -25.530  1.00 60.56    O
ATOM    7   C    ASP A  45   -54.966  76.815 -21.465  1.00 56.69    C
ATOM    8   O    ASP A  45   -54.212  77.423 -20.691  1.00 56.38    O
ATOM    9   N    GLU A  46   -55.347  75.553 -21.277  1.00 58.73    N
ATOM   10   CA   GLU A  46   -55.029  74.804 -20.062  1.00 45.17    C
ATOM   11   CB   GLU A  46    56.108  73.730  19.787  1.00 47.65    C
ATOM   12   CG   GLU A  46   -57.545  74.251 -19.641  1.00 51.14    C
ATOM   13   CD   GLU A  46   -57.760  75.143 -18.418  1.00 52.45    C
ATOM   14   OE1  GLU A  46   -57.219  74.821 -17.336  1.00 54.83    O
ATOM   15   OE2  GLU A  46   -58.472  76.168 -18.532  1.00 50.30    O
ATOM   16   C    GLU A  46   -53.634  76.164 -20.102  1.00 39.33    C
ATOM   17   O    GLU A  46   -53.022  74.019 -21.162  1.00 37.89    O
ATOM   18   N    ALA A  47   -53.142  73.793 -18.926  1.00 34.28    N
ATOM   19   CA   ALA A  47   -51.923  73.013 -18.786  1.00 30.52    C
ATOM   20   CB   ALA A  47   -51.700  72.700 -17.320  1.00 29.00    C
ATOM   21   C    ALA A  47   -51.966  71.707 -19.591  1.00 28.81    C
ATOM   22   O    ALA A  47   -53.016  71.048 -19.867  1.00 28.81    O
ATOM   23   N    LYS A  48   -50.834  71.347 -20.194  1.00 25.63    N
ATOM   24   CA   LYS A  48    50.655  70.022  20.779  1.00 24.41    C
ATOM   25   CB   LYS A  48   -49.537  70.021 -21.914  1.00 26.16    C
ATOM   26   CG   LYS A  48   -50.011  69.730 -23.223  1.00 28.77    C
ATOM   27   CD   LYS A  48   -49.541  68.359 -23.694  1.00 30.57    C
ATOM   28   CE   LYS A  48   -48.218  68.442 -24.548  1.00 31.59    C
ATOM   29   NZ   LYS A  48   -47.781  67.094 -24.909  1.00 31.86    N
ATOM   30   C    LYS A  48   -50.352  69.018 -19.681  1.00 22.34    C
ATOM   31   O    LYS A  48   -49.296  69.075 -19.056  1.00 21.45    O
ATOM   32   N    VAL A  49   -51.292  68.108 -19.451  1.00 20.58    N
ATOM   33   CA   VAL A  49    51.216  67.166  18.339  1.00 19.65    C
ATOM   34   CB   VAL A  49   -52.439  67.326 -17.421  1.00 18.80    C
ATOM   35   CG1  VAL A  49   -52.439  66.285 -16.313  1.00 18.93    C
ATOM   36   CG2  VAL A  49   -52.458  68.726 -16.833  1.00 18.75    C
ATOM   37   C    VAL A  49   -51.050  65.724 -18.824  1.00 19.28    C
ATOM   38   O    VAL A  49   -51.822  65.248 -19.651  1.00 20.38    O
ATOM   39   N    THR A  50   -50.028  65.038 -18.329  1.00 18.29    N
ATOM   40   CA   THR A  50   -49.759  63.668 -18.750  1.00 17.94    C
ATOM   41   CB   THR A  50   -48.456  63.571 -19.585  1.00 17.87    C
ATOM   42   OG1  THR A  50   -48.401  64.623 -20.550  1.00 16.99    O
ATOM   43   CG2  THR A  50   -48.355  62.233 -20.316  1.00 18.23    C
ATOM   44   C    THR A  50   -49.635  62.803 -17.509  1.00 17.62    C
ATOM   45   O    THR A  50   -48.977  63.208 -16.545  1.00 18.20    O
ATOM   46   N    ILE A  51    50.281  61.637  17.505  1.00 17.17    N
ATOM   47   CA   ILE A  51   -50.118  60.703 -16.385  1.00 17.20    C
ATOM   48   CB   ILE A  51   -51.457  60.279 -15.756  1.00 17.27    C
ATOM   49   CG1  ILE A  51   -52.322  61.508 -15.478  1.00 17.36    C
ATOM   50   CD1  ILE A  51   -53.745  61.174 -15.068  1.00 17.27    C
ATOM   51   CG2  ILE A  51   -51.223  59.500 -14.497  1.00 16.79    C
ATOM   52   C    ILE A  51   -49.340  59.466 -16.818  1.00 17.32    C
ATOM   53   O    ILE A  51   -49.667  58.837 -17.833  1.00 17.48    O
ATOM   54   N    ILE A  52   -48.306  59.127 -16.057  1.00 16.77    N
ATOM   55   CA   ILE A  52   -47.524  57.940 -16.347  1.00 17.15    C
ATOM   56   CB   ILE A  52   -46.041  58.255 -16.544  1.00 17.68    C
ATOM   57   CG1  ILE A  52   -45.871  59.466 -17.662  1.00 18.21    C
ATOM   58   CD1  ILE A  52   -44.469  60.027 -17.478  1.00 19.05    C
ATOM   59   CG2  ILE A  52    45.320  57.021  17.078  1.00 17.65    C
ATOM   60   C    ILE A  52   -47.620  56.959 -19.197  1.00 17.72    C
ATOM   61   O    ILE A  52   -47.710  57.263 -14.072  1.00 17.84    O
ATOM   62   N    TYR A  53   -48.156  55.779 -15.480  1.00 17.22    N
ATOM   63   CA   TYR A  53   -48.233  54.740 -14.476  1.00 17.14    C
ATOM   64   CB   TYR A  53   -49.509  53.922 -14.672  1.00 17.15    C
ATOM   65   CG   TYR A  53   -50.804  54.705 -14.560  1.00 16.75    C
ATOM   66   CD1  TYR A  53   -51.456  54.825 -13.339  1.00 16.77    C
ATOM   67   CE1  TYR A  53   -52.655  55.513 -13.231  1.00 16.81    C
ATOM   68   CZ   TYR A  53   -53.222  56.097 -14.357  1.00 16.90    C
ATOM   69   OH   TYR A  53   -54.426  56.790 -14.229  1.00 16.76    O
ATOM   70   CE2  TYR A  53   -52.588  55.988 -15.594  1.00 16.67    C
ATOM   71   CD2  TYR A  53   -51.391  55.299 -15.685  1.00 16.64    C
```

FIG. 22A

```
ATOM    72  C   TYR A  53     -46.995  53.662 -14.622  1.00 17.13           C
ATOM    73  O   TYR A  53     -46.580  53.551 -15.746  1.00 17.48           O
ATOM    74  N   ALA A  54     -46.391  53.493 -13.497  1.00 16.97           N
ATOM    75  CA  ALA A  54     -45.155  52.691  13.520  1.00 18.97           C
ATOM    76  CB  ALA A  54     -43.954  53.566 -13.198  1.00 17.39           C
ATOM    77  C   ALA A  54     -45.194  51.520 -12.560  1.00 16.62           C
ATOM    78  O   ALA A  54     -45.529  51.603 -11.385  1.00 15.83           C
ATOM    79  N   GLY A  55     -44.833  50.342 -13.056  1.00 16.57           N
ATOM    80  CA  GLY A  55     -44.700  49.167 -12.183  1.00 17.11           C
ATOM    81  C   GLY A  55     -43.671  49.382 -11.087  1.00 16.76           C
ATOM    82  O   GLY A  55     -43.809  49.881  -9.982  1.00 16.17           O
ATOM    83  N   LEU A  56     -42.643  50.152 -11.429  1.00 17.53           N
ATOM    84  CA  LEU A  56     -41.565  50.523  10.523  1.00 17.80           C
ATOM    85  CB  LEU A  56     -40.425  49.518 -10.635  1.00 17.51           C
ATOM    86  CG  LEU A  56     -39.206  49.828  -9.795  1.00 17.37           C
ATOM    87  CD1 LEU A  56     -39.576  49.631  -8.335  1.00 17.64           C
ATOM    88  CD2 LEU A  56     -39.064  48.919 -10.209  1.00 17.31           C
ATOM    89  C   LEU A  56     -41.064  51.933 -10.901  1.00 17.97           C
ATOM    90  O   LEU A  56     -40.695  52.194 -12.063  1.00 18.62           O
ATOM    91  N   LEU A  57     -41.078  52.832  -9.925  1.00 16.50           N
ATOM    92  CA  LEU A  57     -40.631  54.189 -10.132  1.00 15.93           C
ATOM    93  CB  LEU A  57     -41.746  55.169  -9.785  1.00 15.70           C
ATOM    94  CG  LEU A  57     -41.489  56.664  -9.944  1.00 16.00           C
ATOM    95  CD1 LEU A  57     -42.798  57.422 -10.163  1.00 15.67           C
ATOM    96  CD2 LEU A  57     -40.680  57.260  -8.792  1.00 15.58           C
ATOM    97  C   LEU A  57     -39.422  54.403  -9.239  1.00 15.81           C
ATOM    98  O   LEU A  57     -39.532  54.317  -8.000  1.00 15.79           C
ATOM    99  N   ILE A  58     -38.274  54.611  -9.883  1.00 15.20           N
ATOM   100  CA  ILE A  58     -36.992  54.890  -9.219  1.00 15.21           C
ATOM   101  CB  ILE A  58     -35.791  54.255  -9.995  1.00 14.91           C
ATOM   102  CG1 ILE A  58     -35.987  52.733 -10.168  1.00 14.29           C
ATOM   103  CD1 ILE A  58     -34.979  52.054 -11.096  1.00 13.73           C
ATOM   104  CG2 ILE A  58     -34.449  54.596  -9.345  1.00 14.14           C
ATOM   105  C   ILE A  58     -36.870  56.422  -9.189  1.00 15.36           C
ATOM   106  O   ILE A  58      36.699  57.032  10.245  1.00 15.17           O
ATOM   107  N   PRO A  59     -36.983  57.048  -7.987  1.00 15.49           N
ATOM   108  CA  PRO A  59     -37.109  58.503  -7.957  1.00 15.57           C
ATOM   109  CB  PRO A  59     -37.646  58.785  -6.543  1.00 15.31           C
ATOM   110  CG  PRO A  59      37.131  57.664   5.725  1.00 15.16           C
ATOM   111  CD  PRO A  59     -37.074  56.464  -6.632  1.00 15.40           C
ATOM   112  C   PRO A  59     -35.781  59.205  -8.191  1.00 15.69           C
ATOM   113  O   PRO A  59     -35.761  60.357  -8.647  1.00 15.85           O
ATOM   114  N   GLY A  60     -34.684  58.523  -7.990  1.00 16.18           N
ATOM   115  CA  GLY A  60     -33.363  59.086  -8.158  1.00 17.16           C
ATOM   116  C   GLY A  60     -32.564  59.182  -6.888  1.00 17.86           C
ATOM   117  O   GLY A  60     -31.395  58.845  -6.872  1.00 18.42           O
ATOM   118  N   ASP A  61     -33.216  59.643  -5.825  1.00 19.45           N
ATOM   119  CA  ASP A  61     -32.671  59.643  -4.473  1.00 20.80           C
ATOM   120  CB  ASP A  61     -32.335  61.079  -4.074  1.00 21.27           C
ATOM   121  CG  ASP A  61     -31.643  61.179  -2.731  1.00 22.32           C
ATOM   122  OD1 ASP A  61     -31.133  60.157  -2.214  1.00 22.79           O
ATOM   123  OD2 ASP A  61     -31.586  62.311  -2.196  1.00 22.84           O
ATOM   124  C   ASP A  61     -33.739  59.069  -3.529  1.00 22.05           C
ATOM   125  O   ASP A  61     -34.784  59.681  -3.357  1.00 22.77           O
ATOM   126  N   GLY A  62     -33.489  57.893  -2.943  1.00 23.85           N
ATOM   127  CA  GLY A  62     -34.426  57.241  -1.992  1.00 24.17           C
ATOM   128  C   GLY A  62     -35.189  56.043  -2.555  1.00 23.86           C
ATOM   129  O   GLY A  62     -35.129  55.777  -3.766  1.00 22.50           O
ATOM   130  N   GLU A  63     -35.916  55.342  -1.679  1.00 23.58           N
ATOM   131  CA  GLU A  63     -36.595  54.074  -2.037  1.00 24.21           C
ATOM   132  CB  GLU A  63      37.308  53.410   0.830  1.00 27.56           C
ATOM   133  CG  GLU A  63     -36.399  52.958   0.325  1.00 31.86           C
ATOM   134  CD  GLU A  63     -35.037  52.416  -0.128  1.00 34.29           C
ATOM   135  OE1 GLU A  63     -34.999  51.417  -0.883  1.00 36.97           O
ATOM   136  OE2 GLU A  63     -34.800  52.992   0.266  1.00 35.37           O
ATOM   137  C   GLU A  63     -37.559  54.175  -3.216  1.00 21.92           C
ATOM   138  O   GLU A  63     -38.432  55.062  -3.234  1.00 20.56           O
ATOM   139  N   PRO A  64     -37.377  53.285  -4.209  1.00 20.80           N
ATOM   140  CA  PRO A  64     -38.238  53.116  -5.369  1.00 20.56           C
ATOM   141  CB  PRO A  64     -37.508  51.953  -6.126  1.00 20.10           C
ATOM   142  CG  PRO A  64     -36.187  51.920  -5.656  1.00 19.54           C
ATOM   143  CD  PRO A  64     -36.218  52.373  -4.250  1.00 20.23           C
ATOM   144  C   PRO A  64     -39.659  52.719  -4.983  1.00 20.24           C
ATOM   145  O   PRO A  64      39.940  51.909   4.083  1.00 19.46           O
ATOM   146  N   LEU A  65     -40.647  53.269  -5.680  1.00 20.43           N
ATOM   147  CA  LEU A  65     -42.040  52.906  -5.450  1.00 21.78           C
ATOM   148  CB  LEU A  65     -42.952  54.137  -5.519  1.00 23.44           C
```

FIG. 22B

| | | | | | | | | | | |
|---|---|---|---|---|---|---|---|---|---|---|
| ATOM | 149 | CG | LEU | A | 65 | -42.536 | 55.395 | -4.735 | 1.00 24.70 | C |
| ATOM | 150 | CD1 | LEU | A | 65 | -43.437 | 56.560 | -5.117 | 1.00 25.86 | C |
| ATOM | 151 | CD2 | LEU | A | 65 | -42.547 | 55.182 | -3.226 | 1.00 25.35 | C |
| ATOM | 152 | C | LEU | A | 65 | -42.532 | 51.839 | -6.433 | 1.00 21.46 | C |
| ATOM | 153 | O | LEU | A | 65 | -42.142 | 51.819 | -7.609 | 1.00 21.31 | O |
| ATOM | 154 | N | ARG | A | 66 | -43.388 | 50.954 | -5.929 | 1.00 20.62 | N |
| ATOM | 155 | CA | ARG | A | 66 | -43.979 | 49.889 | -6.729 | 1.00 20.40 | C |
| ATOM | 156 | CB | ARG | A | 66 | -43.904 | 48.552 | -5.967 | 1.00 22.31 | C |
| ATOM | 157 | CG | ARG | A | 66 | -43.516 | 47.346 | -6.816 | 1.00 24.82 | C |
| ATOM | 158 | CD | ARG | A | 66 | -42.093 | 46.878 | -6.551 | 1.00 27.44 | C |
| ATOM | 159 | NE | ARG | A | 66 | -41.403 | 46.433 | -7.779 | 1.00 29.88 | N |
| ATOM | 160 | CZ | ARG | A | 66 | -40.217 | 45.891 | -7.818 | 1.00 30.73 | C |
| ATOM | 161 | NH1 | ARG | A | 66 | -39.683 | 45.448 | -8.988 | 1.00 31.14 | N |
| ATOM | 162 | NH2 | ARG | A | 66 | -39.551 | 45.516 | -6.699 | 1.00 30.00 | N |
| ATOM | 163 | C | ARG | A | 66 | -45.424 | 50.290 | -7.050 | 1.00 18.63 | C |
| ATOM | 164 | O | ARG | A | 66 | -46.115 | 50.832 | -6.193 | 1.00 17.67 | O |
| ATOM | 165 | N | ASN | A | 67 | -45.861 | 50.059 | -8.292 | 1.00 17.67 | N |
| ATOM | 166 | CA | ASN | A | 67 | -47.214 | 50.436 | -8.746 | 1.00 17.14 | C |
| ATOM | 167 | CB | ASN | A | 67 | -48.289 | 49.520 | -8.134 | 1.00 15.43 | C |
| ATOM | 168 | CG | ASN | A | 67 | -47.986 | 48.044 | -8.366 | 1.00 16.25 | C |
| ATOM | 169 | OD1 | ASN | A | 67 | -47.703 | 47.627 | -9.502 | 1.00 15.84 | O |
| ATOM | 170 | ND2 | ASN | A | 67 | -48.095 | 47.252 | -7.289 | 1.00 15.36 | N |
| ATOM | 171 | C | ASN | A | 67 | -47.482 | 51.913 | -8.470 | 1.00 17.38 | C |
| ATOM | 172 | O | ASN | A | 67 | -48.408 | 52.283 | -7.742 | 1.00 16.95 | O |
| ATOM | 173 | N | ALA | A | 68 | -46.633 | 52.745 | -9.072 | 1.00 17.63 | N |
| ATOM | 174 | CA | ALA | A | 68 | -46.619 | 54.197 | -8.855 | 1.00 17.48 | C |
| ATOM | 175 | CB | ALA | A | 68 | -45.204 | 54.628 | -8.541 | 1.00 17.03 | C |
| ATOM | 176 | C | ALA | A | 68 | -47.173 | 54.979 | -10.046 | 1.00 17.59 | C |
| ATOM | 177 | O | ALA | A | 68 | -47.366 | 54.437 | -11.153 | 1.00 17.67 | O |
| ATOM | 178 | N | ALA | A | 69 | -46.264 | 56.264 | -9.811 | 1.00 17.51 | N |
| ATOM | 179 | CA | ALA | A | 69 | -47.812 | 57.179 | -10.887 | 1.00 17.17 | C |
| ATOM | 180 | CB | ALA | A | 69 | -49.312 | 57.414 | -10.874 | 1.00 16.43 | C |
| ATOM | 181 | C | ALA | A | 69 | -47.038 | 58.503 | -10.784 | 1.00 16.93 | C |
| ATOM | 182 | O | ALA | A | 69 | -46.671 | 58.920 | -9.688 | 1.00 17.46 | O |
| ATOM | 183 | N | LEU | A | 70 | -46.767 | 59.133 | -11.931 | 1.00 16.63 | N |
| ATOM | 184 | CA | LEU | A | 70 | -46.194 | 60.482 | -12.062 | 1.00 15.77 | C |
| ATOM | 185 | CB | LEU | A | 70 | -44.751 | 60.460 | -12.525 | 1.00 15.67 | C |
| ATOM | 186 | CG | LEU | A | 70 | -43.953 | 61.757 | -12.749 | 1.00 15.75 | C |
| ATOM | 187 | CD1 | LEU | A | 70 | -42.461 | 61.509 | -12.610 | 1.00 15.26 | C |
| ATOM | 188 | CD2 | LEU | A | 70 | -44.228 | 62.394 | -14.102 | 1.00 15.75 | C |
| ATOM | 189 | C | LEU | A | 70 | -47.077 | 61.309 | -12.908 | 1.00 15.60 | C |
| ATOM | 190 | O | LEU | A | 70 | -47.537 | 60.834 | -13.948 | 1.00 15.82 | O |
| ATOM | 191 | N | VAL | A | 71 | -47.344 | 62.543 | -12.501 | 1.00 15.65 | N |
| ATOM | 192 | CA | VAL | A | 71 | -48.077 | 63.472 | -13.347 | 1.00 15.44 | C |
| ATOM | 193 | CB | VAL | A | 71 | -49.294 | 64.081 | -12.631 | 1.00 15.23 | C |
| ATOM | 194 | CG1 | VAL | A | 71 | -50.139 | 64.899 | -13.600 | 1.00 15.85 | C |
| ATOM | 195 | CG2 | VAL | A | 71 | -50.139 | 62.987 | -12.019 | 1.00 15.08 | C |
| ATOM | 196 | C | VAL | A | 71 | -47.133 | 64.578 | -13.766 | 1.00 15.70 | C |
| ATOM | 197 | O | VAL | A | 71 | -46.338 | 65.091 | -12.985 | 1.00 15.62 | O |
| ATOM | 198 | N | ILE | A | 72 | -47.215 | 64.921 | -15.068 | 1.00 16.07 | N |
| ATOM | 199 | CA | ILE | A | 72 | -46.501 | 66.065 | -15.614 | 1.00 15.80 | C |
| ATOM | 200 | CB | ILE | A | 72 | -45.744 | 65.707 | -16.898 | 1.00 15.22 | C |
| ATOM | 201 | CG1 | ILE | A | 72 | -44.591 | 64.752 | -16.560 | 1.00 14.79 | C |
| ATOM | 202 | CD1 | ILE | A | 72 | -44.020 | 64.005 | -17.735 | 1.00 14.90 | C |
| ATOM | 203 | CG2 | ILE | A | 72 | -45.264 | 66.976 | -17.600 | 1.00 14.90 | C |
| ATOM | 204 | C | ILE | A | 72 | -47.516 | 67.113 | -15.958 | 1.00 16.21 | C |
| ATOM | 205 | O | ILE | A | 72 | -48.482 | 66.823 | -16.658 | 1.00 16.30 | O |
| ATOM | 206 | N | SER | A | 73 | -47.303 | 68.326 | -15.468 | 1.00 16.85 | N |
| ATOM | 207 | CA | SER | A | 73 | -48.046 | 69.484 | -15.935 | 1.00 17.61 | C |
| ATOM | 208 | CB | SER | A | 73 | -49.754 | 70.179 | -14.767 | 1.00 17.77 | C |
| ATOM | 209 | OG | SER | A | 73 | -49.619 | 71.209 | -15.232 | 1.00 18.12 | O |
| ATOM | 210 | C | SER | A | 73 | -47.091 | 70.430 | -16.681 | 1.00 17.90 | C |
| ATOM | 211 | O | SER | A | 73 | -46.256 | 71.079 | -16.074 | 1.00 17.61 | O |
| ATOM | 212 | N | ASP | A | 74 | -47.208 | 70.492 | -18.005 | 1.00 18.92 | N |
| ATOM | 213 | CA | ASP | A | 74 | -46.332 | 71.313 | -18.858 | 1.00 19.73 | C |
| ATOM | 214 | CB | ASP | A | 74 | -46.956 | 72.815 | -18.623 | 1.00 19.14 | C |
| ATOM | 215 | CG | ASP | A | 74 | -47.968 | 73.242 | -18.971 | 1.00 19.49 | C |
| ATOM | 216 | OD1 | ASP | A | 74 | -48.502 | 72.713 | -19.970 | 1.00 19.64 | O |
| ATOM | 217 | OD2 | ASP | A | 74 | -48.558 | 74.084 | -18.251 | 1.00 19.35 | O |
| ATOM | 218 | C | ASP | A | 74 | -44.869 | 70.915 | -18.740 | 1.00 20.50 | C |
| ATOM | 219 | O | ASP | A | 74 | -44.486 | 69.884 | -19.278 | 1.00 20.61 | O |
| ATOM | 220 | N | LYS | A | 75 | -44.061 | 71.701 | -18.028 | 1.00 22.30 | N |
| ATOM | 221 | CA | LYS | A | 75 | -42.616 | 71.425 | -17.937 | 1.00 24.11 | C |
| ATOM | 222 | CB | LYS | A | 75 | -41.787 | 72.691 | -18.216 | 1.00 25.47 | C |
| ATOM | 223 | CG | LYS | A | 75 | -42.187 | 73.443 | -19.476 | 1.00 27.21 | C |
| ATOM | 224 | CD | LYS | A | 75 | -41.185 | 74.528 | -19.844 | 1.00 29.07 | C |
| ATOM | 225 | CE | LYS | A | 75 | -41.653 | 75.389 | -21.075 | 1.00 30.57 | C |

FIG. 22C

| | | | | | | | | | | |
|---|---|---|---|---|---|---|---|---|---|---|
| ATOM | 226 | NZ | LYS | A | 75 | -41.075 | 76.687 | -21.147 | 1.00 30.90 | N |
| ATOM | 227 | C | LYS | A | 75 | -42.175 | 70.805 | -16.609 | 1.00 24.32 | C |
| ATOM | 228 | O | LYS | A | 75 | -41.038 | 70.353 | -16.483 | 1.00 25.23 | O |
| ATOM | 229 | N | ILE | A | 76 | -43.353 | 70.796 | -15.616 | 1.00 23.10 | N |
| ATOM | 230 | CA | ILE | A | 76 | -42.672 | 70.282 | -14.296 | 1.00 22.92 | C |
| ATOM | 231 | CB | ILE | A | 76 | -42.844 | 71.317 | -13.131 | 1.00 22.59 | C |
| ATOM | 232 | CG1 | ILE | A | 76 | -44.213 | 72.022 | -13.157 | 1.00 23.09 | C |
| ATOM | 233 | CD1 | ILE | A | 76 | -45.391 | 71.214 | -12.622 | 1.00 24.32 | C |
| ATOM | 234 | CG2 | ILE | A | 76 | -41.766 | 72.390 | -13.171 | 1.00 22.19 | C |
| ATOM | 235 | C | ILE | A | 76 | -43.420 | 68.996 | -13.962 | 1.00 23.01 | C |
| ATOM | 236 | O | ILE | A | 76 | -44.342 | 68.580 | -14.679 | 1.00 23.11 | O |
| ATOM | 237 | N | ILE | A | 77 | -43.011 | 68.388 | -12.854 | 1.00 21.41 | N |
| ATOM | 238 | CA | ILE | A | 77 | 43.592 | 67.167 | 12.367 | 1.00 19.52 | C |
| ATOM | 239 | CB | ILE | A | 77 | -42.491 | 66.266 | -11.771 | 1.00 19.08 | C |
| ATOM | 240 | CG1 | ILE | A | 77 | -41.629 | 65.708 | -12.912 | 1.00 18.86 | C |
| ATOM | 241 | CD1 | ILE | A | 77 | -40.256 | 65.208 | -12.513 | 1.00 18.32 | C |
| ATOM | 242 | CG2 | ILE | A | 77 | -43.085 | 65.151 | -10.914 | 1.00 18.55 | C |
| ATOM | 243 | C | ILE | A | 77 | -44.618 | 67.594 | -11.343 | 1.00 19.70 | C |
| ATOM | 244 | O | ILE | A | 77 | -44.283 | 68.262 | -10.346 | 1.00 19.95 | O |
| ATOM | 245 | N | ALA | A | 78 | -45.877 | 67.241 | -11.585 | 1.00 19.24 | N |
| ATOM | 246 | CA | ALA | A | 78 | -46.947 | 67.730 | -10.702 | 1.00 19.08 | C |
| ATOM | 247 | CB | ALA | A | 78 | -48.231 | 67.964 | -11.473 | 1.00 19.12 | C |
| ATOM | 248 | C | ALA | A | 78 | -47.194 | 66.867 | -9.462 | 1.00 19.73 | C |
| ATOM | 249 | O | ALA | A | 78 | -47.577 | 67.375 | -8.431 | 1.00 18.73 | O |
| ATOM | 250 | N | PHE | A | 79 | -46.964 | 65.566 | -9.575 | 1.00 19.85 | N |
| ATOM | 251 | CA | PHE | A | 79 | -47.226 | 64.628 | -8.496 | 1.00 18.59 | C |
| ATOM | 252 | CB | PHE | A | 79 | -48.712 | 64.281 | -8.478 | 1.00 19.28 | C |
| ATOM | 253 | CG | PHE | A | 79 | -49.039 | 63.030 | -7.719 | 1.00 19.21 | C |
| ATOM | 254 | CD1 | PHE | A | 79 | -49.450 | 63.099 | -6.393 | 1.00 18.86 | C |
| ATOM | 255 | CE1 | PHE | A | 79 | -49.766 | 61.953 | -5.689 | 1.00 18.79 | C |
| ATOM | 256 | CZ | PHE | A | 79 | -49.660 | 60.715 | -6.298 | 1.00 18.73 | C |
| ATOM | 257 | CE2 | PHE | A | 79 | -49.249 | 60.628 | -7.622 | 1.00 19.13 | C |
| ATOM | 258 | CD2 | PHE | A | 79 | -48.953 | 61.783 | -8.333 | 1.00 19.11 | C |
| ATOM | 259 | C | PHE | A | 79 | -46.433 | 63.358 | -8.733 | 1.00 18.40 | C |
| ATOM | 260 | O | PHE | A | 79 | 46.330 | 62.894 | 9.870 | 1.00 17.80 | O |
| ATOM | 261 | N | VAL | A | 80 | -45.867 | 62.832 | -7.651 | 1.00 18.34 | N |
| ATOM | 262 | CA | VAL | A | 80 | -45.259 | 61.504 | -7.626 | 1.00 18.31 | C |
| ATOM | 263 | CB | VAL | A | 80 | -43.717 | 61.572 | -7.568 | 1.00 17.92 | C |
| ATOM | 264 | CG1 | VAL | A | 80 | 43.110 | 60.183 | 7.430 | 1.00 17.54 | C |
| ATOM | 265 | CG2 | VAL | A | 80 | -43.157 | 62.243 | -8.808 | 1.00 18.34 | C |
| ATOM | 266 | C | VAL | A | 80 | -45.805 | 60.770 | -6.397 | 1.00 18.23 | C |
| ATOM | 267 | O | VAL | A | 80 | -45.807 | 61.312 | -5.290 | 1.00 19.57 | O |
| ATOM | 268 | N | GLY | A | 81 | -46.281 | 59.549 | -6.593 | 1.00 19.80 | N |
| ATOM | 269 | CA | GLY | A | 81 | -46.822 | 58.739 | -5.502 | 1.00 19.01 | C |
| ATOM | 270 | C | GLY | A | 81 | -47.319 | 57.311 | -6.026 | 1.00 19.73 | C |
| ATOM | 271 | O | GLY | A | 81 | -46.954 | 56.982 | -7.133 | 1.00 20.26 | O |
| ATOM | 272 | N | SER | A | 82 | -48.158 | 56.746 | -5.248 | 1.00 20.05 | N |
| ATOM | 273 | CA | SER | A | 82 | -48.685 | 55.468 | -5.685 | 1.00 20.46 | C |
| ATOM | 274 | CB | SER | A | 82 | -49.079 | 54.642 | -4.473 | 1.00 21.17 | C |
| ATOM | 275 | OG | SER | A | 82 | -50.401 | 54.948 | -4.393 | 1.00 22.40 | O |
| ATOM | 276 | C | SER | A | 82 | -49.882 | 55.691 | -6.620 | 1.00 20.14 | C |
| ATOM | 277 | O | SER | A | 82 | -50.542 | 56.729 | -6.543 | 1.00 20.25 | O |
| ATOM | 278 | N | GLU | A | 83 | -50.144 | 54.735 | -7.509 | 1.00 19.90 | N |
| ATOM | 279 | CA | GLU | A | 83 | -51.307 | 54.800 | -8.422 | 1.00 20.61 | C |
| ATOM | 280 | CB | GLU | A | 83 | -51.483 | 53.460 | -9.178 | 1.00 20.58 | C |
| ATOM | 281 | CG | GLU | A | 83 | -52.728 | 53.328 | -10.054 | 1.00 21.79 | C |
| ATOM | 282 | CD | GLU | A | 83 | -52.549 | 52.360 | -11.232 | 1.00 23.84 | C |
| ATOM | 283 | OE1 | GLU | A | 83 | -53.511 | 52.180 | -12.027 | 1.00 24.15 | O |
| ATOM | 284 | OE2 | GLU | A | 83 | -51.446 | 51.778 | -11.386 | 1.00 24.42 | O |
| ATOM | 285 | C | GLU | A | 83 | -52.601 | 55.214 | -7.689 | 1.00 20.56 | C |
| ATOM | 286 | O | GLU | A | 83 | 53.281 | 56.158 | 8.094 | 1.00 20.28 | O |
| ATOM | 287 | N | ALA | A | 84 | -52.920 | 54.506 | -6.608 | 1.00 21.05 | N |
| ATOM | 288 | CA | ALA | A | 84 | -54.103 | 54.796 | -5.781 | 1.00 22.15 | C |
| ATOM | 289 | CB | ALA | A | 84 | -54.105 | 53.912 | -4.532 | 1.00 21.44 | C |
| ATOM | 290 | C | ALA | A | 84 | -54.236 | 56.276 | -5.378 | 1.00 21.84 | C |
| ATOM | 291 | O | ALA | A | 84 | -55.343 | 56.787 | -5.263 | 1.00 21.76 | O |
| ATOM | 292 | N | ASP | A | 85 | -53.110 | 56.957 | -5.186 | 1.00 22.20 | N |
| ATOM | 293 | CA | ASP | A | 85 | -53.116 | 58.319 | -4.647 | 1.00 22.31 | C |
| ATOM | 294 | CB | ASP | A | 85 | -51.991 | 58.469 | -3.618 | 1.00 22.54 | C |
| ATOM | 295 | CG | ASP | A | 85 | -52.169 | 57.546 | -2.402 | 1.00 23.17 | C |
| ATOM | 296 | OD1 | ASP | A | 85 | -53.297 | 57.092 | -2.117 | 1.00 24.22 | O |
| ATOM | 297 | OD2 | ASP | A | 85 | -51.168 | 57.261 | -1.712 | 1.00 23.33 | O |
| ATOM | 298 | C | ASP | A | 85 | -53.132 | 59.509 | -5.642 | 1.00 22.39 | C |
| ATOM | 299 | O | ASP | A | 85 | 53.098 | 60.646 | 5.194 | 1.00 22.96 | O |
| ATOM | 300 | N | ILE | A | 86 | -53.205 | 59.272 | -6.950 | 1.00 22.67 | N |
| ATOM | 301 | CA | ILE | A | 86 | -53.247 | 60.363 | -7.950 | 1.00 22.79 | C |
| ATOM | 302 | CB | ILE | A | 86 | -53.485 | 59.910 | -9.411 | 1.00 22.19 | C |

FIG. 22D

```
ATOM    303  CG1 ILE A   86     -52.399  58.957  -9.895  1.00 21.62           C
ATOM    304  CD1 ILE A   86     -52.856  58.107 -11.059  1.00 20.86           C
ATOM    305  CG2 ILE A   86     -53.559  61.094 -10.376  1.00 21.61           C
ATOM    306  C   ILE A   86     -54.383  61.343  -7.617  1.00 23.60           C
ATOM    307  O   ILE A   86     -55.527  60.908  -7.463  1.00 24.71           O
ATOM    308  N   PRO A   87     -54.089  62.646  -7.507  1.00 23.89           N
ATOM    309  CA  PRO A   87     -55.192  63.505  -7.235  1.00 25.09           C
ATOM    310  CB  PRO A   87     -54.490  64.946  -7.144  1.00 24.74           C
ATOM    311  CG  PRO A   87     -53.055  64.632  -6.982  1.00 23.79           C
ATOM    312  CD  PRO A   87     -52.779  63.313  -7.535  1.00 23.45           C
ATOM    313  C   PRO A   87     -56.231  63.573  -8.354  1.00 26.45           C
ATOM    314  O   PRO A   87     -55.873  63.445  -9.541  1.00 26.18           O
ATOM    315  N   LYS A   88     -57.508  63.693  -8.002  1.00 28.46           N
ATOM    316  CA  LYS A   88     -58.534  63.543  -8.979  1.00 28.73           C
ATOM    317  CB  LYS A   88     -59.959  63.343  -8.294  1.00 30.83           C
ATOM    318  CG  LYS A   88     -60.221  61.877  -7.945  1.00 33.60           C
ATOM    319  CD  LYS A   88     -61.430  61.642  -7.047  1.00 36.25           C
ATOM    320  CE  LYS A   88     -61.111  61.840  -5.569  1.00 36.54           C
ATOM    321  NZ  LYS A   88     -61.597  63.156  -5.065  1.00 39.85           N
ATOM    322  C   LYS A   88     -58.635  64.627 -10.048  1.00 27.69           C
ATOM    323  O   LYS A   88     -59.142  64.386 -11.142  1.00 28.38           O
ATOM    324  N   LYS A   89     -58.083  65.802  -9.744  1.00 27.16           N
ATOM    325  CA  LYS A   89     -57.997  66.895 -10.729  1.00 26.38           C
ATOM    326  CB  LYS A   89     -57.436  68.173 -10.108  1.00 26.54           C
ATOM    327  CG  LYS A   89     -56.103  68.020  -9.391  1.00 27.40           C
ATOM    328  CD  LYS A   89     -55.508  69.376  -9.044  1.00 27.43           C
ATOM    329  CE  LYS A   89     -54.599  69.259  -7.843  1.00 26.08           C
ATOM    330  NZ  LYS A   89     -53.934  70.557  -7.544  1.00 28.68           N
ATOM    331  C   LYS A   89     -57.189  66.493 -11.966  1.00 26.10           C
ATOM    332  O   LYS A   89     -57.578  66.796 -13.103  1.00 26.46           O
ATOM    333  N   TYR A   90     -56.085  65.787 -11.739  1.00 24.57           N
ATOM    334  CA  TYR A   90     -55.271  65.296 -12.826  1.00 23.43           C
ATOM    335  CB  TYR A   90     -53.887  64.983 -12.323  1.00 23.29           C
ATOM    336  CG  TYR A   90     -53.129  66.016 -11.608  1.00 23.30           C
ATOM    337  CD1 TYR A   90      52.953  67.271  12.192  1.00 22.63           C
ATOM    338  CE1 TYR A   90     -52.252  68.268 -11.531  1.00 22.94           C
ATOM    339  CZ  TYR A   90     -51.709  68.037 -10.273  1.00 22.93           C
ATOM    340  OH  TYR A   90     -51.015  68.974  -9.584  1.00 23.27           O
ATOM    341  CE2 TYR A   90      51.859  66.774   9.688  1.00 22.54           C
ATOM    342  CD2 TYR A   90     -52.559  65.789 -10.351  1.00 22.96           C
ATOM    343  C   TYR A   90     -55.932  64.149 -13.607  1.00 23.41           C
ATOM    344  O   TYR A   90     -55.805  64.081 -14.840  1.00 23.36           O
ATOM    345  N   LEU A   91     -56.642  63.255 -12.916  1.00 22.75           N
ATOM    346  CA  LEU A   91     -57.386  62.208 -13.623  1.00 22.53           C
ATOM    347  CB  LEU A   91     -58.076  61.257 -12.655  1.00 22.43           C
ATOM    348  CG  LEU A   91     -57.247  60.338 -11.751  1.00 22.95           C
ATOM    349  CD1 LEU A   91     -58.151  59.666 -10.715  1.00 21.69           C
ATOM    350  CD2 LEU A   91     -56.450  59.306 -12.549  1.00 22.63           C
ATOM    351  C   LEU A   91     -58.410  62.839 -14.560  1.00 22.69           C
ATOM    352  O   LEU A   91     -58.685  62.319 -15.646  1.00 22.48           O
ATOM    353  N   ARG A   92     -58.947  63.979 -14.139  1.00 22.93           N
ATOM    354  CA  ARG A   92     -59.906  64.721 -14.937  1.00 24.07           C
ATOM    355  CB  ARG A   92     -60.693  65.698 -14.061  1.00 25.03           C
ATOM    356  CG  ARG A   92     -62.055  65.160 -13.691  1.00 26.89           C
ATOM    357  CD  ARG A   92     -62.863  66.146 -12.864  1.00 29.35           C
ATOM    358  NE  ARG A   92     -63.056  65.696 -11.491  1.00 29.76           N
ATOM    359  CZ  ARG A   92     -62.346  66.138 -10.444  1.00 30.13           C
ATOM    360  NH1 ARG A   92     -62.595  65.663  -9.227  1.00 30.57           N
ATOM    361  NH2 ARG A   92     -61.399  67.053 -10.619  1.00 29.09           N
ATOM    362  C   ARG A   92     -59.300  65.438 -16.144  1.00 24.25           C
ATOM    363  O   ARG A   92      59.829  65.338  17.250  1.00 24.89           O
ATOM    364  N   SER A   93     -58.190  66.143 -15.938  1.00 23.76           N
ATOM    365  CA  SER A   93     -57.688  67.078 -16.942  1.00 23.54           C
ATOM    366  CB  SER A   93     -57.075  68.298 -16.250  1.00 23.04           C
ATOM    367  OG  SER A   93     -56.804  67.923 -15.396  1.00 21.89           O
ATOM    368  C   SER A   93     -56.693  66.466 -17.929  1.00 24.09           C
ATOM    369  O   SER A   93     -56.436  67.024 -18.998  1.00 24.85           O
ATOM    370  N   THR A   94     -56.142  65.303 -17.569  1.00 23.65           N
ATOM    371  CA  THR A   94     -55.101  64.635 -18.367  1.00 23.25           C
ATOM    372  CB  THR A   94     -54.716  63.272 -17.747  1.00 22.94           C
ATOM    373  OG1 THR A   94     -53.557  62.732 -18.405  1.00 22.49           O
ATOM    374  CG2 THR A   94     -55.880  62.244 -17.817  1.00 22.10           C
ATOM    375  C   THR A   94     -55.455  64.437 -19.849  1.00 22.92           C
ATOM    376  O   THR A   94      56.558  64.064  20.170  1.00 22.72           O
ATOM    377  N   GLN A   95     -54.509  64.738 -20.741  1.00 24.40           N
ATOM    378  CA  GLN A   95     -54.728  64.588 -22.196  1.00 25.38           C
ATOM    379  CB  GLN A   95     -54.139  65.752 -23.003  1.00 26.78           C
```

FIG. 22E

| ATOM | 380 | CG | GLN | A | 95 | -54.893 | 67.066 | -22.957 | 1.00 | 29.49 | C |
|---|---|---|---|---|---|---|---|---|---|---|---|
| ATOM | 381 | CD | GLN | A | 95 | -54.343 | 67.944 | -21.734 | 1.00 | 31.12 | C |
| ATOM | 382 | OE1 | GLN | A | 95 | -53.426 | 67.547 | -21.000 | 1.00 | 31.13 | O |
| ATOM | 383 | NE2 | GLN | A | 95 | 54.893 | 59.151 | 21.605 | 1.00 | 30.97 | N |
| ATOM | 384 | C | GLN | A | 95 | -54.136 | 63.304 | -22.732 | 1.00 | 24.46 | C |
| ATOM | 385 | O | GLN | A | 95 | -54.530 | 62.836 | -23.796 | 1.00 | 25.58 | O |
| ATOM | 386 | N | SER | A | 96 | -53.158 | 62.750 | -22.030 | 1.00 | 22.32 | N |
| ATOM | 387 | CA | SER | A | 96 | -52.633 | 61.462 | -22.435 | 1.00 | 21.13 | C |
| ATOM | 388 | CB | SER | A | 96 | -51.594 | 61.585 | -23.564 | 1.00 | 21.25 | C |
| ATOM | 389 | OG | SER | A | 96 | -50.328 | 61.956 | -23.069 | 1.00 | 21.05 | O |
| ATOM | 390 | C | SER | A | 96 | -52.865 | 60.750 | -21.238 | 1.00 | 19.98 | C |
| ATOM | 391 | O | SER | A | 96 | -51.527 | 61.371 | -20.333 | 1.00 | 19.76 | O |
| ATOM | 392 | N | THR | A | 97 | 52.223 | 59.438 | 21.239 | 1.00 | 18.72 | N |
| ATOM | 393 | CA | THR | A | 97 | -51.693 | 58.603 | -20.191 | 1.00 | 17.83 | C |
| ATOM | 394 | CB | THR | A | 97 | -52.813 | 57.966 | -19.345 | 1.00 | 17.95 | C |
| ATOM | 395 | OG1 | THR | A | 97 | -53.240 | 56.750 | -19.960 | 1.00 | 19.68 | O |
| ATOM | 396 | CG2 | THR | A | 97 | -54.013 | 58.906 | -19.191 | 1.00 | 17.70 | C |
| ATOM | 397 | C | THR | A | 97 | -50.796 | 57.524 | -20.805 | 1.00 | 17.52 | C |
| ATOM | 398 | O | THR | A | 97 | -50.860 | 57.240 | -22.015 | 1.00 | 17.26 | O |
| ATOM | 399 | N | HIS | A | 98 | -49.941 | 56.949 | -19.966 | 1.00 | 16.98 | N |
| ATOM | 400 | CA | HIS | A | 98 | -48.996 | 55.926 | -20.383 | 1.00 | 16.75 | C |
| ATOM | 401 | CB | HIS | A | 98 | -47.608 | 56.542 | -20.654 | 1.00 | 17.17 | C |
| ATOM | 402 | CG | HIS | A | 98 | -47.571 | 57.484 | -21.825 | 1.00 | 17.02 | C |
| ATOM | 403 | ND1 | HIS | A | 98 | -47.210 | 57.089 | -23.062 | 1.00 | 17.24 | N |
| ATOM | 404 | CE1 | HIS | A | 98 | -47.269 | 58.143 | -23.910 | 1.00 | 17.31 | C |
| ATOM | 405 | NE2 | HIS | A | 98 | -47.662 | 59.221 | -23.203 | 1.00 | 17.43 | N |
| ATOM | 406 | CD2 | HIS | A | 98 | -47.854 | 58.851 | -21.914 | 1.00 | 17.06 | C |
| ATOM | 407 | C | HIS | A | 98 | -48.870 | 54.961 | -19.262 | 1.00 | 16.02 | C |
| ATOM | 408 | O | HIS | A | 98 | -49.049 | 55.339 | -18.101 | 1.00 | 15.28 | O |
| ATOM | 409 | N | ARG | A | 99 | -48.534 | 53.716 | -19.594 | 1.00 | 16.22 | N |
| ATOM | 410 | CA | ARG | A | 99 | -48.727 | 52.729 | -19.553 | 1.00 | 16.36 | C |
| ATOM | 411 | CB | ARG | A | 99 | -49.407 | 51.777 | -18.330 | 1.00 | 16.11 | C |
| ATOM | 412 | CG | ARG | A | 99 | -49.208 | 50.863 | -17.136 | 1.00 | 16.33 | C |
| ATOM | 413 | CD | ARG | A | 99 | -50.440 | 50.037 | -16.831 | 1.00 | 16.50 | C |
| ATOM | 414 | NE | ARG | A | 99 | 51.544 | 50.842 | 16.315 | 1.00 | 17.09 | N |
| ATOM | 415 | CZ | ARG | A | 99 | -51.750 | 51.134 | -15.029 | 1.00 | 17.14 | C |
| ATOM | 416 | NH1 | ARG | A | 99 | -50.929 | 50.701 | -14.077 | 1.00 | 16.55 | N |
| ATOM | 417 | NH2 | ARG | A | 99 | -52.798 | 51.874 | -14.696 | 1.00 | 17.92 | N |
| ATOM | 418 | C | ARG | A | 99 | 46.046 | 51.968 | 18.890 | 1.00 | 16.32 | C |
| ATOM | 419 | O | ARG | A | 99 | -46.691 | 51.253 | -19.892 | 1.00 | 17.13 | O |
| ATOM | 420 | N | VAL | A | 100 | -45.918 | 52.129 | -18.864 | 1.00 | 15.63 | N |
| ATOM | 421 | CA | VAL | A | 100 | -44.619 | 51.537 | -18.356 | 1.00 | 15.79 | C |
| ATOM | 422 | CB | VAL | A | 100 | -43.561 | 52.619 | -18.713 | 1.00 | 15.44 | C |
| ATOM | 423 | CG1 | VAL | A | 100 | -43.946 | 53.371 | -19.974 | 1.00 | 14.07 | C |
| ATOM | 424 | CG2 | VAL | A | 100 | -43.366 | 53.602 | -17.573 | 1.00 | 15.51 | C |
| ATOM | 425 | C | VAL | A | 100 | -44.119 | 50.662 | -17.188 | 1.00 | 16.47 | C |
| ATOM | 426 | O | VAL | A | 100 | -44.524 | 50.873 | -16.034 | 1.00 | 16.91 | O |
| ATOM | 427 | N | PRO | A | 101 | -43.240 | 49.680 | -17.476 | 1.00 | 16.30 | N |
| ATOM | 428 | CA | PRO | A | 101 | -42.677 | 48.865 | -16.394 | 1.00 | 16.58 | C |
| ATOM | 429 | CB | PRO | A | 101 | -41.801 | 47.647 | -17.137 | 1.00 | 16.74 | C |
| ATOM | 430 | CG | PRO | A | 101 | -42.278 | 47.864 | -18.552 | 1.00 | 16.49 | C |
| ATOM | 431 | CD | PRO | A | 101 | -42.780 | 49.240 | -18.807 | 1.00 | 18.36 | C |
| ATOM | 432 | C | PRO | A | 101 | -41.834 | 49.662 | -15.373 | 1.00 | 17.04 | C |
| ATOM | 433 | O | PRO | A | 101 | -41.994 | 49.486 | -14.155 | 1.00 | 17.80 | O |
| ATOM | 434 | N | VAL | A | 102 | -40.975 | 50.552 | -15.864 | 1.00 | 18.51 | N |
| ATOM | 435 | CA | VAL | A | 102 | -39.999 | 51.237 | -15.029 | 1.00 | 16.39 | C |
| ATOM | 436 | CB | VAL | A | 102 | -38.598 | 50.621 | -15.213 | 1.00 | 16.21 | C |
| ATOM | 437 | CG1 | VAL | A | 102 | -37.568 | 51.339 | -14.349 | 1.00 | 16.10 | C |
| ATOM | 438 | CG2 | VAL | A | 102 | -38.626 | 49.130 | -14.900 | 1.00 | 16.14 | C |
| ATOM | 439 | C | VAL | A | 102 | -39.931 | 52.717 | -15.381 | 1.00 | 16.70 | C |
| ATOM | 440 | O | VAL | A | 102 | 39.758 | 53.065 | 16.556 | 1.00 | 16.92 | O |
| ATOM | 441 | N | LEU | A | 103 | -40.056 | 53.584 | -14.373 | 1.00 | 16.69 | N |
| ATOM | 442 | CA | LEU | A | 103 | -39.911 | 55.025 | -14.584 | 1.00 | 17.11 | C |
| ATOM | 443 | CB | LEU | A | 103 | -41.222 | 55.756 | -14.306 | 1.00 | 16.51 | C |
| ATOM | 444 | CG | LEU | A | 103 | -41.420 | 57.099 | -15.034 | 1.00 | 16.53 | C |
| ATOM | 445 | CD1 | LEU | A | 103 | -41.631 | 56.883 | -16.534 | 1.00 | 16.78 | C |
| ATOM | 446 | CD2 | LEU | A | 103 | -42.569 | 57.890 | -14.440 | 1.00 | 15.86 | C |
| ATOM | 447 | C | LEU | A | 103 | -38.796 | 55.597 | -13.709 | 1.00 | 19.65 | C |
| ATOM | 448 | O | LEU | A | 103 | -39.638 | 55.197 | -12.548 | 1.00 | 19.47 | O |
| ATOM | 449 | N | MET | A | 104 | -38.023 | 56.537 | -14.260 | 1.00 | 18.90 | N |
| ATOM | 450 | CA | MET | A | 104 | -36.909 | 57.135 | -13.541 | 1.00 | 18.76 | C |
| ATOM | 451 | CB | MET | A | 104 | -35.708 | 56.187 | -13.559 | 1.00 | 19.18 | C |
| ATOM | 452 | CG | MET | A | 104 | -35.095 | 56.003 | -14.931 | 1.00 | 20.03 | C |
| ATOM | 453 | SD | MET | A | 104 | 33.654 | 54.921 | 14.895 | 1.00 | 22.39 | S |
| ATOM | 454 | CE | MET | A | 104 | -32.398 | 56.053 | -14.272 | 1.00 | 21.65 | C |
| ATOM | 455 | C | MET | A | 104 | -36.536 | 58.494 | -14.151 | 1.00 | 19.01 | C |
| ATOM | 456 | O | MET | A | 104 | -37.022 | 58.832 | -15.246 | 1.00 | 19.93 | O |

FIG. 22F

| | | | | | | | | | |
|---|---|---|---|---|---|---|---|---|---|
| ATOM | 457 | N | PRO | A | 105 | -35.657 | 59.266 | -13.466 | 1.00 | 19.25 | N |
| ATOM | 458 | CA | PRO | A | 105 | -35.181 | 60.531 | -14.044 | 1.00 | 17.98 | C |
| ATOM | 459 | CB | PRO | A | 105 | -34.315 | 61.139 | -12.928 | 1.00 | 17.86 | C |
| ATOM | 460 | CG | PRO | A | 105 | -34.685 | 60.418 | -11.679 | 1.00 | 18.15 | C |
| ATOM | 461 | CD | PRO | A | 105 | -35.118 | 59.047 | -12.107 | 1.00 | 19.01 | C |
| ATOM | 462 | C | PRO | A | 105 | -34.331 | 60.350 | -15.298 | 1.00 | 17.84 | C |
| ATOM | 463 | O | PRO | A | 105 | -33.737 | 59.290 | -15.520 | 1.00 | 17.83 | O |
| ATOM | 464 | N | GLY | A | 106 | -34.286 | 61.387 | -16.122 | 1.00 | 17.81 | N |
| ATOM | 465 | CA | GLY | A | 106 | -33.345 | 61.417 | -17.231 | 1.00 | 17.49 | C |
| ATOM | 466 | C | GLY | A | 106 | -31.941 | 61.311 | -16.656 | 1.00 | 17.41 | C |
| ATOM | 467 | O | GLY | A | 106 | -31.652 | 61.818 | -15.550 | 1.00 | 15.94 | O |
| ATOM | 468 | N | LEU | A | 107 | -31.088 | 60.613 | -17.393 | 1.00 | 17.09 | N |
| ATOM | 469 | CA | LEU | A | 107 | -29.712 | 60.391 | -16.990 | 1.00 | 17.59 | C |
| ATOM | 470 | CB | LEU | A | 107 | -29.182 | 59.132 | -17.667 | 1.00 | 17.11 | C |
| ATOM | 471 | CG | LEU | A | 107 | -29.780 | 57.815 | -17.202 | 1.00 | 17.03 | C |
| ATOM | 472 | CD1 | LEU | A | 107 | -29.613 | 56.782 | -18.303 | 1.00 | 16.69 | C |
| ATOM | 473 | CD2 | LEU | A | 107 | -29.119 | 57.346 | -15.923 | 1.00 | 16.71 | C |
| ATOM | 474 | C | LEU | A | 107 | -28.824 | 61.588 | -17.365 | 1.00 | 18.19 | C |
| ATOM | 475 | O | LEU | A | 107 | -29.093 | 62.312 | -18.335 | 1.00 | 15.78 | O |
| ATOM | 476 | N | TRP | A | 108 | -27.777 | 61.787 | -16.571 | 1.00 | 18.62 | N |
| ATOM | 477 | CA | TRP | A | 108 | -26.734 | 62.758 | -16.855 | 1.00 | 18.46 | C |
| ATOM | 478 | CB | TRP | A | 108 | -26.462 | 63.593 | -15.622 | 1.00 | 19.30 | C |
| ATOM | 479 | CG | TRP | A | 108 | -27.456 | 64.682 | -15.348 | 1.00 | 20.95 | C |
| ATOM | 480 | CD1 | TRP | A | 108 | -28.819 | 64.548 | -15.089 | 1.00 | 21.62 | C |
| ATOM | 481 | NE1 | TRP | A | 108 | -29.395 | 65.775 | -14.869 | 1.00 | 22.60 | N |
| ATOM | 482 | CE2 | TRP | A | 108 | -28.471 | 66.762 | -14.956 | 1.00 | 21.99 | C |
| ATOM | 483 | CD2 | TRP | A | 108 | -27.188 | 66.123 | -15.253 | 1.00 | 21.68 | C |
| ATOM | 484 | CE3 | TRP | A | 108 | -26.058 | 66.920 | -15.395 | 1.00 | 22.05 | C |
| ATOM | 485 | CZ3 | TRP | A | 108 | -26.193 | 68.303 | -15.242 | 1.00 | 21.75 | C |
| ATOM | 486 | CH2 | TRP | A | 108 | -27.425 | 68.893 | -14.947 | 1.00 | 21.69 | C |
| ATOM | 487 | CZ2 | TRP | A | 108 | -28.588 | 68.135 | -14.801 | 1.00 | 22.35 | C |
| ATOM | 488 | C | TRP | A | 108 | -25.458 | 62.065 | -17.191 | 1.00 | 18.31 | C |
| ATOM | 489 | O | TRP | A | 108 | -25.137 | 61.010 | -16.631 | 1.00 | 19.22 | O |
| ATOM | 490 | N | ASP | A | 109 | -24.697 | 62.645 | -18.099 | 1.00 | 17.31 | N |
| ATOM | 491 | CA | ASP | A | 109 | -23.272 | 62.416 | -18.069 | 1.00 | 16.68 | C |
| ATOM | 492 | CB | ASP | A | 109 | -22.766 | 61.799 | -19.373 | 1.00 | 16.77 | C |
| ATOM | 493 | CG | ASP | A | 109 | -21.321 | 61.357 | -19.276 | 1.00 | 17.08 | C |
| ATOM | 494 | OD1 | ASP | A | 109 | -20.436 | 62.181 | -18.959 | 1.00 | 16.98 | O |
| ATOM | 495 | OD2 | ASP | A | 109 | -21.061 | 60.173 | -19.502 | 1.00 | 18.03 | O |
| ATOM | 496 | C | ASP | A | 109 | -22.579 | 63.739 | -17.758 | 1.00 | 15.48 | C |
| ATOM | 497 | O | ASP | A | 109 | -22.825 | 64.732 | -18.395 | 1.00 | 15.54 | O |
| ATOM | 498 | N | CYS | A | 110 | -21.705 | 63.739 | -16.773 | 1.00 | 15.29 | N |
| ATOM | 499 | CA | CYS | A | 110 | -21.105 | 64.977 | -16.289 | 1.00 | 14.87 | C |
| ATOM | 500 | CB | CYS | A | 110 | -21.044 | 64.949 | -14.778 | 1.00 | 14.42 | C |
| ATOM | 501 | SG | CYS | A | 110 | -22.691 | 64.957 | -14.093 | 1.00 | 14.81 | S |
| ATOM | 502 | C | CYS | A | 110 | -19.723 | 65.272 | -16.834 | 1.00 | 14.84 | C |
| ATOM | 503 | O | CYS | A | 110 | -19.037 | 66.175 | -16.327 | 1.00 | 15.09 | O |
| ATOM | 504 | N | HIS | A | 111 | -19.302 | 64.517 | -17.845 | 1.00 | 14.34 | N |
| ATOM | 505 | CA | HIS | A | 111 | -17.995 | 64.736 | -18.419 | 1.00 | 14.92 | C |
| ATOM | 506 | CB | HIS | A | 111 | -16.935 | 63.968 | -17.543 | 1.00 | 14.62 | C |
| ATOM | 507 | CG | HIS | A | 111 | -15.522 | 64.288 | -18.052 | 1.00 | 14.96 | C |
| ATOM | 508 | ND1 | HIS | A | 111 | -14.477 | 64.096 | -17.227 | 1.00 | 15.47 | N |
| ATOM | 509 | CE1 | HIS | A | 111 | -13.336 | 64.448 | -17.851 | 1.00 | 15.75 | C |
| ATOM | 510 | NE2 | HIS | A | 111 | -13.655 | 64.882 | -19.089 | 1.00 | 15.92 | N |
| ATOM | 511 | CD2 | HIS | A | 111 | -15.000 | 64.803 | -19.239 | 1.00 | 15.41 | C |
| ATOM | 512 | C | HIS | A | 111 | -18.008 | 64.365 | -19.867 | 1.00 | 14.59 | C |
| ATOM | 513 | O | HIS | A | 111 | -17.653 | 63.247 | -20.249 | 1.00 | 14.99 | O |
| ATOM | 514 | N | MET | A | 112 | -18.425 | 65.310 | -20.694 | 1.00 | 14.25 | N |
| ATOM | 515 | CA | MET | A | 112 | -18.467 | 65.069 | -22.108 | 1.00 | 14.72 | C |
| ATOM | 516 | CB | MET | A | 112 | -19.889 | 65.263 | -22.594 | 1.00 | 14.51 | C |
| ATOM | 517 | CG | MET | A | 112 | -20.912 | 64.360 | -21.929 | 1.00 | 14.50 | C |
| ATOM | 518 | SD | MET | A | 112 | -20.599 | 62.596 | -22.175 | 1.00 | 15.03 | S |
| ATOM | 519 | CE | MET | A | 112 | -21.054 | 62.454 | -23.908 | 1.00 | 14.84 | C |
| ATOM | 520 | C | MET | A | 112 | -17.509 | 66.027 | -22.905 | 1.00 | 15.33 | C |
| ATOM | 521 | O | MET | A | 112 | -17.097 | 67.012 | -22.207 | 1.00 | 15.94 | O |
| ATOM | 522 | N | HIS | A | 113 | -17.130 | 65.729 | -24.048 | 1.00 | 15.90 | N |
| ATOM | 523 | CA | HIS | A | 113 | -16.460 | 66.709 | -24.917 | 1.00 | 16.27 | C |
| ATOM | 524 | CB | HIS | A | 113 | -14.964 | 66.426 | -25.114 | 1.00 | 16.64 | C |
| ATOM | 525 | CG | HIS | A | 113 | -14.650 | 65.034 | -25.627 | 1.00 | 17.21 | C |
| ATOM | 526 | ND1 | HIS | A | 113 | -14.742 | 64.700 | -26.934 | 1.00 | 17.76 | N |
| ATOM | 527 | CE1 | HIS | A | 113 | -14.398 | 63.455 | -27.098 | 1.00 | 17.19 | C |
| ATOM | 528 | NE2 | HIS | A | 113 | -14.084 | 62.908 | -25.893 | 1.00 | 17.28 | N |
| ATOM | 529 | CD2 | HIS | A | 113 | -14.216 | 63.890 | -24.964 | 1.00 | 17.20 | C |
| ATOM | 530 | C | HIS | A | 113 | -17.178 | 66.858 | -26.231 | 1.00 | 16.77 | C |
| ATOM | 531 | O | HIS | A | 113 | -17.378 | 65.893 | -26.950 | 1.00 | 17.40 | O |
| ATOM | 532 | N | PHE | A | 114 | -17.581 | 68.086 | -26.532 | 1.00 | 17.18 | N |
| ATOM | 533 | CA | PHE | A | 114 | -18.341 | 68.400 | -27.731 | 1.00 | 17.28 | C |

FIG. 22G

| | | | | | | | | | |
|---|---|---|---|---|---|---|---|---|---|
| ATOM | 534 | CB | PHE | A | 114 | -19.339 | 69.513 | -27.419 | 1.00 16.82 | C |
| ATOM | 535 | CG | PHE | A | 114 | -20.875 | 69.022 | -26.942 | 1.00 16.67 | C |
| ATOM | 536 | CD1 | PHE | A | 114 | -20.704 | 68.259 | -25.782 | 1.00 16.70 | C |
| ATOM | 537 | CE1 | PHE | A | 114 | -22.028 | 67.824 | -25.344 | 1.00 16.40 | C |
| ATOM | 538 | CZ | PHE | A | 114 | -23.177 | 68.157 | -26.054 | 1.00 16.53 | C |
| ATOM | 539 | CE2 | PHE | A | 114 | -23.083 | 68.921 | -27.208 | 1.00 16.30 | C |
| ATOM | 540 | CD2 | PHE | A | 114 | -21.843 | 69.349 | -27.648 | 1.00 16.58 | C |
| ATOM | 541 | C | PHE | A | 114 | -17.409 | 68.835 | -29.847 | 1.00 17.32 | C |
| ATOM | 542 | O | PHE | A | 114 | -17.361 | 70.013 | -29.230 | 1.00 17.14 | O |
| ATOM | 543 | N | GLY | A | 115 | -16.649 | 67.868 | -29.350 | 1.00 18.10 | N |
| ATOM | 544 | CA | GLY | A | 115 | -15.587 | 68.099 | -30.349 | 1.00 18.39 | C |
| ATOM | 545 | C | GLY | A | 115 | -15.934 | 67.785 | -31.802 | 1.00 19.18 | C |
| ATOM | 546 | O | GLY | A | 115 | 15.529 | 68.532 | 32.702 | 1.00 20.08 | O |
| ATOM | 547 | N | GLY | A | 116 | -16.640 | 66.678 | -32.050 | 1.00 19.43 | N |
| ATOM | 548 | CA | GLY | A | 116 | -17.047 | 66.299 | -33.410 | 1.00 20.47 | C |
| ATOM | 549 | C | GLY | A | 116 | -15.922 | 66.218 | -34.431 | 1.00 21.73 | C |
| ATOM | 550 | O | GLY | A | 116 | -16.125 | 66.499 | -35.611 | 1.00 21.70 | O |
| ATOM | 551 | N | ASP | A | 117 | -14.742 | 65.817 | -33.959 | 1.00 23.94 | N |
| ATOM | 552 | CA | ASP | A | 117 | -13.497 | 65.757 | -34.738 | 1.00 25.58 | C |
| ATOM | 553 | CB | ASP | A | 117 | -12.359 | 65.178 | -33.870 | 1.00 27.02 | C |
| ATOM | 554 | CG | ASP | A | 117 | -12.042 | 66.029 | -32.631 | 1.00 27.82 | C |
| ATOM | 555 | OD1 | ASP | A | 117 | -10.062 | 66.322 | -32.382 | 1.00 28.33 | O |
| ATOM | 556 | OD2 | ASP | A | 117 | -12.961 | 66.404 | -31.880 | 1.00 29.72 | O |
| ATOM | 557 | C | ASP | A | 117 | -13.602 | 64.960 | -36.039 | 1.00 26.08 | C |
| ATOM | 558 | O | ASP | A | 117 | -14.344 | 63.997 | -36.107 | 1.00 25.01 | O |
| ATOM | 559 | N | ASP | A | 118 | -12.855 | 65.384 | -37.063 | 1.00 27.83 | N |
| ATOM | 560 | CA | ASP | A | 118 | -12.593 | 64.567 | -38.251 | 1.00 29.53 | C |
| ATOM | 561 | CB | ASP | A | 118 | -11.714 | 65.330 | -39.256 | 1.00 29.63 | C |
| ATOM | 562 | CG | ASP | A | 118 | -12.445 | 66.453 | -40.006 | 1.00 28.96 | C |
| ATOM | 563 | OD1 | ASP | A | 118 | -13.676 | 66.452 | -40.131 | 1.00 28.48 | O |
| ATOM | 564 | OD2 | ASP | A | 118 | -11.752 | 67.350 | -40.522 | 1.00 30.46 | O |
| ATOM | 565 | C | ASP | A | 118 | -11.837 | 63.306 | -37.810 | 1.00 31.15 | C |
| ATOM | 566 | O | ASP | A | 118 | -11.043 | 63.352 | -36.863 | 1.00 31.53 | O |
| ATOM | 567 | N | ASP | A | 119 | -12.072 | 62.188 | -38.490 | 1.00 34.14 | N |
| ATOM | 568 | CA | ASP | A | 119 | 11.357 | 60.937 | 38.188 | 1.00 37.48 | C |
| ATOM | 569 | CB | ASP | A | 119 | -11.809 | 59.838 | -39.197 | 1.00 39.59 | C |
| ATOM | 570 | CG | ASP | A | 119 | -11.470 | 58.436 | -38.661 | 1.00 41.55 | C |
| ATOM | 571 | OD1 | ASP | A | 119 | -10.439 | 58.265 | -37.976 | 1.00 42.11 | O |
| ATOM | 572 | OD2 | ASP | A | 119 | 12.237 | 57.492 | 38.962 | 1.00 42.17 | O |
| ATOM | 573 | C | ASP | A | 119 | -9.806 | 61.062 | -38.194 | 1.00 38.35 | C |
| ATOM | 574 | O | ASP | A | 119 | -9.128 | 60.664 | -37.245 | 1.00 39.83 | O |
| ATOM | 575 | N | TYR | A | 120 | -9.285 | 61.692 | -39.261 | 1.00 36.20 | N |
| ATOM | 576 | CA | TYR | A | 120 | -7.959 | 61.953 | -39.525 | 1.00 34.98 | C |
| ATOM | 577 | CB | TYR | A | 120 | -7.767 | 63.231 | -40.422 | 1.00 32.94 | C |
| ATOM | 578 | CG | TYR | A | 120 | -6.545 | 63.257 | -41.285 | 1.00 32.47 | C |
| ATOM | 579 | CD1 | TYR | A | 120 | -6.509 | 62.562 | -42.497 | 1.00 31.96 | C |
| ATOM | 580 | CE1 | TYR | A | 120 | -5.366 | 62.577 | -43.287 | 1.00 32.52 | C |
| ATOM | 581 | CZ | TYR | A | 120 | -4.246 | 63.295 | -42.864 | 1.00 31.17 | C |
| ATOM | 582 | OH | TYR | A | 120 | -3.116 | 63.323 | -43.626 | 1.00 30.32 | O |
| ATOM | 583 | CE2 | TYR | A | 120 | -4.260 | 63.993 | -41.671 | 1.00 31.21 | C |
| ATOM | 584 | CD2 | TYR | A | 120 | -5.406 | 63.966 | -40.889 | 1.00 32.06 | C |
| ATOM | 585 | C | TYR | A | 120 | -6.745 | 62.025 | -38.398 | 1.00 35.32 | C |
| ATOM | 586 | O | TYR | A | 120 | -5.928 | 61.101 | -38.307 | 1.00 36.13 | O |
| ATOM | 587 | N | TYR | A | 121 | -6.681 | 63.030 | -37.591 | 1.00 34.71 | N |
| ATOM | 588 | CA | TYR | A | 121 | -5.639 | 63.242 | -36.571 | 1.00 35.50 | C |
| ATOM | 589 | CB | TYR | A | 121 | -5.358 | 64.706 | -36.227 | 1.00 33.10 | C |
| ATOM | 590 | CG | TYR | A | 121 | -4.614 | 65.525 | -37.250 | 1.00 31.01 | C |
| ATOM | 591 | CD1 | TYR | A | 121 | -3.260 | 65.299 | -37.510 | 1.00 30.45 | C |
| ATOM | 592 | CE1 | TYR | A | 121 | -2.576 | 66.073 | -38.429 | 1.00 29.47 | C |
| ATOM | 593 | CZ | TYR | A | 121 | -3.242 | 67.105 | -39.088 | 1.00 29.20 | C |
| ATOM | 594 | OH | TYR | A | 121 | 2.575 | 67.889 | 40.008 | 1.00 29.74 | O |
| ATOM | 595 | CE2 | TYR | A | 121 | -4.576 | 67.352 | -38.837 | 1.00 28.58 | C |
| ATOM | 596 | CD2 | TYR | A | 121 | -5.255 | 66.568 | -37.925 | 1.00 29.72 | C |
| ATOM | 597 | C | TYR | A | 121 | -5.898 | 62.533 | -35.253 | 1.00 39.54 | C |
| ATOM | 598 | O | TYR | A | 121 | -6.966 | 62.729 | -34.638 | 1.00 40.66 | O |
| ATOM | 599 | N | ASN | A | 122 | -4.929 | 61.758 | -34.780 | 1.00 43.10 | N |
| ATOM | 600 | CA | ASN | A | 122 | -5.176 | 60.904 | -33.616 | 1.00 43.36 | C |
| ATOM | 601 | CB | ASN | A | 122 | -4.330 | 59.625 | -33.588 | 1.00 44.49 | C |
| ATOM | 602 | CG | ASN | A | 122 | -4.734 | 58.733 | -34.856 | 1.00 45.85 | C |
| ATOM | 603 | OD1 | ASN | A | 122 | -3.926 | 58.447 | -35.739 | 1.00 46.05 | O |
| ATOM | 604 | ND2 | ASN | A | 122 | -6.001 | 58.312 | -34.886 | 1.00 45.79 | N |
| ATOM | 605 | C | ASN | A | 122 | -5.132 | 61.566 | -32.229 | 1.00 42.93 | C |
| ATOM | 606 | O | ASN | A | 122 | -5.624 | 61.111 | -31.310 | 1.00 43.61 | O |
| ATOM | 607 | N | ASP | A | 123 | 4.356 | 62.649 | 32.102 | 1.00 41.30 | N |
| ATOM | 608 | CA | ASP | A | 123 | -4.279 | 63.450 | -30.856 | 1.00 42.05 | C |
| ATOM | 609 | CB | ASP | A | 123 | -2.816 | 63.795 | -30.539 | 1.00 42.83 | C |
| ATOM | 610 | CG | ASP | A | 123 | -2.181 | 64.725 | -31.587 | 1.00 41.36 | C |

FIG. 22H

| ATOM | 611 | CD1 | ASP | A | 123 | -2.880 | 65.219 | -32.461 | 1.00 | 40.72 | O |
|------|-----|-----|-----|---|-----|--------|--------|---------|------|-------|---|
| ATOM | 612 | OD2 | ASP | A | 123 | -0.965 | 64.964 | -31.459 | 1.00 | 41.88 | O |
| ATOM | 613 | C | ASP | A | 123 | -5.156 | 64.731 | -30.899 | 1.00 | 42.46 | C |
| ATOM | 614 | O | ASP | A | 123 | 6.124 | 65.805 | 31.666 | 1.00 | 42.05 | O |
| ATOM | 615 | N | TYR | A | 124 | -4.799 | 65.726 | -30.075 | 1.00 | 42.49 | N |
| ATOM | 616 | CA | TYR | A | 124 | -5.534 | 67.004 | -29.968 | 1.00 | 40.26 | C |
| ATOM | 617 | CB | TYR | A | 124 | -5.078 | 67.803 | -28.732 | 1.00 | 44.83 | C |
| ATOM | 618 | CG | TYR | A | 124 | -5.551 | 67.325 | -27.367 | 1.00 | 49.86 | C |
| ATOM | 619 | CD1 | TYR | A | 124 | -6.865 | 66.836 | -27.167 | 1.00 | 50.93 | C |
| ATOM | 620 | CE1 | TYR | A | 124 | -7.291 | 66.411 | -25.913 | 1.00 | 53.95 | C |
| ATOM | 621 | CZ | TYR | A | 124 | -6.409 | 66.497 | -24.831 | 1.00 | 53.83 | C |
| ATOM | 622 | OH | TYR | A | 124 | -6.818 | 66.092 | -23.577 | 1.00 | 56.46 | O |
| ATOM | 623 | CE2 | TYR | A | 124 | 5.115 | 66.993 | 25.000 | 1.00 | 52.83 | C |
| ATOM | 624 | CD2 | TYR | A | 124 | -4.694 | 67.406 | -26.255 | 1.00 | 49.88 | C |
| ATOM | 625 | C | TYR | A | 124 | -5.429 | 67.923 | -31.205 | 1.00 | 36.55 | C |
| ATOM | 626 | O | TYR | A | 124 | -6.109 | 68.955 | -31.244 | 1.00 | 33.75 | O |
| ATOM | 627 | N | THR | A | 125 | -4.573 | 67.559 | -32.177 | 1.00 | 31.85 | N |
| ATOM | 628 | CA | THR | A | 125 | -4.454 | 68.264 | -33.463 | 1.00 | 30.04 | C |
| ATOM | 629 | CB | THR | A | 125 | -3.447 | 67.570 | -34.404 | 1.00 | 29.83 | C |
| ATOM | 630 | OG1 | THR | A | 125 | -2.281 | 67.226 | -33.660 | 1.00 | 32.02 | O |
| ATOM | 631 | CG2 | THR | A | 125 | -3.042 | 68.460 | -35.600 | 1.00 | 26.74 | C |
| ATOM | 632 | C | THR | A | 125 | -5.784 | 68.320 | -34.192 | 1.00 | 29.33 | C |
| ATOM | 633 | O | THR | A | 125 | -6.071 | 69.279 | -34.908 | 1.00 | 27.41 | O |
| ATOM | 634 | N | SER | A | 126 | -6.586 | 67.278 | -34.011 | 1.00 | 30.12 | N |
| ATOM | 635 | CA | SER | A | 126 | -7.896 | 67.189 | -34.655 | 1.00 | 30.70 | C |
| ATOM | 636 | CB | SER | A | 126 | -8.511 | 65.801 | -34.428 | 1.00 | 30.79 | C |
| ATOM | 637 | OG | SER | A | 126 | -8.681 | 65.537 | -33.052 | 1.00 | 31.96 | O |
| ATOM | 638 | C | SER | A | 126 | -8.838 | 68.312 | -34.184 | 1.00 | 29.46 | C |
| ATOM | 639 | O | SER | A | 126 | -9.580 | 68.880 | -34.980 | 1.00 | 28.57 | O |
| ATOM | 640 | N | GLY | A | 127 | -8.792 | 68.629 | -32.891 | 1.00 | 29.25 | N |
| ATOM | 641 | CA | GLY | A | 127 | -9.521 | 69.747 | -32.333 | 1.00 | 27.44 | C |
| ATOM | 642 | C | GLY | A | 127 | -9.204 | 71.060 | -33.032 | 1.00 | 28.09 | C |
| ATOM | 643 | O | GLY | A | 127 | -10.111 | 71.875 | -33.253 | 1.00 | 29.02 | O |
| ATOM | 644 | N | LEU | A | 128 | -7.930 | 71.273 | -33.387 | 1.00 | 25.97 | N |
| ATOM | 645 | CA | LEU | A | 128 | 7.546 | 72.483 | 34.134 | 1.00 | 23.60 | C |
| ATOM | 646 | CB | LEU | A | 128 | -6.049 | 72.810 | -33.980 | 1.00 | 21.94 | C |
| ATOM | 647 | CG | LEU | A | 128 | -5.445 | 73.982 | -34.770 | 1.00 | 20.67 | C |
| ATOM | 648 | CD1 | LEU | A | 128 | -4.378 | 74.671 | -33.965 | 1.00 | 19.43 | C |
| ATOM | 649 | CD2 | LEU | A | 128 | 4.909 | 73.575 | 36.148 | 1.00 | 20.13 | C |
| ATOM | 650 | C | LEU | A | 128 | -7.942 | 72.409 | -35.604 | 1.00 | 23.68 | C |
| ATOM | 651 | O | LEU | A | 128 | -8.511 | 73.354 | -36.130 | 1.00 | 25.48 | O |
| ATOM | 652 | N | ALA | A | 129 | -7.646 | 71.287 | -36.249 | 1.00 | 22.44 | N |
| ATOM | 653 | CA | ALA | A | 129 | -7.710 | 71.162 | -37.687 | 1.00 | 20.43 | C |
| ATOM | 654 | CB | ALA | A | 129 | -6.821 | 70.026 | -38.113 | 1.00 | 19.54 | C |
| ATOM | 655 | C | ALA | A | 129 | -9.119 | 70.947 | -38.225 | 1.00 | 21.50 | C |
| ATOM | 656 | O | ALA | A | 129 | -9.403 | 71.302 | -39.386 | 1.00 | 24.05 | O |
| ATOM | 657 | N | THR | A | 130 | -9.998 | 70.327 | -37.434 | 1.00 | 20.97 | N |
| ATOM | 658 | CA | THR | A | 130 | -11.393 | 70.002 | -37.841 | 1.00 | 18.27 | C |
| ATOM | 659 | CB | THR | A | 130 | -12.121 | 69.095 | -36.905 | 1.00 | 17.96 | C |
| ATOM | 660 | OG1 | THR | A | 130 | -11.374 | 67.878 | -36.828 | 1.00 | 18.32 | O |
| ATOM | 661 | CG2 | THR | A | 130 | -13.521 | 68.778 | -37.424 | 1.00 | 17.33 | C |
| ATOM | 662 | C | THR | A | 130 | -12.160 | 71.385 | -37.853 | 1.00 | 17.45 | C |
| ATOM | 663 | O | THR | A | 130 | -12.253 | 72.095 | -36.818 | 1.00 | 16.46 | O |
| ATOM | 664 | N | HIS | A | 131 | -12.715 | 71.680 | -39.026 | 1.00 | 15.69 | N |
| ATOM | 665 | CA | HIS | A | 131 | -13.513 | 72.870 | -39.209 | 1.00 | 15.76 | C |
| ATOM | 666 | CB | HIS | A | 131 | -13.879 | 73.036 | -40.579 | 1.00 | 15.32 | C |
| ATOM | 667 | CG | HIS | A | 131 | -14.469 | 74.367 | -41.001 | 1.00 | 14.95 | C |
| ATOM | 668 | ND1 | HIS | A | 131 | -15.669 | 74.741 | -40.551 | 1.00 | 15.24 | N |
| ATOM | 669 | CE1 | HIS | A | 131 | -15.946 | 75.982 | -40.989 | 1.00 | 15.22 | C |
| ATOM | 670 | NE2 | HIS | A | 131 | -14.915 | 76.399 | -41.730 | 1.00 | 15.11 | N |
| ATOM | 671 | CD2 | HIS | A | 131 | 13.984 | 75.428 | 41.757 | 1.00 | 15.26 | C |
| ATOM | 672 | C | HIS | A | 131 | -14.757 | 72.736 | -38.379 | 1.00 | 16.05 | C |
| ATOM | 673 | O | HIS | A | 131 | -15.390 | 71.679 | -38.388 | 1.00 | 17.39 | O |
| ATOM | 674 | N | PRO | A | 132 | -15.134 | 73.794 | -37.626 | 1.00 | 15.64 | N |
| ATOM | 675 | CA | PRO | A | 132 | -16.260 | 73.671 | -36.705 | 1.00 | 14.91 | C |
| ATOM | 676 | CB | PRO | A | 132 | -16.345 | 75.059 | -36.092 | 1.00 | 15.28 | C |
| ATOM | 677 | CG | PRO | A | 132 | -14.930 | 75.527 | -36.124 | 1.00 | 15.16 | C |
| ATOM | 678 | CD | PRO | A | 132 | -14.440 | 75.081 | -37.457 | 1.00 | 14.97 | C |
| ATOM | 679 | C | PRO | A | 132 | -17.566 | 73.311 | -37.371 | 1.00 | 14.54 | C |
| ATOM | 680 | O | PRO | A | 132 | -18.418 | 72.707 | -36.735 | 1.00 | 13.70 | O |
| ATOM | 681 | N | ALA | A | 133 | -17.712 | 73.634 | -38.654 | 1.00 | 14.60 | N |
| ATOM | 682 | CA | ALA | A | 133 | -18.932 | 73.270 | -39.361 | 1.00 | 14.58 | C |
| ATOM | 683 | CB | ALA | A | 133 | -18.970 | 73.867 | -40.762 | 1.00 | 14.69 | C |
| ATOM | 684 | C | ALA | A | 133 | 19.059 | 71.756 | 39.399 | 1.00 | 15.02 | C |
| ATOM | 685 | O | ALA | A | 133 | -20.138 | 71.222 | -39.112 | 1.00 | 16.15 | O |
| ATOM | 686 | N | SER | A | 134 | -17.970 | 71.055 | -39.720 | 1.00 | 14.45 | N |
| ATOM | 687 | CA | SER | A | 134 | -17.955 | 69.600 | -39.602 | 1.00 | 14.80 | C |

FIG. 22I

| | | | | | | | | | |
|---|---|---|---|---|---|---|---|---|---|
| ATOM | 688 | CB | SER | A | 134 | -16.615 | 69.061 | -40.035 | 1.00 14.05 | C |
| ATOM | 689 | OG | SER | A | 134 | -16.255 | 69.596 | -41.284 | 1.00 14.76 | O |
| ATOM | 690 | C | SER | A | 134 | -18.261 | 69.130 | -38.158 | 1.00 13.84 | C |
| ATOM | 691 | O | SER | A | 134 | -19.057 | 68.219 | -37.951 | 1.00 13.99 | O |
| ATOM | 692 | N | SER | A | 135 | -17.659 | 69.757 | -37.159 | 1.00 13.55 | N |
| ATOM | 693 | CA | SER | A | 135 | -17.882 | 69.317 | -35.772 | 1.00 13.68 | C |
| ATOM | 694 | CB | SER | A | 135 | -17.072 | 70.151 | -34.796 | 1.00 13.56 | C |
| ATOM | 695 | OG | SER | A | 135 | -15.730 | 70.270 | -35.246 | 1.00 14.59 | O |
| ATOM | 696 | C | SER | A | 135 | -19.352 | 69.420 | -35.426 | 1.00 13.70 | C |
| ATOM | 697 | O | SER | A | 135 | -19.934 | 68.482 | -34.872 | 1.00 13.47 | O |
| ATOM | 698 | N | GLY | A | 136 | -19.949 | 70.554 | -35.797 | 1.00 13.55 | N |
| ATOM | 699 | CA | GLY | A | 136 | -21.338 | 70.823 | -35.525 | 1.00 13.56 | C |
| ATOM | 700 | C | GLY | A | 136 | -22.233 | 69.780 | -36.157 | 1.00 14.46 | C |
| ATOM | 701 | O | GLY | A | 136 | -23.140 | 69.261 | -35.486 | 1.00 14.29 | O |
| ATOM | 702 | N | ALA | A | 137 | -21.985 | 69.460 | -37.438 | 1.00 14.38 | N |
| ATOM | 703 | CA | ALA | A | 137 | -22.781 | 68.444 | -38.118 | 1.00 14.25 | C |
| ATOM | 704 | CB | ALA | A | 137 | -22.296 | 68.203 | -39.528 | 1.00 13.84 | C |
| ATOM | 705 | C | ALA | A | 137 | -22.764 | 67.159 | -37.294 | 1.00 14.64 | C |
| ATOM | 706 | O | ALA | A | 137 | -23.833 | 66.655 | -36.911 | 1.00 14.46 | O |
| ATOM | 707 | N | ARG | A | 138 | -21.556 | 66.671 | -36.981 | 1.00 14.68 | N |
| ATOM | 708 | CA | ARG | A | 138 | -21.372 | 65.419 | -36.243 | 1.00 14.61 | C |
| ATOM | 709 | CB | ARG | A | 138 | -19.890 | 65.024 | -36.149 | 1.00 15.10 | C |
| ATOM | 710 | CG | ARG | A | 138 | -19.179 | 64.858 | -37.480 | 1.00 16.33 | C |
| ATOM | 711 | CD | ARG | A | 138 | -17.668 | 64.076 | -37.393 | 1.00 17.62 | C |
| ATOM | 712 | NE | ARG | A | 138 | -16.800 | 64.802 | -38.106 | 1.00 20.62 | N |
| ATOM | 713 | CZ | ARG | A | 138 | -16.391 | 64.509 | -39.334 | 1.00 21.69 | C |
| ATOM | 714 | NH1 | ARG | A | 138 | -15.446 | 65.211 | -39.907 | 1.00 23.42 | N |
| ATOM | 715 | NH2 | ARG | A | 138 | -16.924 | 63.504 | -39.993 | 1.00 22.73 | N |
| ATOM | 716 | C | ARG | A | 138 | -21.975 | 65.482 | -34.838 | 1.00 14.57 | C |
| ATOM | 717 | O | ARG | A | 138 | -22.544 | 64.490 | -34.356 | 1.00 15.58 | O |
| ATOM | 718 | N | LEU | A | 139 | -21.866 | 66.629 | -34.177 | 1.00 13.36 | N |
| ATOM | 719 | CA | LEU | A | 139 | -22.434 | 66.776 | -32.839 | 1.00 13.05 | C |
| ATOM | 720 | CB | LEU | A | 139 | -21.917 | 68.043 | -32.164 | 1.00 12.61 | C |
| ATOM | 721 | CG | LEU | A | 139 | -20.398 | 68.037 | -31.945 | 1.00 12.30 | C |
| ATOM | 722 | CD1 | LEU | A | 139 | -19.839 | 69.437 | -31.740 | 1.00 12.39 | C |
| ATOM | 723 | CD2 | LEU | A | 139 | -20.011 | 67.106 | -30.808 | 1.00 12.17 | C |
| ATOM | 724 | C | LEU | A | 139 | -23.979 | 66.706 | -32.818 | 1.00 13.50 | C |
| ATOM | 725 | O | LEU | A | 139 | -24.586 | 66.356 | -31.775 | 1.00 13.75 | O |
| ATOM | 726 | N | ALA | A | 140 | -24.609 | 67.009 | -33.960 | 1.00 12.66 | N |
| ATOM | 727 | CA | ALA | A | 140 | -26.036 | 66.912 | -34.075 | 1.00 12.45 | C |
| ATOM | 728 | CB | ALA | A | 140 | -26.558 | 67.644 | -35.286 | 1.00 12.30 | C |
| ATOM | 729 | C | ALA | A | 140 | -26.459 | 65.447 | -34.065 | 1.00 13.26 | C |
| ATOM | 730 | O | ALA | A | 140 | -27.368 | 65.078 | -33.301 | 1.00 14.02 | O |
| ATOM | 731 | N | ARG | A | 141 | -25.797 | 64.585 | -34.841 | 1.00 13.10 | N |
| ATOM | 732 | CA | ARG | A | 141 | -26.081 | 63.157 | -34.715 | 1.00 12.80 | C |
| ATOM | 733 | CB | ARG | A | 141 | -25.189 | 62.341 | -35.611 | 1.00 12.50 | C |
| ATOM | 734 | CG | ARG | A | 141 | -25.388 | 60.851 | -35.438 | 1.00 12.44 | C |
| ATOM | 735 | CD | ARG | A | 141 | -26.748 | 60.448 | -35.962 | 1.00 12.78 | C |
| ATOM | 736 | NE | ARG | A | 141 | -26.951 | 59.010 | -35.999 | 1.00 12.74 | N |
| ATOM | 737 | CZ | ARG | A | 141 | -26.523 | 58.203 | -36.961 | 1.00 12.89 | C |
| ATOM | 738 | NH1 | ARG | A | 141 | -26.797 | 56.897 | -36.882 | 1.00 12.80 | N |
| ATOM | 739 | NH2 | ARG | A | 141 | -25.835 | 58.691 | -37.999 | 1.00 12.29 | N |
| ATOM | 740 | C | ARG | A | 141 | -25.904 | 62.698 | -33.259 | 1.00 13.37 | C |
| ATOM | 741 | O | ARG | A | 141 | -26.771 | 62.020 | -32.699 | 1.00 13.67 | O |
| ATOM | 742 | N | GLY | A | 142 | -24.792 | 63.093 | -32.648 | 1.00 13.64 | N |
| ATOM | 743 | CA | GLY | A | 142 | -24.443 | 62.655 | -31.290 | 1.00 14.28 | C |
| ATOM | 744 | C | GLY | A | 142 | -25.480 | 63.015 | -30.250 | 1.00 14.21 | C |
| ATOM | 745 | O | GLY | A | 142 | -25.826 | 62.194 | -29.405 | 1.00 14.38 | O |
| ATOM | 746 | N | CYS | A | 143 | -25.993 | 64.237 | -30.339 | 1.00 14.22 | N |
| ATOM | 747 | CA | CYS | A | 143 | -27.011 | 64.721 | -29.423 | 1.00 14.02 | C |
| ATOM | 748 | CB | CYS | A | 143 | -27.137 | 66.242 | -29.531 | 1.00 14.38 | C |
| ATOM | 749 | SG | CYS | A | 143 | -25.762 | 67.176 | -28.811 | 1.00 13.67 | S |
| ATOM | 750 | C | CYS | A | 143 | -28.371 | 64.065 | -29.639 | 1.00 13.91 | C |
| ATOM | 751 | O | CYS | A | 143 | -29.133 | 63.868 | -28.690 | 1.00 14.12 | O |
| ATOM | 752 | N | TRP | A | 144 | -28.668 | 63.725 | -30.883 | 1.00 14.08 | N |
| ATOM | 753 | CA | TRP | A | 144 | -29.876 | 62.951 | -31.214 | 1.00 14.25 | C |
| ATOM | 754 | CB | TRP | A | 144 | -30.010 | 62.748 | -32.725 | 1.00 13.34 | C |
| ATOM | 755 | CG | TRP | A | 144 | -31.265 | 61.997 | -33.038 | 1.00 13.15 | C |
| ATOM | 756 | CD1 | TRP | A | 144 | -32.547 | 62.504 | -33.161 | 1.00 13.01 | C |
| ATOM | 757 | NE1 | TRP | A | 144 | -33.444 | 61.511 | -33.405 | 1.00 13.08 | N |
| ATOM | 758 | CE2 | TRP | A | 144 | -32.838 | 60.305 | -33.455 | 1.00 12.94 | C |
| ATOM | 759 | CD2 | TRP | A | 144 | -31.421 | 60.534 | -33.209 | 1.00 12.88 | C |
| ATOM | 760 | CE3 | TRP | A | 144 | -30.553 | 59.443 | -33.206 | 1.00 13.31 | C |
| ATOM | 761 | CZ3 | TRP | A | 144 | -31.081 | 58.165 | -33.445 | 1.00 13.27 | C |
| ATOM | 762 | CH2 | TRP | A | 144 | -32.495 | 57.968 | -33.672 | 1.00 12.94 | C |
| ATOM | 763 | CZ2 | TRP | A | 144 | -33.357 | 59.031 | -33.684 | 1.00 12.98 | C |
| ATOM | 764 | C | TRP | A | 144 | -29.752 | 61.629 | -30.573 | 1.00 15.06 | C |

FIG. 22J

| | | | | | | | | | |
|---|---|---|---|---|---|---|---|---|---|
| ATOM | 765 | O | TRP | A | 144 | -30.675 | 61.121 | -29.952 | 1.00 15.72 | O |
| ATOM | 766 | N | GLU | A | 145 | -28.574 | 61.051 | -30.744 | 1.00 15.98 | N |
| ATOM | 767 | CA | GLU | A | 145 | -28.275 | 59.737 | -30.263 | 1.00 16.46 | C |
| ATOM | 768 | CB | GLU | A | 145 | -26.934 | 59.344 | -30.867 | 1.00 17.10 | C |
| ATOM | 769 | CG | GLU | A | 145 | -26.813 | 57.884 | -31.217 | 1.00 19.54 | C |
| ATOM | 770 | CD | GLU | A | 145 | -27.660 | 57.417 | -32.396 | 1.00 20.45 | C |
| ATOM | 771 | OE1 | GLU | A | 145 | -27.405 | 57.827 | -33.549 | 1.00 21.12 | O |
| ATOM | 772 | OE2 | GLU | A | 145 | -28.545 | 56.571 | -32.168 | 1.00 21.42 | O |
| ATOM | 773 | C | GLU | A | 145 | -28.309 | 59.701 | -28.722 | 1.00 16.40 | C |
| ATOM | 774 | O | GLU | A | 145 | -28.775 | 58.734 | -28.134 | 1.00 16.17 | O |
| ATOM | 775 | N | ALA | A | 146 | -27.873 | 60.780 | -28.072 | 1.00 16.69 | N |
| ATOM | 776 | CA | ALA | A | 146 | -27.858 | 60.861 | -26.601 | 1.00 17.10 | C |
| ATOM | 777 | CB | ALA | A | 146 | -27.223 | 62.156 | -26.138 | 1.00 16.72 | C |
| ATOM | 778 | C | ALA | A | 146 | -29.262 | 60.767 | -26.041 | 1.00 17.97 | C |
| ATOM | 779 | O | ALA | A | 146 | -29.515 | 60.023 | -25.076 | 1.00 17.69 | O |
| ATOM | 780 | N | LEU | A | 147 | -30.175 | 61.520 | -26.656 | 1.00 18.13 | N |
| ATOM | 781 | CA | LEU | A | 147 | -31.574 | 61.557 | -26.243 | 1.00 17.56 | C |
| ATOM | 782 | CB | LEU | A | 147 | -32.338 | 62.643 | -27.014 | 1.00 16.86 | C |
| ATOM | 783 | CG | LEU | A | 147 | -33.303 | 63.517 | -26.211 | 1.00 16.66 | C |
| ATOM | 784 | CD1 | LEU | A | 147 | -32.773 | 63.923 | -24.844 | 1.00 16.04 | C |
| ATOM | 785 | CD2 | LEU | A | 147 | -33.644 | 64.753 | -27.007 | 1.00 16.51 | C |
| ATOM | 786 | C | LEU | A | 147 | -32.225 | 60.190 | -26.404 | 1.00 17.48 | C |
| ATOM | 787 | O | LEU | A | 147 | -32.991 | 59.735 | -25.536 | 1.00 17.89 | O |
| ATOM | 788 | N | GLN | A | 148 | -31.900 | 59.509 | -27.489 | 1.00 17.81 | N |
| ATOM | 789 | CA | GLN | A | 148 | -32.432 | 58.164 | -27.695 | 1.00 19.19 | C |
| ATOM | 790 | CB | GLN | A | 148 | -32.104 | 57.652 | -29.099 | 1.00 18.88 | C |
| ATOM | 791 | CG | GLN | A | 148 | -32.649 | 58.542 | -30.208 | 1.00 18.89 | C |
| ATOM | 792 | CD | GLN | A | 148 | -34.142 | 58.356 | -30.454 | 1.00 19.56 | C |
| ATOM | 793 | OE1 | GLN | A | 148 | -34.613 | 57.244 | -30.752 | 1.00 19.79 | O |
| ATOM | 794 | NE2 | GLN | A | 148 | -34.894 | 59.448 | -30.348 | 1.00 18.92 | N |
| ATOM | 795 | C | GLN | A | 148 | -32.008 | 57.156 | -26.602 | 1.00 20.00 | C |
| ATOM | 796 | O | GLN | A | 148 | -32.739 | 56.199 | -26.342 | 1.00 20.44 | O |
| ATOM | 797 | N | ASN | A | 149 | -30.860 | 57.377 | -25.956 | 1.00 20.41 | N |
| ATOM | 798 | CA | ASN | A | 149 | -30.459 | 56.556 | -24.811 | 1.00 21.38 | C |
| ATOM | 799 | CB | ASN | A | 149 | -28.945 | 56.473 | -24.704 | 1.00 25.01 | C |
| ATOM | 800 | CG | ASN | A | 149 | -28.346 | 55.529 | -25.713 | 1.00 30.06 | C |
| ATOM | 801 | OD1 | ASN | A | 149 | -27.779 | 55.954 | -26.722 | 1.00 32.63 | O |
| ATOM | 802 | ND2 | ASN | A | 149 | -28.462 | 54.234 | -25.451 | 1.00 32.13 | N |
| ATOM | 803 | C | ASN | A | 149 | -30.992 | 56.998 | -23.450 | 1.00 20.24 | C |
| ATOM | 804 | O | ASN | A | 149 | -30.588 | 56.441 | -22.424 | 1.00 19.70 | O |
| ATOM | 805 | N | GLY | A | 150 | -31.850 | 58.012 | -23.421 | 1.00 18.46 | N |
| ATOM | 806 | CA | GLY | A | 150 | -32.357 | 58.515 | -22.154 | 1.00 17.58 | C |
| ATOM | 807 | C | GLY | A | 150 | -31.393 | 59.440 | -21.431 | 1.00 17.46 | C |
| ATOM | 808 | O | GLY | A | 150 | -31.516 | 59.664 | -20.221 | 1.00 16.80 | O |
| ATOM | 809 | N | TYR | A | 151 | -30.419 | 59.974 | -22.166 | 1.00 16.77 | N |
| ATOM | 810 | CA | TYR | A | 151 | -29.542 | 60.990 | -21.613 | 1.00 16.14 | C |
| ATOM | 811 | CB | TYR | A | 151 | -28.117 | 60.797 | -22.122 | 1.00 15.29 | C |
| ATOM | 812 | CG | TYR | A | 151 | -27.390 | 59.797 | -21.269 | 1.00 15.19 | C |
| ATOM | 813 | CD1 | TYR | A | 151 | -26.504 | 60.224 | -20.280 | 1.00 14.45 | C |
| ATOM | 814 | CE1 | TYR | A | 151 | -25.839 | 59.315 | -19.485 | 1.00 14.11 | C |
| ATOM | 815 | CZ | TYR | A | 151 | -26.099 | 57.967 | -19.629 | 1.00 14.23 | C |
| ATOM | 816 | OH | TYR | A | 151 | -25.426 | 57.089 | -18.800 | 1.00 14.53 | O |
| ATOM | 817 | CE2 | TYR | A | 151 | -26.982 | 57.504 | -20.581 | 1.00 14.02 | C |
| ATOM | 818 | CD2 | TYR | A | 151 | -27.632 | 58.415 | -21.396 | 1.00 14.56 | C |
| ATOM | 819 | C | TYR | A | 151 | -30.111 | 62.375 | -21.921 | 1.00 16.24 | C |
| ATOM | 820 | O | TYR | A | 151 | -30.190 | 62.787 | -23.095 | 1.00 16.44 | O |
| ATOM | 821 | N | THR | A | 152 | -30.542 | 63.064 | -20.866 | 1.00 15.13 | N |
| ATOM | 822 | CA | THR | A | 152 | -31.261 | 64.338 | -21.017 | 1.00 14.86 | C |
| ATOM | 823 | CB | THR | A | 152 | -32.620 | 64.318 | -20.285 | 1.00 14.64 | C |
| ATOM | 824 | OG1 | THR | A | 152 | -32.432 | 63.972 | -18.894 | 1.00 14.60 | O |
| ATOM | 825 | CG2 | THR | A | 152 | -33.569 | 63.327 | -20.969 | 1.00 13.77 | C |
| ATOM | 826 | C | THR | A | 152 | -30.445 | 65.553 | -20.570 | 1.00 14.52 | C |
| ATOM | 827 | O | THR | A | 152 | -30.897 | 66.694 | -20.676 | 1.00 14.60 | O |
| ATOM | 828 | N | SER | A | 153 | -29.234 | 65.296 | -20.097 | 1.00 14.39 | N |
| ATOM | 829 | CA | SER | A | 153 | -28.324 | 66.351 | -19.654 | 1.00 14.83 | C |
| ATOM | 830 | CB | SER | A | 153 | -28.540 | 66.734 | -18.179 | 1.00 14.99 | C |
| ATOM | 831 | OG | SER | A | 153 | -29.763 | 67.418 | -17.996 | 1.00 14.58 | O |
| ATOM | 832 | C | SER | A | 153 | -26.895 | 65.884 | -19.840 | 1.00 14.91 | C |
| ATOM | 833 | O | SER | A | 153 | -26.559 | 64.739 | -19.553 | 1.00 14.81 | O |
| ATOM | 834 | N | TYR | A | 154 | -26.064 | 66.797 | -20.317 | 1.00 14.89 | N |
| ATOM | 835 | CA | TYR | A | 154 | -24.668 | 66.552 | -20.576 | 1.00 14.45 | C |
| ATOM | 836 | CB | TYR | A | 154 | -24.420 | 66.567 | -22.095 | 1.00 14.22 | C |
| ATOM | 837 | CG | TYR | A | 154 | -24.500 | 65.215 | -22.793 | 1.00 14.21 | C |
| ATOM | 838 | CD1 | TYR | A | 154 | -24.655 | 64.016 | -22.079 | 1.00 13.98 | C |
| ATOM | 839 | CE1 | TYR | A | 154 | -24.698 | 62.791 | -22.742 | 1.00 13.91 | C |
| ATOM | 840 | CZ | TYR | A | 154 | -24.566 | 62.750 | -24.131 | 1.00 14.03 | C |
| ATOM | 841 | OH | TYR | A | 154 | -24.588 | 61.561 | -24.840 | 1.00 13.97 | O |

FIG. 22K

| | | | | | | | | | |
|---|---|---|---|---|---|---|---|---|---|
| ATOM | 842 | CE2 | TYR A 154 | -24.401 | 63.915 | -24.638 | 1.00 | 14.08 | C |
| ATOM | 843 | CD2 | TYR A 154 | -24.358 | 65.130 | -24.170 | 1.00 | 14.20 | C |
| ATOM | 844 | C | TYR A 154 | -24.007 | 67.762 | -19.971 | 1.00 | 14.59 | C |
| ATOM | 845 | O | TYR A 154 | 24.552 | 68.872 | 20.070 | 1.00 | 15.03 | O |
| ATOM | 846 | N | ARG A 155 | -22.870 | 67.569 | -19.313 | 1.00 | 14.18 | N |
| ATOM | 847 | CA | ARG A 155 | -22.020 | 68.696 | -18.961 | 1.00 | 14.28 | C |
| ATOM | 848 | CB | ARG A 155 | -21.651 | 68.715 | -17.467 | 1.00 | 14.25 | C |
| ATOM | 849 | CG | ARG A 155 | -20.649 | 69.810 | -17.114 | 1.00 | 14.11 | C |
| ATOM | 850 | CD | ARG A 155 | -20.275 | 69.806 | -15.649 | 1.00 | 14.34 | C |
| ATOM | 851 | NE | ARG A 155 | -19.423 | 68.675 | -15.297 | 1.00 | 14.67 | N |
| ATOM | 852 | CZ | ARG A 155 | -18.651 | 68.623 | -14.269 | 1.00 | 14.78 | C |
| ATOM | 853 | NH1 | ARG A 155 | -18.625 | 69.657 | -13.364 | 1.00 | 14.37 | N |
| ATOM | 854 | NH2 | ARG A 155 | 17.897 | 67.545 | 13.973 | 1.00 | 14.12 | N |
| ATOM | 855 | C | ARG A 155 | -20.797 | 68.558 | -19.845 | 1.00 | 14.74 | C |
| ATOM | 856 | O | ARG A 155 | -19.936 | 67.676 | -19.626 | 1.00 | 14.77 | O |
| ATOM | 857 | N | ASP A 156 | -20.747 | 69.398 | -20.880 | 1.00 | 14.43 | N |
| ATOM | 858 | CA | ASP A 156 | -19.642 | 69.473 | -21.811 | 1.00 | 13.97 | C |
| ATOM | 859 | CB | ASP A 156 | -20.075 | 70.294 | -23.030 | 1.00 | 13.55 | C |
| ATOM | 860 | CG | ASP A 156 | -19.928 | 70.585 | -23.992 | 1.00 | 13.49 | C |
| ATOM | 861 | OD1 | ASP A 156 | -17.977 | 69.768 | -24.091 | 1.00 | 12.89 | O |
| ATOM | 862 | OD2 | ASP A 156 | -18.986 | 71.647 | -24.658 | 1.00 | 13.56 | O |
| ATOM | 863 | C | ASP A 156 | -18.457 | 70.148 | -21.122 | 1.00 | 13.94 | C |
| ATOM | 864 | O | ASP A 156 | -18.560 | 71.303 | -20.719 | 1.00 | 14.18 | O |
| ATOM | 865 | N | LEU A 157 | -17.335 | 69.440 | -21.007 | 1.00 | 13.82 | N |
| ATOM | 866 | CA | LEU A 157 | -16.143 | 70.010 | -20.369 | 1.00 | 14.45 | C |
| ATOM | 867 | CB | LEU A 157 | -15.559 | 69.058 | -19.311 | 1.00 | 14.20 | C |
| ATOM | 868 | CG | LEU A 157 | -16.475 | 68.834 | -18.099 | 1.00 | 13.95 | C |
| ATOM | 869 | CD1 | LEU A 157 | -15.733 | 68.050 | -17.028 | 1.00 | 14.21 | C |
| ATOM | 870 | CD2 | LEU A 157 | -16.977 | 70.164 | -17.560 | 1.00 | 13.69 | C |
| ATOM | 871 | C | LEU A 157 | -15.031 | 70.523 | -21.292 | 1.00 | 14.92 | C |
| ATOM | 872 | O | LEU A 157 | -13.986 | 70.947 | -20.794 | 1.00 | 15.75 | O |
| ATOM | 873 | N | ALA A 158 | -15.254 | 70.506 | -22.605 | 1.00 | 14.85 | N |
| ATOM | 874 | CA | ALA A 158 | -14.334 | 71.088 | -23.573 | 1.00 | 15.21 | C |
| ATOM | 875 | CB | ALA A 158 | -13.005 | 70.352 | -23.539 | 1.00 | 15.38 | C |
| ATOM | 876 | C | ALA A 158 | 14.933 | 70.985 | 24.978 | 1.00 | 16.43 | C |
| ATOM | 877 | O | ALA A 158 | -15.039 | 69.870 | -25.527 | 1.00 | 17.58 | O |
| ATOM | 878 | N | GLY A 159 | -15.330 | 72.105 | -25.378 | 1.00 | 15.00 | N |
| ATOM | 879 | CA | GLY A 159 | -15.705 | 72.029 | -26.981 | 1.00 | 16.10 | C |
| ATOM | 880 | C | GLY A 159 | 16.770 | 73.069 | 27.371 | 1.00 | 16.63 | C |
| ATOM | 881 | O | GLY A 159 | -16.780 | 74.139 | -26.882 | 1.00 | 18.04 | O |
| ATOM | 882 | N | TYR A 160 | -17.697 | 72.555 | -28.209 | 1.00 | 16.27 | N |
| ATOM | 883 | CA | TYR A 160 | -18.720 | 73.435 | -28.803 | 1.00 | 16.13 | C |
| ATOM | 884 | CB | TYR A 160 | -18.906 | 73.160 | -30.313 | 1.00 | 15.43 | C |
| ATOM | 885 | CG | TYR A 160 | -17.500 | 73.424 | -31.002 | 1.00 | 14.86 | C |
| ATOM | 886 | CD1 | TYR A 160 | -17.033 | 74.738 | -31.165 | 1.00 | 15.50 | C |
| ATOM | 887 | CE1 | TYR A 160 | -15.820 | 75.008 | -31.784 | 1.00 | 14.88 | C |
| ATOM | 888 | CZ | TYR A 160 | -15.061 | 73.960 | -32.239 | 1.00 | 14.99 | C |
| ATOM | 889 | OH | TYR A 160 | -13.865 | 74.248 | -32.856 | 1.00 | 15.44 | O |
| ATOM | 890 | CE2 | TYR A 160 | -15.494 | 72.641 | -32.078 | 1.00 | 14.66 | C |
| ATOM | 891 | CD2 | TYR A 160 | -16.701 | 72.383 | -31.447 | 1.00 | 14.46 | C |
| ATOM | 892 | C | TYR A 160 | -20.123 | 73.413 | -28.152 | 1.00 | 16.32 | C |
| ATOM | 893 | O | TYR A 160 | -21.126 | 73.808 | -28.783 | 1.00 | 16.25 | O |
| ATOM | 894 | N | GLY A 161 | -20.185 | 73.001 | -26.885 | 1.00 | 16.07 | N |
| ATOM | 895 | CA | GLY A 161 | -21.453 | 72.873 | -26.192 | 1.00 | 16.24 | C |
| ATOM | 896 | C | GLY A 161 | -22.310 | 74.110 | -26.333 | 1.00 | 16.72 | C |
| ATOM | 897 | O | GLY A 161 | -23.481 | 74.036 | -26.706 | 1.00 | 17.29 | O |
| ATOM | 898 | N | CYS A 162 | -21.724 | 75.266 | -26.064 | 1.00 | 16.07 | N |
| ATOM | 899 | CA | CYS A 162 | -22.477 | 76.502 | -26.124 | 1.00 | 16.50 | C |
| ATOM | 900 | CB | CYS A 162 | -21.582 | 77.678 | -25.735 | 1.00 | 17.05 | C |
| ATOM | 901 | SG | CYS A 162 | -20.907 | 77.444 | -24.093 | 1.00 | 17.84 | S |
| ATOM | 902 | C | CYS A 162 | 23.047 | 76.727 | 27.504 | 1.00 | 16.16 | C |
| ATOM | 903 | O | CYS A 162 | -24.207 | 77.133 | -27.651 | 1.00 | 15.28 | O |
| ATOM | 904 | N | GLU A 163 | -22.221 | 76.442 | -28.511 | 1.00 | 16.42 | N |
| ATOM | 905 | CA | GLU A 163 | -22.559 | 76.787 | -29.877 | 1.00 | 16.70 | C |
| ATOM | 906 | CB | GLU A 163 | -21.317 | 76.831 | -30.759 | 1.00 | 16.67 | C |
| ATOM | 907 | CG | GLU A 163 | -20.472 | 78.067 | -30.469 | 1.00 | 17.53 | C |
| ATOM | 908 | CD | GLU A 163 | -19.602 | 77.929 | -29.230 | 1.00 | 18.66 | C |
| ATOM | 909 | OE1 | GLU A 163 | -19.204 | 76.791 | -28.903 | 1.00 | 19.85 | O |
| ATOM | 910 | OE2 | GLU A 163 | -19.293 | 78.948 | -28.578 | 1.00 | 19.86 | O |
| ATOM | 911 | C | GLU A 163 | -23.640 | 75.849 | -30.386 | 1.00 | 16.52 | C |
| ATOM | 912 | O | GLU A 163 | -24.583 | 76.279 | -31.060 | 1.00 | 16.43 | O |
| ATOM | 913 | N | VAL A 164 | -23.537 | 74.584 | -29.984 | 1.00 | 15.89 | N |
| ATOM | 914 | CA | VAL A 164 | -24.491 | 73.579 | -30.415 | 1.00 | 15.68 | C |
| ATOM | 915 | CB | VAL A 164 | 23.852 | 72.162 | 30.422 | 1.00 | 15.07 | C |
| ATOM | 916 | CG1 | VAL A 164 | -24.904 | 71.055 | -30.513 | 1.00 | 14.27 | C |
| ATOM | 917 | CG2 | VAL A 164 | -22.821 | 72.061 | -31.541 | 1.00 | 14.07 | C |
| ATOM | 918 | C | VAL A 164 | -25.803 | 73.697 | -29.622 | 1.00 | 16.40 | C |

FIG. 22L

| | | | | | | | | | | |
|---|---|---|---|---|---|---|---|---|---|---|
| ATOM | 919 | O | VAL | A | 164 | -26.879 | 73.430 | -30.163 | 1.00 16.65 | O |
| ATOM | 920 | N | ALA | A | 165 | -25.734 | 74.147 | -28.368 | 1.00 16.89 | N |
| ATOM | 921 | CA | ALA | A | 165 | -26.961 | 74.328 | -27.590 | 1.00 17.02 | C |
| ATOM | 922 | CB | ALA | A | 165 | 26.675 | 74.725 | 26.151 | 1.00 17.01 | C |
| ATOM | 923 | C | ALA | A | 165 | -27.921 | 75.318 | -28.252 | 1.00 18.58 | C |
| ATOM | 924 | O | ALA | A | 165 | -29.140 | 75.198 | -28.090 | 1.00 20.38 | O |
| ATOM | 925 | N | LYS | A | 166 | -27.391 | 76.271 | -29.015 | 1.00 19.20 | N |
| ATOM | 926 | CA | LYS | A | 166 | -28.236 | 77.253 | -29.722 | 1.00 19.11 | C |
| ATOM | 927 | CB | LYS | A | 166 | -27.381 | 78.293 | -30.450 | 1.00 19.39 | C |
| ATOM | 928 | CG | LYS | A | 166 | -26.556 | 79.122 | -29.479 | 1.00 20.28 | C |
| ATOM | 929 | CD | LYS | A | 166 | -25.817 | 80.276 | -30.133 | 1.00 20.81 | C |
| ATOM | 930 | CE | LYS | A | 166 | -25.744 | 81.447 | -29.163 | 1.00 20.60 | C |
| ATOM | 931 | NZ | LYS | A | 166 | 24.379 | 82.037 | 29.144 | 1.00 20.49 | N |
| ATOM | 932 | C | LYS | A | 166 | -29.182 | 76.580 | -30.701 | 1.00 19.78 | C |
| ATOM | 933 | O | LYS | A | 166 | -30.342 | 76.992 | -30.832 | 1.00 18.68 | O |
| ATOM | 934 | N | ALA | A | 167 | -28.680 | 75.543 | -31.374 | 1.00 17.94 | N |
| ATOM | 935 | CA | ALA | A | 167 | -29.446 | 74.831 | -32.383 | 1.00 17.66 | C |
| ATOM | 936 | CB | ALA | A | 167 | -28.521 | 74.111 | -33.344 | 1.00 17.05 | C |
| ATOM | 937 | C | ALA | A | 167 | -30.416 | 73.852 | -31.718 | 1.00 18.16 | C |
| ATOM | 938 | O | ALA | A | 167 | -31.396 | 73.430 | -32.342 | 1.00 18.45 | O |
| ATOM | 939 | N | ILE | A | 168 | -30.141 | 73.490 | -30.459 | 1.00 17.82 | N |
| ATOM | 940 | CA | ILE | A | 168 | -31.066 | 72.678 | -29.671 | 1.00 17.53 | C |
| ATOM | 941 | CB | ILE | A | 168 | -30.362 | 71.963 | -28.499 | 1.00 17.09 | C |
| ATOM | 942 | CG1 | ILE | A | 168 | -29.420 | 70.869 | -29.004 | 1.00 16.28 | C |
| ATOM | 943 | CD1 | ILE | A | 168 | -28.603 | 70.250 | -27.889 | 1.00 16.24 | C |
| ATOM | 944 | CG2 | ILE | A | 168 | -31.276 | 71.390 | -27.515 | 1.00 16.81 | C |
| ATOM | 945 | C | ILE | A | 168 | -32.167 | 73.599 | -29.142 | 1.00 18.12 | C |
| ATOM | 946 | O | ILE | A | 168 | -33.335 | 73.251 | -29.160 | 1.00 17.82 | O |
| ATOM | 947 | N | ASN | A | 169 | -31.795 | 74.791 | -28.696 | 1.00 19.78 | N |
| ATOM | 948 | CA | ASN | A | 169 | -32.764 | 75.672 | -28.065 | 1.00 19.55 | C |
| ATOM | 949 | CB | ASN | A | 169 | -32.061 | 76.714 | -27.218 | 1.00 20.24 | C |
| ATOM | 950 | CG | ASN | A | 169 | -31.400 | 76.094 | -26.003 | 1.00 21.91 | C |
| ATOM | 951 | OD1 | ASN | A | 169 | -30.564 | 76.723 | -25.330 | 1.00 22.67 | O |
| ATOM | 952 | ND2 | ASN | A | 169 | -31.751 | 74.829 | -25.724 | 1.00 22.28 | N |
| ATOM | 953 | C | ASN | A | 169 | 33.753 | 76.306 | 29.015 | 1.00 19.89 | C |
| ATOM | 954 | O | ASN | A | 169 | -34.923 | 76.449 | -28.677 | 1.00 19.97 | O |
| ATOM | 955 | N | ASP | A | 170 | -33.282 | 76.658 | -30.211 | 1.00 19.66 | N |
| ATOM | 956 | CA | ASP | A | 170 | -34.115 | 77.295 | -31.206 | 1.00 19.88 | C |
| ATOM | 957 | CB | ASP | A | 170 | 33.258 | 78.126 | 32.173 | 1.00 19.46 | C |
| ATOM | 958 | CG | ASP | A | 170 | -32.508 | 77.277 | -33.210 | 1.00 18.44 | C |
| ATOM | 959 | OD1 | ASP | A | 170 | -32.569 | 76.035 | -33.155 | 1.00 18.56 | O |
| ATOM | 960 | OD2 | ASP | A | 170 | -31.847 | 77.863 | -34.078 | 1.00 17.55 | O |
| ATOM | 961 | C | ASP | A | 170 | -34.924 | 76.244 | -31.950 | 1.00 19.99 | C |
| ATOM | 962 | O | ASP | A | 170 | -35.634 | 76.557 | -32.908 | 1.00 19.35 | O |
| ATOM | 963 | N | GLY | A | 171 | -34.784 | 74.992 | -31.520 | 1.00 18.74 | N |
| ATOM | 964 | CA | GLY | A | 171 | -35.613 | 73.910 | -32.024 | 1.00 17.96 | C |
| ATOM | 965 | C | GLY | A | 171 | -35.107 | 73.199 | -33.260 | 1.00 16.21 | C |
| ATOM | 966 | O | GLY | A | 171 | -35.678 | 72.189 | -33.633 | 1.00 19.43 | O |
| ATOM | 967 | N | THR | A | 172 | -34.044 | 73.705 | -33.892 | 1.00 17.31 | N |
| ATOM | 968 | CA | THR | A | 172 | -33.524 | 73.146 | -35.142 | 1.00 16.39 | C |
| ATOM | 969 | CB | THR | A | 172 | -32.335 | 73.962 | -35.684 | 1.00 16.67 | C |
| ATOM | 970 | OG1 | THR | A | 172 | -32.661 | 75.352 | -35.657 | 1.00 17.39 | C |
| ATOM | 971 | CG2 | THR | A | 172 | -32.030 | 73.596 | -37.121 | 1.00 16.40 | C |
| ATOM | 972 | C | THR | A | 172 | -33.089 | 71.691 | -35.032 | 1.00 16.06 | C |
| ATOM | 973 | O | THR | A | 172 | -33.319 | 70.892 | -35.952 | 1.00 16.27 | O |
| ATOM | 974 | N | ILE | A | 173 | -32.429 | 71.346 | -33.937 | 1.00 15.19 | N |
| ATOM | 975 | CA | ILE | A | 173 | -32.040 | 69.959 | -33.715 | 1.00 15.01 | C |
| ATOM | 976 | CB | ILE | A | 173 | -30.511 | 69.678 | -33.856 | 1.00 14.80 | C |
| ATOM | 977 | CG1 | ILE | A | 173 | -29.680 | 70.512 | -32.887 | 1.00 14.48 | C |
| ATOM | 978 | CD1 | ILE | A | 173 | -28.327 | 69.916 | -32.591 | 1.00 14.14 | C |
| ATOM | 979 | CG2 | ILE | A | 173 | 30.059 | 69.901 | 35.295 | 1.00 14.98 | C |
| ATOM | 980 | C | ILE | A | 173 | -32.570 | 69.551 | -32.379 | 1.00 15.13 | C |
| ATOM | 981 | O | ILE | A | 173 | -33.332 | 70.293 | -31.767 | 1.00 16.62 | O |
| ATOM | 982 | N | VAL | A | 174 | -32.189 | 68.374 | -31.924 | 1.00 14.73 | N |
| ATOM | 983 | CA | VAL | A | 174 | -32.778 | 67.810 | -30.717 | 1.00 14.84 | C |
| ATOM | 984 | CB | VAL | A | 174 | -33.772 | 66.689 | -31.139 | 1.00 14.46 | C |
| ATOM | 985 | CG1 | VAL | A | 174 | -33.727 | 65.500 | -30.207 | 1.00 14.53 | C |
| ATOM | 986 | CG2 | VAL | A | 174 | -35.184 | 67.242 | -31.283 | 1.00 14.10 | C |
| ATOM | 987 | C | VAL | A | 174 | -31.618 | 67.291 | -29.862 | 1.00 14.65 | C |
| ATOM | 988 | O | VAL | A | 174 | -30.625 | 66.784 | -30.420 | 1.00 14.91 | O |
| ATOM | 989 | N | GLY | A | 175 | -31.703 | 67.423 | -28.544 | 1.00 13.03 | N |
| ATOM | 990 | CA | GLY | A | 175 | -30.629 | 66.907 | -27.706 | 1.00 12.87 | C |
| ATOM | 991 | C | GLY | A | 175 | -30.859 | 67.062 | -26.217 | 1.00 12.86 | C |
| ATOM | 992 | O | GLY | A | 175 | 31.909 | 67.562 | 25.793 | 1.00 12.68 | O |
| ATOM | 993 | N | PRO | A | 176 | -29.872 | 66.646 | -25.402 | 1.00 12.93 | N |
| ATOM | 994 | CA | PRO | A | 176 | -29.971 | 66.817 | -23.932 | 1.00 12.66 | C |
| ATOM | 995 | CB | PRO | A | 176 | -28.726 | 66.073 | -23.401 | 1.00 12.85 | C |

FIG. 22M

| ATOM | 996 | CG | PRO | A | 176 | -28.235 | 65.225 | -24.537 | 1.00 | 12.91 | C |
|---|---|---|---|---|---|---|---|---|---|---|---|
| ATOM | 997 | CD | PRO | A | 176 | -28.621 | 65.970 | -25.797 | 1.00 | 12.81 | C |
| ATOM | 998 | C | PRO | A | 176 | -29.883 | 68.284 | -23.548 | 1.00 | 12.97 | C |
| ATOM | 999 | O | PRO | A | 176 | 29.461 | 69.112 | 24.359 | 1.00 | 12.79 | O |
| ATOM | 1000 | N | ASN | A | 177 | -30.280 | 68.627 | -22.327 | 1.00 | 13.26 | N |
| ATOM | 1001 | CA | ASN | A | 177 | -29.838 | 69.908 | -21.777 | 1.00 | 13.23 | C |
| ATOM | 1002 | CB | ASN | A | 177 | -30.382 | 70.110 | -20.368 | 1.00 | 13.33 | C |
| ATOM | 1003 | CG | ASN | A | 177 | -31.889 | 70.252 | -20.339 | 1.00 | 13.14 | C |
| ATOM | 1004 | OD1 | ASN | A | 177 | -32.425 | 71.286 | -20.731 | 1.00 | 13.56 | O |
| ATOM | 1005 | ND2 | ASN | A | 177 | -32.581 | 69.221 | -19.848 | 1.00 | 12.53 | N |
| ATOM | 1006 | C | ASN | A | 177 | -28.292 | 69.929 | -21.772 | 1.00 | 13.26 | C |
| ATOM | 1007 | O | ASN | A | 177 | -27.653 | 68.990 | -21.311 | 1.00 | 13.28 | O |
| ATOM | 1008 | N | VAL | A | 178 | 27.697 | 70.974 | 22.330 | 1.00 | 13.78 | N |
| ATOM | 1009 | CA | VAL | A | 178 | -26.243 | 71.074 | -22.440 | 1.00 | 13.98 | C |
| ATOM | 1010 | CB | VAL | A | 178 | -25.830 | 71.276 | -23.904 | 1.00 | 13.30 | C |
| ATOM | 1011 | CG1 | VAL | A | 178 | -24.356 | 71.392 | -24.026 | 1.00 | 13.32 | C |
| ATOM | 1012 | CG2 | VAL | A | 178 | -26.151 | 70.023 | -24.684 | 1.00 | 13.02 | C |
| ATOM | 1013 | C | VAL | A | 178 | -25.725 | 72.198 | -21.560 | 1.00 | 14.86 | C |
| ATOM | 1014 | O | VAL | A | 178 | -26.067 | 73.374 | -21.756 | 1.00 | 15.60 | O |
| ATOM | 1015 | N | TYR | A | 179 | -24.956 | 71.824 | -20.546 | 1.00 | 15.21 | N |
| ATOM | 1016 | CA | TYR | A | 179 | -24.292 | 72.786 | -19.692 | 1.00 | 15.11 | C |
| ATOM | 1017 | CB | TYR | A | 179 | -24.440 | 72.416 | -18.227 | 1.00 | 15.94 | C |
| ATOM | 1018 | CG | TYR | A | 179 | -25.864 | 72.315 | -17.819 | 1.00 | 17.46 | C |
| ATOM | 1019 | CD1 | TYR | A | 179 | -26.530 | 73.418 | -17.305 | 1.00 | 17.88 | C |
| ATOM | 1020 | CE1 | TYR | A | 179 | -27.860 | 73.338 | -16.942 | 1.00 | 19.30 | C |
| ATOM | 1021 | CZ | TYR | A | 179 | -28.540 | 72.136 | -17.084 | 1.00 | 20.28 | C |
| ATOM | 1022 | OH | TYR | A | 179 | -29.863 | 72.070 | -16.712 | 1.00 | 21.67 | O |
| ATOM | 1023 | CE2 | TYR | A | 179 | -27.898 | 71.017 | -17.586 | 1.00 | 19.37 | C |
| ATOM | 1024 | CD2 | TYR | A | 179 | -26.566 | 71.114 | -17.955 | 1.00 | 18.17 | C |
| ATOM | 1025 | C | TYR | A | 179 | -22.955 | 72.680 | -20.081 | 1.00 | 14.61 | C |
| ATOM | 1026 | O | TYR | A | 179 | -22.229 | 71.642 | -19.836 | 1.00 | 14.14 | O |
| ATOM | 1027 | N | SER | A | 180 | -22.333 | 73.744 | -20.686 | 1.00 | 14.25 | N |
| ATOM | 1028 | CA | SER | A | 180 | -21.506 | 73.696 | -21.293 | 1.00 | 14.56 | C |
| ATOM | 1029 | CB | SER | A | 180 | -21.097 | 73.927 | -22.807 | 1.00 | 13.37 | C |
| ATOM | 1030 | OG | SER | A | 180 | 19.801 | 73.996 | 23.362 | 1.00 | 14.05 | O |
| ATOM | 1031 | C | SER | A | 180 | -19.992 | 74.627 | -20.651 | 1.00 | 14.82 | C |
| ATOM | 1032 | O | SER | A | 180 | -20.343 | 75.698 | -20.078 | 1.00 | 15.28 | O |
| ATOM | 1033 | N | SER | A | 181 | -18.726 | 74.254 | -20.765 | 1.00 | 15.27 | N |
| ATOM | 1034 | CA | SER | A | 181 | 17.618 | 75.055 | 20.259 | 1.00 | 15.23 | C |
| ATOM | 1035 | CB | SER | A | 181 | -16.512 | 74.126 | -19.613 | 1.00 | 15.10 | C |
| ATOM | 1036 | OG | SER | A | 181 | -16.079 | 73.349 | -20.918 | 1.00 | 14.58 | O |
| ATOM | 1037 | C | SER | A | 181 | -17.051 | 76.017 | -21.316 | 1.00 | 15.73 | C |
| ATOM | 1038 | O | SER | A | 181 | -16.238 | 76.902 | -21.002 | 1.00 | 15.31 | O |
| ATOM | 1039 | N | GLY | A | 182 | -17.470 | 75.845 | -22.567 | 1.00 | 15.38 | N |
| ATOM | 1040 | CA | GLY | A | 182 | -16.754 | 76.472 | -23.652 | 1.00 | 15.47 | C |
| ATOM | 1041 | C | GLY | A | 182 | -15.411 | 75.788 | -23.711 | 1.00 | 15.76 | C |
| ATOM | 1042 | O | GLY | A | 182 | -15.334 | 74.566 | -23.691 | 1.00 | 16.35 | O |
| ATOM | 1043 | N | ALA | A | 183 | -14.351 | 76.509 | -24.004 | 1.00 | 15.50 | N |
| ATOM | 1044 | CA | ALA | A | 183 | -13.002 | 75.959 | -23.968 | 1.00 | 15.26 | C |
| ATOM | 1045 | CB | ALA | A | 183 | -12.022 | 77.001 | -24.471 | 1.00 | 14.68 | C |
| ATOM | 1046 | C | ALA | A | 183 | -12.619 | 75.534 | -22.547 | 1.00 | 15.34 | C |
| ATOM | 1047 | O | ALA | A | 183 | -12.932 | 76.236 | -21.587 | 1.00 | 15.29 | C |
| ATOM | 1048 | N | ALA | A | 184 | -11.952 | 74.386 | -22.420 | 1.00 | 15.65 | N |
| ATOM | 1049 | CA | ALA | A | 184 | -11.180 | 74.064 | -21.201 | 1.00 | 15.89 | C |
| ATOM | 1050 | CB | ALA | A | 184 | -10.672 | 72.631 | -21.246 | 1.00 | 15.41 | C |
| ATOM | 1051 | C | ALA | A | 184 | -10.092 | 75.038 | -21.076 | 1.00 | 15.87 | C |
| ATOM | 1052 | O | ALA | A | 184 | -9.310 | 75.337 | -22.068 | 1.00 | 15.69 | O |
| ATOM | 1053 | N | LEU | A | 185 | -9.791 | 75.545 | -19.871 | 1.00 | 16.07 | N |
| ATOM | 1054 | CA | LEU | A | 185 | -8.646 | 76.420 | -19.593 | 1.00 | 16.75 | C |
| ATOM | 1055 | CB | LEU | A | 185 | -8.947 | 77.417 | -18.462 | 1.00 | 16.71 | C |
| ATOM | 1056 | CG | LEU | A | 185 | 10.259 | 78.217 | 18.519 | 1.00 | 16.74 | C |
| ATOM | 1057 | CD1 | LEU | A | 185 | -10.081 | 79.542 | -17.790 | 1.00 | 16.47 | C |
| ATOM | 1058 | CD2 | LEU | A | 185 | -10.739 | 78.436 | -19.939 | 1.00 | 16.00 | C |
| ATOM | 1059 | C | LEU | A | 185 | -7.407 | 75.611 | -19.230 | 1.00 | 17.42 | C |
| ATOM | 1060 | O | LEU | A | 185 | -7.429 | 74.779 | -18.302 | 1.00 | 18.38 | O |
| ATOM | 1061 | N | SER | A | 186 | -6.327 | 75.877 | -19.957 | 1.00 | 17.20 | N |
| ATOM | 1062 | CA | SER | A | 186 | -5.046 | 75.242 | -19.712 | 1.00 | 17.29 | C |
| ATOM | 1063 | CB | SER | A | 186 | -4.801 | 74.194 | -20.806 | 1.00 | 17.50 | C |
| ATOM | 1064 | OG | SER | A | 186 | -3.630 | 73.466 | -20.556 | 1.00 | 17.47 | O |
| ATOM | 1065 | C | SER | A | 186 | -3.914 | 76.279 | -19.609 | 1.00 | 17.20 | C |
| ATOM | 1066 | O | SER | A | 186 | -3.984 | 77.293 | -20.396 | 1.00 | 18.37 | O |
| ATOM | 1067 | N | GLN | A | 187 | -2.981 | 76.036 | -18.889 | 1.00 | 16.24 | N |
| ATOM | 1068 | CA | GLN | A | 187 | -1.662 | 76.838 | -18.966 | 1.00 | 15.97 | C |
| ATOM | 1069 | CB | GLN | A | 187 | 0.804 | 76.695 | 17.699 | 1.00 | 16.01 | C |
| ATOM | 1070 | CG | GLN | A | 187 | -0.579 | 75.258 | -17.304 | 1.00 | 16.95 | C |
| ATOM | 1071 | CD | GLN | A | 187 | 0.854 | 75.105 | -16.589 | 1.00 | 17.70 | C |
| ATOM | 1072 | OE1 | GLN | A | 187 | 0.920 | 75.081 | -15.356 | 1.00 | 15.99 | O |

FIG. 22N

| | | | | | | | | | | |
|---|---|---|---|---|---|---|---|---|---|---|
| ATOM | 1073 | NE2 | GLN | A | 187 | 1.925 | 74.990 | -17.359 | 1.00 17.50 | N |
| ATOM | 1074 | C | GLN | A | 187 | -0.874 | 76.371 | -20.178 | 1.00 16.29 | C |
| ATOM | 1075 | O | GLN | A | 187 | -1.123 | 75.251 | -20.586 | 1.00 16.82 | O |
| ATOM | 1076 | N | THR | A | 188 | 0.065 | 77.202 | -20.648 | 1.00 15.49 | N |
| ATOM | 1077 | CA | THR | A | 188 | 1.025 | 76.751 | -21.651 | 1.00 15.22 | C |
| ATOM | 1078 | CB | THR | A | 188 | 2.056 | 77.833 | -22.029 | 1.00 15.14 | C |
| ATOM | 1079 | OG1 | THR | A | 188 | 1.378 | 78.983 | -22.545 | 1.00 14.76 | O |
| ATOM | 1080 | CG2 | THR | A | 188 | 3.029 | 77.317 | -23.117 | 1.00 14.54 | C |
| ATOM | 1081 | C | THR | A | 188 | 1.763 | 75.531 | -21.111 | 1.00 15.53 | C |
| ATOM | 1082 | O | THR | A | 188 | 2.183 | 75.512 | -19.944 | 1.00 15.25 | O |
| ATOM | 1083 | N | ALA | A | 189 | 1.904 | 74.511 | -21.958 | 1.00 15.39 | N |
| ATOM | 1084 | CA | ALA | A | 189 | 2.525 | 73.252 | -21.568 | 1.00 15.87 | C |
| ATOM | 1085 | CB | ALA | A | 189 | 3.898 | 73.480 | -20.954 | 1.00 14.85 | C |
| ATOM | 1086 | C | ALA | A | 189 | 1.634 | 72.472 | -20.606 | 1.00 16.74 | C |
| ATOM | 1087 | O | ALA | A | 189 | 2.107 | 71.556 | -19.952 | 1.00 17.42 | O |
| ATOM | 1088 | N | GLY | A | 190 | 0.356 | 72.843 | -20.522 | 1.00 17.37 | N |
| ATOM | 1089 | CA | GLY | A | 190 | -0.598 | 72.165 | -19.652 | 1.00 17.93 | C |
| ATOM | 1090 | C | GLY | A | 190 | -1.277 | 71.028 | -20.396 | 1.00 19.37 | C |
| ATOM | 1091 | O | GLY | A | 190 | -1.003 | 70.801 | -21.588 | 1.00 19.57 | O |
| ATOM | 1092 | N | HIS | A | 191 | -2.169 | 70.320 | -19.706 | 1.00 20.62 | N |
| ATOM | 1093 | CA | HIS | A | 191 | -2.840 | 69.132 | -20.266 | 1.00 22.20 | C |
| ATOM | 1094 | CB | HIS | A | 191 | -1.671 | 68.404 | -19.205 | 1.00 24.82 | C |
| ATOM | 1095 | CG | HIS | A | 191 | -4.307 | 67.115 | -19.707 | 1.00 29.36 | C |
| ATOM | 1096 | ND1 | HIS | A | 191 | -3.607 | 65.956 | -19.846 | 1.00 31.45 | N |
| ATOM | 1097 | CE1 | HIS | A | 191 | -4.423 | 64.992 | -20.310 | 1.00 31.52 | C |
| ATOM | 1098 | NE2 | HIS | A | 191 | -5.652 | 65.529 | -20.481 | 1.00 31.38 | N |
| ATOM | 1099 | CD2 | HIS | A | 191 | -5.616 | 66.834 | -20.122 | 1.00 30.50 | C |
| ATOM | 1100 | C | HIS | A | 191 | -3.690 | 69.451 | -21.456 | 1.00 21.58 | C |
| ATOM | 1101 | O | HIS | A | 191 | -3.942 | 68.592 | -22.282 | 1.00 22.84 | O |
| ATOM | 1102 | N | GLY | A | 192 | -4.141 | 70.693 | -21.554 | 1.00 20.93 | N |
| ATOM | 1103 | CA | GLY | A | 192 | -4.899 | 71.140 | -22.709 | 1.00 20.91 | C |
| ATOM | 1104 | C | GLY | A | 192 | -4.078 | 71.445 | -23.947 | 1.00 20.15 | C |
| ATOM | 1105 | O | GLY | A | 192 | -4.610 | 71.433 | -25.060 | 1.00 19.74 | O |
| ATOM | 1106 | N | ASP | A | 193 | -2.785 | 71.712 | -23.757 | 1.00 19.37 | N |
| ATOM | 1107 | CA | ASP | A | 193 | 1.898 | 72.119 | -24.857 | 1.00 19.51 | C |
| ATOM | 1108 | CB | ASP | A | 193 | -0.536 | 72.544 | -24.306 | 1.00 18.37 | C |
| ATOM | 1109 | CG | ASP | A | 193 | 0.228 | 73.433 | -25.264 | 1.00 17.84 | C |
| ATOM | 1110 | OD1 | ASP | A | 193 | 1.180 | 74.100 | -24.781 | 1.00 17.38 | O |
| ATOM | 1111 | OD2 | ASP | A | 193 | 0.119 | 73.464 | -26.484 | 1.00 16.32 | O |
| ATOM | 1112 | C | ASP | A | 193 | -1.712 | 71.023 | -25.901 | 1.00 19.10 | C |
| ATOM | 1113 | O | ASP | A | 193 | -1.800 | 69.855 | -25.565 | 1.00 20.71 | O |
| ATOM | 1114 | N | ILE | A | 194 | -1.464 | 71.399 | -27.154 | 1.00 18.96 | N |
| ATOM | 1115 | CA | ILE | A | 194 | -1.215 | 70.430 | -28.246 | 1.00 18.73 | C |
| ATOM | 1116 | CB | ILE | A | 194 | -1.930 | 70.843 | -29.545 | 1.00 18.13 | C |
| ATOM | 1117 | CG1 | ILE | A | 194 | -3.410 | 71.042 | -29.293 | 1.00 18.59 | C |
| ATOM | 1118 | CD1 | ILE | A | 194 | -4.021 | 72.092 | -30.183 | 1.00 18.89 | C |
| ATOM | 1119 | CG2 | ILE | A | 194 | -1.741 | 69.810 | -30.641 | 1.00 17.44 | C |
| ATOM | 1120 | C | ILE | A | 194 | 0.281 | 70.334 | -28.534 | 1.00 18.89 | C |
| ATOM | 1121 | O | ILE | A | 194 | 0.796 | 70.975 | -29.453 | 1.00 19.48 | O |
| ATOM | 1122 | N | PHE | A | 195 | 0.966 | 69.506 | -27.763 | 1.00 19.58 | N |
| ATOM | 1123 | CA | PHE | A | 195 | 2.427 | 69.412 | -27.783 | 1.00 20.35 | C |
| ATOM | 1124 | CB | PHE | A | 195 | 2.913 | 68.389 | -26.753 | 1.00 20.27 | C |
| ATOM | 1125 | CG | PHE | A | 195 | 2.801 | 68.871 | -25.340 | 1.00 20.92 | C |
| ATOM | 1126 | CD1 | PHE | A | 195 | 1.562 | 68.903 | -24.691 | 1.00 21.96 | C |
| ATOM | 1127 | CE1 | PHE | A | 195 | 1.456 | 69.359 | -23.369 | 1.00 22.51 | C |
| ATOM | 1128 | CZ | PHE | A | 195 | 2.598 | 69.781 | -22.685 | 1.00 21.03 | C |
| ATOM | 1129 | CE2 | PHE | A | 195 | 3.829 | 69.743 | -23.326 | 1.00 20.98 | C |
| ATOM | 1130 | CD2 | PHE | A | 195 | 3.927 | 69.292 | -24.644 | 1.00 20.95 | C |
| ATOM | 1131 | C | PHE | A | 195 | 3.036 | 69.114 | -29.142 | 1.00 20.77 | C |
| ATOM | 1132 | O | PHE | A | 195 | 4.154 | 69.510 | -29.414 | 1.00 21.38 | O |
| ATOM | 1133 | N | ALA | A | 196 | 2.302 | 68.434 | -30.004 | 1.00 21.27 | N |
| ATOM | 1134 | CA | ALA | A | 196 | 2.851 | 68.074 | -31.292 | 1.00 21.07 | C |
| ATOM | 1135 | CB | ALA | A | 196 | 2.017 | 66.998 | -31.935 | 1.00 21.47 | C |
| ATOM | 1136 | C | ALA | A | 196 | 3.003 | 69.268 | -32.234 | 1.00 21.61 | C |
| ATOM | 1137 | O | ALA | A | 196 | 3.900 | 69.253 | -33.097 | 1.00 22.67 | O |
| ATOM | 1138 | N | LEU | A | 197 | 2.145 | 70.284 | -32.086 | 1.00 19.86 | N |
| ATOM | 1139 | CA | LEU | A | 197 | 2.263 | 71.510 | -32.890 | 1.00 18.59 | C |
| ATOM | 1140 | CB | LEU | A | 197 | 0.896 | 72.161 | -33.117 | 1.00 19.48 | C |
| ATOM | 1141 | CG | LEU | A | 197 | 0.018 | 71.453 | -34.156 | 1.00 19.12 | C |
| ATOM | 1142 | CD1 | LEU | A | 197 | -1.399 | 72.017 | -34.130 | 1.00 19.05 | C |
| ATOM | 1143 | CD2 | LEU | A | 197 | 0.607 | 71.539 | -35.556 | 1.00 18.74 | C |
| ATOM | 1144 | C | LEU | A | 197 | 3.211 | 72.479 | -32.198 | 1.00 17.37 | C |
| ATOM | 1145 | O | LEU | A | 197 | 3.367 | 72.391 | -30.997 | 1.00 17.86 | O |
| ATOM | 1146 | N | PRO | A | 198 | 3.864 | 73.383 | -32.949 | 1.00 16.61 | N |
| ATOM | 1147 | CA | PRO | A | 198 | 4.696 | 74.396 | -32.283 | 1.00 16.62 | C |
| ATOM | 1148 | CB | PRO | A | 198 | 5.374 | 75.131 | -33.442 | 1.00 15.85 | C |
| ATOM | 1149 | CG | PRO | A | 198 | 5.231 | 74.240 | -34.812 | 1.00 15.72 | C |

FIG. 22O

| | | | | | | | | | |
|---|---|---|---|---|---|---|---|---|---|
| ATOM | 1150 | CD | PRO A 198 | 3.941 | 73.515 | -34.412 | 1.00 | 16.17 | C |
| ATOM | 1151 | C | PRO A 198 | 3.839 | 75.365 | -31.493 | 1.00 | 16.83 | C |
| ATOM | 1152 | O | PRO A 198 | 2.652 | 75.512 | -31.802 | 1.00 | 17.11 | O |
| ATOM | 1153 | N | ALA A 199 | 4.442 | 76.015 | -30.497 | 1.00 | 17.10 | N |
| ATOM | 1154 | CA | ALA A 199 | 3.735 | 76.933 | -29.578 | 1.00 | 16.85 | C |
| ATOM | 1155 | CB | ALA A 199 | 4.699 | 77.502 | -28.547 | 1.00 | 16.50 | C |
| ATOM | 1156 | C | ALA A 199 | 2.948 | 78.064 | -30.262 | 1.00 | 16.95 | C |
| ATOM | 1157 | O | ALA A 199 | 1.802 | 78.324 | -29.897 | 1.00 | 16.55 | O |
| ATOM | 1158 | N | GLY A 200 | 3.550 | 78.715 | -31.264 | 1.00 | 17.00 | N |
| ATOM | 1159 | CA | GLY A 200 | 2.895 | 79.820 | -31.958 | 1.00 | 16.37 | C |
| ATOM | 1160 | C | GLY A 200 | 1.547 | 79.462 | -32.561 | 1.00 | 16.45 | C |
| ATOM | 1161 | O | GLY A 200 | 0.609 | 80.247 | -32.520 | 1.00 | 16.39 | O |
| ATOM | 1162 | N | GLU A 201 | 1.441 | 78.269 | -33.124 | 1.00 | 17.05 | N |
| ATOM | 1163 | CA | GLU A 201 | 0.216 | 77.859 | -33.805 | 1.00 | 17.29 | C |
| ATOM | 1164 | CB | GLU A 201 | 0.428 | 76.565 | -34.613 | 1.00 | 18.10 | C |
| ATOM | 1165 | CG | GLU A 201 | 1.149 | 76.746 | -35.942 | 1.00 | 19.04 | C |
| ATOM | 1166 | CD | GLU A 201 | 2.628 | 77.134 | -35.809 | 1.00 | 20.52 | C |
| ATOM | 1167 | OE1 | GLU A 201 | 3.186 | 77.002 | -34.695 | 1.00 | 22.86 | O |
| ATOM | 1168 | OE2 | GLU A 201 | 3.264 | 77.560 | -36.813 | 1.00 | 20.76 | O |
| ATOM | 1169 | C | GLU A 201 | -0.870 | 77.673 | -32.779 | 1.00 | 16.72 | C |
| ATOM | 1170 | O | GLU A 201 | -2.015 | 78.066 | -32.992 | 1.00 | 16.54 | O |
| ATOM | 1171 | N | VAL A 202 | -0.490 | 77.108 | -31.639 | 1.00 | 16.66 | N |
| ATOM | 1172 | CA | VAL A 202 | -1.457 | 76.794 | -30.598 | 1.00 | 16.45 | C |
| ATOM | 1173 | CB | VAL A 202 | -0.918 | 75.785 | -29.598 | 1.00 | 15.94 | C |
| ATOM | 1174 | CG1 | VAL A 202 | -2.020 | 75.370 | -28.629 | 1.00 | 15.66 | C |
| ATOM | 1175 | CG2 | VAL A 202 | -0.381 | 74.541 | -30.335 | 1.00 | 15.39 | C |
| ATOM | 1176 | C | VAL A 202 | -1.958 | 78.043 | -29.880 | 1.00 | 17.00 | C |
| ATOM | 1177 | O | VAL A 202 | -3.165 | 78.225 | -29.714 | 1.00 | 17.08 | O |
| ATOM | 1178 | N | LEU A 203 | -1.043 | 78.912 | -29.467 | 1.00 | 17.49 | N |
| ATOM | 1179 | CA | LEU A 203 | -1.453 | 80.157 | -28.930 | 1.00 | 17.90 | C |
| ATOM | 1180 | CB | LEU A 203 | -0.314 | 80.791 | -28.050 | 1.00 | 18.05 | C |
| ATOM | 1181 | CG | LEU A 203 | -0.182 | 80.078 | -26.704 | 1.00 | 19.56 | C |
| ATOM | 1182 | CD1 | LEU A 203 | 0.658 | 78.786 | -26.848 | 1.00 | 19.55 | C |
| ATOM | 1183 | CD2 | LEU A 203 | 0.350 | 81.020 | -25.618 | 1.00 | 18.26 | C |
| ATOM | 1184 | C | LEU A 203 | 2.071 | 81.141 | -29.821 | 1.00 | 17.84 | C |
| ATOM | 1185 | O | LEU A 203 | -2.898 | 81.967 | -29.450 | 1.00 | 18.00 | O |
| ATOM | 1186 | N | GLY A 204 | -1.690 | 81.054 | -31.081 | 1.00 | 17.15 | N |
| ATOM | 1187 | CA | GLY A 204 | -2.367 | 81.868 | -32.065 | 1.00 | 18.32 | C |
| ATOM | 1188 | C | GLY A 204 | 3.845 | 81.499 | 32.097 | 1.00 | 18.30 | C |
| ATOM | 1189 | O | GLY A 204 | -4.713 | 82.353 | -32.168 | 1.00 | 17.73 | O |
| ATOM | 1190 | N | SER A 205 | -4.112 | 80.295 | -31.990 | 1.00 | 18.34 | N |
| ATOM | 1191 | CA | SER A 205 | -5.442 | 79.690 | -32.156 | 1.00 | 18.18 | C |
| ATOM | 1192 | CB | SER A 205 | -5.401 | 79.196 | -32.456 | 1.00 | 19.17 | C |
| ATOM | 1193 | OG | SER A 205 | -5.440 | 77.976 | -33.847 | 1.00 | 18.43 | O |
| ATOM | 1194 | C | SER A 205 | -6.246 | 79.896 | -30.919 | 1.00 | 18.60 | C |
| ATOM | 1195 | O | SER A 205 | -7.403 | 80.251 | -31.018 | 1.00 | 20.32 | O |
| ATOM | 1196 | N | TYR A 206 | -5.637 | 79.686 | -29.759 | 1.00 | 18.54 | N |
| ATOM | 1197 | CA | TYR A 206 | -6.365 | 79.480 | -28.534 | 1.00 | 18.25 | C |
| ATOM | 1198 | CB | TYR A 206 | -6.177 | 78.031 | -28.109 | 1.00 | 19.51 | C |
| ATOM | 1199 | CG | TYR A 206 | -6.724 | 77.017 | -29.071 | 1.00 | 20.92 | C |
| ATOM | 1200 | CD1 | TYR A 206 | -7.912 | 77.246 | -29.760 | 1.00 | 22.12 | C |
| ATOM | 1201 | CE1 | TYR A 206 | -8.439 | 76.308 | -30.637 | 1.00 | 22.00 | C |
| ATOM | 1202 | CZ | TYR A 206 | -7.789 | 75.121 | -30.817 | 1.00 | 22.17 | C |
| ATOM | 1203 | OH | TYR A 206 | -8.329 | 74.175 | -31.665 | 1.00 | 22.86 | O |
| ATOM | 1204 | CE2 | TYR A 206 | -6.617 | 74.862 | -30.129 | 1.00 | 22.97 | C |
| ATOM | 1205 | CD2 | TYR A 206 | -6.097 | 75.803 | -29.253 | 1.00 | 21.84 | C |
| ATOM | 1206 | C | TYR A 206 | -5.965 | 80.378 | -27.372 | 1.00 | 18.23 | C |
| ATOM | 1207 | O | TYR A 206 | -6.447 | 80.197 | -26.248 | 1.00 | 17.97 | O |
| ATOM | 1208 | N | GLY A 207 | -5.065 | 81.322 | -27.632 | 1.00 | 18.27 | N |
| ATOM | 1209 | CA | GLY A 207 | -4.585 | 82.248 | -26.604 | 1.00 | 17.02 | C |
| ATOM | 1210 | C | GLY A 207 | 5.555 | 83.400 | 26.464 | 1.00 | 17.37 | C |
| ATOM | 1211 | O | GLY A 207 | -6.425 | 83.590 | -27.326 | 1.00 | 17.66 | O |
| ATOM | 1212 | N | VAL A 208 | -5.414 | 84.168 | -25.384 | 1.00 | 17.61 | N |
| ATOM | 1213 | CA | VAL A 208 | -6.337 | 85.268 | -25.099 | 1.00 | 17.79 | C |
| ATOM | 1214 | CB | VAL A 208 | -6.891 | 85.219 | -23.657 | 1.00 | 16.92 | C |
| ATOM | 1215 | CG1 | VAL A 208 | -7.939 | 83.874 | -23.400 | 1.00 | 15.92 | C |
| ATOM | 1216 | CG2 | VAL A 208 | -5.804 | 85.534 | -22.633 | 1.00 | 16.92 | C |
| ATOM | 1217 | C | VAL A 208 | -5.743 | 86.647 | -25.428 | 1.00 | 19.54 | C |
| ATOM | 1218 | O | VAL A 208 | -6.291 | 87.683 | -25.045 | 1.00 | 17.88 | O |
| ATOM | 1219 | N | MET A 209 | -4.629 | 86.636 | -26.157 | 1.00 | 19.39 | N |
| ATOM | 1220 | CA | MET A 209 | -4.034 | 87.843 | -26.720 | 1.00 | 20.15 | C |
| ATOM | 1221 | CB | MET A 209 | -2.505 | 87.793 | -26.607 | 1.00 | 21.01 | C |
| ATOM | 1222 | CG | MET A 209 | -1.897 | 86.787 | -27.527 | 1.00 | 21.06 | C |
| ATOM | 1223 | SD | MET A 209 | 2.047 | 85.059 | 27.037 | 1.00 | 23.65 | S |
| ATOM | 1224 | CE | MET A 209 | -1.293 | 85.071 | -25.438 | 1.00 | 22.17 | C |
| ATOM | 1225 | C | MET A 209 | -4.393 | 87.895 | -28.179 | 1.00 | 20.75 | C |
| ATOM | 1226 | O | MET A 209 | -4.904 | 86.912 | -29.727 | 1.00 | 21.63 | O |

FIG. 22P

| | | | | | | | | | | |
|---|---|---|---|---|---|---|---|---|---|---|
| ATOM | 1227 | N | ASN | A | 210 | -4.091 | 89.024 | -28.808 | 1.00 20.70 | N |
| ATOM | 1228 | CA | ASN | A | 210 | -4.154 | 89.145 | -30.257 | 1.00 21.14 | C |
| ATOM | 1229 | CB | ASN | A | 210 | -3.067 | 88.273 | -30.914 | 1.00 23.96 | C |
| ATOM | 1230 | CG | ASN | A | 210 | 1.643 | 88.806 | 30.703 | 1.00 27.68 | C |
| ATOM | 1231 | OD1 | ASN | A | 210 | -1.419 | 89.950 | -30.278 | 1.00 32.02 | O |
| ATOM | 1232 | ND2 | ASN | A | 210 | -0.661 | 87.969 | -31.030 | 1.00 30.51 | N |
| ATOM | 1233 | C | ASN | A | 210 | -5.552 | 88.835 | -30.831 | 1.00 19.30 | C |
| ATOM | 1234 | O | ASN | A | 210 | -5.709 | 87.925 | -31.655 | 1.00 19.67 | O |
| ATOM | 1235 | N | PRO | A | 211 | -6.979 | 89.590 | -30.396 | 1.00 17.92 | N |
| ATOM | 1236 | CA | PRO | A | 211 | -7.919 | 89.447 | -31.017 | 1.00 17.36 | C |
| ATOM | 1237 | CB | PRO | A | 211 | -8.725 | 90.590 | -30.379 | 1.00 16.70 | C |
| ATOM | 1238 | CG | PRO | A | 211 | -7.718 | 91.545 | -29.846 | 1.00 16.56 | C |
| ATOM | 1239 | CD | PRO | A | 211 | 6.567 | 90.704 | 29.434 | 1.00 16.27 | C |
| ATOM | 1240 | C | PRO | A | 211 | -7.846 | 89.644 | -32.537 | 1.00 16.21 | C |
| ATOM | 1241 | O | PRO | A | 211 | -7.096 | 90.482 | -33.003 | 1.00 15.49 | O |
| ATOM | 1242 | N | ARG | A | 212 | -8.643 | 88.879 | -33.276 | 1.00 16.71 | N |
| ATOM | 1243 | CA | ARG | A | 212 | -8.582 | 89.795 | -34.756 | 1.00 17.18 | C |
| ATOM | 1244 | CB | ARG | A | 212 | -7.485 | 87.817 | -35.210 | 1.00 18.71 | C |
| ATOM | 1245 | CG | ARG | A | 212 | -7.232 | 86.653 | -34.258 | 1.00 20.70 | C |
| ATOM | 1246 | CD | ARG | A | 212 | -6.622 | 85.438 | -34.945 | 1.00 22.47 | C |
| ATOM | 1247 | NE | ARG | A | 212 | -7.659 | 84.428 | -34.993 | 1.00 25.31 | N |
| ATOM | 1248 | CZ | ARG | A | 212 | -7.799 | 83.464 | -34.106 | 1.00 24.16 | C |
| ATOM | 1249 | NH1 | ARG | A | 212 | -6.941 | 83.323 | -33.130 | 1.00 23.93 | N |
| ATOM | 1250 | NH2 | ARG | A | 212 | -9.800 | 82.627 | -34.224 | 1.00 27.46 | N |
| ATOM | 1251 | C | ARG | A | 212 | -9.864 | 88.247 | -35.317 | 1.00 16.40 | C |
| ATOM | 1252 | O | ARG | A | 212 | -10.657 | 87.676 | -34.576 | 1.00 15.38 | O |
| ATOM | 1253 | N | PRO | A | 213 | -10.053 | 88.375 | -36.649 | 1.00 16.42 | N |
| ATOM | 1254 | CA | PRO | A | 213 | -11.140 | 87.623 | -37.300 | 1.00 16.53 | C |
| ATOM | 1255 | CB | PRO | A | 213 | -11.035 | 88.040 | -38.775 | 1.00 15.77 | C |
| ATOM | 1256 | CG | PRO | A | 213 | -10.269 | 89.322 | -38.773 | 1.00 15.92 | C |
| ATOM | 1257 | CD | PRO | A | 213 | -9.324 | 89.237 | -37.600 | 1.00 15.79 | C |
| ATOM | 1258 | C | PRO | A | 213 | -10.955 | 86.089 | -37.135 | 1.00 16.56 | C |
| ATOM | 1259 | O | PRO | A | 213 | -9.840 | 85.620 | -36.849 | 1.00 16.47 | O |
| ATOM | 1260 | N | GLY | A | 214 | -12.044 | 85.323 | -37.267 | 1.00 16.86 | N |
| ATOM | 1261 | CA | GLY | A | 214 | 11.965 | 83.858 | 37.228 | 1.00 16.87 | C |
| ATOM | 1262 | C | GLY | A | 214 | -12.451 | 83.246 | -35.922 | 1.00 18.06 | C |
| ATOM | 1263 | O | GLY | A | 214 | -11.888 | 82.256 | -35.436 | 1.00 19.33 | O |
| ATOM | 1264 | N | TYR | A | 215 | -13.489 | 83.845 | -35.334 | 1.00 17.14 | N |
| ATOM | 1265 | CA | TYR | A | 215 | 14.159 | 83.257 | 34.187 | 1.00 16.70 | C |
| ATOM | 1266 | CB | TYR | A | 215 | -14.905 | 81.970 | -34.587 | 1.00 16.65 | C |
| ATOM | 1267 | CG | TYR | A | 215 | -15.897 | 82.224 | -35.707 | 1.00 16.86 | C |
| ATOM | 1268 | CD1 | TYR | A | 215 | -17.073 | 82.956 | -35.499 | 1.00 16.29 | C |
| ATOM | 1269 | CE1 | TYR | A | 215 | -17.964 | 83.217 | -36.530 | 1.00 16.81 | C |
| ATOM | 1270 | CZ | TYR | A | 215 | -17.681 | 82.737 | -37.817 | 1.00 17.48 | C |
| ATOM | 1271 | OH | TYR | A | 215 | -18.529 | 82.964 | -38.898 | 1.00 17.44 | O |
| ATOM | 1272 | CE2 | TYR | A | 215 | -16.511 | 82.060 | -38.050 | 1.00 17.21 | C |
| ATOM | 1273 | CD2 | TYR | A | 215 | -15.627 | 81.790 | -37.000 | 1.00 17.02 | C |
| ATOM | 1274 | C | TYR | A | 215 | -13.206 | 83.076 | -33.015 | 1.00 16.67 | C |
| ATOM | 1275 | O | TYR | A | 215 | -13.254 | 82.085 | -32.279 | 1.00 16.76 | O |
| ATOM | 1276 | N | TRP | A | 216 | -12.364 | 84.085 | -32.852 | 1.00 16.49 | N |
| ATOM | 1277 | CA | TRP | A | 216 | -11.446 | 84.216 | -31.724 | 1.00 16.24 | C |
| ATOM | 1278 | CB | TRP | A | 216 | -10.874 | 85.624 | -31.740 | 1.00 15.47 | C |
| ATOM | 1279 | CG | TRP | A | 216 | -9.724 | 85.847 | -30.818 | 1.00 15.57 | C |
| ATOM | 1280 | CD1 | TRP | A | 216 | -8.417 | 85.417 | -30.977 | 1.00 15.75 | C |
| ATOM | 1281 | NE1 | TRP | A | 216 | -7.634 | 85.827 | -29.922 | 1.00 16.29 | N |
| ATOM | 1282 | CE2 | TRP | A | 216 | -8.357 | 86.546 | -29.038 | 1.00 15.69 | C |
| ATOM | 1283 | CD2 | TRP | A | 216 | -9.728 | 86.597 | -29.545 | 1.00 15.94 | C |
| ATOM | 1284 | CE3 | TRP | A | 216 | -10.694 | 87.278 | -28.817 | 1.00 15.29 | C |
| ATOM | 1285 | CZ3 | TRP | A | 216 | -10.317 | 87.883 | -27.634 | 1.00 15.41 | C |
| ATOM | 1286 | CH2 | TRP | A | 216 | -8.998 | 87.817 | -27.169 | 1.00 16.03 | C |
| ATOM | 1287 | CZ2 | TRP | A | 216 | 7.996 | 87.145 | 27.870 | 1.00 15.67 | C |
| ATOM | 1288 | C | TRP | A | 216 | -12.110 | 83.960 | -30.402 | 1.00 16.16 | C |
| ATOM | 1289 | O | TRP | A | 216 | -13.135 | 84.551 | -30.080 | 1.00 16.24 | O |
| ATOM | 1290 | N | GLY | A | 217 | -11.525 | 83.077 | -29.621 | 1.00 16.52 | N |
| ATOM | 1291 | CA | GLY | A | 217 | -11.981 | 82.850 | -28.256 | 1.00 17.77 | C |
| ATOM | 1292 | C | GLY | A | 217 | -13.139 | 81.893 | -28.226 | 1.00 18.58 | C |
| ATOM | 1293 | O | GLY | A | 217 | -13.827 | 81.798 | -27.233 | 1.00 20.05 | O |
| ATOM | 1294 | N | ALA | A | 218 | -13.377 | 81.179 | -29.312 | 1.00 18.31 | N |
| ATOM | 1295 | CA | ALA | A | 218 | -14.530 | 80.293 | -29.340 | 1.00 18.61 | C |
| ATOM | 1296 | CB | ALA | A | 218 | -15.656 | 80.892 | -30.186 | 1.00 19.52 | C |
| ATOM | 1297 | C | ALA | A | 218 | -14.124 | 78.934 | -29.882 | 1.00 18.87 | C |
| ATOM | 1298 | O | ALA | A | 218 | -14.671 | 78.488 | -30.893 | 1.00 18.94 | O |
| ATOM | 1299 | N | GLY | A | 219 | -13.145 | 78.306 | -29.228 | 1.00 18.56 | N |
| ATOM | 1300 | CA | GLY | A | 219 | 12.683 | 76.960 | 29.588 | 1.00 18.06 | C |
| ATOM | 1301 | C | GLY | A | 219 | -12.733 | 75.973 | -28.421 | 1.00 17.72 | C |
| ATOM | 1302 | O | GLY | A | 219 | -13.251 | 75.263 | -27.352 | 1.00 17.29 | O |
| ATOM | 1303 | N | PRO | A | 220 | -12.202 | 74.760 | -28.625 | 1.00 17.59 | N |

FIG. 22Q

| | | | | | | | | | |
|---|---|---|---|---|---|---|---|---|---|
| ATOM | 1304 | CA | PRO | A | 220 | -12.335 | 73.693 | -27.629 | 1.00 17.34 | C |
| ATOM | 1305 | CB | PRO | A | 220 | -11.927 | 72.442 | -28.404 | 1.00 16.93 | C |
| ATOM | 1306 | CG | PRO | A | 220 | -11.983 | 72.835 | -29.644 | 1.00 16.72 | C |
| ATOM | 1307 | CD | PRO | A | 220 | 11.597 | 74.269 | 29.970 | 1.00 17.07 | C |
| ATOM | 1308 | C | PRO | A | 220 | -11.391 | 73.907 | -26.474 | 1.00 16.94 | C |
| ATOM | 1309 | O | PRO | A | 220 | -11.561 | 73.337 | -25.408 | 1.00 16.26 | O |
| ATOM | 1310 | N | LEU | A | 221 | -10.414 | 74.762 | -26.702 | 1.00 17.61 | N |
| ATOM | 1311 | CA | LEU | A | 221 | -9.345 | 74.973 | -25.756 | 1.00 18.25 | C |
| ATOM | 1312 | CB | LEU | A | 221 | -8.132 | 74.166 | -26.195 | 1.00 19.13 | C |
| ATOM | 1313 | CG | LEU | A | 221 | -6.828 | 74.506 | -25.495 | 1.00 21.19 | C |
| ATOM | 1314 | CD1 | LEU | A | 221 | -6.826 | 73.957 | -24.055 | 1.00 22.20 | C |
| ATOM | 1315 | CD2 | LEU | A | 221 | -5.686 | 73.945 | -26.332 | 1.00 21.78 | C |
| ATOM | 1316 | C | LEU | A | 221 | 9.007 | 76.459 | 25.629 | 1.00 18.03 | C |
| ATOM | 1317 | O | LEU | A | 221 | -9.171 | 77.248 | -26.570 | 1.00 17.55 | O |
| ATOM | 1318 | N | CYS | A | 222 | -8.562 | 76.829 | -24.440 | 1.00 18.33 | N |
| ATOM | 1319 | CA | CYS | A | 222 | -8.143 | 78.194 | -24.160 | 1.00 19.20 | C |
| ATOM | 1320 | CB | CYS | A | 222 | -9.247 | 78.916 | -23.430 | 1.00 18.21 | C |
| ATOM | 1321 | SG | CYS | A | 222 | -8.776 | 80.597 | -23.078 | 1.00 19.26 | S |
| ATOM | 1322 | C | CYS | A | 222 | -6.874 | 78.160 | -23.305 | 1.00 18.41 | C |
| ATOM | 1323 | O | CYS | A | 222 | -6.874 | 77.596 | -22.202 | 1.00 19.52 | O |
| ATOM | 1324 | N | ILE | A | 223 | -5.797 | 78.743 | -23.835 | 1.00 16.92 | N |
| ATOM | 1325 | CA | ILE | A | 223 | -4.517 | 78.806 | -23.161 | 1.00 15.71 | C |
| ATOM | 1326 | CB | ILE | A | 223 | -3.386 | 78.339 | -24.096 | 1.00 15.82 | C |
| ATOM | 1327 | CG1 | ILE | A | 223 | -3.267 | 76.834 | -23.987 | 1.00 16.22 | C |
| ATOM | 1328 | CD1 | ILE | A | 223 | -3.243 | 76.167 | -25.317 | 1.00 16.46 | C |
| ATOM | 1329 | CG2 | ILE | A | 223 | -2.040 | 78.943 | -23.708 | 1.00 15.32 | C |
| ATOM | 1330 | C | ILE | A | 223 | -4.269 | 80.216 | -22.620 | 1.00 15.52 | C |
| ATOM | 1331 | O | ILE | A | 223 | -4.380 | 81.204 | -23.354 | 1.00 15.13 | O |
| ATOM | 1332 | N | ALA | A | 224 | -3.937 | 80.288 | -21.327 | 1.00 14.24 | N |
| ATOM | 1333 | CA | ALA | A | 224 | -3.801 | 81.542 | -20.619 | 1.00 13.19 | C |
| ATOM | 1334 | CB | ALA | A | 224 | -5.126 | 81.931 | -19.953 | 1.00 12.79 | C |
| ATOM | 1335 | C | ALA | A | 224 | -2.700 | 81.375 | -19.576 | 1.00 12.65 | C |
| ATOM | 1336 | O | ALA | A | 224 | -2.643 | 80.345 | -18.897 | 1.00 12.51 | O |
| ATOM | 1337 | N | ASP | A | 225 | -1.823 | 82.371 | -19.457 | 1.00 11.77 | N |
| ATOM | 1338 | CA | ASP | A | 225 | 0.742 | 82.282 | 18.508 | 1.00 11.85 | C |
| ATOM | 1339 | CB | ASP | A | 225 | 0.595 | 82.048 | -19.221 | 1.00 12.03 | C |
| ATOM | 1340 | CG | ASP | A | 225 | 0.606 | 80.755 | -20.020 | 1.00 12.41 | C |
| ATOM | 1341 | OD1 | ASP | A | 225 | 0.535 | 79.650 | -19.421 | 1.00 12.07 | O |
| ATOM | 1342 | OD2 | ASP | A | 225 | 0.659 | 80.854 | 21.268 | 1.00 12.92 | O |
| ATOM | 1343 | C | ASP | A | 225 | -0.709 | 83.558 | -17.738 | 1.00 11.69 | C |
| ATOM | 1344 | O | ASP | A | 225 | -0.635 | 84.633 | -18.345 | 1.00 12.11 | O |
| ATOM | 1345 | N | GLY | A | 226 | -0.789 | 83.454 | -16.414 | 1.00 10.99 | N |
| ATOM | 1346 | CA | GLY | A | 226 | -0.770 | 84.630 | -15.563 | 1.00 10.99 | C |
| ATOM | 1347 | C | GLY | A | 226 | -2.151 | 85.093 | -15.160 | 1.00 11.21 | C |
| ATOM | 1348 | O | GLY | A | 226 | -3.123 | 84.827 | -15.857 | 1.00 11.05 | O |
| ATOM | 1349 | N | VAL | A | 227 | -2.237 | 85.798 | -14.028 | 1.00 11.50 | N |
| ATOM | 1350 | CA | VAL | A | 227 | -3.513 | 86.242 | -13.471 | 1.00 11.56 | C |
| ATOM | 1351 | CB | VAL | A | 227 | -3.310 | 86.972 | -12.110 | 1.00 11.19 | C |
| ATOM | 1352 | CG1 | VAL | A | 227 | -4.463 | 87.930 | -11.771 | 1.00 10.94 | C |
| ATOM | 1353 | CG2 | VAL | A | 227 | -3.101 | 85.953 | -11.016 | 1.00 10.80 | C |
| ATOM | 1354 | C | VAL | A | 227 | -4.325 | 87.069 | -14.479 | 1.00 12.28 | C |
| ATOM | 1355 | O | VAL | A | 227 | -5.549 | 86.865 | -14.624 | 1.00 13.11 | O |
| ATOM | 1356 | N | GLU | A | 228 | -3.651 | 87.966 | -15.194 | 1.00 12.71 | N |
| ATOM | 1357 | CA | GLU | A | 228 | -4.319 | 88.864 | -16.161 | 1.00 13.23 | C |
| ATOM | 1358 | CB | GLU | A | 228 | -3.342 | 89.851 | -16.748 | 1.00 13.15 | C |
| ATOM | 1359 | CG | GLU | A | 228 | -2.594 | 90.667 | -15.703 | 1.00 13.43 | C |
| ATOM | 1360 | CD | GLU | A | 228 | -3.502 | 91.544 | -14.842 | 1.00 14.02 | C |
| ATOM | 1361 | OE1 | GLU | A | 228 | -4.206 | 92.458 | -15.362 | 1.00 14.29 | O |
| ATOM | 1362 | OE2 | GLU | A | 228 | -3.484 | 91.341 | -13.620 | 1.00 14.07 | O |
| ATOM | 1363 | C | GLU | A | 228 | -4.989 | 88.065 | -17.276 | 1.00 13.65 | C |
| ATOM | 1364 | O | GLU | A | 228 | 6.145 | 98.332 | 17.617 | 1.00 14.42 | O |
| ATOM | 1365 | N | GLU | A | 229 | -4.287 | 87.080 | -17.822 | 1.00 14.06 | N |
| ATOM | 1366 | CA | GLU | A | 229 | -4.794 | 86.357 | -18.990 | 1.00 14.96 | C |
| ATOM | 1367 | CB | GLU | A | 229 | -3.674 | 85.563 | -19.668 | 1.00 14.72 | C |
| ATOM | 1368 | CG | GLU | A | 229 | -2.926 | 86.386 | -20.696 | 1.00 14.24 | C |
| ATOM | 1369 | CD | GLU | A | 229 | -1.847 | 85.622 | -21.434 | 1.00 14.45 | C |
| ATOM | 1370 | OE1 | GLU | A | 229 | -0.871 | 86.281 | -21.836 | 1.00 14.25 | O |
| ATOM | 1371 | OE2 | GLU | A | 229 | -1.944 | 84.380 | -21.600 | 1.00 14.49 | O |
| ATOM | 1372 | C | GLU | A | 229 | -5.951 | 85.460 | -18.603 | 1.00 15.26 | C |
| ATOM | 1373 | O | GLU | A | 229 | -6.894 | 85.200 | -19.373 | 1.00 16.12 | O |
| ATOM | 1374 | N | VAL | A | 230 | -5.878 | 85.013 | -17.372 | 1.00 15.11 | N |
| ATOM | 1375 | CA | VAL | A | 230 | -6.776 | 84.001 | -16.865 | 1.00 14.72 | C |
| ATOM | 1376 | CB | VAL | A | 230 | -6.093 | 83.355 | -15.636 | 1.00 14.06 | C |
| ATOM | 1377 | CG1 | VAL | A | 230 | 6.953 | 83.332 | 14.396 | 1.00 14.76 | C |
| ATOM | 1378 | CG2 | VAL | A | 230 | -5.563 | 81.990 | -15.986 | 1.00 13.59 | C |
| ATOM | 1379 | C | VAL | A | 230 | -8.155 | 84.629 | -16.642 | 1.00 14.74 | C |
| ATOM | 1380 | O | VAL | A | 230 | -9.186 | 83.975 | -16.827 | 1.00 15.10 | O |

FIG. 22R

```
ATOM   1381  N    ARG A 231      -8.175   85.903  -16.279  1.00  14.63           N
ATOM   1382  CA   ARG A 231      -9.418   86.665  -16.203  1.00  14.27           C
ATOM   1383  CB   ARG A 231      -9.149   88.092  -15.719  1.00  14.02           C
ATOM   1384  CG   ARG A 231      -9.925   88.203   14.219  1.00  13.42           C
ATOM   1385  CD   ARG A 231      -8.875   89.670  -13.769  1.00  12.92           C
ATOM   1386  NE   ARG A 231      -8.215   89.854  -12.464  1.00  12.58           N
ATOM   1387  CZ   ARG A 231      -8.739   89.531  -11.268  1.00  12.52           C
ATOM   1388  NH1  ARG A 231      -8.035   89.771  -10.163  1.00  12.13           N
ATOM   1389  NH2  ARG A 231      -9.961   88.974  -11.161  1.00  11.79           N
ATOM   1390  C    ARG A 231     -10.138   86.693  -17.558  1.00  14.31           C
ATOM   1391  O    ARG A 231     -11.330   86.372  -17.651  1.00  14.85           O
ATOM   1392  N    ARG A 232      -9.425   87.041  -18.624  1.00  13.83           N
ATOM   1393  CA   ARG A 232     -10.068   87.056   19.945  1.00  13.28           C
ATOM   1394  CB   ARG A 232      -9.191   87.731  -20.984  1.00  12.65           C
ATOM   1395  CG   ARG A 232      -9.727   87.581  -22.392  1.00  12.20           C
ATOM   1396  CD   ARG A 232      -9.603   88.858  -23.190  1.00  11.75           C
ATOM   1397  NE   ARG A 232      -8.216   89.236  -23.370  1.00  11.31           N
ATOM   1398  CZ   ARG A 232      -7.703   90.420  -23.045  1.00  11.56           C
ATOM   1399  NH1  ARG A 232      -8.448   91.392  -22.499  1.00  11.32           N
ATOM   1400  NH2  ARG A 232      -6.414   90.631  -23.268  1.00  11.69           N
ATOM   1401  C    ARG A 232     -10.441   85.651  -20.416  1.00  14.02           C
ATOM   1402  O    ARG A 232     -11.375   85.488  -21.220  1.00  14.40           O
ATOM   1403  N    ALA A 233      -9.705   84.647  -19.925  1.00  13.82           N
ATOM   1404  CA   ALA A 233      -9.988   83.293  -20.251  1.00  13.66           C
ATOM   1405  CB   ALA A 233      -8.893   82.309  -19.760  1.00  13.43           C
ATOM   1406  C    ALA A 233     -11.243   82.813  -19.735  1.00  13.53           C
ATOM   1407  O    ALA A 233     -12.083   82.157  -20.467  1.00  13.45           O
ATOM   1408  N    VAL A 234     -11.677   83.148  -18.489  1.00  13.61           N
ATOM   1409  CA   VAL A 234     -12.990   82.745  -17.971  1.00  13.47           C
ATOM   1410  CB   VAL A 234     -13.134   82.994  -16.464  1.00  13.64           C
ATOM   1411  CG1  VAL A 234     -14.583   82.733  -16.025  1.00  12.99           C
ATOM   1412  CG2  VAL A 234     -12.126   82.158  -15.677  1.00  13.75           C
ATOM   1413  C    VAL A 234     -14.061   83.559  -18.694  1.00  13.35           C
ATOM   1414  O    VAL A 234     -15.031   83.003  -19.238  1.00  13.07           O
ATOM   1415  N    ARG A 235      13.860   84.379   18.708  1.00  12.99           N
ATOM   1416  CA   ARG A 235     -14.816   85.783  -19.319  1.00  12.71           C
ATOM   1417  CB   ARG A 235     -14.346   87.233  -19.215  1.00  12.37           C
ATOM   1418  CG   ARG A 235     -14.291   87.712  -17.767  1.00  11.55           C
ATOM   1419  CD   ARG A 235      13.569   89.027   17.627  1.00  10.84           C
ATOM   1420  NE   ARG A 235     -13.324   89.302  -16.227  1.00  10.76           N
ATOM   1421  CZ   ARG A 235     -12.766   90.414  -15.759  1.00  10.72           C
ATOM   1422  NH1  ARG A 235     -12.407   91.380  -16.584  1.00  10.95           N
ATOM   1423  NH2  ARG A 235     -12.561   90.570  -14.460  1.00  10.63           N
ATOM   1424  C    ARG A 235     -15.140   85.391  -20.757  1.00  12.97           C
ATOM   1425  O    ARG A 235     -16.297   85.521  -21.173  1.00  12.65           O
ATOM   1426  N    LEU A 236     -14.152   84.867  -21.490  1.00  13.38           N
ATOM   1427  CA   LEU A 236     -14.393   84.392  -22.863  1.00  14.13           C
ATOM   1428  CB   LEU A 236     -13.096   84.059  -23.594  1.00  13.92           C
ATOM   1429  CG   LEU A 236     -12.348   85.275  -24.141  1.00  13.99           C
ATOM   1430  CD1  LEU A 236     -11.025   84.803  -24.719  1.00  14.07           C
ATOM   1431  CD2  LEU A 236     -13.126   86.072  -25.175  1.00  13.28           C
ATOM   1432  C    LEU A 236     -15.374   83.226  -22.953  1.00  14.40           C
ATOM   1433  O    LEU A 236     -16.171   83.145  -23.886  1.00  15.04           O
ATOM   1434  N    GLN A 237     -15.316   82.319  -21.993  1.00  14.44           N
ATOM   1435  CA   GLN A 237     -16.266   81.207  -21.959  1.00  14.63           C
ATOM   1436  CB   GLN A 237     -15.500   80.106  -21.010  1.00  14.88           C
ATOM   1437  CG   GLN A 237     -14.436   79.446  -21.310  1.00  15.14           C
ATOM   1438  CD   GLN A 237     -13.826   79.839  -22.626  1.00  15.51           C
ATOM   1439  OE1  GLN A 237     -14.395   79.458  -23.718  1.00  16.57           O
ATOM   1440  NE2  GLN A 237     -12.747   80.603  -22.543  1.00  15.49           N
ATOM   1441  C    GLN A 237      17.673   81.684   21.566  1.00  14.87           C
ATOM   1442  O    GLN A 237     -18.646   81.309  -22.226  1.00  15.88           O
ATOM   1443  N    ILE A 238     -17.789   82.511  -20.522  1.00  14.10           N
ATOM   1444  CA   ILE A 238     -19.069   83.140  -20.179  1.00  14.16           C
ATOM   1445  CB   ILE A 238     -18.956   84.103  -18.951  1.00  13.71           C
ATOM   1446  CG1  ILE A 238     -18.348   83.403  -17.715  1.00  13.46           C
ATOM   1447  CD1  ILE A 238     -19.091   82.159  -17.231  1.00  13.55           C
ATOM   1448  CG2  ILE A 238     -20.311   84.692  -18.593  1.00  13.05           C
ATOM   1449  C    ILE A 238     -19.693   83.859  -21.400  1.00  14.66           C
ATOM   1450  O    ILE A 238     -20.910   83.773  -21.647  1.00  13.93           O
ATOM   1451  N    ARG A 239     -18.848   84.526  -22.160  1.00  15.12           N
ATOM   1452  CA   ARG A 239     -19.310   85.211  -23.384  1.00  16.22           C
ATOM   1453  CB   ARG A 239     -18.153   85.842  -24.161  1.00  16.15           C
ATOM   1454  CG   ARG A 239      18.557   87.173   24.749  1.00  16.95           C
ATOM   1455  CD   ARG A 239     -17.489   87.795  -25.633  1.00  17.14           C
ATOM   1456  NE   ARG A 239     -17.837   87.537  -27.010  1.00  16.95           N
ATOM   1457  CZ   ARG A 239     -18.212   89.467  -27.968  1.00  16.86           C
```

FIG. 22S

| | | | | | | | | | |
|---|---|---|---|---|---|---|---|---|---|
| ATOM | 1458 | NH1 | ARG A 239 | -18.256 | 89.740 | -27.507 | 1.00 | 16.03 | N |
| ATOM | 1459 | NH2 | ARG A 239 | -19.509 | 88.112 | -29.105 | 1.00 | 16.57 | N |
| ATOM | 1460 | C | ARG A 239 | -20.109 | 84.295 | -24.310 | 1.00 | 17.26 | C |
| ATOM | 1461 | O | ARG A 239 | -21.152 | 84.711 | -24.871 | 1.00 | 17.98 | O |
| ATOM | 1462 | N | ARG A 240 | -19.638 | 83.056 | -24.475 | 1.00 | 17.12 | N |
| ATOM | 1463 | CA | ARG A 240 | -20.330 | 82.130 | -25.361 | 1.00 | 17.31 | C |
| ATOM | 1464 | CB | ARG A 240 | -19.392 | 81.131 | -26.067 | 1.00 | 16.63 | C |
| ATOM | 1465 | CG | ARG A 240 | -19.124 | 80.776 | -25.330 | 1.00 | 16.39 | C |
| ATOM | 1466 | CD | ARG A 240 | -16.959 | 80.597 | -26.263 | 1.00 | 15.50 | C |
| ATOM | 1467 | NE | ARG A 240 | -17.063 | 79.407 | -27.113 | 1.00 | 15.27 | N |
| ATOM | 1468 | CZ | ARG A 240 | -16.261 | 78.354 | -27.085 | 1.00 | 15.02 | C |
| ATOM | 1469 | NH1 | ARG A 240 | -15.225 | 78.321 | -26.252 | 1.00 | 14.50 | N |
| ATOM | 1470 | NH2 | ARG A 240 | -16.459 | 77.338 | -27.923 | 1.00 | 14.75 | N |
| ATOM | 1471 | C | ARG A 240 | -21.522 | 81.446 | -24.716 | 1.00 | 18.12 | C |
| ATOM | 1472 | O | ARG A 240 | -22.252 | 80.755 | -25.408 | 1.00 | 19.63 | O |
| ATOM | 1473 | N | GLY A 241 | -21.736 | 81.633 | -23.417 | 1.00 | 17.70 | N |
| ATOM | 1474 | CA | GLY A 241 | -22.847 | 80.980 | -22.754 | 1.00 | 17.92 | C |
| ATOM | 1475 | C | GLY A 241 | -22.445 | 79.869 | -21.814 | 1.00 | 19.53 | C |
| ATOM | 1476 | O | GLY A 241 | -23.311 | 79.087 | -21.348 | 1.00 | 20.25 | O |
| ATOM | 1477 | N | ALA A 242 | -21.148 | 79.739 | -21.503 | 1.00 | 19.19 | N |
| ATOM | 1478 | CA | ALA A 242 | -20.668 | 78.687 | -20.597 | 1.00 | 18.78 | C |
| ATOM | 1479 | CB | ALA A 242 | -19.173 | 78.816 | -20.321 | 1.00 | 17.91 | C |
| ATOM | 1480 | C | ALA A 242 | -21.451 | 78.644 | -19.289 | 1.00 | 18.25 | C |
| ATOM | 1481 | O | ALA A 242 | -21.638 | 79.665 | -18.634 | 1.00 | 18.67 | O |
| ATOM | 1482 | N | LYS A 243 | -21.902 | 77.454 | -18.924 | 1.00 | 18.24 | N |
| ATOM | 1483 | CA | LYS A 243 | -22.657 | 77.255 | -17.688 | 1.00 | 19.05 | C |
| ATOM | 1484 | CB | LYS A 243 | -23.909 | 76.404 | -17.942 | 1.00 | 20.12 | C |
| ATOM | 1485 | CG | LYS A 243 | -25.241 | 77.145 | -17.851 | 1.00 | 21.71 | C |
| ATOM | 1486 | CD | LYS A 243 | -25.674 | 77.755 | -19.166 | 1.00 | 22.70 | C |
| ATOM | 1487 | CE | LYS A 243 | -27.091 | 77.323 | -19.602 | 1.00 | 23.94 | C |
| ATOM | 1488 | NZ | LYS A 243 | -28.172 | 77.484 | -18.600 | 1.00 | 25.96 | N |
| ATOM | 1489 | C | LYS A 243 | -21.791 | 76.625 | -16.610 | 1.00 | 17.85 | C |
| ATOM | 1490 | O | LYS A 243 | -22.273 | 76.295 | -15.534 | 1.00 | 17.69 | O |
| ATOM | 1491 | N | VAL A 244 | -20.514 | 76.434 | -16.928 | 1.00 | 16.67 | N |
| ATOM | 1492 | CA | VAL A 244 | 19.527 | 75.918 | 15.983 | 1.00 | 15.74 | C |
| ATOM | 1493 | CB | VAL A 244 | -19.635 | 74.373 | -15.729 | 1.00 | 15.50 | C |
| ATOM | 1494 | CG1 | VAL A 244 | -19.275 | 73.657 | -17.086 | 1.00 | 15.36 | C |
| ATOM | 1495 | CG2 | VAL A 244 | -18.789 | 73.868 | -14.637 | 1.00 | 14.49 | C |
| ATOM | 1496 | C | VAL A 244 | 18.173 | 76.329 | 16.552 | 1.00 | 15.25 | C |
| ATOM | 1497 | O | VAL A 244 | -18.067 | 76.570 | -17.741 | 1.00 | 15.09 | O |
| ATOM | 1498 | N | ILE A 245 | -17.165 | 76.453 | -15.689 | 1.00 | 15.08 | N |
| ATOM | 1499 | CA | ILE A 245 | -15.790 | 76.701 | -16.104 | 1.00 | 14.42 | C |
| ATOM | 1500 | CB | ILE A 245 | -15.225 | 77.973 | -15.432 | 1.00 | 13.51 | C |
| ATOM | 1501 | CG1 | ILE A 245 | -16.034 | 79.213 | -15.845 | 1.00 | 12.70 | C |
| ATOM | 1502 | CD1 | ILE A 245 | -16.525 | 79.506 | -17.337 | 1.00 | 12.42 | C |
| ATOM | 1503 | CG2 | ILE A 245 | -13.743 | 78.122 | -15.716 | 1.00 | 12.83 | C |
| ATOM | 1504 | C | ILE A 245 | -16.923 | 75.478 | -15.762 | 1.00 | 15.26 | C |
| ATOM | 1505 | O | ILE A 245 | -14.993 | 74.944 | -14.655 | 1.00 | 15.41 | O |
| ATOM | 1506 | N | LYS A 246 | -14.108 | 75.042 | -16.717 | 1.00 | 16.06 | N |
| ATOM | 1507 | CA | LYS A 246 | -13.302 | 73.839 | -16.573 | 1.00 | 16.69 | C |
| ATOM | 1508 | CB | LYS A 246 | -13.640 | 72.902 | -17.722 | 1.00 | 16.62 | C |
| ATOM | 1509 | CG | LYS A 246 | -12.621 | 71.805 | -17.932 | 1.00 | 16.91 | C |
| ATOM | 1510 | CD | LYS A 246 | -12.703 | 70.763 | -16.846 | 1.00 | 17.32 | C |
| ATOM | 1511 | CE | LYS A 246 | -11.840 | 69.573 | -17.212 | 1.00 | 19.00 | C |
| ATOM | 1512 | NZ | LYS A 246 | -12.292 | 68.409 | -16.352 | 1.00 | 19.16 | N |
| ATOM | 1513 | C | LYS A 246 | -11.810 | 74.154 | -16.515 | 1.00 | 16.94 | C |
| ATOM | 1514 | O | LYS A 246 | -11.363 | 74.753 | -17.575 | 1.00 | 17.82 | O |
| ATOM | 1515 | N | VAL A 247 | -11.043 | 73.754 | -15.599 | 1.00 | 17.42 | N |
| ATOM | 1516 | CA | VAL A 247 | -9.572 | 73.913 | -15.641 | 1.00 | 17.76 | C |
| ATOM | 1517 | CB | VAL A 247 | -8.997 | 74.640 | -14.403 | 1.00 | 16.91 | C |
| ATOM | 1518 | CG1 | VAL A 247 | 9.398 | 76.085 | 14.397 | 1.00 | 17.00 | C |
| ATOM | 1519 | CG2 | VAL A 247 | -9.453 | 73.972 | -13.126 | 1.00 | 17.24 | C |
| ATOM | 1520 | C | VAL A 247 | -8.821 | 72.592 | -15.739 | 1.00 | 18.11 | C |
| ATOM | 1521 | O | VAL A 247 | -9.247 | 71.598 | -15.165 | 1.00 | 19.52 | O |
| ATOM | 1522 | N | MET A 248 | -7.687 | 72.593 | -16.438 | 1.00 | 18.99 | N |
| ATOM | 1523 | CA | MET A 248 | -6.699 | 71.517 | -16.282 | 1.00 | 19.02 | C |
| ATOM | 1524 | CB | MET A 248 | -5.860 | 71.378 | -17.546 | 1.00 | 19.99 | C |
| ATOM | 1525 | CG | MET A 248 | -6.681 | 71.225 | -18.807 | 1.00 | 21.12 | C |
| ATOM | 1526 | SD | MET A 248 | -7.849 | 69.848 | -18.730 | 1.00 | 23.48 | S |
| ATOM | 1527 | CE | MET A 248 | -8.249 | 69.704 | -20.495 | 1.00 | 22.51 | C |
| ATOM | 1528 | C | MET A 248 | -5.799 | 71.879 | -15.101 | 1.00 | 18.74 | C |
| ATOM | 1529 | O | MET A 248 | -5.009 | 72.816 | -15.188 | 1.00 | 19.34 | O |
| ATOM | 1530 | N | ALA A 249 | -5.938 | 71.167 | -13.984 | 1.00 | 18.52 | N |
| ATOM | 1531 | CA | ALA A 249 | 5.105 | 71.447 | 12.824 | 1.00 | 18.26 | C |
| ATOM | 1532 | CB | ALA A 249 | -5.962 | 71.795 | -11.624 | 1.00 | 18.50 | C |
| ATOM | 1533 | C | ALA A 249 | -4.046 | 70.371 | -12.489 | 1.00 | 19.20 | C |
| ATOM | 1534 | O | ALA A 249 | -3.455 | 70.373 | -11.416 | 1.00 | 18.28 | O |

FIG. 22T

| ATOM | 1535 | N   | SER A 250 | -3.798 | 69.465 | -13.418 | 1.00 | 19.43 | N |
|------|------|-----|-----------|--------|--------|---------|------|-------|---|
| ATOM | 1536 | CA  | SER A 250 | -2.683 | 68.552 | -13.286 | 1.00 | 20.54 | C |
| ATOM | 1537 | CB  | SER A 250 | -2.974 | 67.430 | -12.274 | 1.00 | 20.55 | C |
| ATOM | 1538 | OG  | SER A 250 | 3.662  | 66.379 | 12.873  | 1.00 | 20.37 | O |
| ATOM | 1539 | C   | SER A 250 | -2.353 | 67.977 | -14.633 | 1.00 | 22.16 | C |
| ATOM | 1540 | O   | SER A 250 | -3.094 | 68.172 | -15.590 | 1.00 | 21.65 | O |
| ATOM | 1541 | N   | GLY A 251 | -1.224 | 67.282 | -14.703 | 1.00 | 25.57 | N |
| ATOM | 1542 | CA  | GLY A 251 | -0.832 | 66.570 | -15.911 | 1.00 | 29.68 | C |
| ATOM | 1543 | C   | GLY A 251 | -1.641 | 65.293 | -16.069 | 1.00 | 35.36 | C |
| ATOM | 1544 | O   | GLY A 251 | -2.235 | 64.855 | -15.023 | 1.00 | 36.56 | O |
| ATOM | 1545 | N   | GLY A 252 | -1.694 | 64.716 | -17.208 | 1.00 | 39.16 | N |
| ATOM | 1546 | CA  | GLY A 252 | -2.233 | 63.381 | -17.402 | 1.00 | 41.18 | C |
| ATOM | 1547 | C   | GLY A 252 | 1.114  | 62.386 | 17.656  | 1.00 | 43.96 | C |
| ATOM | 1548 | O   | GLY A 252 | -0.198 | 62.247 | -16.842 | 1.00 | 40.78 | O |
| ATOM | 1549 | N   | VAL A 253 | -1.209 | 61.689 | -18.790 | 1.00 | 47.84 | N |
| ATOM | 1550 | CA  | VAL A 253 | -0.159 | 60.796 | -19.306 | 1.00 | 50.90 | C |
| ATOM | 1551 | CB  | VAL A 253 | -0.164 | 59.377 | -18.653 | 1.00 | 49.30 | C |
| ATOM | 1552 | CG1 | VAL A 253 | 0.969  | 59.223 | -17.639 | 1.00 | 47.60 | C |
| ATOM | 1553 | CG2 | VAL A 253 | -1.529 | 59.023 | -18.054 | 1.00 | 46.89 | C |
| ATOM | 1554 | C   | VAL A 253 | -0.323 | 60.670 | -20.826 | 1.00 | 54.47 | C |
| ATOM | 1555 | O   | VAL A 253 | -1.136 | 59.874 | -21.294 | 1.00 | 55.19 | O |
| ATOM | 1556 | N   | MET A 254 | 0.427  | 61.470 | -21.588 | 1.00 | 57.54 | N |
| ATOM | 1557 | CA  | MET A 254 | 0.349  | 61.456 | -23.066 | 1.00 | 56.55 | C |
| ATOM | 1558 | CB  | MET A 254 | -0.631 | 62.525 | -23.606 | 1.00 | 61.22 | C |
| ATOM | 1559 | CG  | MET A 254 | -0.852 | 63.762 | -22.727 | 1.00 | 63.98 | C |
| ATOM | 1560 | SD  | MET A 254 | -2.079 | 64.966 | -23.356 | 1.00 | 65.56 | S |
| ATOM | 1561 | CE  | MET A 254 | -3.507 | 63.878 | -23.600 | 1.00 | 61.45 | C |
| ATOM | 1562 | C   | MET A 254 | 1.702  | 61.539 | -23.776 | 1.00 | 51.64 | C |
| ATOM | 1563 | O   | MET A 254 | 2.688  | 60.956 | -23.325 | 1.00 | 46.81 | O |
| ATOM | 1564 | N   | ASP A 258 | 5.602  | 63.604 | -19.630 | 1.00 | 35.87 | N |
| ATOM | 1565 | CA  | ASP A 258 | 4.556  | 64.207 | -18.804 | 1.00 | 36.84 | C |
| ATOM | 1566 | CB  | ASP A 258 | 3.276  | 64.475 | -19.639 | 1.00 | 37.89 | C |
| ATOM | 1567 | CG  | ASP A 258 | 2.019  | 64.774 | -18.770 | 1.00 | 37.19 | C |
| ATOM | 1568 | OD1 | ASP A 258 | 2.042  | 65.697 | -17.906 | 1.00 | 34.85 | O |
| ATOM | 1569 | OD2 | ASP A 258 | 1.000  | 64.074 | 18.984  | 1.00 | 35.25 | O |
| ATOM | 1570 | C   | ASP A 258 | 4.253  | 63.362 | -17.555 | 1.00 | 36.33 | C |
| ATOM | 1571 | O   | ASP A 258 | 4.360  | 62.131 | -17.585 | 1.00 | 36.24 | O |
| ATOM | 1572 | N   | ASN A 259 | 3.867  | 64.047 | -16.474 | 1.00 | 34.40 | N |
| ATOM | 1573 | CA  | ASN A 259 | 3.625  | 63.436 | 15.177  | 1.00 | 32.26 | C |
| ATOM | 1574 | CB  | ASN A 259 | 4.742  | 63.626 | -14.204 | 1.00 | 30.15 | C |
| ATOM | 1575 | CG  | ASN A 259 | 4.839  | 62.905 | -13.003 | 1.00 | 30.54 | C |
| ATOM | 1576 | OD1 | ASN A 259 | 3.837  | 62.537 | -12.412 | 1.00 | 32.36 | O |
| ATOM | 1577 | ND2 | ASN A 259 | 6.058  | 62.541 | -12.625 | 1.00 | 29.64 | N |
| ATOM | 1578 | C   | ASN A 259 | 2.265  | 63.869 | -14.643 | 1.00 | 32.27 | C |
| ATOM | 1579 | O   | ASN A 259 | 1.975  | 65.064 | -14.591 | 1.00 | 33.52 | O |
| ATOM | 1580 | N   | PRO A 260 | 1.410  | 62.892 | -14.275 | 1.00 | 32.74 | N |
| ATOM | 1581 | CA  | PRO A 260 | 0.127  | 63.190 | -13.621 | 1.00 | 31.43 | C |
| ATOM | 1582 | CB  | PRO A 260 | -0.557 | 61.006 | -13.556 | 1.00 | 31.76 | C |
| ATOM | 1583 | CG  | PRO A 260 | 0.548  | 60.896 | -13.658 | 1.00 | 31.86 | C |
| ATOM | 1584 | CD  | PRO A 260 | 1.575  | 61.446 | -14.546 | 1.00 | 32.50 | C |
| ATOM | 1585 | C   | PRO A 260 | -0.291 | 63.718 | -12.211 | 1.00 | 29.49 | C |
| ATOM | 1586 | O   | PRO A 260 | -0.646 | 64.297 | -11.669 | 1.00 | 29.35 | O |
| ATOM | 1587 | N   | ASN A 261 | 1.460  | 63.522 | -11.617 | 1.00 | 29.47 | N |
| ATOM | 1588 | CA  | ASN A 261 | 1.681  | 63.963 | -10.245 | 1.00 | 29.06 | C |
| ATOM | 1589 | CB  | ASN A 261 | 2.835  | 63.206 | -9.593  | 1.00 | 32.96 | C |
| ATOM | 1590 | CG  | ASN A 261 | 2.501  | 61.740 | -9.351  | 1.00 | 36.94 | C |
| ATOM | 1591 | OD1 | ASN A 261 | 1.887  | 61.373 | -8.336  | 1.00 | 38.63 | O |
| ATOM | 1592 | ND2 | ASN A 261 | 2.892  | 60.891 | -10.301 | 1.00 | 36.47 | N |
| ATOM | 1593 | C   | ASN A 261 | 1.875  | 65.452 | -10.105 | 1.00 | 26.63 | C |
| ATOM | 1594 | O   | ASN A 261 | 1.613  | 65.996 | -9.034  | 1.00 | 27.99 | O |
| ATOM | 1595 | N   | PHE A 262 | 2.292  | 66.121 | 11.180  | 1.00 | 22.48 | N |
| ATOM | 1596 | CA  | PHE A 262 | 2.521  | 67.572 | -11.158 | 1.00 | 20.09 | C |
| ATOM | 1597 | CB  | PHE A 262 | 3.531  | 67.991 | -12.230 | 1.00 | 19.03 | C |
| ATOM | 1598 | CG  | PHE A 262 | 4.921  | 67.207 | -12.212 | 1.00 | 19.55 | C |
| ATOM | 1599 | CD1 | PHE A 262 | 5.266  | 66.559 | -11.047 | 1.00 | 18.36 | C |
| ATOM | 1600 | CE1 | PHE A 262 | 6.441  | 65.835 | -11.044 | 1.00 | 17.70 | C |
| ATOM | 1601 | CZ  | PHE A 262 | 7.205  | 65.756 | -12.198 | 1.00 | 17.71 | C |
| ATOM | 1602 | CE2 | PHE A 262 | 6.787  | 66.410 | -13.349 | 1.00 | 17.97 | C |
| ATOM | 1603 | CD2 | PHE A 262 | 5.602  | 67.128 | -13.356 | 1.00 | 17.88 | C |
| ATOM | 1604 | C   | PHE A 262 | 1.236  | 68.395 | -11.323 | 1.00 | 19.09 | C |
| ATOM | 1605 | O   | PHE A 262 | 0.442  | 68.158 | -12.247 | 1.00 | 19.20 | O |
| ATOM | 1606 | N   | ALA A 263 | 1.043  | 69.352 | -10.415 | 1.00 | 17.63 | N |
| ATOM | 1607 | CA  | ALA A 263 | -0.049 | 70.340 | -10.480 | 1.00 | 16.64 | C |
| ATOM | 1608 | CB  | ALA A 263 | 0.066  | 71.169 | 9.194   | 1.00 | 15.86 | C |
| ATOM | 1609 | C   | ALA A 263 | 0.112  | 71.260 | -11.702 | 1.00 | 15.99 | C |
| ATOM | 1610 | O   | ALA A 263 | 1.229  | 71.419 | -12.229 | 1.00 | 15.49 | O |
| ATOM | 1611 | N   | GLN A 264 | -0.986 | 71.861 | -12.163 | 1.00 | 15.43 | N |

FIG. 22U

| | | | | | | | | | |
|---|---|---|---|---|---|---|---|---|---|
| ATOM | 1612 | CA | GLN A 264 | -0.896 | 72.847 | -13.265 | 1.00 | 14.57 | C |
| ATOM | 1613 | CB | GLN A 264 | -1.433 | 72.268 | -14.567 | 1.00 | 13.73 | C |
| ATOM | 1614 | CG | GLN A 264 | -0.529 | 71.225 | -15.187 | 1.00 | 13.01 | C |
| ATOM | 1615 | CD | GLN A 264 | 1.070 | 70.704 | 16.493 | 1.00 | 12.68 | C |
| ATOM | 1616 | OE1 | GLN A 264 | -2.139 | 71.116 | -16.943 | 1.00 | 12.55 | O |
| ATOM | 1617 | NE2 | GLN A 264 | -0.337 | 69.794 | -17.111 | 1.00 | 12.44 | N |
| ATOM | 1618 | C | GLN A 264 | -1.633 | 74.133 | -12.912 | 1.00 | 14.55 | C |
| ATOM | 1619 | O | GLN A 264 | -2.596 | 74.095 | -12.141 | 1.00 | 13.74 | O |
| ATOM | 1620 | N | PHE A 265 | -1.180 | 75.255 | -13.497 | 1.00 | 14.70 | N |
| ATOM | 1621 | CA | PHE A 265 | -1.568 | 76.613 | -13.041 | 1.00 | 14.95 | C |
| ATOM | 1622 | CB | PHE A 265 | -3.098 | 76.838 | -13.015 | 1.00 | 14.93 | C |
| ATOM | 1623 | CG | PHE A 265 | -3.717 | 77.093 | -14.364 | 1.00 | 14.98 | C |
| ATOM | 1624 | CD1 | PHE A 265 | 3.398 | 78.256 | 15.063 | 1.00 | 15.17 | C |
| ATOM | 1625 | CE1 | PHE A 265 | -3.983 | 78.530 | -16.304 | 1.00 | 15.84 | C |
| ATOM | 1626 | CZ | PHE A 265 | -4.911 | 77.639 | -16.847 | 1.00 | 15.63 | C |
| ATOM | 1627 | CE2 | PHE A 265 | -5.236 | 76.475 | -16.151 | 1.00 | 15.11 | C |
| ATOM | 1628 | CD2 | PHE A 265 | -4.646 | 76.210 | -14.923 | 1.00 | 14.76 | C |
| ATOM | 1629 | C | PHE A 265 | -1.018 | 76.894 | -11.633 | 1.00 | 15.25 | C |
| ATOM | 1630 | O | PHE A 265 | -0.842 | 75.970 | -10.828 | 1.00 | 15.46 | O |
| ATOM | 1631 | N | SER A 266 | -0.710 | 78.159 | -11.350 | 1.00 | 14.93 | N |
| ATOM | 1632 | CA | SER A 266 | -0.392 | 78.590 | -9.987 | 1.00 | 14.97 | C |
| ATOM | 1633 | CB | SER A 266 | 0.229 | 79.988 | -10.009 | 1.00 | 14.78 | C |
| ATOM | 1634 | OG | SER A 266 | -0.648 | 80.924 | -10.627 | 1.00 | 15.13 | O |
| ATOM | 1635 | C | SER A 266 | -1.662 | 78.620 | -9.120 | 1.00 | 15.03 | C |
| ATOM | 1636 | O | SER A 266 | -2.750 | 78.796 | -9.657 | 1.00 | 14.96 | O |
| ATOM | 1637 | N | PRO A 267 | -1.518 | 78.476 | -7.781 | 1.00 | 15.15 | N |
| ATOM | 1638 | CA | PRO A 267 | -2.585 | 78.825 | -6.845 | 1.00 | 15.03 | C |
| ATOM | 1639 | CB | PRO A 267 | -1.868 | 78.888 | -5.500 | 1.00 | 14.86 | C |
| ATOM | 1640 | CG | PRO A 267 | -0.707 | 77.970 | -5.637 | 1.00 | 14.67 | C |
| ATOM | 1641 | CD | PRO A 267 | -0.310 | 77.986 | -7.081 | 1.00 | 14.69 | C |
| ATOM | 1642 | C | PRO A 267 | -3.159 | 80.207 | -7.156 | 1.00 | 15.74 | C |
| ATOM | 1643 | O | PRO A 267 | -4.380 | 80.389 | -7.092 | 1.00 | 16.29 | O |
| ATOM | 1644 | N | GLU A 268 | -2.288 | 81.173 | -7.468 | 1.00 | 15.99 | N |
| ATOM | 1645 | CA | GLU A 268 | -2.722 | 82.525 | -7.838 | 1.00 | 16.63 | C |
| ATOM | 1646 | CB | GLU A 268 | 1.529 | 93.436 | 8.138 | 1.00 | 17.42 | C |
| ATOM | 1647 | CG | GLU A 268 | -0.651 | 83.792 | -6.938 | 1.00 | 19.19 | C |
| ATOM | 1648 | CD | GLU A 268 | 0.592 | 82.874 | -6.736 | 1.00 | 20.86 | C |
| ATOM | 1649 | OE1 | GLU A 268 | 0.489 | 81.697 | -6.690 | 1.00 | 20.12 | O |
| ATOM | 1650 | OE2 | GLU A 268 | 1.676 | 83.451 | 6.561 | 1.00 | 21.46 | C |
| ATOM | 1651 | C | GLU A 268 | -3.704 | 82.534 | -9.026 | 1.00 | 16.91 | C |
| ATOM | 1652 | O | GLU A 268 | -4.760 | 83.180 | -8.958 | 1.00 | 17.64 | O |
| ATOM | 1653 | N | GLU A 269 | -3.374 | 81.829 | -10.111 | 1.00 | 16.12 | N |
| ATOM | 1654 | CA | GLU A 269 | -4.278 | 81.787 | -11.245 | 1.00 | 15.65 | C |
| ATOM | 1655 | CB | GLU A 269 | -3.614 | 81.145 | -12.459 | 1.00 | 15.07 | C |
| ATOM | 1656 | CG | GLU A 269 | -2.576 | 81.992 | -13.154 | 1.00 | 14.29 | C |
| ATOM | 1657 | CD | GLU A 269 | -1.488 | 81.139 | -13.777 | 1.00 | 14.13 | C |
| ATOM | 1658 | OE1 | GLU A 269 | -1.283 | 81.169 | -15.009 | 1.00 | 14.80 | O |
| ATOM | 1659 | OE2 | GLU A 269 | -0.825 | 80.410 | -13.028 | 1.00 | 14.57 | O |
| ATOM | 1660 | C | GLU A 269 | -5.572 | 81.037 | -10.894 | 1.00 | 16.04 | C |
| ATOM | 1661 | O | GLU A 269 | -6.667 | 81.435 | -11.317 | 1.00 | 16.25 | O |
| ATOM | 1662 | N | LEU A 270 | -5.449 | 79.957 | -10.121 | 1.00 | 15.51 | N |
| ATOM | 1663 | CA | LEU A 270 | -6.607 | 79.123 | -9.783 | 1.00 | 15.17 | C |
| ATOM | 1664 | CB | LEU A 270 | -6.184 | 77.825 | -9.087 | 1.00 | 14.55 | C |
| ATOM | 1665 | CG | LEU A 270 | -5.509 | 76.712 | -9.908 | 1.00 | 13.89 | C |
| ATOM | 1666 | CD1 | LEU A 270 | -5.194 | 75.541 | -9.009 | 1.00 | 12.98 | C |
| ATOM | 1667 | CD2 | LEU A 270 | -6.379 | 76.266 | -11.072 | 1.00 | 14.03 | C |
| ATOM | 1668 | C | LEU A 270 | -7.602 | 79.897 | -8.930 | 1.00 | 15.51 | C |
| ATOM | 1669 | O | LEU A 270 | -8.807 | 79.850 | -9.186 | 1.00 | 15.60 | O |
| ATOM | 1670 | N | LYS A 271 | -7.095 | 80.633 | -7.941 | 1.00 | 15.75 | N |
| ATOM | 1671 | CA | LYS A 271 | -7.936 | 81.463 | -7.088 | 1.00 | 15.59 | C |
| ATOM | 1672 | CB | LYS A 271 | 7.092 | 82.207 | 6.061 | 1.00 | 15.80 | C |
| ATOM | 1673 | CG | LYS A 271 | -7.698 | 83.125 | -5.156 | 1.00 | 16.97 | C |
| ATOM | 1674 | CD | LYS A 271 | -7.183 | 83.356 | -3.823 | 1.00 | 17.80 | C |
| ATOM | 1675 | CE | LYS A 271 | -7.944 | 84.339 | -2.952 | 1.00 | 18.05 | C |
| ATOM | 1676 | NZ | LYS A 271 | -7.699 | 85.754 | -3.404 | 1.00 | 18.94 | N |
| ATOM | 1677 | C | LYS A 271 | -8.710 | 82.449 | -7.946 | 1.00 | 15.47 | C |
| ATOM | 1678 | O | LYS A 271 | -9.933 | 82.597 | -7.821 | 1.00 | 15.33 | O |
| ATOM | 1679 | N | VAL A 272 | -7.997 | 83.117 | -8.940 | 1.00 | 15.18 | N |
| ATOM | 1680 | CA | VAL A 272 | -8.665 | 84.073 | -9.699 | 1.00 | 15.15 | C |
| ATOM | 1681 | CB | VAL A 272 | -7.650 | 84.926 | -10.477 | 1.00 | 14.42 | C |
| ATOM | 1682 | CG1 | VAL A 272 | -8.312 | 85.583 | -11.664 | 1.00 | 13.81 | C |
| ATOM | 1683 | CG2 | VAL A 272 | -7.073 | 85.961 | -9.545 | 1.00 | 14.12 | C |
| ATOM | 1684 | C | VAL A 272 | -9.697 | 83.380 | -10.593 | 1.00 | 14.85 | C |
| ATOM | 1685 | O | VAL A 272 | 10.803 | 83.866 | 10.759 | 1.00 | 15.14 | O |
| ATOM | 1686 | N | ILE A 273 | -9.348 | 92.237 | -11.147 | 1.00 | 15.00 | N |
| ATOM | 1687 | CA | ILE A 273 | -10.277 | 81.556 | -12.032 | 1.00 | 15.27 | C |
| ATOM | 1688 | CB | ILE A 273 | -9.664 | 80.301 | -12.672 | 1.00 | 14.93 | C |

FIG. 22V

| | | | | | | | | | |
|---|---|---|---|---|---|---|---|---|---|
| ATOM | 1689 | CG1 | ILE | A | 273 | -8.619 | 80.711 | -13.717 | 1.00 14.90 | C |
| ATOM | 1690 | CD1 | ILE | A | 273 | -7.821 | 79.585 | -14.317 | 1.00 14.77 | C |
| ATOM | 1691 | CG2 | ILE | A | 273 | -10.754 | 79.475 | -13.343 | 1.00 15.39 | C |
| ATOM | 1692 | C | ILE | A | 273 | 11.576 | 81.234 | 11.289 | 1.00 15.74 | C |
| ATOM | 1693 | O | ILE | A | 273 | -12.658 | 81.543 | -11.790 | 1.00 16.00 | O |
| ATOM | 1694 | N | VAL | A | 274 | -11.460 | 80.640 | -10.094 | 1.00 15.72 | N |
| ATOM | 1695 | CA | VAL | A | 274 | -12.622 | 80.344 | -9.248 | 1.00 15.41 | C |
| ATOM | 1696 | CB | VAL | A | 274 | -12.238 | 79.717 | -7.883 | 1.00 14.99 | C |
| ATOM | 1697 | CG1 | VAL | A | 274 | -13.430 | 79.710 | -6.952 | 1.00 14.16 | C |
| ATOM | 1698 | CG2 | VAL | A | 274 | -11.727 | 78.267 | -8.072 | 1.00 14.52 | C |
| ATOM | 1699 | C | VAL | A | 274 | -13.461 | 81.597 | -9.068 | 1.00 15.65 | C |
| ATOM | 1700 | O | VAL | A | 274 | -14.664 | 81.596 | -9.354 | 1.00 16.51 | O |
| ATOM | 1701 | N | GLU | A | 275 | 12.805 | 82.679 | 8.650 | 1.00 15.65 | N |
| ATOM | 1702 | CA | GLU | A | 275 | -13.466 | 83.938 | -8.355 | 1.00 15.47 | C |
| ATOM | 1703 | CB | GLU | A | 275 | -12.438 | 84.940 | -7.871 | 1.00 16.36 | C |
| ATOM | 1704 | CG | GLU | A | 275 | -12.078 | 84.792 | -6.402 | 1.00 16.93 | C |
| ATOM | 1705 | CD | GLU | A | 275 | -10.861 | 85.615 | -5.998 | 1.00 17.33 | C |
| ATOM | 1706 | OE1 | GLU | A | 275 | -10.326 | 86.591 | -6.822 | 1.00 16.65 | O |
| ATOM | 1707 | OE2 | GLU | A | 275 | -10.426 | 85.463 | -4.838 | 1.00 18.19 | O |
| ATOM | 1708 | C | GLU | A | 275 | -14.231 | 84.525 | -9.529 | 1.00 15.54 | C |
| ATOM | 1709 | O | GLU | A | 275 | -15.303 | 85.097 | -9.349 | 1.00 16.43 | O |
| ATOM | 1710 | N | GLU | A | 276 | -13.672 | 84.409 | -10.725 | 1.00 15.01 | N |
| ATOM | 1711 | CA | GLU | A | 276 | -14.281 | 84.963 | -11.919 | 1.00 14.34 | C |
| ATOM | 1712 | CB | GLU | A | 276 | -13.302 | 84.878 | -13.086 | 1.00 14.14 | C |
| ATOM | 1713 | CG | GLU | A | 276 | -12.212 | 85.927 | -13.027 | 1.00 13.71 | C |
| ATOM | 1714 | CD | GLU | A | 276 | -12.721 | 87.321 | -13.375 | 1.00 13.96 | C |
| ATOM | 1715 | OE1 | GLU | A | 276 | -13.699 | 87.444 | -14.176 | 1.00 13.53 | O |
| ATOM | 1716 | OE2 | GLU | A | 276 | -12.130 | 88.304 | -12.846 | 1.00 13.97 | O |
| ATOM | 1717 | C | GLU | A | 276 | -15.571 | 84.209 | -12.234 | 1.00 14.54 | C |
| ATOM | 1718 | O | GLU | A | 276 | -16.560 | 84.300 | -12.647 | 1.00 14.40 | O |
| ATOM | 1719 | N | ALA | A | 277 | -15.554 | 82.900 | -12.006 | 1.00 14.51 | N |
| ATOM | 1720 | CA | ALA | A | 277 | -16.711 | 82.064 | -12.234 | 1.00 13.81 | C |
| ATOM | 1721 | CB | ALA | A | 277 | -16.310 | 80.599 | -12.189 | 1.00 13.68 | C |
| ATOM | 1722 | C | ALA | A | 277 | -17.754 | 82.374 | -11.180 | 1.00 13.51 | C |
| ATOM | 1723 | O | ALA | A | 277 | 18.925 | 82.571 | 11.402 | 1.00 12.84 | O |
| ATOM | 1724 | N | ALA | A | 278 | -17.305 | 82.433 | -9.925 | 1.00 13.72 | N |
| ATOM | 1725 | CA | ALA | A | 278 | -18.191 | 82.665 | -8.792 | 1.00 13.43 | C |
| ATOM | 1726 | CB | ALA | A | 278 | -17.402 | 82.694 | -7.498 | 1.00 12.95 | C |
| ATOM | 1727 | C | ALA | A | 278 | 18.981 | 83.957 | 8.987 | 1.00 13.95 | C |
| ATOM | 1728 | O | ALA | A | 278 | -20.147 | 84.023 | -8.612 | 1.00 14.45 | O |
| ATOM | 1729 | N | ARG | A | 279 | -18.369 | 84.965 | -9.617 | 1.00 14.15 | N |
| ATOM | 1730 | CA | ARG | A | 279 | -19.023 | 86.269 | -9.780 | 1.00 14.18 | C |
| ATOM | 1731 | CB | ARG | A | 279 | -19.055 | 87.356 | -10.241 | 1.00 15.01 | C |
| ATOM | 1732 | CG | ARG | A | 279 | -18.621 | 88.772 | -10.173 | 1.00 15.75 | C |
| ATOM | 1733 | CD | ARG | A | 279 | -17.552 | 89.863 | -10.184 | 1.00 17.16 | C |
| ATOM | 1734 | NE | ARG | A | 279 | -16.364 | 89.516 | -10.970 | 1.00 18.36 | N |
| ATOM | 1735 | CZ | ARG | A | 279 | -15.193 | 89.210 | -10.424 | 1.00 18.78 | C |
| ATOM | 1736 | NH1 | ARG | A | 279 | -14.175 | 90.095 | -11.200 | 1.00 18.57 | N |
| ATOM | 1737 | NH2 | ARG | A | 279 | -15.044 | 89.219 | -9.091 | 1.00 19.50 | N |
| ATOM | 1738 | C | ARG | A | 279 | -20.178 | 86.179 | -10.719 | 1.00 13.63 | C |
| ATOM | 1739 | O | ARG | A | 279 | -21.108 | 86.970 | -10.641 | 1.00 12.89 | O |
| ATOM | 1740 | N | GLN | A | 280 | -20.128 | 85.168 | -11.595 | 1.00 14.16 | N |
| ATOM | 1741 | CA | GLN | A | 280 | -21.243 | 84.953 | -12.501 | 1.00 14.55 | C |
| ATOM | 1742 | CB | GLN | A | 280 | -20.761 | 84.878 | -13.937 | 1.00 15.00 | C |
| ATOM | 1743 | CG | GLN | A | 280 | -19.928 | 86.077 | -14.349 | 1.00 15.48 | C |
| ATOM | 1744 | CD | GLN | A | 280 | -20.673 | 87.397 | -14.156 | 1.00 16.60 | C |
| ATOM | 1745 | OE1 | GLN | A | 280 | -20.107 | 88.357 | -13.638 | 1.00 17.73 | O |
| ATOM | 1746 | NE2 | GLN | A | 280 | -21.944 | 87.430 | -14.574 | 1.00 16.33 | N |
| ATOM | 1747 | C | GLN | A | 280 | -22.055 | 83.735 | -12.128 | 1.00 14.49 | C |
| ATOM | 1748 | O | GLN | A | 280 | -22.833 | 83.247 | -12.932 | 1.00 15.06 | O |
| ATOM | 1749 | N | ASN | A | 281 | 21.894 | 83.257 | 10.900 | 1.00 14.53 | N |
| ATOM | 1750 | CA | ASN | A | 281 | -22.658 | 82.119 | -10.431 | 1.00 15.01 | C |
| ATOM | 1751 | CB | ASN | A | 281 | -24.161 | 82.426 | -10.509 | 1.00 15.54 | C |
| ATOM | 1752 | CG | ASN | A | 281 | -24.953 | 82.444 | -9.150 | 1.00 15.91 | C |
| ATOM | 1753 | OD1 | ASN | A | 281 | -24.247 | 82.218 | -8.104 | 1.00 17.03 | O |
| ATOM | 1754 | ND2 | ASN | A | 281 | -26.148 | 82.697 | -9.173 | 1.00 15.85 | N |
| ATOM | 1755 | C | ASN | A | 281 | -22.365 | 80.819 | -11.197 | 1.00 14.99 | C |
| ATOM | 1756 | O | ASN | A | 281 | -23.261 | 79.991 | -11.374 | 1.00 15.16 | O |
| ATOM | 1757 | N | ARG | A | 282 | -21.127 | 80.662 | -11.672 | 1.00 14.97 | N |
| ATOM | 1758 | CA | ARG | A | 282 | -20.612 | 79.357 | -12.134 | 1.00 14.44 | C |
| ATOM | 1759 | CB | ARG | A | 282 | -19.803 | 79.488 | -13.410 | 1.00 13.34 | C |
| ATOM | 1760 | CG | ARG | A | 282 | -20.605 | 79.542 | -14.685 | 1.00 12.79 | C |
| ATOM | 1761 | CD | ARG | A | 282 | -21.529 | 80.734 | -14.756 | 1.00 12.40 | C |
| ATOM | 1762 | NE | ARG | A | 282 | 22.074 | 80.842 | 16.104 | 1.00 11.96 | N |
| ATOM | 1763 | CZ | ARG | A | 282 | -22.959 | 81.752 | -16.468 | 1.00 11.63 | C |
| ATOM | 1764 | NH1 | ARG | A | 282 | -23.394 | 91.787 | -17.721 | 1.00 11.35 | N |
| ATOM | 1765 | NH2 | ARG | A | 282 | -23.393 | 82.640 | -15.578 | 1.00 11.66 | N |

FIG. 22W

| ATOM | 1766 | C | ARG A 282 | -19.707 | 78.755 | -11.077 | 1.00 | 14.64 | C |
| ATOM | 1767 | O | ARG A 282 | -19.206 | 79.456 | -10.217 | 1.00 | 14.97 | O |
| ATOM | 1768 | N | ILE A 283 | -19.521 | 77.444 | -11.140 | 1.00 | 15.76 | N |
| ATOM | 1769 | CA | ILE A 283 | -19.473 | 76.770 | -10.379 | 1.00 | 15.71 | C |
| ATOM | 1770 | CB | ILE A 283 | -19.000 | 75.549 | -9.611 | 1.00 | 15.64 | C |
| ATOM | 1771 | CG1 | ILE A 283 | -19.663 | 74.550 | -10.575 | 1.00 | 15.09 | C |
| ATOM | 1772 | CD1 | ILE A 283 | -19.748 | 73.155 | -9.995 | 1.00 | 14.99 | C |
| ATOM | 1773 | CG2 | ILE A 283 | -19.907 | 75.979 | -8.458 | 1.00 | 14.90 | C |
| ATOM | 1774 | C | ILE A 283 | -17.369 | 76.322 | -11.326 | 1.00 | 16.01 | C |
| ATOM | 1775 | O | ILE A 283 | -17.509 | 76.377 | -12.565 | 1.00 | 16.65 | O |
| ATOM | 1776 | N | VAL A 284 | -16.261 | 75.891 | -10.747 | 1.00 | 16.25 | N |
| ATOM | 1777 | CA | VAL A 284 | -15.147 | 75.400 | -11.539 | 1.00 | 16.20 | C |
| ATOM | 1778 | CB | VAL A 284 | -13.839 | 76.182 | -11.294 | 1.00 | 16.15 | C |
| ATOM | 1779 | CG1 | VAL A 284 | -12.681 | 75.518 | -12.014 | 1.00 | 16.14 | C |
| ATOM | 1780 | CG2 | VAL A 284 | -13.980 | 77.605 | -11.807 | 1.00 | 16.68 | C |
| ATOM | 1781 | C | VAL A 284 | -14.953 | 73.916 | -11.261 | 1.00 | 16.42 | C |
| ATOM | 1782 | O | VAL A 284 | -15.022 | 73.440 | -10.119 | 1.00 | 16.58 | O |
| ATOM | 1783 | N | SER A 285 | -14.756 | 73.207 | -12.386 | 1.00 | 16.06 | N |
| ATOM | 1784 | CA | SER A 285 | -14.457 | 71.793 | -12.409 | 1.00 | 16.56 | C |
| ATOM | 1785 | CB | SER A 285 | -15.307 | 71.147 | -13.482 | 1.00 | 16.57 | C |
| ATOM | 1786 | OG | SER A 285 | -15.920 | 70.002 | -12.955 | 1.00 | 17.70 | O |
| ATOM | 1787 | C | SER A 285 | -12.990 | 71.589 | -12.766 | 1.00 | 16.96 | C |
| ATOM | 1788 | O | SER A 285 | -12.511 | 72.087 | -13.817 | 1.00 | 16.79 | O |
| ATOM | 1789 | N | ALA A 286 | -12.280 | 70.846 | -11.919 | 1.00 | 16.67 | N |
| ATOM | 1790 | CA | ALA A 286 | -10.853 | 70.641 | -12.122 | 1.00 | 17.08 | C |
| ATOM | 1791 | CB | ALA A 286 | -10.076 | 71.126 | -10.917 | 1.00 | 16.47 | C |
| ATOM | 1792 | C | ALA A 286 | -10.457 | 69.196 | -12.500 | 1.00 | 18.26 | C |
| ATOM | 1793 | O | ALA A 286 | -10.771 | 68.229 | -11.789 | 1.00 | 17.79 | O |
| ATOM | 1794 | N | HIS A 287 | -9.788 | 69.085 | -13.650 | 1.00 | 19.34 | N |
| ATOM | 1795 | CA | HIS A 287 | -9.127 | 67.868 | -14.089 | 1.00 | 20.02 | C |
| ATOM | 1796 | CB | HIS A 287 | -8.723 | 68.017 | -15.551 | 1.00 | 20.31 | C |
| ATOM | 1797 | CG | HIS A 287 | -7.733 | 66.983 | -16.021 | 1.00 | 21.31 | C |
| ATOM | 1798 | ND1 | HIS A 287 | -8.111 | 65.840 | -16.647 | 1.00 | 21.86 | N |
| ATOM | 1799 | CE1 | HIS A 287 | -7.014 | 65.111 | -16.950 | 1.00 | 21.66 | C |
| ATOM | 1800 | NE2 | HIS A 287 | 5.925 | 65.793 | 16.526 | 1.00 | 22.13 | N |
| ATOM | 1801 | CD2 | HIS A 287 | -6.334 | 66.946 | -15.938 | 1.00 | 21.19 | C |
| ATOM | 1802 | C | HIS A 287 | -7.922 | 67.692 | -13.213 | 1.00 | 21.00 | C |
| ATOM | 1803 | O | HIS A 287 | -6.999 | 68.513 | -13.255 | 1.00 | 22.30 | O |
| ATOM | 1804 | N | VAL A 288 | 7.927 | 66.661 | 12.367 | 1.00 | 20.84 | N |
| ATOM | 1805 | CA | VAL A 288 | -6.791 | 66.411 | -11.480 | 1.00 | 19.57 | C |
| ATOM | 1806 | CB | VAL A 288 | -6.971 | 67.039 | -10.085 | 1.00 | 19.24 | C |
| ATOM | 1807 | CG1 | VAL A 288 | -6.729 | 68.531 | -10.137 | 1.00 | 19.05 | C |
| ATOM | 1808 | CG2 | VAL A 288 | -8.354 | 66.755 | -9.534 | 1.00 | 19.45 | C |
| ATOM | 1809 | C | VAL A 288 | -6.534 | 64.927 | -11.316 | 1.00 | 19.34 | C |
| ATOM | 1810 | O | VAL A 288 | -7.481 | 64.132 | -11.297 | 1.00 | 19.33 | O |
| ATOM | 1811 | N | HIS A 289 | -5.248 | 64.576 | -11.202 | 1.00 | 18.61 | N |
| ATOM | 1812 | CA | HIS A 289 | -4.780 | 63.223 | -10.912 | 1.00 | 17.90 | C |
| ATOM | 1813 | CB | HIS A 289 | -3.099 | 62.696 | -12.026 | 1.00 | 17.10 | C |
| ATOM | 1814 | CG | HIS A 289 | -4.647 | 62.333 | -13.260 | 1.00 | 16.67 | C |
| ATOM | 1815 | ND1 | HIS A 289 | -5.504 | 61.297 | -13.304 | 1.00 | 16.65 | N |
| ATOM | 1816 | CE1 | HIS A 289 | -6.033 | 61.205 | -14.539 | 1.00 | 16.53 | C |
| ATOM | 1817 | NE2 | HIS A 289 | -5.504 | 62.187 | -15.288 | 1.00 | 16.92 | N |
| ATOM | 1818 | CD2 | HIS A 289 | -4.649 | 62.903 | -14.524 | 1.00 | 16.71 | C |
| ATOM | 1819 | C | HIS A 289 | -4.010 | 63.209 | -9.629 | 1.00 | 19.40 | C |
| ATOM | 1820 | O | HIS A 289 | -4.496 | 62.706 | -8.606 | 1.00 | 18.75 | O |
| ATOM | 1821 | N | GLY A 290 | -2.803 | 63.761 | -9.676 | 1.00 | 17.89 | N |
| ATOM | 1822 | CA | GLY A 290 | -1.920 | 63.805 | -8.524 | 1.00 | 18.69 | C |
| ATOM | 1823 | C | GLY A 290 | -2.468 | 64.649 | -7.388 | 1.00 | 18.46 | C |
| ATOM | 1824 | O | GLY A 290 | -3.222 | 65.577 | -7.618 | 1.00 | 17.75 | O |
| ATOM | 1825 | N | LYS A 291 | -2.067 | 64.311 | -6.163 | 1.00 | 19.09 | N |
| ATOM | 1826 | CA | LYS A 291 | 2.592 | 64.934 | 4.952 | 1.00 | 18.98 | C |
| ATOM | 1827 | CB | LYS A 291 | -2.869 | 64.210 | -3.701 | 1.00 | 19.91 | C |
| ATOM | 1828 | CG | LYS A 291 | -2.702 | 64.698 | -2.411 | 1.00 | 20.95 | C |
| ATOM | 1829 | CD | LYS A 291 | -2.332 | 63.630 | -1.226 | 1.00 | 22.32 | C |
| ATOM | 1830 | CE | LYS A 291 | -3.278 | 64.125 | -0.073 | 1.00 | 23.17 | C |
| ATOM | 1831 | NZ | LYS A 291 | -2.651 | 63.886 | 1.255 | 1.00 | 23.89 | N |
| ATOM | 1832 | C | LYS A 291 | -2.281 | 66.432 | -4.898 | 1.00 | 18.49 | C |
| ATOM | 1833 | O | LYS A 291 | -3.126 | 67.229 | -4.492 | 1.00 | 19.82 | O |
| ATOM | 1834 | N | ALA A 292 | -1.086 | 66.824 | -5.324 | 1.00 | 19.11 | N |
| ATOM | 1835 | CA | ALA A 292 | -0.741 | 68.243 | -5.366 | 1.00 | 17.85 | C |
| ATOM | 1836 | CB | ALA A 292 | 0.679 | 68.438 | -5.875 | 1.00 | 16.90 | C |
| ATOM | 1837 | C | ALA A 292 | -1.763 | 69.022 | -6.223 | 1.00 | 18.00 | C |
| ATOM | 1838 | O | ALA A 292 | -2.202 | 70.101 | -5.832 | 1.00 | 17.96 | O |
| ATOM | 1839 | N | GLY A 293 | 2.144 | 68.458 | 7.376 | 1.00 | 17.66 | N |
| ATOM | 1840 | CA | GLY A 293 | -3.176 | 69.045 | -8.221 | 1.00 | 18.16 | C |
| ATOM | 1841 | C | GLY A 293 | -4.525 | 69.121 | -7.519 | 1.00 | 19.90 | C |
| ATOM | 1842 | O | GLY A 293 | -5.115 | 70.210 | -7.393 | 1.00 | 19.28 | O |

FIG. 22X

| | | | | | | | | | | |
|---|---|---|---|---|---|---|---|---|---|---|
| ATOM | 1843 | N | ILE | A | 294 | -5.008 | 67.961 | -7.066 | 1.00 18.20 | N |
| ATOM | 1844 | CA | ILE | A | 294 | -6.227 | 67.858 | -6.246 | 1.00 19.25 | C |
| ATOM | 1845 | CB | ILE | A | 294 | -6.348 | 66.456 | -5.598 | 1.00 17.92 | C |
| ATOM | 1846 | CG1 | ILE | A | 294 | 6.521 | 65.375 | 6.670 | 1.00 17.41 | C |
| ATOM | 1847 | CD1 | ILE | A | 294 | -6.359 | 63.965 | -6.140 | 1.00 17.16 | C |
| ATOM | 1848 | CG2 | ILE | A | 294 | -7.497 | 66.401 | -4.594 | 1.00 17.56 | C |
| ATOM | 1849 | C | ILE | A | 294 | -6.271 | 68.940 | -5.156 | 1.00 19.56 | C |
| ATOM | 1850 | O | ILE | A | 294 | -7.237 | 69.728 | -5.096 | 1.00 19.55 | O |
| ATOM | 1851 | N | MET | A | 295 | -5.225 | 68.990 | -4.323 | 1.00 17.49 | N |
| ATOM | 1852 | CA | MET | A | 295 | -5.189 | 69.912 | -3.196 | 1.00 19.03 | C |
| ATOM | 1853 | CB | MET | A | 295 | -3.960 | 69.681 | -2.305 | 1.00 19.58 | C |
| ATOM | 1854 | CG | MET | A | 295 | -3.951 | 68.313 | -1.648 | 1.00 18.86 | C |
| ATOM | 1855 | SD | MET | A | 295 | 5.418 | 68.052 | 0.636 | 1.00 21.01 | S |
| ATOM | 1856 | CE | MET | A | 295 | -4.839 | 68.812 | 0.901 | 1.00 19.03 | C |
| ATOM | 1857 | C | MET | A | 295 | -5.279 | 71.363 | -3.603 | 1.00 18.10 | C |
| ATOM | 1858 | O | MET | A | 295 | -6.006 | 72.117 | -2.990 | 1.00 19.71 | O |
| ATOM | 1859 | N | ALA | A | 296 | -4.532 | 71.753 | -4.625 | 1.00 18.57 | N |
| ATOM | 1860 | CA | ALA | A | 296 | -4.561 | 73.114 | -5.157 | 1.00 17.91 | C |
| ATOM | 1861 | CB | ALA | A | 296 | -3.544 | 73.261 | -6.287 | 1.00 16.31 | C |
| ATOM | 1862 | C | ALA | A | 296 | -5.974 | 73.502 | -5.631 | 1.00 17.77 | C |
| ATOM | 1863 | O | ALA | A | 296 | -6.501 | 74.561 | -5.254 | 1.00 17.56 | O |
| ATOM | 1864 | N | ALA | A | 297 | -6.578 | 72.648 | -6.455 | 1.00 17.58 | N |
| ATOM | 1865 | CA | ALA | A | 297 | -7.946 | 72.878 | -6.947 | 1.00 17.82 | C |
| ATOM | 1866 | CB | ALA | A | 297 | -8.383 | 71.757 | -7.875 | 1.00 17.10 | C |
| ATOM | 1867 | C | ALA | A | 297 | -8.943 | 73.041 | -5.785 | 1.00 17.50 | C |
| ATOM | 1868 | O | ALA | A | 297 | -9.756 | 73.967 | -5.790 | 1.00 16.73 | O |
| ATOM | 1869 | N | ILE | A | 298 | -8.860 | 72.150 | -4.792 | 1.00 17.54 | N |
| ATOM | 1870 | CA | ILE | A | 298 | -9.667 | 72.280 | -3.546 | 1.00 17.06 | C |
| ATOM | 1871 | CB | ILE | A | 298 | -9.416 | 71.136 | -2.533 | 1.00 15.79 | C |
| ATOM | 1872 | CG1 | ILE | A | 298 | -10.026 | 69.849 | -3.072 | 1.00 15.29 | C |
| ATOM | 1873 | CD1 | ILE | A | 298 | -9.430 | 68.602 | -2.494 | 1.00 15.04 | C |
| ATOM | 1874 | CG2 | ILE | A | 298 | -10.835 | 71.442 | -1.189 | 1.00 15.91 | C |
| ATOM | 1875 | C | ILE | A | 298 | -9.409 | 73.629 | -2.900 | 1.00 17.30 | C |
| ATOM | 1876 | O | ILE | A | 298 | -10.349 | 74.394 | -2.677 | 1.00 18.26 | O |
| ATOM | 1877 | N | LYS | A | 299 | 8.137 | 73.924 | 2.647 | 1.00 17.07 | N |
| ATOM | 1878 | CA | LYS | A | 299 | -7.724 | 75.129 | -1.964 | 1.00 17.15 | C |
| ATOM | 1879 | CB | LYS | A | 299 | -6.205 | 75.156 | -1.900 | 1.00 18.10 | C |
| ATOM | 1880 | CG | LYS | A | 299 | -5.615 | 76.486 | -1.435 | 1.00 20.12 | C |
| ATOM | 1881 | CD | LYS | A | 299 | 5.765 | 76.670 | 0.075 | 1.00 21.40 | C |
| ATOM | 1882 | CE | LYS | A | 299 | -4.397 | 76.718 | 0.736 | 1.00 22.42 | C |
| ATOM | 1883 | NZ | LYS | A | 299 | -3.856 | 78.097 | 0.575 | 1.00 22.41 | N |
| ATOM | 1884 | C | LYS | A | 299 | -8.276 | 76.368 | -2.649 | 1.00 17.43 | C |
| ATOM | 1885 | O | LYS | A | 299 | -8.705 | 77.306 | -1.985 | 1.00 17.24 | O |
| ATOM | 1886 | N | ALA | A | 300 | -8.292 | 76.348 | -3.981 | 1.00 18.18 | N |
| ATOM | 1887 | CA | ALA | A | 300 | -8.740 | 77.485 | -4.780 | 1.00 19.36 | C |
| ATOM | 1888 | CB | ALA | A | 300 | -8.288 | 77.335 | -6.238 | 1.00 18.02 | C |
| ATOM | 1889 | C | ALA | A | 300 | -10.253 | 77.708 | -4.721 | 1.00 18.21 | C |
| ATOM | 1890 | O | ALA | A | 300 | -10.712 | 78.831 | -4.915 | 1.00 19.27 | O |
| ATOM | 1891 | N | GLY | A | 301 | -11.025 | 76.648 | -4.489 | 1.00 17.68 | N |
| ATOM | 1892 | CA | GLY | A | 301 | -12.477 | 76.762 | -4.409 | 1.00 17.10 | C |
| ATOM | 1893 | C | GLY | A | 301 | -13.243 | 76.014 | -5.689 | 1.00 16.67 | C |
| ATOM | 1894 | O | GLY | A | 301 | -14.429 | 76.294 | -5.731 | 1.00 16.39 | O |
| ATOM | 1895 | N | CYS | A | 302 | -12.590 | 75.057 | -6.142 | 1.00 16.46 | N |
| ATOM | 1896 | CA | CYS | A | 302 | -13.287 | 74.229 | -7.121 | 1.00 16.97 | C |
| ATOM | 1897 | CB | CYS | A | 302 | -12.319 | 73.410 | -7.964 | 1.00 17.74 | C |
| ATOM | 1898 | SG | CYS | A | 302 | -11.094 | 74.412 | -8.811 | 1.00 20.49 | S |
| ATOM | 1899 | C | CYS | A | 302 | -14.297 | 73.329 | -6.435 | 1.00 16.47 | C |
| ATOM | 1900 | O | CYS | A | 302 | -14.048 | 72.797 | -5.363 | 1.00 17.08 | O |
| ATOM | 1901 | N | LYS | A | 303 | -15.451 | 73.177 | -7.055 | 1.00 16.52 | N |
| ATOM | 1902 | CA | LYS | A | 303 | -16.547 | 72.441 | -6.461 | 1.00 16.68 | C |
| ATOM | 1903 | CB | LYS | A | 303 | 17.839 | 73.273 | 6.498 | 1.00 17.28 | C |
| ATOM | 1904 | CG | LYS | A | 303 | -17.803 | 74.561 | -5.701 | 1.00 18.28 | C |
| ATOM | 1905 | CD | LYS | A | 303 | -17.447 | 74.338 | -4.244 | 1.00 19.60 | C |
| ATOM | 1906 | CE | LYS | A | 303 | -18.662 | 73.924 | -3.443 | 1.00 20.89 | C |
| ATOM | 1907 | NZ | LYS | A | 303 | -18.567 | 74.645 | -2.159 | 1.00 22.00 | N |
| ATOM | 1908 | C | LYS | A | 303 | -16.777 | 71.147 | -7.205 | 1.00 16.21 | C |
| ATOM | 1909 | O | LYS | A | 303 | -17.775 | 70.496 | -6.983 | 1.00 16.66 | O |
| ATOM | 1910 | N | SER | A | 304 | -15.875 | 70.794 | -8.109 | 1.00 15.80 | N |
| ATOM | 1911 | CA | SER | A | 304 | -16.013 | 69.573 | -8.884 | 1.00 15.98 | C |
| ATOM | 1912 | CB | SER | A | 304 | -16.900 | 69.781 | -10.044 | 1.00 15.57 | C |
| ATOM | 1913 | OG | SER | A | 304 | -17.121 | 68.596 | -10.808 | 1.00 15.86 | O |
| ATOM | 1914 | C | SER | A | 304 | -14.641 | 69.167 | -9.390 | 1.00 16.09 | C |
| ATOM | 1915 | O | SER | A | 304 | -13.847 | 69.907 | -9.893 | 1.00 16.32 | O |
| ATOM | 1916 | N | LEU | A | 305 | 14.371 | 67.811 | 9.238 | 1.00 15.88 | N |
| ATOM | 1917 | CA | LEU | A | 305 | -13.075 | 67.212 | -9.599 | 1.00 15.50 | C |
| ATOM | 1918 | CB | LEU | A | 305 | -12.302 | 66.605 | -8.327 | 1.00 14.63 | C |
| ATOM | 1919 | CG | LEU | A | 305 | -12.015 | 67.914 | -7.309 | 1.00 14.37 | C |

FIG. 2Y

| | | | | | | | | | |
|---|---|---|---|---|---|---|---|---|---|
| ATOM | 1920 | CD1 | LEU A 305 | -11.204 | 67.384 | -6.159 | 1.00 | 13.10 | C |
| ATOM | 1921 | CD2 | LEU A 305 | -11.285 | 69.095 | -7.982 | 1.00 | 13.94 | C |
| ATOM | 1922 | C | LEU A 305 | -13.270 | 65.998 | -10.522 | 1.00 | 15.61 | C |
| ATOM | 1923 | O | LEU A 305 | -14.031 | 65.074 | -10.198 | 1.00 | 15.16 | O |
| ATOM | 1924 | N | GLU A 306 | -12.603 | 65.993 | -11.671 | 1.00 | 15.86 | N |
| ATOM | 1925 | CA | GLU A 306 | -12.659 | 64.802 | -12.498 | 1.00 | 17.28 | C |
| ATOM | 1926 | CB | GLU A 306 | -12.959 | 65.071 | -13.980 | 1.00 | 17.63 | C |
| ATOM | 1927 | CG | GLU A 306 | -13.555 | 66.406 | -14.407 | 1.00 | 19.57 | C |
| ATOM | 1928 | CD | GLU A 306 | -14.569 | 67.063 | -13.465 | 1.00 | 20.20 | C |
| ATOM | 1929 | OE1 | GLU A 306 | -15.544 | 66.427 | -13.006 | 1.00 | 19.90 | O |
| ATOM | 1930 | OE2 | GLU A 306 | -14.393 | 68.291 | -13.223 | 1.00 | 21.29 | O |
| ATOM | 1931 | C | GLU A 306 | -11.412 | 63.930 | -12.331 | 1.00 | 17.70 | C |
| ATOM | 1932 | O | GLU A 306 | 10.318 | 64.442 | 12.107 | 1.00 | 18.73 | O |
| ATOM | 1933 | N | HIS A 307 | -11.592 | 62.616 | -12.449 | 1.00 | 17.67 | N |
| ATOM | 1934 | CA | HIS A 307 | -10.524 | 61.628 | -12.298 | 1.00 | 17.44 | C |
| ATOM | 1935 | CB | HIS A 307 | -9.331 | 61.945 | -13.189 | 1.00 | 18.06 | C |
| ATOM | 1936 | CG | HIS A 307 | -9.702 | 62.044 | -14.642 | 1.00 | 19.48 | C |
| ATOM | 1937 | ND1 | HIS A 307 | -10.059 | 60.961 | -15.376 | 1.00 | 20.40 | N |
| ATOM | 1938 | CE1 | HIS A 307 | -10.379 | 61.355 | -16.624 | 1.00 | 20.40 | C |
| ATOM | 1939 | NE2 | HIS A 307 | -10.243 | 62.694 | -16.690 | 1.00 | 20.10 | N |
| ATOM | 1940 | CD2 | HIS A 307 | -9.827 | 63.150 | -15.485 | 1.00 | 19.72 | C |
| ATOM | 1941 | C | HIS A 307 | -10.153 | 61.453 | -10.863 | 1.00 | 17.21 | C |
| ATOM | 1942 | O | HIS A 307 | -10.401 | 60.398 | -10.293 | 1.00 | 17.22 | O |
| ATOM | 1943 | N | VAL A 308 | -9.593 | 62.491 | -10.252 | 1.00 | 16.89 | N |
| ATOM | 1944 | CA | VAL A 308 | -9.219 | 62.484 | -8.828 | 1.00 | 16.96 | C |
| ATOM | 1945 | CB | VAL A 308 | -10.453 | 62.568 | -7.871 | 1.00 | 16.62 | C |
| ATOM | 1946 | CG1 | VAL A 308 | -10.139 | 63.453 | -6.678 | 1.00 | 16.53 | C |
| ATOM | 1947 | CG2 | VAL A 308 | -11.686 | 63.116 | -8.574 | 1.00 | 16.20 | C |
| ATOM | 1948 | C | VAL A 308 | -9.365 | 61.261 | -8.474 | 1.00 | 16.89 | C |
| ATOM | 1949 | O | VAL A 308 | -9.467 | 60.736 | -7.390 | 1.00 | 16.79 | O |
| ATOM | 1950 | N | SER A 309 | -7.500 | 60.850 | -9.395 | 1.00 | 17.56 | N |
| ATOM | 1951 | CA | SER A 309 | -6.837 | 59.537 | -9.352 | 1.00 | 18.18 | C |
| ATOM | 1952 | CB | SER A 309 | -5.988 | 59.320 | -10.602 | 1.00 | 18.15 | C |
| ATOM | 1953 | OG | SER A 309 | -6.749 | 59.639 | -11.770 | 1.00 | 19.32 | O |
| ATOM | 1954 | C | SER A 309 | 6.007 | 59.229 | 8.129 | 1.00 | 19.51 | C |
| ATOM | 1955 | O | SER A 309 | -5.843 | 58.064 | -7.773 | 1.00 | 19.60 | O |
| ATOM | 1956 | N | TYR A 310 | -5.470 | 60.251 | -7.482 | 1.00 | 18.93 | N |
| ATOM | 1957 | CA | TYR A 310 | -4.670 | 60.007 | -6.300 | 1.00 | 19.23 | C |
| ATOM | 1958 | CB | TYR A 310 | 3.251 | 60.607 | 6.447 | 1.00 | 19.62 | C |
| ATOM | 1959 | CG | TYR A 310 | -2.360 | 59.614 | -7.396 | 1.00 | 19.33 | C |
| ATOM | 1960 | CD1 | TYR A 310 | -1.458 | 58.841 | -6.921 | 1.00 | 19.78 | C |
| ATOM | 1961 | CE1 | TYR A 310 | -0.662 | 58.102 | -7.800 | 1.00 | 19.52 | C |
| ATOM | 1962 | CZ | TYR A 310 | -0.774 | 58.344 | -9.173 | 1.00 | 20.07 | C |
| ATOM | 1963 | OH | TYR A 310 | -0.015 | 57.673 | -10.107 | 1.00 | 20.56 | O |
| ATOM | 1964 | CE2 | TYR A 310 | -1.656 | 59.298 | -9.644 | 1.00 | 19.46 | C |
| ATOM | 1965 | CD2 | TYR A 310 | -2.435 | 60.022 | -8.764 | 1.00 | 18.98 | C |
| ATOM | 1966 | C | TYR A 310 | -5.386 | 60.436 | -5.023 | 1.00 | 19.66 | C |
| ATOM | 1967 | O | TYR A 310 | -4.746 | 60.705 | -4.005 | 1.00 | 20.92 | O |
| ATOM | 1968 | N | ALA A 311 | -6.714 | 60.474 | -5.068 | 1.00 | 19.39 | N |
| ATOM | 1969 | CA | ALA A 311 | -7.504 | 60.830 | -3.891 | 1.00 | 20.32 | C |
| ATOM | 1970 | CB | ALA A 311 | -8.974 | 60.930 | -4.243 | 1.00 | 19.15 | C |
| ATOM | 1971 | C | ALA A 311 | -7.302 | 59.817 | -2.777 | 1.00 | 21.15 | C |
| ATOM | 1972 | O | ALA A 311 | -7.405 | 58.622 | -3.006 | 1.00 | 22.08 | O |
| ATOM | 1973 | N | ASP A 312 | -7.016 | 60.301 | -1.574 | 1.00 | 22.98 | N |
| ATOM | 1974 | CA | ASP A 312 | -6.864 | 59.439 | -0.404 | 1.00 | 23.63 | C |
| ATOM | 1975 | CB | ASP A 312 | -5.407 | 59.436 | 0.051 | 1.00 | 25.67 | C |
| ATOM | 1976 | CG | ASP A 312 | -4.981 | 60.771 | 0.657 | 1.00 | 28.17 | C |
| ATOM | 1977 | OD1 | ASP A 312 | -5.499 | 61.809 | 0.210 | 1.00 | 29.59 | O |
| ATOM | 1978 | OD2 | ASP A 312 | -4.147 | 60.785 | 1.612 | 1.00 | 28.67 | O |
| ATOM | 1979 | C | ASP A 312 | -7.772 | 59.933 | 0.717 | 1.00 | 23.61 | C |
| ATOM | 1980 | O | ASP A 312 | 8.606 | 60.815 | 0.492 | 1.00 | 23.24 | O |
| ATOM | 1981 | N | GLU A 313 | -7.592 | 59.371 | 1.916 | 1.00 | 24.81 | N |
| ATOM | 1982 | CA | GLU A 313 | -8.357 | 59.721 | 3.125 | 1.00 | 25.02 | C |
| ATOM | 1983 | CB | GLU A 313 | -7.665 | 59.126 | 4.353 | 1.00 | 27.46 | C |
| ATOM | 1984 | CG | GLU A 313 | -8.597 | 58.402 | 5.337 | 1.00 | 31.57 | C |
| ATOM | 1985 | CD | GLU A 313 | -8.777 | 59.144 | 6.658 | 1.00 | 33.11 | C |
| ATOM | 1986 | OE1 | GLU A 313 | -7.901 | 58.995 | 7.531 | 1.00 | 34.19 | O |
| ATOM | 1987 | OE2 | GLU A 313 | -9.789 | 59.868 | 6.831 | 1.00 | 33.23 | O |
| ATOM | 1988 | C | GLU A 313 | -8.508 | 61.240 | 3.261 | 1.00 | 24.19 | C |
| ATOM | 1989 | O | GLU A 313 | -9.616 | 61.777 | 3.408 | 1.00 | 23.17 | O |
| ATOM | 1990 | N | GLU A 314 | -7.377 | 61.924 | 3.158 | 1.00 | 23.53 | N |
| ATOM | 1991 | CA | GLU A 314 | -7.314 | 63.368 | 3.280 | 1.00 | 22.77 | C |
| ATOM | 1992 | CB | GLU A 314 | -5.865 | 63.792 | 3.105 | 1.00 | 22.94 | C |
| ATOM | 1993 | CG | GLU A 314 | 5.624 | 65.283 | 3.186 | 1.00 | 24.48 | C |
| ATOM | 1994 | CD | GLU A 314 | -4.209 | 65.634 | 3.623 | 1.00 | 25.21 | C |
| ATOM | 1995 | OE1 | GLU A 314 | -4.032 | 65.826 | 3.972 | 1.00 | 25.97 | O |
| ATOM | 1996 | OE2 | GLU A 314 | -3.304 | 64.740 | 3.647 | 1.00 | 24.40 | O |

FIG. 22Z

```
ATOM   1997  C    GLU A 314      -6.250  64.072   2.289  1.00 21.64           C
ATOM   1998  O    GLU A 314      -9.051  64.914   2.674  1.00 21.37           O
ATOM   1999  N    THR A 315      -9.155  63.691   1.011  1.00 21.19           N
ATOM   2000  CA   THR A 315      -9.029  64.199   0.350  1.00 20.79           C
ATOM   2001  CB   THR A 315      -8.607  63.675  -1.444  1.00 21.49           C
ATOM   2002  OG1  THR A 315      -7.284  64.151  -1.751  1.00 23.47           O
ATOM   2003  CG2  THR A 315      -9.556  64.157  -2.510  1.00 20.30           C
ATOM   2004  C    THR A 315     -10.511  63.894   0.169  1.00 19.54           C
ATOM   2005  O    THR A 315     -11.336  64.776  -0.012  1.00 18.91           O
ATOM   2006  N    TRP A 316     -10.855  62.663   0.547  1.00 19.26           N
ATOM   2007  CA   TRP A 316     -12.264  62.335   0.737  1.00 17.89           C
ATOM   2008  CB   TRP A 316     -12.486  60.866   1.096  1.00 16.65           C
ATOM   2009  CG   TRP A 316      11.760  59.920   0.196  1.00 15.72           C
ATOM   2010  CD1  TRP A 316     -11.550  60.047  -1.171  1.00 15.42           C
ATOM   2011  NE1  TRP A 316     -10.834  58.984  -1.655  1.00 15.39           N
ATOM   2012  CE2  TRP A 316     -10.542  58.107  -0.667  1.00 15.37           C
ATOM   2013  CD2  TRP A 316     -11.127  58.645   0.567  1.00 15.64           C
ATOM   2014  CE3  TRP A 316     -10.966  57.930   1.764  1.00 15.54           C
ATOM   2015  CZ3  TRP A 316     -10.256  56.723   1.728  1.00 15.05           C
ATOM   2016  CH2  TRP A 316      -9.704  56.225   0.535  1.00 15.00           C
ATOM   2017  CZ2  TRP A 316      -9.830  56.906  -0.684  1.00 15.23           C
ATOM   2018  C    TRP A 316     -12.891  63.229   1.764  1.00 19.61           C
ATOM   2019  O    TRP A 316     -13.925  63.838   1.498  1.00 18.40           O
ATOM   2020  N    GLU A 317     -12.258  63.339   2.934  1.00 19.82           N
ATOM   2021  CA   GLU A 317     -12.812  64.131   4.022  1.00 20.98           C
ATOM   2022  CB   GLU A 317     -12.029  63.941   5.328  1.00 22.62           C
ATOM   2023  CG   GLU A 317     -11.914  62.498   5.789  1.00 25.61           C
ATOM   2024  CD   GLU A 317     -13.255  61.824   6.138  1.00 28.76           C
ATOM   2025  OE1  GLU A 317     -14.249  62.546   6.386  1.00 31.19           O
ATOM   2026  OE2  GLU A 317     -13.324  60.568   6.189  1.00 29.25           O
ATOM   2027  C    GLU A 317     -12.933  65.609   3.645  1.00 20.66           C
ATOM   2028  O    GLU A 317     -13.892  66.276   4.056  1.00 20.70           O
ATOM   2029  N    LEU A 318     -11.992  66.124   2.850  1.00 19.86           N
ATOM   2030  CA   LEU A 318     -12.054  67.550   2.473  1.00 18.81           C
ATOM   2031  CB   LEU A 318      10.726  68.079   1.901  1.00 18.15           C
ATOM   2032  CG   LEU A 318      -9.752  68.856   2.818  1.00 18.27           C
ATOM   2033  CD1  LEU A 318      -8.373  68.930   2.179  1.00 17.86           C
ATOM   2034  CD2  LEU A 318     -10.235  70.255   3.192  1.00 17.06           C
ATOM   2035  C    LEU A 318      13.211  67.792   1.511  1.00 18.53           C
ATOM   2036  O    LEU A 318     -13.891  68.833   1.582  1.00 18.44           O
ATOM   2037  N    MET A 319     -13.428  66.820   0.627  1.00 17.96           N
ATOM   2038  CA   MET A 319     -14.415  66.923  -0.433  1.00 17.44           C
ATOM   2039  CB   MET A 319     -14.209  65.807  -1.464  1.00 16.73           C
ATOM   2040  CG   MET A 319     -12.996  65.990  -2.374  1.00 16.65           C
ATOM   2041  SD   MET A 319     -12.828  64.765  -3.713  1.00 17.18           S
ATOM   2042  CE   MET A 319     -14.131  65.275  -4.839  1.00 15.56           C
ATOM   2043  C    MET A 319     -15.800  66.855   0.222  1.00 16.80           C
ATOM   2044  O    MET A 319     -16.717  67.592  -0.155  1.00 17.59           O
ATOM   2045  N    LYS A 320     -15.931  65.995   1.233  1.00 19.40           N
ATOM   2046  CA   LYS A 320     -17.174  65.906   1.995  1.00 18.98           C
ATOM   2047  CB   LYS A 320     -17.161  64.732   2.970  1.00 18.78           C
ATOM   2048  CG   LYS A 320     -17.175  63.375   2.291  1.00 19.48           C
ATOM   2049  CD   LYS A 320     -17.775  62.267   3.158  1.00 20.97           C
ATOM   2050  CE   LYS A 320     -16.843  61.876   4.296  1.00 21.64           C
ATOM   2051  NZ   LYS A 320     -17.649  61.646   5.526  1.00 21.75           N
ATOM   2052  C    LYS A 320     -17.391  67.207   2.731  1.00 19.63           C
ATOM   2053  O    LYS A 320     -18.435  67.814   2.602  1.00 19.97           O
ATOM   2054  N    GLU A 321     -16.377  67.647   3.469  1.00 21.22           N
ATOM   2055  CA   GLU A 321     -16.444  68.872   4.239  1.00 22.07           C
ATOM   2056  CB   GLU A 321     -15.130  69.121   4.972  1.00 24.65           C
ATOM   2057  CG   GLU A 321      15.187  70.261   5.979  1.00 28.06           C
ATOM   2058  CD   GLU A 321     -13.612  70.830   6.295  1.00 32.19           C
ATOM   2059  OE1  GLU A 321     -12.896  70.650   6.651  1.00 35.59           O
ATOM   2060  OE2  GLU A 321     -13.647  72.065   6.188  1.00 33.17           O
ATOM   2061  C    GLU A 321     -16.806  70.076   3.379  1.00 21.41           C
ATOM   2062  O    GLU A 321     -17.621  70.887   3.786  1.00 21.72           O
ATOM   2063  N    LYS A 322     -16.220  70.197   2.192  1.00 20.74           N
ATOM   2064  CA   LYS A 322     -16.459  71.368   1.376  1.00 19.04           C
ATOM   2065  CB   LYS A 322     -15.165  71.897   0.727  1.00 19.04           C
ATOM   2066  CG   LYS A 322     -14.102  72.263   1.746  1.00 18.42           C
ATOM   2067  CD   LYS A 322     -12.956  73.092   1.187  1.00 18.20           C
ATOM   2068  CE   LYS A 322     -12.173  73.727   2.328  1.00 17.56           C
ATOM   2069  NZ   LYS A 322     -12.170  75.208   2.192  1.00 17.15           N
ATOM   2070  C    LYS A 322      17.546  71.179   0.346  1.00 18.66           C
ATOM   2071  O    LYS A 322     -17.803  72.070  -0.456  1.00 20.16           O
ATOM   2072  N    GLY A 323     -16.183  70.013   0.366  1.00 17.24           N
ATOM   2073  CA   GLY A 323     -19.213  69.703  -0.619  1.00 16.43           C
```

FIG. 22AA

| | | | | | | | | | |
|---|---|---|---|---|---|---|---|---|---|
| ATOM | 2074 | C | GLY | A | 323 | -18.710 | 69.787 | -2.053 | 1.00 16.16 | C |
| ATOM | 2075 | O | GLY | A | 323 | -19.246 | 70.546 | -2.873 | 1.00 15.79 | O |
| ATOM | 2076 | N | ILE | A | 324 | -17.667 | 69.087 | -2.345 | 1.00 16.07 | N |
| ATOM | 2077 | CA | ILE | A | 324 | 17.818 | 69.002 | 3.662 | 1.00 16.27 | C |
| ATOM | 2078 | CB | ILE | A | 324 | -15.481 | 69.115 | -3.532 | 1.00 15.91 | C |
| ATOM | 2079 | CG1 | ILE | A | 324 | -15.102 | 70.355 | -2.708 | 1.00 15.75 | C |
| ATOM | 2080 | CD1 | ILE | A | 324 | -13.661 | 70.395 | -2.251 | 1.00 15.52 | C |
| ATOM | 2081 | CG2 | ILE | A | 324 | -14.817 | 69.136 | -4.895 | 1.00 15.55 | C |
| ATOM | 2082 | C | ILE | A | 324 | -17.395 | 67.718 | -4.603 | 1.00 16.57 | C |
| ATOM | 2083 | O | ILE | A | 324 | -17.223 | 66.601 | -3.897 | 1.00 17.50 | O |
| ATOM | 2084 | N | LEU | A | 325 | -17.918 | 67.862 | -5.606 | 1.00 15.97 | N |
| ATOM | 2085 | CA | LEU | A | 325 | -18.351 | 66.752 | -6.418 | 1.00 16.11 | C |
| ATOM | 2086 | CB | LEU | A | 325 | 19.193 | 67.234 | 7.605 | 1.00 15.31 | C |
| ATOM | 2087 | CG | LEU | A | 325 | -20.060 | 66.132 | -8.210 | 1.00 15.99 | C |
| ATOM | 2088 | CD1 | LEU | A | 325 | -21.109 | 65.622 | -7.212 | 1.00 16.21 | C |
| ATOM | 2089 | CD2 | LEU | A | 325 | -20.695 | 66.565 | -9.533 | 1.00 15.41 | C |
| ATOM | 2090 | C | LEU | A | 325 | -17.155 | 65.912 | -6.889 | 1.00 15.12 | C |
| ATOM | 2091 | O | LEU | A | 325 | -16.116 | 66.474 | -7.257 | 1.00 16.51 | O |
| ATOM | 2092 | N | TYR | A | 326 | -17.305 | 64.580 | -6.829 | 1.00 15.67 | N |
| ATOM | 2093 | CA | TYR | A | 326 | -16.304 | 63.616 | -7.319 | 1.00 15.44 | C |
| ATOM | 2094 | CB | TYR | A | 326 | -16.097 | 62.544 | -6.245 | 1.00 14.69 | C |
| ATOM | 2095 | CG | TYR | A | 326 | -14.068 | 61.656 | -6.379 | 1.00 14.08 | C |
| ATOM | 2096 | CD1 | TYR | A | 326 | -14.809 | 60.631 | -7.332 | 1.00 14.05 | C |
| ATOM | 2097 | CE1 | TYR | A | 326 | -13.702 | 59.802 | -7.423 | 1.00 14.22 | C |
| ATOM | 2098 | CZ | TYR | A | 326 | -12.621 | 59.991 | -6.548 | 1.00 14.34 | C |
| ATOM | 2099 | OH | TYR | A | 326 | -11.487 | 59.185 | -6.632 | 1.00 14.39 | O |
| ATOM | 2100 | CE2 | TYR | A | 326 | -12.670 | 60.997 | -5.600 | 1.00 13.86 | C |
| ATOM | 2101 | CD2 | TYR | A | 326 | -13.785 | 61.813 | -5.517 | 1.00 13.69 | C |
| ATOM | 2102 | C | TYR | A | 326 | -16.604 | 62.965 | -8.617 | 1.00 15.49 | C |
| ATOM | 2103 | O | TYR | A | 326 | -17.798 | 62.208 | -8.573 | 1.00 16.66 | O |
| ATOM | 2104 | N | VAL | A | 327 | -15.138 | 63.196 | -9.746 | 1.00 14.94 | N |
| ATOM | 2105 | CA | VAL | A | 327 | -16.483 | 62.570 | -11.051 | 1.00 14.97 | C |
| ATOM | 2106 | CB | VAL | A | 327 | -16.813 | 63.598 | -12.190 | 1.00 14.29 | C |
| ATOM | 2107 | CG1 | VAL | A | 327 | -17.119 | 62.880 | -13.500 | 1.00 14.38 | C |
| ATOM | 2108 | CG2 | VAL | A | 327 | 19.005 | 64.461 | 11.836 | 1.00 13.83 | C |
| ATOM | 2109 | C | VAL | A | 327 | -15.315 | 61.711 | -11.502 | 1.00 15.31 | C |
| ATOM | 2110 | O | VAL | A | 327 | -14.378 | 62.198 | -12.125 | 1.00 14.97 | O |
| ATOM | 2111 | N | ALA | A | 328 | -15.372 | 60.431 | -11.177 | 1.00 16.15 | N |
| ATOM | 2112 | CA | ALA | A | 328 | 14.247 | 59.824 | 11.419 | 1.00 16.74 | C |
| ATOM | 2113 | CB | ALA | A | 328 | -14.538 | 58.148 | -10.841 | 1.00 16.25 | C |
| ATOM | 2114 | C | ALA | A | 328 | -13.839 | 59.418 | -12.886 | 1.00 17.20 | C |
| ATOM | 2115 | O | ALA | A | 328 | -12.654 | 59.413 | -13.179 | 1.00 17.05 | O |
| ATOM | 2116 | N | THR | A | 329 | -14.910 | 59.343 | -13.798 | 1.00 19.59 | N |
| ATOM | 2117 | CA | THR | A | 329 | -14.526 | 59.172 | -15.240 | 1.00 20.40 | C |
| ATOM | 2118 | CB | THR | A | 329 | -13.835 | 60.432 | -15.819 | 1.00 21.09 | C |
| ATOM | 2119 | OG1 | THR | A | 329 | -14.493 | 61.597 | -15.294 | 1.00 22.16 | O |
| ATOM | 2120 | CG2 | THR | A | 329 | -13.910 | 60.465 | -17.351 | 1.00 20.71 | C |
| ATOM | 2121 | C | THR | A | 329 | -13.737 | 57.956 | -15.510 | 1.00 20.92 | C |
| ATOM | 2122 | O | THR | A | 329 | -12.746 | 57.801 | -16.279 | 1.00 21.42 | O |
| ATOM | 2123 | N | ARG | A | 330 | -14.218 | 56.792 | -14.884 | 1.00 21.12 | N |
| ATOM | 2124 | CA | ARG | A | 330 | -13.557 | 55.502 | -14.893 | 1.00 20.89 | C |
| ATOM | 2125 | CB | ARG | A | 330 | -14.261 | 54.543 | -13.929 | 1.00 20.57 | C |
| ATOM | 2126 | CG | ARG | A | 330 | -13.579 | 53.198 | -13.779 | 1.00 20.51 | C |
| ATOM | 2127 | CD | ARG | A | 330 | -12.207 | 53.311 | -13.126 | 1.00 20.33 | C |
| ATOM | 2128 | NE | ARG | A | 330 | -11.465 | 52.065 | -13.285 | 1.00 19.98 | N |
| ATOM | 2129 | CZ | ARG | A | 330 | -10.255 | 51.826 | -12.789 | 1.00 19.96 | C |
| ATOM | 2130 | NH1 | ARG | A | 330 | -9.616 | 52.754 | -12.073 | 1.00 19.13 | N |
| ATOM | 2131 | NH2 | ARG | A | 330 | -9.684 | 50.647 | -13.019 | 1.00 19.52 | N |
| ATOM | 2132 | C | ARG | A | 330 | -13.454 | 54.917 | -16.298 | 1.00 20.98 | C |
| ATOM | 2133 | O | ARG | A | 330 | -12.539 | 54.144 | -16.585 | 1.00 20.65 | O |
| ATOM | 2134 | N | SER | A | 331 | 14.365 | 55.309 | 17.180 | 1.00 21.29 | N |
| ATOM | 2135 | CA | SER | A | 331 | -14.364 | 54.772 | -16.540 | 1.00 21.71 | C |
| ATOM | 2136 | CB | SER | A | 331 | -15.575 | 55.271 | -19.323 | 1.00 20.99 | C |
| ATOM | 2137 | OG | SER | A | 331 | -16.785 | 54.736 | -18.811 | 1.00 19.62 | O |
| ATOM | 2138 | C | SER | A | 331 | -13.042 | 55.061 | -19.273 | 1.00 23.24 | C |
| ATOM | 2139 | O | SER | A | 331 | -12.527 | 54.296 | -19.992 | 1.00 22.16 | O |
| ATOM | 2140 | N | VAL | A | 332 | -12.488 | 56.257 | -19.060 | 1.00 25.31 | N |
| ATOM | 2141 | CA | VAL | A | 332 | -11.212 | 56.635 | -19.674 | 1.00 26.35 | C |
| ATOM | 2142 | CB | VAL | A | 332 | -10.760 | 58.076 | -19.319 | 1.00 26.84 | C |
| ATOM | 2143 | CG1 | VAL | A | 332 | -9.363 | 58.350 | -19.064 | 1.00 26.93 | C |
| ATOM | 2144 | CG2 | VAL | A | 332 | -11.721 | 59.103 | -19.879 | 1.00 26.24 | C |
| ATOM | 2145 | C | VAL | A | 332 | -10.124 | 55.651 | -19.262 | 1.00 26.90 | C |
| ATOM | 2146 | O | VAL | A | 332 | -9.413 | 55.123 | -20.114 | 1.00 27.57 | O |
| ATOM | 2147 | N | ILE | A | 333 | 9.999 | 55.397 | 17.965 | 1.00 26.70 | N |
| ATOM | 2148 | CA | ILE | A | 333 | -8.979 | 54.462 | -17.500 | 1.00 27.09 | C |
| ATOM | 2149 | CB | ILE | A | 333 | -8.908 | 54.370 | -15.955 | 1.00 28.23 | C |
| ATOM | 2150 | CG1 | ILE | A | 333 | -8.208 | 55.597 | -15.349 | 1.00 29.24 | C |

FIG. 22BB

```
ATOM   2151  CD1 ILE A 333      -8.975  56.988 -15.444  1.00 31.38           C
ATOM   2152  CG2 ILE A 333      -9.110  53.157 -15.536  1.00 27.20           C
ATOM   2153  C   ILE A 333      -9.239  53.097 -18.134  1.00 26.53           C
ATOM   2154  O   ILE A 333      -9.306  52.481  18.681  1.00 27.02           O
ATOM   2155  N   GLU A 334     -10.486  52.656 -18.114  1.00 25.34           N
ATOM   2156  CA  GLU A 334     -10.829  51.330 -18.624  1.00 25.44           C
ATOM   2157  CB  GLU A 334     -12.300  50.962 -18.380  1.00 24.21           C
ATOM   2158  CG  GLU A 334     -12.705  50.872 -16.907  1.00 23.69           C
ATOM   2159  CD  GLU A 334     -12.091  49.689 -16.175  1.00 23.36           C
ATOM   2160  OE1 GLU A 334     -11.866  48.640 -16.796  1.00 23.76           O
ATOM   2161  OE2 GLU A 334     -11.823  49.801 -14.970  1.00 23.81           O
ATOM   2162  C   GLU A 334     -10.457  51.133 -20.086  1.00 26.55           C
ATOM   2163  O   GLU A 334      10.139  50.007  20.479  1.00 25.89           O
ATOM   2164  N   ILE A 335     -10.471  52.214 -20.877  1.00 25.69           N
ATOM   2165  CA  ILE A 335     -10.106  52.126 -22.307  1.00 33.65           C
ATOM   2166  CB  ILE A 335     -10.283  53.446 -23.092  1.00 29.77           C
ATOM   2167  CC1 ILE A 335     -11.769  53.746 -23.304  1.00 28.93           C
ATOM   2168  CD1 ILE A 335     -12.019  55.158 -23.784  1.00 28.26           C
ATOM   2169  CG2 ILE A 335      -9.569  53.368 -24.444  1.00 28.39           C
ATOM   2170  C   ILE A 335      -8.677  51.635 -22.465  1.00 33.59           C
ATOM   2171  O   ILE A 335      -8.437  50.609 -23.109  1.00 34.33           O
ATOM   2172  N   PHE A 336      -7.731  52.346 -21.862  1.00 36.84           N
ATOM   2173  CA  PHE A 336      -6.351  51.938 -22.017  1.00 40.15           C
ATOM   2174  CB  PHE A 336      -5.359  53.115 -21.922  1.00 46.59           C
ATOM   2175  CG  PHE A 336      -5.410  53.894 -20.630  1.00 50.23           C
ATOM   2176  CD1 PHE A 336      -5.684  53.289 -19.402  1.00 51.20           C
ATOM   2177  CE1 PHE A 336      -5.102  54.021 -18.216  1.00 52.56           C
ATOM   2178  CZ  PHE A 336      -5.425  55.375 -18.251  1.00 54.12           C
ATOM   2179  CE2 PHE A 336      -5.728  56.000 -19.470  1.00 53.73           C
ATOM   2180  CD2 PHE A 336      -5.710  55.264 -20.651  1.00 51.50           C
ATOM   2181  C   PHE A 336      -5.943  50.711 -21.195  1.00 39.99           C
ATOM   2182  O   PHE A 336      -4.928  50.089 -21.504  1.00 40.91           O
ATOM   2183  N   LEU A 337      -6.732  50.348 -20.178  1.00 39.92           N
ATOM   2184  CA  LEU A 337      -6.550  49.047 -19.519  1.00 38.46           C
ATOM   2185  CB  LEU A 337       7.386  48.902  18.244  1.00 34.74           C
ATOM   2186  CG  LEU A 337      -6.880  49.439 -16.926  1.00 33.08           C
ATOM   2187  CD1 LEU A 337      -7.874  49.238 -15.811  1.00 32.87           C
ATOM   2188  CD2 LEU A 337      -5.525  48.960 -16.520  1.00 31.85           C
ATOM   2189  C   LEU A 337       6.878  47.922  20.493  1.00 41.71           C
ATOM   2190  O   LEU A 337      -6.298  46.839 -20.408  1.00 46.04           O
ATOM   2191  N   ALA A 338      -7.784  48.188 -21.434  1.00 43.73           N
ATOM   2192  CA  ALA A 338      -8.167  47.198 -22.452  1.00 44.87           C
ATOM   2193  CB  ALA A 338      -9.596  47.446 -22.919  1.00 41.97           C
ATOM   2194  C   ALA A 338      -7.196  47.071 -23.659  1.00 46.14           C
ATOM   2195  O   ALA A 338      -7.458  46.312 -24.588  1.00 45.15           O
ATOM   2196  N   SER A 339      -6.083  47.805 -23.633  1.00 49.37           N
ATOM   2197  CA  SER A 339      -5.045  47.724 -24.674  1.00 51.70           C
ATOM   2198  CB  SER A 339      -4.337  49.069 -24.836  1.00 52.07           C
ATOM   2199  OG  SER A 339      -5.208  50.033 -25.399  1.00 52.82           O
ATOM   2200  C   SER A 339      -3.992  46.653 -24.396  1.00 54.71           C
ATOM   2201  O   SER A 339      -3.559  45.966 -25.323  1.00 54.83           O
ATOM   2202  N   ASN A 340      -3.584  46.541 -23.125  1.00 57.50           N
ATOM   2203  CA  ASN A 340      -2.544  45.600 -22.649  1.00 59.04           C
ATOM   2204  CB  ASN A 340      -2.854  44.157 -23.058  1.00 57.59           C
ATOM   2205  CG  ASN A 340      -3.723  43.450 -22.055  1.00 56.37           C
ATOM   2206  OD1 ASN A 340      -4.892  43.181 -22.320  1.00 56.77           O
ATOM   2207  ND2 ASN A 340      -3.163  43.154 -20.888  1.00 54.52           N
ATOM   2208  C   ASN A 340      -1.895  45.934 -23.012  1.00 62.30           C
ATOM   2209  O   ASN A 340      -0.229  45.052 -22.996  1.00 63.16           O
ATOM   2210  N   GLY A 341      -0.832  47.202 -23.322  1.00 65.26           N
ATOM   2211  CA  GLY A 341       0.507  47.634  23.725  1.00 67.39           C
ATOM   2212  C   GLY A 341       0.836  47.219 -25.146  1.00 68.36           C
ATOM   2213  O   GLY A 341       1.896  46.640 -25.414  1.00 66.98           O
ATOM   2214  N   GLU A 342      -0.094  47.506 -26.052  1.00 71.37           N
ATOM   2215  CA  GLU A 342       0.094  47.261 -27.475  1.00 75.95           C
ATOM   2216  CB  GLU A 342      -1.236  46.877 -28.122  1.00 76.70           C
ATOM   2217  CG  GLU A 342      -1.098  45.996 -29.354  1.00 75.98           C
ATOM   2218  CD  GLU A 342      -2.412  45.808 -30.092  1.00 75.76           C
ATOM   2219  OE1 GLU A 342      -3.337  46.637 -29.918  1.00 71.09           O
ATOM   2220  OE2 GLU A 342      -2.513  44.027 -30.059  1.00 75.59           O
ATOM   2221  C   GLU A 342       0.672  48.532 -28.097  1.00 79.05           C
ATOM   2222  O   GLU A 342      -0.025  49.551 -28.227  1.00 74.79           O
ATOM   2223  N   GLY A 343       1.954  48.457 -28.469  1.00 80.61           N
ATOM   2224  CA  GLY A 343       2.713  49.616  28.948  1.00 76.37           C
ATOM   2225  C   GLY A 343       3.056  50.544 -27.797  1.00 73.59           C
ATOM   2226  O   GLY A 343       2.724  51.733 -27.019  1.00 73.09           O
ATOM   2227  N   LEU A 344       3.714  49.983 -26.782  1.00 69.40           N
```

FIG. 22CC

| ATOM | 2228 | CA | LEU A 344 | 4.101 | 50.708 | -25.573 | 1.00 | 61.34 | C |
|---|---|---|---|---|---|---|---|---|---|
| ATOM | 2229 | CB | LEU A 344 | 2.964 | 50.699 | -24.542 | 1.00 | 61.13 | C |
| ATOM | 2230 | CG | LEU A 344 | 1.778 | 51.654 | -24.705 | 1.00 | 60.98 | C |
| ATOM | 2231 | CD1 | LEU A 344 | 0.722 | 51.388 | 23.851 | 1.00 | 58.85 | C |
| ATOM | 2232 | CD2 | LEU A 344 | 2.242 | 53.104 | -24.666 | 1.00 | 59.42 | C |
| ATOM | 2233 | C | LEU A 344 | 5.323 | 50.056 | -24.962 | 1.00 | 56.50 | C |
| ATOM | 2234 | O | LEU A 344 | 5.434 | 48.833 | -24.942 | 1.00 | 53.70 | O |
| ATOM | 2235 | N | VAL A 345 | 6.237 | 50.873 | -24.455 | 1.00 | 54.97 | N |
| ATOM | 2236 | CA | VAL A 345 | 7.385 | 50.346 | -23.729 | 1.00 | 54.01 | C |
| ATOM | 2237 | CB | VAL A 345 | 8.484 | 51.414 | -23.502 | 1.00 | 55.19 | C |
| ATOM | 2238 | CG1 | VAL A 345 | 9.869 | 50.765 | -23.499 | 1.00 | 53.93 | C |
| ATOM | 2239 | CG2 | VAL A 345 | 8.410 | 52.503 | -24.564 | 1.00 | 54.52 | C |
| ATOM | 2240 | C | VAL A 345 | 6.893 | 49.771 | 22.393 | 1.00 | 54.46 | C |
| ATOM | 2241 | O | VAL A 345 | 5.849 | 50.186 | -21.980 | 1.00 | 52.46 | O |
| ATOM | 2242 | N | LYS A 346 | 7.637 | 48.805 | -21.851 | 1.00 | 54.12 | N |
| ATOM | 2243 | CA | LYS A 346 | 7.280 | 48.133 | -20.599 | 1.00 | 52.07 | C |
| ATOM | 2244 | CB | LYS A 346 | 8.331 | 47.092 | -20.229 | 1.00 | 51.11 | C |
| ATOM | 2245 | CG | LYS A 346 | 8.206 | 45.789 | -21.022 | 1.00 | 50.59 | C |
| ATOM | 2246 | CD | LYS A 346 | 9.565 | 45.165 | -21.304 | 1.00 | 49.89 | C |
| ATOM | 2247 | CE | LYS A 346 | 10.289 | 45.907 | -22.418 | 1.00 | 48.21 | C |
| ATOM | 2248 | NZ | LYS A 346 | 11.735 | 45.563 | -22.633 | 1.00 | 46.75 | N |
| ATOM | 2249 | C | LYS A 346 | 7.053 | 49.101 | -19.438 | 1.00 | 51.76 | C |
| ATOM | 2250 | O | LYS A 346 | 6.042 | 49.000 | -18.749 | 1.00 | 49.57 | O |
| ATOM | 2251 | N | GLU A 347 | 7.984 | 50.039 | -19.241 | 1.00 | 53.61 | N |
| ATOM | 2252 | CA | GLU A 347 | 7.880 | 51.049 | -18.170 | 1.00 | 54.62 | C |
| ATOM | 2253 | CB | GLU A 347 | 9.187 | 51.840 | -18.002 | 1.00 | 55.14 | C |
| ATOM | 2254 | CG | GLU A 347 | 10.349 | 51.051 | -17.408 | 1.00 | 57.29 | C |
| ATOM | 2255 | CD | GLU A 347 | 11.286 | 50.459 | -18.459 | 1.00 | 59.35 | C |
| ATOM | 2256 | OE1 | GLU A 347 | 10.983 | 50.548 | -19.677 | 1.00 | 60.60 | O |
| ATOM | 2257 | OE2 | GLU A 347 | 12.338 | 49.903 | -18.062 | 1.00 | 57.40 | O |
| ATOM | 2258 | C | GLU A 347 | 6.719 | 52.019 | -18.396 | 1.00 | 53.20 | C |
| ATOM | 2259 | O | GLU A 347 | 6.118 | 52.514 | -17.435 | 1.00 | 52.42 | O |
| ATOM | 2260 | N | SER A 348 | 6.422 | 52.283 | -19.669 | 1.00 | 51.29 | N |
| ATOM | 2261 | CA | SER A 348 | 5.301 | 53.134 | -20.069 | 1.00 | 50.38 | C |
| ATOM | 2262 | CB | SER A 348 | 5.395 | 53.451 | 21.570 | 1.00 | 53.00 | C |
| ATOM | 2263 | OG | SER A 348 | 4.378 | 54.342 | -21.995 | 1.00 | 55.08 | O |
| ATOM | 2264 | C | SER A 348 | 3.945 | 52.492 | -19.717 | 1.00 | 47.06 | C |
| ATOM | 2265 | O | SER A 348 | 3.027 | 53.172 | -19.265 | 1.00 | 44.75 | O |
| ATOM | 2266 | N | TRP A 349 | 3.845 | 51.180 | 19.922 | 1.00 | 45.43 | N |
| ATOM | 2267 | CA | TRP A 349 | 2.660 | 50.395 | -19.554 | 1.00 | 43.90 | C |
| ATOM | 2268 | CB | TRP A 349 | 2.598 | 49.128 | -20.432 | 1.00 | 44.12 | C |
| ATOM | 2269 | CG | TRP A 349 | 1.536 | 48.125 | -20.034 | 1.00 | 44.33 | C |
| ATOM | 2270 | CD1 | TRP A 349 | 1.724 | 46.795 | -19.652 | 1.00 | 43.99 | C |
| ATOM | 2271 | NE1 | TRP A 349 | 0.523 | 46.196 | -19.354 | 1.00 | 44.09 | N |
| ATOM | 2272 | CE2 | TRP A 349 | -0.504 | 47.064 | -19.511 | 1.00 | 44.22 | C |
| ATOM | 2273 | CD2 | TRP A 349 | 0.076 | 48.343 | -19.950 | 1.00 | 43.57 | C |
| ATOM | 2274 | CE3 | TRP A 349 | -0.772 | 49.425 | -20.183 | 1.00 | 42.61 | C |
| ATOM | 2275 | CZ3 | TRP A 349 | -2.145 | 49.251 | -19.986 | 1.00 | 42.93 | C |
| ATOM | 2276 | CH2 | TRP A 349 | -2.682 | 48.019 | -19.567 | 1.00 | 43.49 | C |
| ATOM | 2277 | CZ2 | TRP A 349 | -1.874 | 46.983 | -19.322 | 1.00 | 44.42 | C |
| ATOM | 2278 | C | TRP A 349 | 2.588 | 50.092 | -18.072 | 1.00 | 42.07 | C |
| ATOM | 2279 | O | TRP A 349 | 1.504 | 49.874 | -17.515 | 1.00 | 39.66 | O |
| ATOM | 2280 | N | ALA A 350 | 3.743 | 50.100 | -17.412 | 1.00 | 41.93 | N |
| ATOM | 2281 | CA | ALA A 350 | 3.821 | 49.993 | -15.951 | 1.00 | 41.54 | C |
| ATOM | 2282 | CB | ALA A 350 | 5.268 | 49.796 | -15.499 | 1.00 | 40.15 | C |
| ATOM | 2283 | C | ALA A 350 | 3.193 | 51.209 | -15.253 | 1.00 | 40.17 | C |
| ATOM | 2284 | O | ALA A 350 | 2.462 | 51.051 | -14.270 | 1.00 | 40.17 | O |
| ATOM | 2285 | N | LYS A 351 | 3.475 | 52.411 | -15.767 | 1.00 | 41.71 | N |
| ATOM | 2286 | CA | LYS A 351 | 2.922 | 53.656 | -15.203 | 1.00 | 42.28 | C |
| ATOM | 2287 | CB | LYS A 351 | 3.675 | 54.896 | -15.717 | 1.00 | 45.21 | C |
| ATOM | 2288 | CG | LYS A 351 | 4.976 | 55.222 | 14.973 | 1.00 | 46.95 | C |
| ATOM | 2289 | CD | LYS A 351 | 5.618 | 56.510 | -15.490 | 1.00 | 49.95 | C |
| ATOM | 2290 | CE | LYS A 351 | 6.440 | 56.284 | -16.764 | 1.00 | 51.85 | C |
| ATOM | 2291 | NZ | LYS A 351 | 6.598 | 57.485 | -17.646 | 1.00 | 49.10 | N |
| ATOM | 2292 | C | LYS A 351 | 1.404 | 53.815 | -15.415 | 1.00 | 39.79 | C |
| ATOM | 2293 | O | LYS A 351 | 0.719 | 54.365 | -14.554 | 1.00 | 36.24 | O |
| ATOM | 2294 | N | LEU A 352 | 0.891 | 53.327 | -16.546 | 1.00 | 36.44 | N |
| ATOM | 2295 | CA | LEU A 352 | -0.556 | 53.331 | -16.797 | 1.00 | 35.50 | C |
| ATOM | 2296 | CB | LEU A 352 | -0.907 | 52.973 | -18.254 | 1.00 | 34.57 | C |
| ATOM | 2297 | CG | LEU A 352 | -0.594 | 54.036 | -19.327 | 1.00 | 35.34 | C |
| ATOM | 2298 | CD1 | LEU A 352 | -0.783 | 53.494 | -20.738 | 1.00 | 34.59 | C |
| ATOM | 2299 | CD2 | LEU A 352 | -1.389 | 55.328 | -19.144 | 1.00 | 34.85 | C |
| ATOM | 2300 | C | LEU A 352 | -1.318 | 52.442 | -15.821 | 1.00 | 34.94 | C |
| ATOM | 2301 | O | LEU A 352 | 2.383 | 52.843 | 15.342 | 1.00 | 36.01 | O |
| ATOM | 2302 | N | GLN A 353 | -0.776 | 51.258 | -15.524 | 1.00 | 33.36 | N |
| ATOM | 2303 | CA | GLN A 353 | -1.395 | 50.325 | -14.573 | 1.00 | 32.47 | C |
| ATOM | 2304 | CB | GLN A 353 | -0.727 | 48.942 | -14.622 | 1.00 | 32.94 | C |

FIG. 22DD

| | | | | | | | | | |
|---|---|---|---|---|---|---|---|---|---|
| ATOM | 2305 | CG | GLN | A | 353 | -1.271 | 48.061 | -15.695 | 1.00 34.43 | C |
| ATOM | 2306 | CD | GLN | A | 353 | -0.371 | 46.779 | -15.956 | 1.00 36.11 | C |
| ATOM | 2307 | OE1 | GLN | A | 353 | 0.772 | 46.993 | -16.418 | 1.00 35.44 | O |
| ATOM | 2308 | NE2 | GLN | A | 353 | 0.901 | 45.588 | 15.681 | 1.00 35.06 | N |
| ATOM | 2309 | C | GLN | A | 353 | -1.377 | 50.898 | -13.150 | 1.00 32.00 | C |
| ATOM | 2310 | O | GLN | A | 353 | -2.386 | 50.840 | -12.439 | 1.00 31.17 | O |
| ATOM | 2311 | N | ALA | A | 354 | -0.234 | 51.463 | -12.756 | 1.00 31.39 | N |
| ATOM | 2312 | CA | ALA | A | 354 | -0.078 | 52.141 | -11.461 | 1.00 30.65 | C |
| ATOM | 2313 | CB | ALA | A | 354 | 1.353 | 52.615 | -11.270 | 1.00 30.56 | C |
| ATOM | 2314 | C | ALA | A | 354 | -1.052 | 53.305 | -11.273 | 1.00 29.99 | C |
| ATOM | 2315 | O | ALA | A | 354 | -1.637 | 53.441 | -10.197 | 1.00 29.47 | O |
| ATOM | 2316 | N | LEU | A | 355 | -1.225 | 54.135 | -12.307 | 1.00 29.26 | N |
| ATOM | 2317 | CA | LEU | A | 355 | 2.244 | 55.195 | 12.265 | 1.00 28.35 | C |
| ATOM | 2318 | CB | LEU | A | 355 | -2.159 | 56.153 | -13.462 | 1.00 27.43 | C |
| ATOM | 2319 | CG | LEU | A | 355 | -3.348 | 57.140 | -13.555 | 1.00 27.51 | C |
| ATOM | 2320 | CD1 | LEU | A | 355 | -3.101 | 58.417 | -12.774 | 1.00 26.49 | C |
| ATOM | 2321 | CD2 | LEU | A | 355 | -3.697 | 57.477 | -14.996 | 1.00 27.40 | C |
| ATOM | 2322 | C | LEU | A | 355 | -3.648 | 54.987 | -12.169 | 1.00 27.53 | C |
| ATOM | 2323 | O | LEU | A | 355 | -4.436 | 54.971 | -11.293 | 1.00 26.19 | O |
| ATOM | 2324 | N | ALA | A | 356 | -3.940 | 53.643 | -13.073 | 1.00 26.89 | N |
| ATOM | 2325 | CA | ALA | A | 356 | -5.221 | 52.927 | -13.094 | 1.00 25.34 | C |
| ATOM | 2326 | CB | ALA | A | 356 | -5.240 | 51.877 | -14.185 | 1.00 24.40 | C |
| ATOM | 2327 | C | ALA | A | 356 | -5.525 | 52.294 | -11.749 | 1.00 24.86 | C |
| ATOM | 2328 | O | ALA | A | 356 | -6.674 | 52.266 | -11.343 | 1.00 25.19 | O |
| ATOM | 2329 | N | ASP | A | 357 | -4.498 | 51.811 | -11.060 | 1.00 24.88 | N |
| ATOM | 2330 | CA | ASP | A | 357 | -4.712 | 51.204 | -9.755 | 1.00 25.48 | C |
| ATOM | 2331 | CB | ASP | A | 357 | -3.579 | 50.259 | -9.368 | 1.00 27.41 | C |
| ATOM | 2332 | CG | ASP | A | 357 | -3.817 | 48.849 | -9.884 | 1.00 29.55 | C |
| ATOM | 2333 | OD1 | ASP | A | 357 | -4.941 | 48.310 | -9.698 | 1.00 30.96 | O |
| ATOM | 2334 | OD2 | ASP | A | 357 | -2.875 | 48.289 | -10.489 | 1.00 29.94 | O |
| ATOM | 2335 | C | ASP | A | 357 | -4.999 | 52.192 | -8.658 | 1.00 24.81 | C |
| ATOM | 2336 | O | ASP | A | 357 | -5.900 | 51.966 | -7.867 | 1.00 26.42 | O |
| ATOM | 2337 | N | SER | A | 358 | -4.247 | 53.291 | -8.607 | 1.00 23.69 | N |
| ATOM | 2338 | CA | SER | A | 358 | -4.589 | 54.403 | -7.725 | 1.00 22.65 | C |
| ATOM | 2339 | CB | SER | A | 358 | 3.663 | 55.597 | 7.923 | 1.00 22.19 | C |
| ATOM | 2340 | OG | SER | A | 358 | -2.331 | 55.153 | -7.875 | 1.00 24.91 | O |
| ATOM | 2341 | C | SER | A | 358 | -5.981 | 54.870 | -8.038 | 1.00 22.05 | C |
| ATOM | 2342 | O | SER | A | 358 | -6.770 | 55.086 | -7.137 | 1.00 22.66 | O |
| ATOM | 2343 | N | HIS | A | 359 | 6.290 | 55.029 | 9.320 | 1.00 21.39 | N |
| ATOM | 2344 | CA | HIS | A | 359 | -7.993 | 55.538 | -9.682 | 1.00 20.60 | C |
| ATOM | 2345 | CB | HIS | A | 359 | -7.789 | 55.578 | -11.180 | 1.00 20.16 | C |
| ATOM | 2346 | CG | HIS | A | 359 | -9.076 | 56.244 | -11.593 | 1.00 20.19 | C |
| ATOM | 2347 | ND1 | HIS | A | 359 | -10.251 | 55.597 | -11.610 | 1.00 20.25 | N |
| ATOM | 2348 | CE1 | HIS | A | 359 | -11.219 | 56.435 | -12.009 | 1.00 19.76 | C |
| ATOM | 2349 | NE2 | HIS | A | 359 | -10.658 | 57.620 | -12.269 | 1.00 19.57 | N |
| ATOM | 2350 | CD2 | HIS | A | 359 | -9.339 | 57.543 | -12.011 | 1.00 20.19 | C |
| ATOM | 2351 | C | HIS | A | 359 | -8.644 | 54.710 | -9.020 | 1.00 19.94 | C |
| ATOM | 2352 | O | HIS | A | 359 | -9.551 | 55.257 | -8.410 | 1.00 20.02 | O |
| ATOM | 2353 | N | LEU | A | 360 | -8.502 | 53.387 | -9.109 | 1.00 19.74 | N |
| ATOM | 2354 | CA | LEU | A | 360 | -9.469 | 52.453 | -8.543 | 1.00 19.27 | C |
| ATOM | 2355 | CB | LEU | A | 360 | -9.164 | 51.003 | -8.950 | 1.00 18.64 | C |
| ATOM | 2356 | CG | LEU | A | 360 | -10.209 | 49.933 | -8.569 | 1.00 18.93 | C |
| ATOM | 2357 | CD1 | LEU | A | 360 | -11.521 | 50.142 | -9.314 | 1.00 18.60 | C |
| ATOM | 2358 | CD2 | LEU | A | 360 | -9.699 | 48.513 | -8.781 | 1.00 17.70 | C |
| ATOM | 2359 | C | LEU | A | 360 | -9.583 | 52.629 | -7.032 | 1.00 19.35 | C |
| ATOM | 2360 | O | LEU | A | 360 | -10.668 | 52.939 | -6.550 | 1.00 19.33 | O |
| ATOM | 2361 | N | LYS | A | 361 | -8.476 | 52.468 | -6.300 | 1.00 20.47 | N |
| ATOM | 2362 | CA | LYS | A | 361 | -8.431 | 52.751 | -4.843 | 1.00 21.32 | C |
| ATOM | 2363 | CB | LYS | A | 361 | -6.989 | 52.792 | -4.342 | 1.00 23.00 | C |
| ATOM | 2364 | CG | LYS | A | 361 | -6.516 | 51.577 | -3.547 | 1.00 25.31 | C |
| ATOM | 2365 | CD | LYS | A | 361 | 5.103 | 51.810 | 2.994 | 1.00 26.70 | C |
| ATOM | 2366 | CE | LYS | A | 361 | -4.415 | 50.516 | -2.547 | 1.00 29.27 | C |
| ATOM | 2367 | NZ | LYS | A | 361 | -4.310 | 50.313 | -1.060 | 1.00 29.55 | N |
| ATOM | 2368 | C | LYS | A | 361 | -9.151 | 54.063 | -4.456 | 1.00 20.60 | C |
| ATOM | 2369 | O | LYS | A | 361 | -10.050 | 54.064 | -3.622 | 1.00 20.51 | O |
| ATOM | 2370 | N | ALA | A | 362 | -8.755 | 55.166 | -5.080 | 1.00 20.05 | N |
| ATOM | 2371 | CA | ALA | A | 362 | -9.385 | 56.468 | -4.881 | 1.00 19.94 | C |
| ATOM | 2372 | CB | ALA | A | 362 | -8.787 | 57.496 | -5.846 | 1.00 19.26 | C |
| ATOM | 2373 | C | ALA | A | 362 | -10.922 | 56.468 | -5.001 | 1.00 19.71 | C |
| ATOM | 2374 | O | ALA | A | 362 | -11.634 | 56.953 | -4.114 | 1.00 19.33 | O |
| ATOM | 2375 | N | TYR | A | 363 | -11.418 | 55.878 | -6.095 | 1.00 18.63 | N |
| ATOM | 2376 | CA | TYR | A | 363 | -12.844 | 55.822 | -6.369 | 1.00 19.31 | C |
| ATOM | 2377 | CB | TYR | A | 363 | -13.080 | 55.197 | -7.735 | 1.00 17.81 | C |
| ATOM | 2378 | CG | TYR | A | 363 | 14.455 | 55.413 | 8.344 | 1.00 16.97 | C |
| ATOM | 2379 | CD1 | TYR | A | 363 | -15.387 | 55.296 | -7.762 | 1.00 16.39 | C |
| ATOM | 2380 | CE1 | TYR | A | 363 | -16.622 | 56.539 | -8.347 | 1.00 16.71 | C |
| ATOM | 2381 | CZ | TYR | A | 363 | -16.935 | 55.839 | -9.557 | 1.00 16.61 | C |

FIG. 22EE

```
ATOM  2382  OH  TYR A 363     -18.123  56.032 -10.175  1.00 15.74           O
ATOM  2383  CE2 TYR A 363     -16.447  56.957 -10.140  1.00 16.79           C
ATOM  2384  CD2 TYR A 363     -14.805  56.758  -9.541  1.00 16.88           C
ATOM  2385  C   TYR A 363     -13.561  55.003   5.320  1.00 19.35           C
ATOM  2386  O   TYR A 363     -14.528  55.465  -4.722  1.00 20.77           O
ATOM  2387  N   GLN A 364     -13.084  53.778  -5.112  1.00 19.97           N
ATOM  2388  CA  GLN A 364     -13.613  52.874  -4.096  1.00 20.31           C
ATOM  2389  CB  GLN A 364     -12.802  51.576  -4.077  1.00 20.28           C
ATOM  2390  CG  GLN A 364     -12.840  50.079  -5.426  1.00 21.11           C
ATOM  2391  CD  GLN A 364     -12.256  49.484  -5.436  1.00 21.74           C
ATOM  2392  OE1 GLN A 364     -11.309  49.174  -4.725  1.00 22.43           O
ATOM  2393  NE2 GLN A 364     -12.819  48.635  -6.278  1.00 22.59           N
ATOM  2394  C   GLN A 364      13.652  53.505   2.715  1.00 20.85           C
ATOM  2395  O   GLN A 364     -14.623  53.323  -1.960  1.00 21.32           O
ATOM  2396  N   GLY A 365     -12.612  54.272  -2.405  1.00 20.77           N
ATOM  2397  CA  GLY A 365     -12.494  54.900  -1.105  1.00 21.69           C
ATOM  2398  C   GLY A 365     -13.457  56.056  -0.953  1.00 22.86           C
ATOM  2399  O   GLY A 365     -14.029  56.266   0.121  1.00 25.03           O
ATOM  2400  N   ALA A 366     -13.636  56.809  -2.029  1.00 21.51           N
ATOM  2401  CA  ALA A 366     -14.556  57.923  -2.027  1.00 21.12           C
ATOM  2402  CB  ALA A 366     -14.419  58.725  -3.315  1.00 19.98           C
ATOM  2403  C   ALA A 366     -15.993  57.426  -1.836  1.00 21.62           C
ATOM  2404  O   ALA A 366     -16.761  58.037  -1.088  1.00 22.29           O
ATOM  2405  N   ILE A 367     -16.345  56.323  -2.501  1.00 21.22           N
ATOM  2406  CA  ILE A 367     -17.664  55.693  -2.343  1.00 21.04           C
ATOM  2407  CB  ILE A 367     -17.850  54.518  -3.327  1.00 20.78           C
ATOM  2408  CG1 ILE A 367     -17.776  55.034  -4.763  1.00 19.49           C
ATOM  2409  CD1 ILE A 367     -17.693  53.947  -5.811  1.00 19.37           C
ATOM  2410  CG2 ILE A 367     -19.154  53.750  -3.049  1.00 19.41           C
ATOM  2411  C   ILE A 367     -17.886  55.220  -0.902  1.00 21.16           C
ATOM  2412  O   ILE A 367     -18.860  55.617  -0.249  1.00 20.43           O
ATOM  2413  N   LYS A 368     -16.966  54.399  -0.399  1.00 22.79           N
ATOM  2414  CA  LYS A 368     -17.052  53.946   0.996  1.00 24.29           C
ATOM  2415  CB  LYS A 368     -15.961  52.919   1.342  1.00 26.65           C
ATOM  2416  CG  LYS A 368      16.096  52.339   2.744  1.00 30.27           C
ATOM  2417  CD  LYS A 368     -14.807  51.691   3.256  1.00 34.57           C
ATOM  2418  CE  LYS A 368     -14.834  50.161   3.272  1.00 37.03           C
ATOM  2419  NZ  LYS A 368     -14.753  49.615   1.828  1.00 39.29           N
ATOM  2420  C   LYS A 368      17.076  55.121   1.990  1.00 22.89           C
ATOM  2421  O   LYS A 368     -17.902  55.133   2.882  1.00 23.46           O
ATOM  2422  N   ALA A 369     -16.210  56.118   1.801  1.00 21.47           N
ATOM  2423  CA  ALA A 369     -16.178  57.303   2.664  1.00 20.49           C
ATOM  2424  CB  ALA A 369     -14.935  58.130   2.400  1.00 19.57           C
ATOM  2425  C   ALA A 369     -17.423  58.175   2.525  1.00 21.05           C
ATOM  2426  O   ALA A 369     -17.655  59.059  -3.364  1.00 20.75           O
ATOM  2427  N   GLY A 370     -18.207  57.944   1.466  1.00 20.35           N
ATOM  2428  CA  GLY A 370     -19.469  58.651   1.269  1.00 19.55           C
ATOM  2429  C   GLY A 370     -19.312  60.091   0.814  1.00 19.66           C
ATOM  2430  O   GLY A 370     -20.115  60.963   1.161  1.00 19.54           O
ATOM  2431  N   VAL A 371     -18.242  60.334   0.061  1.00 19.67           N
ATOM  2432  CA  VAL A 371     -18.085  61.503  -0.807  1.00 18.79           C
ATOM  2433  CB  VAL A 371     -16.754  61.360  -1.598  1.00 18.50           C
ATOM  2434  CG1 VAL A 371     -16.625  62.364  -2.748  1.00 17.50           C
ATOM  2435  CG2 VAL A 371     -15.583  61.424  -0.625  1.00 17.09           C
ATOM  2436  C   VAL A 371     -19.249  61.514  -1.791  1.00 18.88           C
ATOM  2437  O   VAL A 371     -19.622  60.466  -2.300  1.00 20.17           O
ATOM  2438  N   THR A 372     -19.830  62.679  -2.052  1.00 19.96           N
ATOM  2439  CA  THR A 372     -20.880  62.805  -3.069  1.00 18.88           C
ATOM  2440  CB  THR A 372     -21.538  64.192  -3.030  1.00 18.58           C
ATOM  2441  OG1 THR A 372     -22.000  64.456  -1.706  1.00 18.33           O
ATOM  2442  CG2 THR A 372      22.704  64.256   3.996  1.00 18.62           C
ATOM  2443  C   THR A 372     -20.305  62.576  -4.469  1.00 18.80           C
ATOM  2444  O   THR A 372     -19.321  63.210  -4.851  1.00 19.39           O
ATOM  2445  N   ILE A 373     -20.931  61.685  -5.231  1.00 19.78           N
ATOM  2446  CA  ILE A 373     -20.395  61.275  -6.534  1.00 19.25           C
ATOM  2447  CB  ILE A 373     -19.877  59.822  -6.458  1.00 19.11           C
ATOM  2448  CG1 ILE A 373     -18.740  59.776  -5.423  1.00 18.63           C
ATOM  2449  CD1 ILE A 373     -18.325  58.396  -5.028  1.00 19.51           C
ATOM  2450  CG2 ILE A 373     -19.443  59.307  -7.831  1.00 18.05           C
ATOM  2451  C   ILE A 373     -21.378  61.452  -7.687  1.00 19.60           C
ATOM  2452  O   ILE A 373     -22.579  61.206  -7.519  1.00 20.40           O
ATOM  2453  N   ALA A 374     -20.875  61.902  -8.838  1.00 18.94           N
ATOM  2454  CA  ALA A 374     -21.646  61.834 -10.082  1.00 18.93           C
ATOM  2455  CB  ALA A 374      22.073  63.216  10.566  1.00 18.81           C
ATOM  2456  C   ALA A 374     -20.824  61.193 -11.144  1.00 19.05           C
ATOM  2457  O   ALA A 374     -19.656  60.787 -10.900  1.00 19.44           O
ATOM  2458  N   LEU A 375     -21.443  60.823 -12.300  1.00 19.51           N
```

FIG. 22FF

| | | | | | | | | | |
|---|---|---|---|---|---|---|---|---|---|
|ATOM|2459|CA|LEU|A|375|-20.815|60.014|-13.342|1.00 19.66|C|
|ATOM|2460|CB|LEU|A|375|-21.871|58.782|-13.665|1.00 19.74|C|
|ATOM|2461|CG|LEU|A|375|-22.063|57.850|-12.527|1.00 19.30|C|
|ATOM|2462|CD1|LEU|A|375|-22.800|56.660|-13.120|1.00 19.47|C|
|ATOM|2463|CD2|LEU|A|375|-20.855|57.401|-11.725|1.00 17.69|C|
|ATOM|2464|C|LEU|A|375|-20.538|60.766|-14.639|1.00 18.92|C|
|ATOM|2465|O|LEU|A|375|-21.351|61.580|-15.095|1.00 18.62|O|
|ATOM|2466|N|GLY|A|376|-19.394|60.451|-15.245|1.00 18.65|N|
|ATOM|2467|CA|GLY|A|376|-19.004|61.011|-16.526|1.00 17.74|C|
|ATOM|2468|C|GLY|A|376|-18.060|60.039|-17.189|1.00 18.08|C|
|ATOM|2469|O|GLY|A|376|-17.495|59.161|-16.531|1.00 18.10|O|
|ATOM|2470|N|THR|A|377|-17.869|60.195|-18.493|1.00 18.35|N|
|ATOM|2471|CA|THR|A|377|-17.147|59.201|-19.262|1.00 18.74|C|
|ATOM|2472|CB|THR|A|377|-16.102|58.416|-20.177|1.00 18.65|C|
|ATOM|2473|OG1|THR|A|377|-18.834|59.339|-20.979|1.00 19.01|O|
|ATOM|2474|CG2|THR|A|377|-19.091|57.599|-19.367|1.00 19.16|C|
|ATOM|2475|C|THR|A|377|-16.050|59.793|-20.127|1.00 19.53|C|
|ATOM|2476|O|THR|A|377|-15.251|59.065|-20.693|1.00 19.72|O|
|ATOM|2477|N|ASP|A|378|-16.016|61.127|-20.231|1.00 20.21|N|
|ATOM|2478|CA|ASP|A|378|-15.141|61.836|-21.182|1.00 20.60|C|
|ATOM|2479|CB|ASP|A|378|-13.651|61.802|-20.753|1.00 20.84|C|
|ATOM|2480|CG|ASP|A|378|-12.788|62.850|-21.481|1.00 22.02|C|
|ATOM|2481|OD1|ASP|A|378|-13.326|63.783|-22.108|1.00 22.13|O|
|ATOM|2482|OD2|ASP|A|378|-11.544|62.756|-21.416|1.00 24.64|O|
|ATOM|2483|C|ASP|A|378|-15.310|61.297|-22.609|1.00 19.90|C|
|ATOM|2484|O|ASP|A|378|-14.337|60.927|-23.255|1.00 19.35|O|
|ATOM|2485|N|THR|A|379|-16.541|61.229|-23.089|1.00 18.66|N|
|ATOM|2486|CA|THR|A|379|-16.767|60.791|-24.455|1.00 19.46|C|
|ATOM|2487|CB|THR|A|379|-17.588|59.471|-24.518|1.00 20.41|C|
|ATOM|2488|OG1|THR|A|379|-18.835|59.653|-23.831|1.00 20.63|O|
|ATOM|2489|CG2|THR|A|379|-16.836|58.310|-23.883|1.00 19.89|C|
|ATOM|2490|C|THR|A|379|-17.457|61.885|-25.295|1.00 18.83|C|
|ATOM|2491|O|THR|A|379|-17.648|62.944|-24.788|1.00 17.88|O|
|ATOM|2492|N|ALA|A|380|-17.580|61.612|-26.589|1.00 18.05|N|
|ATOM|2493|CA|ALA|A|380|-18.320|62.465|-27.486|1.00 17.69|C|
|ATOM|2494|CB|ALA|A|380|-17.953|62.125|-28.911|1.00 17.93|C|
|ATOM|2495|C|ALA|A|380|-19.805|62.219|-27.267|1.00 17.58|C|
|ATOM|2496|O|ALA|A|380|-20.184|61.106|-26.970|1.00 18.43|O|
|ATOM|2497|N|PRO|A|381|-20.654|63.240|-27.449|1.00 17.25|N|
|ATOM|2498|CA|PRO|A|381|-22.106|62.985|-27.461|1.00 17.16|C|
|ATOM|2499|CB|PRO|A|381|-22.666|64.217|-28.215|1.00 16.98|C|
|ATOM|2500|CG|PRO|A|381|-21.642|65.295|-27.994|1.00 16.98|C|
|ATOM|2501|CD|PRO|A|381|-20.309|64.627|-27.934|1.00 17.09|C|
|ATOM|2502|C|PRO|A|381|-22.471|61.717|-28.262|1.00 17.43|C|
|ATOM|2503|O|PRO|A|381|-21.979|61.537|-29.413|1.00 16.81|O|
|ATOM|2504|N|GLY|A|382|-23.330|60.869|-27.709|1.00 17.43|N|
|ATOM|2505|CA|GLY|A|382|-23.760|59.601|-28.335|1.00 17.07|C|
|ATOM|2506|C|GLY|A|382|-22.886|58.409|-27.966|1.00 17.36|C|
|ATOM|2507|O|GLY|A|382|-23.212|57.242|-28.248|1.00 17.56|O|
|ATOM|2508|N|GLY|A|383|-21.766|58.699|-27.326|1.00 17.14|N|
|ATOM|2509|CA|GLY|A|383|-20.847|57.662|-26.892|1.00 17.31|C|
|ATOM|2510|C|GLY|A|383|-21.429|56.767|-25.803|1.00 17.54|C|
|ATOM|2511|O|GLY|A|383|-22.597|56.915|-25.401|1.00 16.86|O|
|ATOM|2512|N|PRO|A|384|-20.609|55.820|-25.329|1.00 17.08|N|
|ATOM|2513|CA|PRO|A|384|-21.100|54.701|-24.451|1.00 17.22|C|
|ATOM|2514|CB|PRO|A|384|-20.062|53.697|-24.609|1.00 16.69|C|
|ATOM|2515|CG|PRO|A|384|-18.789|54.403|-24.926|1.00 16.47|C|
|ATOM|2516|CD|PRO|A|384|-19.204|55.598|-25.728|1.00 17.02|C|
|ATOM|2517|C|PRO|A|384|-21.181|55.307|-23.015|1.00 17.79|C|
|ATOM|2518|O|PRO|A|384|-20.459|54.820|-22.132|1.00 18.04|O|
|ATOM|2519|N|THR|A|385|-22.054|56.282|-22.785|1.00 17.67|N|
|ATOM|2520|CA|THR|A|385|-22.160|56.885|-21.458|1.00 19.80|C|
|ATOM|2521|CB|THR|A|385|-23.014|58.178|-21.456|1.00 18.27|C|
|ATOM|2522|OG1|THR|A|385|-24.233|57.963|-22.172|1.00 16.91|O|
|ATOM|2523|CG2|THR|A|385|-22.243|59.315|-22.126|1.00 17.61|C|
|ATOM|2524|C|THR|A|385|-22.650|55.905|-20.401|1.00 19.99|C|
|ATOM|2525|O|THR|A|385|-22.236|55.978|-19.256|1.00 21.38|O|
|ATOM|2526|N|ALA|A|386|-23.485|54.950|-20.810|1.00 21.17|N|
|ATOM|2527|CA|ALA|A|386|-24.040|53.945|-19.909|1.00 20.40|C|
|ATOM|2528|CB|ALA|A|386|-25.056|53.096|-20.639|1.00 20.74|C|
|ATOM|2529|C|ALA|A|386|-22.972|53.069|-19.256|1.00 20.92|C|
|ATOM|2530|O|ALA|A|386|-23.128|52.633|-18.080|1.00 20.73|O|
|ATOM|2531|N|LEU|A|387|-21.889|52.818|-19.988|1.00 19.73|N|
|ATOM|2532|CA|LEU|A|387|-20.773|52.076|-19.404|1.00 20.25|C|
|ATOM|2533|CB|LEU|A|387|-19.532|52.112|-20.300|1.00 20.74|C|
|ATOM|2534|CG|LEU|A|387|-19.335|51.043|-21.366|1.00 22.15|C|
|ATOM|2535|CD1|LEU|A|387|-17.971|51.195|-22.023|1.00 22.35|C|

FIG. 22GG

| | | | | | | | | | | |
|---|---|---|---|---|---|---|---|---|---|---|
| ATOM | 2536 | CD2 | LEU | A | 387 | -19.471 | 49.647 | -20.779 | 1.00 22.05 | C |
| ATOM | 2537 | C | LEU | A | 387 | -20.409 | 52.566 | -17.993 | 1.00 19.99 | C |
| ATOM | 2538 | O | LEU | A | 387 | -20.017 | 51.773 | -17.137 | 1.00 19.56 | O |
| ATOM | 2539 | N | GLU | A | 388 | -20.537 | 53.866 | -17.745 | 1.00 19.60 | N |
| ATOM | 2540 | CA | GLU | A | 388 | -20.062 | 54.391 | -16.469 | 1.00 20.45 | C |
| ATOM | 2541 | CB | GLU | A | 388 | -19.963 | 55.925 | -16.478 | 1.00 20.84 | C |
| ATOM | 2542 | CG | GLU | A | 388 | -19.137 | 56.523 | -15.338 | 1.00 21.23 | C |
| ATOM | 2543 | CD | GLU | A | 388 | -17.629 | 56.271 | -15.442 | 1.00 22.02 | C |
| ATOM | 2544 | OE1 | GLU | A | 388 | -16.923 | 56.482 | -14.427 | 1.00 22.69 | O |
| ATOM | 2545 | OE2 | GLU | A | 388 | -17.133 | 55.883 | -16.519 | 1.00 22.06 | O |
| ATOM | 2546 | C | GLU | A | 388 | -20.883 | 53.876 | -15.285 | 1.00 20.39 | C |
| ATOM | 2547 | O | GLU | A | 388 | -20.347 | 53.725 | -14.190 | 1.00 19.75 | O |
| ATOM | 2548 | N | LEU | A | 389 | -22.168 | 53.585 | -15.523 | 1.00 20.23 | N |
| ATOM | 2549 | CA | LEU | A | 389 | -23.030 | 52.919 | -14.522 | 1.00 18.68 | C |
| ATOM | 2550 | CB | LEU | A | 389 | -24.497 | 52.850 | -14.992 | 1.00 17.88 | C |
| ATOM | 2551 | CG | LEU | A | 389 | -25.164 | 54.244 | -15.081 | 1.00 17.67 | C |
| ATOM | 2552 | CD1 | LEU | A | 389 | -25.958 | 54.422 | -16.363 | 1.00 17.59 | C |
| ATOM | 2553 | CD2 | LEU | A | 389 | -26.011 | 54.601 | -13.863 | 1.00 17.14 | C |
| ATOM | 2554 | C | LEU | A | 389 | -22.474 | 51.553 | -14.198 | 1.00 17.96 | C |
| ATOM | 2555 | O | LEU | A | 389 | -22.355 | 51.200 | -13.028 | 1.00 19.00 | O |
| ATOM | 2556 | N | GLN | A | 390 | -22.068 | 50.815 | -15.222 | 1.00 17.44 | N |
| ATOM | 2557 | CA | GLN | A | 390 | -21.466 | 49.504 | -15.008 | 1.00 17.98 | C |
| ATOM | 2558 | CB | GLN | A | 390 | -21.124 | 48.817 | -16.341 | 1.00 18.26 | C |
| ATOM | 2559 | CG | GLN | A | 390 | -20.804 | 47.332 | -16.208 | 1.00 18.68 | C |
| ATOM | 2560 | CD | GLN | A | 390 | -20.334 | 46.694 | -17.506 | 1.00 19.51 | C |
| ATOM | 2561 | OE1 | GLN | A | 390 | -20.878 | 46.961 | -18.596 | 1.00 19.80 | O |
| ATOM | 2562 | NE2 | GLN | A | 390 | -19.323 | 45.854 | -17.393 | 1.00 19.81 | N |
| ATOM | 2563 | C | GLN | A | 390 | -20.232 | 49.560 | -14.095 | 1.00 17.66 | C |
| ATOM | 2564 | O | GLN | A | 390 | -20.122 | 48.784 | -13.143 | 1.00 17.48 | O |
| ATOM | 2565 | N | PHE | A | 391 | -19.316 | 50.476 | -14.395 | 1.00 17.46 | N |
| ATOM | 2566 | CA | PHE | A | 391 | -18.103 | 50.657 | -13.600 | 1.00 17.35 | C |
| ATOM | 2567 | CB | PHE | A | 391 | -17.108 | 51.551 | -14.337 | 1.00 17.25 | C |
| ATOM | 2568 | CG | PHE | A | 391 | -16.708 | 51.019 | -15.679 | 1.00 17.66 | C |
| ATOM | 2569 | CD1 | PHE | A | 391 | -16.412 | 49.656 | -15.846 | 1.00 17.67 | C |
| ATOM | 2570 | CE1 | PHE | A | 391 | -16.033 | 49.157 | -17.094 | 1.00 17.48 | C |
| ATOM | 2571 | CZ | PHE | A | 391 | -15.947 | 50.015 | -18.188 | 1.00 17.37 | C |
| ATOM | 2572 | CE2 | PHE | A | 391 | -16.231 | 51.369 | -18.032 | 1.00 17.70 | C |
| ATOM | 2573 | CD2 | PHE | A | 391 | -16.610 | 51.867 | -16.784 | 1.00 17.42 | C |
| ATOM | 2574 | C | PHE | A | 391 | -18.391 | 51.214 | -12.204 | 1.00 17.34 | C |
| ATOM | 2575 | O | PHE | A | 391 | -17.731 | 50.843 | -11.225 | 1.00 17.40 | O |
| ATOM | 2576 | N | ALA | A | 392 | -19.385 | 52.081 | -12.097 | 1.00 17.15 | N |
| ATOM | 2577 | CA | ALA | A | 392 | -19.773 | 52.549 | -10.791 | 1.00 17.84 | C |
| ATOM | 2578 | CB | ALA | A | 392 | -20.948 | 53.501 | -10.993 | 1.00 17.43 | C |
| ATOM | 2579 | C | ALA | A | 392 | -20.067 | 51.335 | -9.868 | 1.00 18.71 | C |
| ATOM | 2580 | O | ALA | A | 392 | -19.735 | 51.319 | -8.695 | 1.00 18.55 | O |
| ATOM | 2581 | N | VAL | A | 393 | -20.712 | 50.312 | -10.474 | 1.00 18.10 | N |
| ATOM | 2582 | CA | VAL | A | 393 | -21.101 | 49.142 | -9.715 | 1.00 19.42 | C |
| ATOM | 2583 | CB | VAL | A | 393 | -22.327 | 48.437 | -10.359 | 1.00 17.99 | C |
| ATOM | 2584 | CG1 | VAL | A | 393 | -22.633 | 47.125 | -9.657 | 1.00 16.55 | C |
| ATOM | 2585 | CG2 | VAL | A | 393 | -23.546 | 49.356 | -10.330 | 1.00 17.78 | C |
| ATOM | 2586 | C | VAL | A | 393 | -19.931 | 48.154 | -9.534 | 1.00 19.18 | C |
| ATOM | 2587 | O | VAL | A | 393 | -19.607 | 47.743 | -8.407 | 1.00 19.02 | O |
| ATOM | 2588 | N | GLU | A | 394 | -19.300 | 47.785 | -10.649 | 1.00 19.54 | N |
| ATOM | 2589 | CA | GLU | A | 394 | -18.401 | 46.633 | -10.668 | 1.00 20.21 | C |
| ATOM | 2590 | CB | GLU | A | 394 | -18.497 | 45.942 | -12.027 | 1.00 20.51 | C |
| ATOM | 2591 | CG | GLU | A | 394 | -19.926 | 45.594 | -12.420 | 1.00 20.92 | C |
| ATOM | 2592 | CD | GLU | A | 394 | -20.002 | 44.826 | -13.715 | 1.00 21.67 | C |
| ATOM | 2593 | OE1 | GLU | A | 394 | -18.941 | 44.595 | -14.318 | 1.00 22.06 | O |
| ATOM | 2594 | OE2 | GLU | A | 394 | -21.123 | 44.462 | -14.135 | 1.00 22.42 | O |
| ATOM | 2595 | C | GLU | A | 394 | -16.953 | 46.972 | -10.356 | 1.00 20.77 | C |
| ATOM | 2596 | O | GLU | A | 394 | -16.177 | 46.082 | -10.037 | 1.00 21.56 | O |
| ATOM | 2597 | N | ARG | A | 395 | -16.593 | 48.248 | -10.491 | 1.00 20.59 | N |
| ATOM | 2598 | CA | ARG | A | 395 | -15.284 | 48.760 | -10.124 | 1.00 20.80 | C |
| ATOM | 2599 | CB | ARG | A | 395 | -14.792 | 49.769 | -11.156 | 1.00 22.81 | C |
| ATOM | 2600 | CG | ARG | A | 395 | -14.546 | 49.188 | -12.523 | 1.00 25.89 | C |
| ATOM | 2601 | CD | ARG | A | 395 | -13.267 | 48.392 | -12.502 | 1.00 28.14 | C |
| ATOM | 2602 | NE | ARG | A | 395 | -13.489 | 47.098 | -13.106 | 1.00 30.95 | N |
| ATOM | 2603 | CZ | ARG | A | 395 | -12.535 | 46.384 | -13.672 | 1.00 34.81 | C |
| ATOM | 2604 | NH1 | ARG | A | 395 | -12.832 | 45.202 | -14.185 | 1.00 36.37 | N |
| ATOM | 2605 | NH2 | ARG | A | 395 | -11.200 | 46.856 | -13.732 | 1.00 37.42 | N |
| ATOM | 2606 | C | ARG | A | 395 | -15.454 | 49.517 | -8.843 | 1.00 20.13 | C |
| ATOM | 2607 | O | ARG | A | 395 | -14.779 | 49.254 | -7.846 | 1.00 19.63 | O |
| ATOM | 2608 | N | GLY | A | 396 | -16.362 | 50.481 | -8.887 | 1.00 19.19 | N |
| ATOM | 2609 | CA | GLY | A | 396 | -16.591 | 51.345 | -7.752 | 1.00 19.99 | C |
| ATOM | 2610 | C | GLY | A | 396 | -17.117 | 50.580 | -6.549 | 1.00 19.72 | C |
| ATOM | 2611 | O | GLY | A | 396 | -16.663 | 50.798 | -5.426 | 1.00 19.19 | O |
| ATOM | 2612 | N | GLY | A | 397 | -18.068 | 49.688 | -6.791 | 1.00 19.15 | N |

FIG. 22HH

```
ATOM   2613  CA   GLY A 397     -18.689  48.962  -5.708  1.00 19.61           C
ATOM   2614  C    GLY A 397     -19.955  49.623  -5.208  1.00 20.20           C
ATOM   2615  O    GLY A 397     -20.410  49.311  -4.115  1.00 20.46           O
ATOM   2616  N    MET A 398      20.516  50.543   5.990  1.00 20.15           N
ATOM   2617  CA   MET A 398     -21.853  51.064  -5.717  1.00 21.10           C
ATOM   2618  CB   MET A 398     -22.187  52.225  -6.658  1.00 21.31           C
ATOM   2619  CG   MET A 398     -21.515  53.548  -6.340  1.00 21.80           C
ATOM   2620  SD   MET A 398     -22.140  54.842  -7.442  1.00 22.87           S
ATOM   2621  CE   MET A 398     -20.949  56.128  -7.103  1.00 22.92           C
ATOM   2622  C    MET A 398     -22.924  49.966  -5.897  1.00 21.65           C
ATOM   2623  O    MET A 398     -22.745  49.018  -6.696  1.00 21.82           O
ATOM   2624  N    THR A 399     -24.039  50.098  -5.174  1.00 21.11           N
ATOM   2625  CA   THR A 399      25.215  49.288   5.473  1.00 21.34           C
ATOM   2626  CB   THR A 399     -26.300  49.363  -4.374  1.00 21.68           C
ATOM   2627  OG1  THR A 399     -26.763  50.715  -4.242  1.00 22.64           O
ATOM   2628  CG2  THR A 399     -25.791  48.842  -3.036  1.00 20.63           C
ATOM   2629  C    THR A 399     -25.796  49.855  -6.752  1.00 21.34           C
ATOM   2630  O    THR A 399     -25.596  51.033  -7.046  1.00 22.49           O
ATOM   2631  N    PRO A 400     -26.536  49.045  -7.519  1.00 21.42           N
ATOM   2632  CA   PRO A 400     -27.099  49.667  -8.733  1.00 21.47           C
ATOM   2633  CB   PRO A 400     -27.980  48.555  -9.326  1.00 21.56           C
ATOM   2634  CG   PRO A 400     -27.370  47.282  -8.792  1.00 21.48           C
ATOM   2635  CD   PRO A 400     -26.846  47.603  -7.427  1.00 20.97           C
ATOM   2636  C    PRO A 400     -27.921  50.931  -8.441  1.00 20.67           C
ATOM   2637  O    PRO A 400     -27.927  51.857  -9.264  1.00 19.60           O
ATOM   2638  N    LEU A 401     -28.594  50.955  -7.284  1.00 20.32           N
ATOM   2639  CA   LEU A 401     -29.425  52.093  -6.873  1.00 19.89           C
ATOM   2640  CB   LEU A 401     -30.299  51.762  -5.658  1.00 19.49           C
ATOM   2641  CG   LEU A 401     -31.333  52.801  -5.201  1.00 18.78           C
ATOM   2642  CD1  LEU A 401     -32.440  53.011  -6.234  1.00 17.62           C
ATOM   2643  CD2  LEU A 401     -31.898  52.384  -3.854  1.00 18.14           C
ATOM   2644  C    LEU A 401     -28.586  53.315  -6.580  1.00 20.37           C
ATOM   2645  O    LEU A 401     -29.047  54.420  -6.777  1.00 21.39           O
ATOM   2646  N    GLU A 402     -27.357  53.115  -6.112  1.00 21.46           N
ATOM   2647  CA   GLU A 402      26.421  54.227   5.886  1.00 21.70           C
ATOM   2648  CB   GLU A 402     -25.289  53.794  -4.950  1.00 21.97           C
ATOM   2649  CG   GLU A 402     -25.689  53.811  -3.485  1.00 22.83           C
ATOM   2650  CD   GLU A 402     -24.775  52.993  -2.573  1.00 24.78           C
ATOM   2651  OE1  GLU A 402      23.897  52.212   3.048  1.00 24.60           O
ATOM   2652  OE2  GLU A 402     -24.970  53.107  -1.345  1.00 24.96           O
ATOM   2653  C    GLU A 402     -25.875  54.781  -7.209  1.00 21.38           C
ATOM   2654  O    GLU A 402     -25.741  56.003  -7.386  1.00 21.71           O
ATOM   2655  N    ALA A 403     -25.588  53.871  -8.137  1.00 20.62           N
ATOM   2656  CA   ALA A 403     -25.132  54.223  -9.469  1.00 19.82           C
ATOM   2657  CB   ALA A 403     -24.883  52.976 -10.301  1.00 19.19           C
ATOM   2658  C    ALA A 403     -26.169  55.112 -10.132  1.00 20.12           C
ATOM   2659  O    ALA A 403     -25.831  56.100 -10.797  1.00 20.93           O
ATOM   2660  N    ILE A 404     -27.440  54.775  -9.950  1.00 19.89           N
ATOM   2661  CA   ILE A 404     -28.480  55.570 -10.560  1.00 19.39           C
ATOM   2662  CB   ILE A 404     -29.820  54.828 -10.553  1.00 19.58           C
ATOM   2663  CG1  ILE A 404     -29.840  53.878 -11.754  1.00 19.02           C
ATOM   2664  CD1  ILE A 404     -30.731  52.672 -11.614  1.00 18.41           C
ATOM   2665  CG2  ILE A 404     -30.989  55.807 -10.672  1.00 20.22           C
ATOM   2666  C    ILE A 404     -28.511  56.971  -9.939  1.00 19.52           C
ATOM   2667  O    ILE A 404     -28.605  57.966 -10.660  1.00 18.37           O
ATOM   2668  N    LYS A 405     -28.365  57.032  -8.610  1.00 20.09           N
ATOM   2669  CA   LYS A 405     -28.283  58.285  -7.867  1.00 19.99           C
ATOM   2670  CB   LYS A 405     -28.042  57.981  -6.397  1.00 21.23           C
ATOM   2671  CG   LYS A 405     -28.372  59.096  -5.422  1.00 21.73           C
ATOM   2672  CD   LYS A 405     -27.581  58.861  -4.138  1.00 23.52           C
ATOM   2673  CE   LYS A 405      28.256  59.429   2.904  1.00 23.62           C
ATOM   2674  NZ   LYS A 405     -28.161  60.902  -2.656  1.00 24.09           N
ATOM   2675  C    LYS A 405     -27.154  59.164  -8.417  1.00 20.11           C
ATOM   2676  O    LYS A 405     -27.348  60.356  -8.694  1.00 20.93           O
ATOM   2677  N    ALA A 406     -25.979  58.576  -8.601  1.00 19.31           N
ATOM   2678  CA   ALA A 406     -24.857  59.279  -9.222  1.00 18.43           C
ATOM   2679  CB   ALA A 406     -23.637  58.385  -9.292  1.00 17.93           C
ATOM   2680  C    ALA A 406     -25.178  59.829 -10.619  1.00 18.38           C
ATOM   2681  O    ALA A 406     -24.607  60.850 -11.025  1.00 17.95           O
ATOM   2682  N    ALA A 407     -26.074  59.163 -11.351  1.00 17.44           N
ATOM   2683  CA   ALA A 407     -26.318  59.550 -12.745  1.00 17.79           C
ATOM   2684  CB   ALA A 407     -26.447  58.324 -13.648  1.00 17.99           C
ATOM   2685  C    ALA A 407     -27.517  60.471 -12.904  1.00 17.57           C
ATOM   2686  O    ALA A 407      27.793  60.933  14.025  1.00 17.19           O
ATOM   2687  N    THR A 408     -28.203  60.734 -11.780  1.00 17.01           N
ATOM   2688  CA   THR A 408     -29.435  61.526 -11.747  1.00 16.93           C
ATOM   2689  CB   THR A 408     -30.699  60.622 -11.650  1.00 16.79           C
```

FIG. 22II

| | | | | | | | | | |
|---|---|---|---|---|---|---|---|---|---|
| ATOM | 2690 | CG1 | THR A 408 | -30.566 | 59.764 | -10.503 | 1.00 | 16.54 | O |
| ATOM | 2691 | CG2 | THR A 408 | -30.900 | 59.769 | -12.909 | 1.00 | 15.75 | C |
| ATOM | 2692 | C | THR A 408 | -29.442 | 62.559 | -10.594 | 1.00 | 17.73 | C |
| ATOM | 2693 | O | THR A 408 | -29.832 | 63.712 | -10.739 | 1.00 | 18.50 | O |
| ATOM | 2694 | N | ALA A 409 | -29.922 | 62.164 | -9.410 | 1.00 | 17.32 | N |
| ATOM | 2695 | CA | ALA A 409 | -30.057 | 63.099 | -8.265 | 1.00 | 17.33 | C |
| ATOM | 2696 | CB | ALA A 409 | -30.522 | 62.359 | -7.025 | 1.00 | 16.33 | C |
| ATOM | 2697 | C | ALA A 409 | -28.790 | 63.945 | -7.953 | 1.00 | 17.39 | C |
| ATOM | 2698 | O | ALA A 409 | -28.876 | 65.164 | -7.874 | 1.00 | 17.60 | O |
| ATOM | 2699 | N | ASN A 410 | -27.639 | 63.297 | -7.771 | 1.00 | 16.53 | N |
| ATOM | 2700 | CA | ASN A 410 | -26.373 | 64.004 | -7.619 | 1.00 | 16.87 | C |
| ATOM | 2701 | CB | ASN A 410 | -25.278 | 63.004 | -7.278 | 1.00 | 16.96 | C |
| ATOM | 2702 | CG | ASN A 410 | -25.395 | 62.446 | -5.878 | 1.00 | 17.21 | C |
| ATOM | 2703 | OD1 | ASN A 410 | -26.170 | 62.935 | -5.030 | 1.00 | 16.81 | O |
| ATOM | 2704 | ND2 | ASN A 410 | -24.592 | 61.414 | -5.617 | 1.00 | 16.87 | N |
| ATOM | 2705 | C | ASN A 410 | -25.859 | 64.811 | -8.830 | 1.00 | 17.31 | C |
| ATOM | 2706 | O | ASN A 410 | -25.087 | 65.734 | -8.657 | 1.00 | 17.55 | O |
| ATOM | 2707 | N | ALA A 411 | -26.237 | 64.438 | -10.052 | 1.00 | 17.48 | N |
| ATOM | 2708 | CA | ALA A 411 | -25.602 | 65.085 | -11.241 | 1.00 | 17.64 | C |
| ATOM | 2709 | CB | ALA A 411 | -26.193 | 64.301 | -12.494 | 1.00 | 17.69 | C |
| ATOM | 2710 | C | ALA A 411 | -25.692 | 66.546 | -11.406 | 1.00 | 18.39 | C |
| ATOM | 2711 | O | ALA A 411 | -24.707 | 67.170 | -11.819 | 1.00 | 19.07 | O |
| ATOM | 2712 | N | PRO A 412 | -26.865 | 67.165 | -11.115 | 1.00 | 18.70 | N |
| ATOM | 2713 | CA | PRO A 412 | -26.902 | 68.625 | -11.265 | 1.00 | 18.79 | C |
| ATOM | 2714 | CB | PRO A 412 | -28.353 | 69.003 | -10.912 | 1.00 | 19.60 | C |
| ATOM | 2715 | CG | PRO A 412 | -29.059 | 67.739 | -10.581 | 1.00 | 18.91 | C |
| ATOM | 2716 | CD | PRO A 412 | -28.226 | 66.607 | -11.120 | 1.00 | 19.07 | C |
| ATOM | 2717 | C | PRO A 412 | -25.910 | 69.416 | -10.395 | 1.00 | 18.42 | C |
| ATOM | 2718 | O | PRO A 412 | -25.637 | 70.580 | -10.706 | 1.00 | 19.84 | O |
| ATOM | 2719 | N | LEU A 413 | -25.367 | 68.815 | -9.334 | 1.00 | 17.98 | N |
| ATOM | 2720 | CA | LEU A 413 | -24.352 | 69.519 | -8.520 | 1.00 | 17.25 | C |
| ATOM | 2721 | CB | LEU A 413 | -23.886 | 68.675 | -7.338 | 1.00 | 16.47 | C |
| ATOM | 2722 | CG | LEU A 413 | -24.987 | 68.332 | -6.352 | 1.00 | 15.54 | C |
| ATOM | 2723 | CD1 | LEU A 413 | -24.662 | 66.978 | -5.782 | 1.00 | 14.92 | C |
| ATOM | 2724 | CD2 | LEU A 413 | -25.124 | 69.397 | -5.268 | 1.00 | 15.39 | C |
| ATOM | 2725 | C | LEU A 413 | -23.151 | 69.934 | -9.370 | 1.00 | 17.11 | C |
| ATOM | 2726 | O | LEU A 413 | -22.491 | 70.929 | -9.063 | 1.00 | 17.20 | O |
| ATOM | 2727 | N | SER A 414 | -22.924 | 69.206 | -10.464 | 1.00 | 16.59 | N |
| ATOM | 2728 | CA | SER A 414 | -21.811 | 69.474 | -11.346 | 1.00 | 16.44 | C |
| ATOM | 2729 | CB | SER A 414 | -21.712 | 68.367 | -12.378 | 1.00 | 16.65 | C |
| ATOM | 2730 | OG | SER A 414 | -22.840 | 68.423 | -13.216 | 1.00 | 17.62 | O |
| ATOM | 2731 | C | SER A 414 | -21.899 | 70.824 | -12.063 | 1.00 | 16.68 | C |
| ATOM | 2732 | O | SER A 414 | -20.960 | 71.204 | -12.783 | 1.00 | 17.19 | O |
| ATOM | 2733 | N | VAL A 415 | -23.022 | 71.528 | -11.909 | 1.00 | 15.79 | N |
| ATOM | 2734 | CA | VAL A 415 | -23.127 | 72.896 | -12.411 | 1.00 | 15.50 | C |
| ATOM | 2735 | CB | VAL A 415 | -23.988 | 72.990 | -13.708 | 1.00 | 15.83 | C |
| ATOM | 2736 | CG1 | VAL A 415 | -23.352 | 72.171 | -14.830 | 1.00 | 16.06 | C |
| ATOM | 2737 | CG2 | VAL A 415 | -25.412 | 72.490 | -13.500 | 1.00 | 16.16 | C |
| ATOM | 2738 | C | VAL A 415 | -23.494 | 73.895 | -11.305 | 1.00 | 15.93 | C |
| ATOM | 2739 | O | VAL A 415 | -23.735 | 75.071 | -11.560 | 1.00 | 15.89 | O |
| ATOM | 2740 | N | GLY A 416 | -23.472 | 73.445 | -10.055 | 1.00 | 16.46 | N |
| ATOM | 2741 | CA | GLY A 416 | -23.729 | 74.346 | -8.926 | 1.00 | 17.03 | C |
| ATOM | 2742 | C | GLY A 416 | -25.012 | 75.165 | -9.076 | 1.00 | 17.36 | C |
| ATOM | 2743 | O | GLY A 416 | -26.078 | 74.611 | -9.388 | 1.00 | 18.58 | O |
| ATOM | 2744 | N | PRO A 417 | -24.926 | 76.489 | -8.874 | 1.00 | 16.60 | N |
| ATOM | 2745 | CA | PRO A 417 | -26.126 | 77.337 | -8.957 | 1.00 | 15.95 | C |
| ATOM | 2746 | CB | PRO A 417 | -25.648 | 78.688 | -8.423 | 1.00 | 15.69 | C |
| ATOM | 2747 | CG | PRO A 417 | -24.165 | 78.653 | -8.548 | 1.00 | 15.80 | C |
| ATOM | 2748 | CD | PRO A 417 | -23.727 | 77.233 | -8.464 | 1.00 | 15.82 | C |
| ATOM | 2749 | C | PRO A 417 | -26.726 | 77.476 | -10.365 | 1.00 | 15.89 | C |
| ATOM | 2750 | O | PRO A 417 | -27.717 | 78.158 | -10.537 | 1.00 | 15.26 | O |
| ATOM | 2751 | N | GLN A 418 | -26.156 | 76.803 | -11.361 | 1.00 | 16.81 | N |
| ATOM | 2752 | CA | GLN A 418 | -26.713 | 76.849 | -12.733 | 1.00 | 17.21 | C |
| ATOM | 2753 | CB | GLN A 418 | -25.605 | 76.758 | -13.784 | 1.00 | 17.14 | C |
| ATOM | 2754 | CG | GLN A 418 | -24.669 | 77.952 | -13.792 | 1.00 | 17.45 | C |
| ATOM | 2755 | CD | GLN A 418 | -25.352 | 79.214 | -14.279 | 1.00 | 18.20 | C |
| ATOM | 2756 | OE1 | GLN A 418 | -26.029 | 79.218 | -15.320 | 1.00 | 18.91 | O |
| ATOM | 2757 | NE2 | GLN A 418 | -25.173 | 80.301 | -13.536 | 1.00 | 18.40 | N |
| ATOM | 2758 | C | GLN A 418 | -27.756 | 75.794 | -12.967 | 1.00 | 17.79 | C |
| ATOM | 2759 | O | GLN A 418 | -28.461 | 75.742 | -13.987 | 1.00 | 17.79 | O |
| ATOM | 2760 | N | ALA A 419 | -27.849 | 74.839 | -12.007 | 1.00 | 18.00 | N |
| ATOM | 2761 | CA | ALA A 419 | -28.804 | 73.741 | -12.074 | 1.00 | 17.89 | C |
| ATOM | 2762 | CB | ALA A 419 | -28.338 | 72.584 | -11.201 | 1.00 | 18.33 | C |
| ATOM | 2763 | C | ALA A 419 | -30.217 | 74.164 | -11.677 | 1.00 | 17.54 | C |
| ATOM | 2764 | O | ALA A 419 | -30.416 | 74.824 | -10.633 | 1.00 | 16.42 | O |
| ATOM | 2765 | N | PRO A 420 | -31.210 | 73.755 | -12.469 | 1.00 | 15.63 | N |
| ATOM | 2766 | CA | PRO A 420 | -32.694 | 73.877 | -12.346 | 1.00 | 16.36 | C |

FIG. 22JJ

```
ATOM   2767  CB  PRO A 420     -33.415  73.624 -13.333  1.00 16.43           C
ATOM   2768  CG  PRO A 420     -32.417  73.340 -14.431  1.00 16.49           C
ATOM   2769  CD  PRO A 420     -31.088  73.084 -13.797  1.00 16.49           C
ATOM   2770  C   PRO A 420     -32.889  72.791  11.015  1.00 15.99           C
ATOM   2771  O   PRO A 420     -32.015  71.976 -10.738  1.00 16.24           O
ATOM   2772  N   LEU A 421     -34.097  72.747 -10.471  1.00 15.42           N
ATOM   2773  CA  LEU A 421     -34.503  71.592  -9.680  1.00 15.09           C
ATOM   2774  CB  LEU A 421     -35.780  71.907  -8.918  1.00 15.31           C
ATOM   2775  CG  LEU A 421     -35.608  72.772  -7.666  1.00 15.92           C
ATOM   2776  CD1 LEU A 421     -36.970  73.152  -7.020  1.00 15.64           C
ATOM   2777  CD2 LEU A 421     -34.720  72.073  -6.624  1.00 16.08           C
ATOM   2778  C   LEU A 421     -34.726  70.402 -10.606  1.00 14.59           C
ATOM   2779  O   LEU A 421      35.735  70.288  11.185  1.00 15.05           O
ATOM   2780  N   THR A 422     -33.738  69.521 -10.750  1.00 13.91           N
ATOM   2781  CA  THR A 422     -33.834  68.430 -11.723  1.00 14.13           C
ATOM   2782  CB  THR A 422     -33.370  68.890 -13.136  1.00 13.94           C
ATOM   2783  OG1 THR A 422     -33.772  67.935 -14.113  1.00 13.37           O
ATOM   2784  CG2 THR A 422     -31.847  69.092 -13.224  1.00 13.91           C
ATOM   2785  C   THR A 422     -33.133  67.139 -11.274  1.00 14.53           C
ATOM   2786  O   THR A 422     -32.583  67.088 -10.183  1.00 14.68           O
ATOM   2787  N   GLY A 423     -33.207  66.090 -12.096  1.00 15.25           N
ATOM   2788  CA  GLY A 423     -32.597  64.795 -11.792  1.00 16.35           C
ATOM   2789  C   GLY A 423     -33.294  63.989 -10.696  1.00 17.57           C
ATOM   2790  O   GLY A 423     -32.715  63.041 -10.137  1.00 17.89           O
ATOM   2791  N   GLN A 424     -34.536  64.353 -10.378  1.00 17.77           N
ATOM   2792  CA  GLN A 424     -35.327  63.592  -9.418  1.00 18.44           C
ATOM   2793  CB  GLN A 424     -35.217  64.192  -8.019  1.00 18.31           C
ATOM   2794  CG  GLN A 424     -33.883  63.943  -7.347  1.00 19.04           C
ATOM   2795  CD  GLN A 424     -33.819  64.522  -5.956  1.00 19.75           C
ATOM   2796  OE1 GLN A 424     -34.584  64.136  -5.074  1.00 21.55           O
ATOM   2797  NE2 GLN A 424     -32.917  65.460  -5.753  1.00 19.70           N
ATOM   2798  C   GLN A 424     -36.789  63.533  -9.839  1.00 19.16           C
ATOM   2799  O   GLN A 424     -37.323  64.513 -10.369  1.00 18.97           O
ATOM   2800  N   LEU A 425     -37.436  62.391  -9.588  1.00 19.25           N
ATOM   2801  CA  LEU A 425      38.868  62.267   9.835  1.00 19.17           C
ATOM   2802  CB  LEU A 425     -39.279  60.839 -10.177  1.00 19.02           C
ATOM   2803  CG  LEU A 425     -38.640  60.256 -11.431  1.00 19.09           C
ATOM   2804  CD1 LEU A 425     -39.379  58.968 -11.780  1.00 18.77           C
ATOM   2805  CD2 LEU A 425      38.625  61.226  12.608  1.00 18.82           C
ATOM   2806  C   LEU A 425     -39.550  62.736  -8.602  1.00 19.63           C
ATOM   2807  O   LEU A 425     -39.794  61.974  -7.673  1.00 19.62           O
ATOM   2808  N   ARG A 426     -39.836  64.024  -8.608  1.00 21.02           N
ATOM   2809  CA  ARG A 426     -40.242  64.729  -7.426  1.00 21.99           C
ATOM   2810  CB  ARG A 426     -39.008  65.237  -6.705  1.00 23.54           C
ATOM   2811  CG  ARG A 426     -39.088  65.041  -5.213  1.00 26.71           C
ATOM   2812  CD  ARG A 426     -38.358  66.136  -4.466  1.00 27.76           C
ATOM   2813  NE  ARG A 426     -37.019  65.747  -4.065  1.00 29.29           N
ATOM   2814  CZ  ARG A 426     -36.427  66.204  -2.967  1.00 30.88           C
ATOM   2815  NH1 ARG A 426     -37.080  67.045  -2.172  1.00 29.69           N
ATOM   2816  NH2 ARG A 426     -35.191  65.817  -2.659  1.00 31.83           N
ATOM   2817  C   ARG A 426     -41.103  65.905  -7.847  1.00 22.56           C
ATOM   2818  O   ARG A 426     -40.881  66.522  -8.886  1.00 22.54           O
ATOM   2819  N   GLU A 427     -42.100  66.199  -7.033  1.00 23.87           N
ATOM   2820  CA  GLU A 427     -42.963  67.341  -7.235  1.00 24.61           C
ATOM   2821  CB  GLU A 427     -43.936  67.423  -6.067  1.00 26.92           C
ATOM   2822  CG  GLU A 427     -45.256  68.071  -6.425  1.00 30.37           C
ATOM   2823  CD  GLU A 427     -45.726  69.025  -5.355  1.00 33.22           C
ATOM   2824  OE1 GLU A 427     -44.857  69.767  -4.828  1.00 35.81           O
ATOM   2825  OE2 GLU A 427     -46.947  69.043  -5.058  1.00 32.53           O
ATOM   2826  C   GLU A 427     -42.155  68.648  -7.335  1.00 23.32           C
ATOM   2827  O   GLU A 427      41.293  68.926   6.507  1.00 21.60           O
ATOM   2828  N   GLY A 428     -42.440  69.441  -8.359  1.00 22.49           N
ATOM   2829  CA  GLY A 428     -41.772  70.721  -8.534  1.00 22.02           C
ATOM   2830  C   GLY A 428     -40.488  70.661  -9.343  1.00 21.76           C
ATOM   2831  O   GLY A 428     -40.058  71.678  -9.889  1.00 22.41           O
ATOM   2832  N   TYR A 429     -39.861  69.484  -9.467  1.00 21.09           N
ATOM   2833  CA  TYR A 429     -38.662  69.279 -10.229  1.00 20.65           C
ATOM   2834  CB  TYR A 429     -37.921  68.019  -9.818  1.00 19.96           C
ATOM   2835  CG  TYR A 429     -37.151  68.191  -8.549  1.00 19.67           C
ATOM   2836  CD1 TYR A 429     -35.785  67.950  -8.517  1.00 19.21           C
ATOM   2837  CE1 TYR A 429     -35.064  68.109  -7.355  1.00 19.32           C
ATOM   2838  CZ  TYR A 429     -35.711  68.516  -6.208  1.00 19.68           C
ATOM   2839  OH  TYR A 429     -34.989  68.682  -5.069  1.00 20.45           O
ATOM   2840  CE2 TYR A 429      37.067  68.777   6.203  1.00 19.57           C
ATOM   2841  CD2 TYR A 429     -37.784  68.609  -7.372  1.00 19.70           C
ATOM   2842  C   TYR A 429     -39.029  69.197 -11.686  1.00 20.84           C
ATOM   2843  O   TYR A 429     -40.170  69.868 -12.321  1.00 21.54           O
```

FIG. 22KK

```
ATOM   2844  N    GLU A 430     -38.043  69.462 -12.536  1.00 21.15           N
ATOM   2845  CA   GLU A 430     -38.209  69.485 -13.968  1.00 21.97           C
ATOM   2846  CB   GLU A 430     -36.910  69.925 -14.672  1.00 22.94           C
ATOM   2847  CG   GLU A 430     -36.587  71.383  14.479  1.00 24.44           C
ATOM   2848  CD   GLU A 430     -36.227  72.083 -15.781  1.00 26.71           C
ATOM   2849  OE1  GLU A 430     -35.306  71.636 -16.544  1.00 25.61           O
ATOM   2850  OE2  GLU A 430     -36.874  73.117 -16.020  1.00 27.49           O
ATOM   2851  C    GLU A 430     -38.618  68.139 -14.557  1.00 21.27           C
ATOM   2852  O    GLU A 430     -38.561  67.117 -14.180  1.00 22.79           O
ATOM   2853  N    ALA A 431     -39.555  68.149 -15.493  1.00 20.53           N
ATOM   2854  CA   ALA A 431     -40.042  66.921 -16.127  1.00 19.31           C
ATOM   2855  CB   ALA A 431     -41.355  67.200 -16.844  1.00 19.47           C
ATOM   2856  C    ALA A 431      39.066  66.241  17.080  1.00 19.13           C
ATOM   2857  O    ALA A 431     -39.345  66.111 -18.267  1.00 19.00           O
ATOM   2858  N    ASP A 432     -37.928  65.802 -16.569  1.00 17.59           N
ATOM   2859  CA   ASP A 432     -36.978  65.039 -17.382  1.00 17.59           C
ATOM   2860  CB   ASP A 432     -35.531  65.546 -17.200  1.00 18.24           C
ATOM   2861  CG   ASP A 432     -35.260  66.870 -17.914  1.00 19.11           C
ATOM   2862  OD1  ASP A 432     -36.176  67.457 -18.537  1.00 19.50           O
ATOM   2863  OD2  ASP A 432     -34.107  67.339 -17.847  1.00 19.42           O
ATOM   2864  C    ASP A 432     -37.087  63.567 -16.993  1.00 17.09           C
ATOM   2865  O    ASP A 432     -36.465  63.118 -16.030  1.00 17.23           O
ATOM   2866  N    VAL A 433     -37.873  62.815 -17.747  1.00 17.01           N
ATOM   2867  CA   VAL A 433     -38.303  61.492 -17.300  1.00 17.11           C
ATOM   2868  CB   VAL A 433     -39.802  61.505 -16.917  1.00 16.33           C
ATOM   2869  CG1  VAL A 433     -40.234  60.145 -16.425  1.00 16.06           C
ATOM   2870  CG2  VAL A 433     -40.103  62.556 -15.845  1.00 15.25           C
ATOM   2871  C    VAL A 433     -38.055  60.438 -18.368  1.00 17.94           C
ATOM   2872  O    VAL A 433     -38.304  60.690 -19.559  1.00 19.25           O
ATOM   2873  N    ILE A 434     -37.552  59.270 -17.966  1.00 17.92           N
ATOM   2874  CA   ILE A 434     -37.419  58.156 -18.925  1.00 18.49           C
ATOM   2875  CB   ILE A 434     -35.956  57.862 -19.348  1.00 18.54           C
ATOM   2876  CG1  ILE A 434     -35.128  57.379 -18.161  1.00 18.74           C
ATOM   2877  CD1  ILE A 434     -33.742  56.932 -18.553  1.00 19.40           C
ATOM   2878  CG2  ILE A 434      35.323  59.075  20.027  1.00 19.91           C
ATOM   2879  C    ILE A 434     -38.079  56.861 -18.465  1.00 18.46           C
ATOM   2880  O    ILE A 434     -38.224  56.596 -17.264  1.00 18.62           O
ATOM   2881  N    ALA A 435     -38.463  56.056 -19.445  1.00 18.66           N
ATOM   2882  CA   ALA A 435      39.149  54.798  19.192  1.00 18.44           C
ATOM   2883  CB   ALA A 435     -40.547  54.836 -19.788  1.00 17.19           C
ATOM   2884  C    ALA A 435     -38.350  53.653 -19.795  1.00 18.60           C
ATOM   2885  O    ALA A 435     -37.900  53.727 -20.947  1.00 18.30           O
ATOM   2886  N    LEU A 436     -38.199  52.595 -19.002  1.00 19.34           N
ATOM   2887  CA   LEU A 436     -37.484  51.400 -19.412  1.00 19.85           C
ATOM   2888  CB   LEU A 436     -36.306  51.161 -18.484  1.00 20.12           C
ATOM   2889  CG   LEU A 436     -35.045  52.014 -18.495  1.00 19.75           C
ATOM   2890  CD1  LEU A 436     -35.292  53.426 -18.018  1.00 20.02           C
ATOM   2891  CD2  LEU A 436     -34.060  51.350 -17.561  1.00 20.36           C
ATOM   2892  C    LEU A 436     -38.386  50.172 -19.375  1.00 21.15           C
ATOM   2893  O    LEU A 436     -39.365  50.108 -18.627  1.00 20.24           O
ATOM   2894  N    GLU A 437     -38.029  49.185 -20.185  1.00 23.58           N
ATOM   2895  CA   GLU A 437     -38.747  47.922 -20.261  1.00 25.44           C
ATOM   2896  CB   GLU A 437     -38.436  47.294 -21.598  1.00 27.82           C
ATOM   2897  CG   GLU A 437     -39.593  46.571 -22.256  1.00 31.51           C
ATOM   2898  CD   GLU A 437     -39.560  46.757 -23.766  1.00 33.01           C
ATOM   2899  OE1  GLU A 437     -39.478  47.121 -24.320  1.00 33.54           O
ATOM   2900  OE2  GLU A 437     -40.620  46.565 -24.390  1.00 32.82           O
ATOM   2901  C    GLU A 437     -38.276  46.968 -19.165  1.00 24.88           C
ATOM   2902  O    GLU A 437     -39.013  46.102 -18.718  1.00 23.29           O
ATOM   2903  N    GLU A 438     -37.034  47.158 -18.746  1.00 24.59           N
ATOM   2904  CA   GLU A 438      36.322  46.227  17.899  1.00 24.99           C
ATOM   2905  CB   GLU A 438     -35.055  45.801 -18.625  1.00 27.99           C
ATOM   2906  CG   GLU A 438     -35.265  44.858 -19.779  1.00 31.98           C
ATOM   2907  CD   GLU A 438     -34.890  43.472 -19.356  1.00 39.35           C
ATOM   2908  OE1  GLU A 438     -33.673  43.252 -19.109  1.00 41.29           O
ATOM   2909  OE2  GLU A 438     -35.809  42.620 -19.230  1.00 41.75           O
ATOM   2910  C    GLU A 438     -35.919  46.956 -16.629  1.00 23.17           C
ATOM   2911  O    GLU A 438     -35.674  48.164 -16.649  1.00 21.95           O
ATOM   2912  N    ASN A 439     -35.822  46.210 -15.537  1.00 21.48           N
ATOM   2913  CA   ASN A 439     -35.463  46.776 -14.242  1.00 20.21           C
ATOM   2914  CB   ASN A 439     -36.128  45.990 -13.112  1.00 19.85           C
ATOM   2915  CG   ASN A 439     -35.749  46.492 -11.727  1.00 19.14           C
ATOM   2916  OD1  ASN A 439     -35.947  45.787 -10.746  1.00 18.97           O
ATOM   2917  ND2  ASN A 439      35.219  47.706  11.638  1.00 18.97           N
ATOM   2918  C    ASN A 439     -33.950  46.835 -14.046  1.00 19.57           C
ATOM   2919  O    ASN A 439     -33.302  45.801 -13.820  1.00 19.51           O
ATOM   2920  N    PRO A 440     -33.386  48.053 -14.116  1.00 19.71           N
```

FIG. 22LL

| ATOM | 2921 | CA | PRO | A | 440 | -31.349 | 48.237 | -14.065 | 1.00 | 18.78 | C |
| ATOM | 2922 | CB | PRO | A | 440 | -31.778 | 49.716 | -14.460 | 1.00 | 18.72 | C |
| ATOM | 2923 | CG | PRO | A | 440 | -33.037 | 50.342 | -13.934 | 1.00 | 18.73 | C |
| ATOM | 2924 | CD | PRO | A | 440 | 34.087 | 49.337 | 14.289 | 1.00 | 18.62 | C |
| ATOM | 2925 | C | PRO | A | 440 | -31.347 | 47.943 | -12.706 | 1.00 | 19.29 | C |
| ATOM | 2926 | O | PRO | A | 440 | -30.134 | 47.839 | -12.610 | 1.00 | 19.85 | O |
| ATOM | 2927 | N | LEU | A | 441 | -32.177 | 47.820 | -11.673 | 1.00 | 19.68 | N |
| ATOM | 2928 | CA | LEU | A | 441 | -31.698 | 47.512 | -10.331 | 1.00 | 21.03 | C |
| ATOM | 2929 | CB | LEU | A | 441 | -32.769 | 47.039 | -9.279 | 1.00 | 20.56 | C |
| ATOM | 2930 | CG | LEU | A | 441 | -33.143 | 49.325 | -9.173 | 1.00 | 20.41 | C |
| ATOM | 2931 | CD1 | LEU | A | 441 | -34.336 | 49.555 | -8.266 | 1.00 | 19.35 | C |
| ATOM | 2932 | CD2 | LEU | A | 441 | -31.957 | 50.165 | -8.721 | 1.00 | 20.10 | C |
| ATOM | 2933 | C | LEU | A | 441 | 31.258 | 46.057 | 10.242 | 1.00 | 22.32 | C |
| ATOM | 2934 | O | LEU | A | 441 | -30.462 | 45.680 | -9.363 | 1.00 | 22.72 | O |
| ATOM | 2935 | N | GLU | A | 442 | -31.772 | 45.261 | -11.176 | 1.00 | 23.83 | N |
| ATOM | 2936 | CA | GLU | A | 442 | -31.444 | 43.849 | -11.299 | 1.00 | 25.79 | C |
| ATOM | 2937 | CB | GLU | A | 442 | -32.676 | 43.070 | -11.748 | 1.00 | 28.97 | C |
| ATOM | 2938 | CG | GLU | A | 442 | -33.726 | 43.029 | -10.652 | 1.00 | 32.39 | C |
| ATOM | 2939 | CD | GLU | A | 442 | -34.714 | 41.906 | -10.816 | 1.00 | 35.40 | C |
| ATOM | 2940 | OE1 | GLU | A | 442 | -34.293 | 40.778 | -11.146 | 1.00 | 39.94 | O |
| ATOM | 2941 | OE2 | GLU | A | 442 | -35.918 | 42.143 | -10.591 | 1.00 | 37.65 | O |
| ATOM | 2942 | C | GLU | A | 442 | -30.261 | 43.586 | -12.231 | 1.00 | 25.31 | C |
| ATOM | 2943 | O | GLU | A | 442 | -29.488 | 42.661 | -12.011 | 1.00 | 26.26 | O |
| ATOM | 2944 | N | ASP | A | 443 | -30.118 | 44.406 | -13.262 | 1.00 | 25.11 | N |
| ATOM | 2945 | CA | ASP | A | 443 | -28.970 | 44.340 | -14.160 | 1.00 | 24.36 | C |
| ATOM | 2946 | CB | ASP | A | 443 | -29.283 | 43.399 | -15.323 | 1.00 | 24.63 | C |
| ATOM | 2947 | CG | ASP | A | 443 | -28.135 | 43.276 | -16.317 | 1.00 | 26.21 | C |
| ATOM | 2948 | OD1 | ASP | A | 443 | -26.968 | 43.592 | -15.955 | 1.00 | 25.45 | O |
| ATOM | 2949 | OD2 | ASP | A | 443 | -28.416 | 42.850 | -17.470 | 1.00 | 26.53 | O |
| ATOM | 2950 | C | ASP | A | 443 | -28.593 | 45.754 | -14.650 | 1.00 | 23.53 | C |
| ATOM | 2951 | O | ASP | A | 443 | -29.269 | 46.329 | -15.519 | 1.00 | 21.97 | O |
| ATOM | 2952 | N | ILE | A | 444 | -27.536 | 46.315 | -14.081 | 1.00 | 22.08 | N |
| ATOM | 2953 | CA | ILE | A | 444 | -27.173 | 47.701 | -14.393 | 1.00 | 21.95 | C |
| ATOM | 2954 | CB | ILE | A | 444 | -26.085 | 48.248 | -13.431 | 1.00 | 21.68 | C |
| ATOM | 2955 | CG1 | ILE | A | 444 | 26.059 | 49.785 | 13.428 | 1.00 | 20.92 | C |
| ATOM | 2956 | CD1 | ILE | A | 444 | -27.209 | 50.455 | -12.693 | 1.00 | 20.32 | C |
| ATOM | 2957 | CG2 | ILE | A | 444 | -24.719 | 47.638 | -13.738 | 1.00 | 21.89 | C |
| ATOM | 2958 | C | ILE | A | 444 | -26.763 | 47.917 | -15.855 | 1.00 | 21.93 | C |
| ATOM | 2959 | O | ILE | A | 444 | 26.772 | 49.042 | 16.334 | 1.00 | 20.86 | O |
| ATOM | 2960 | N | LYS | A | 445 | -26.400 | 46.830 | -16.537 | 1.00 | 22.24 | N |
| ATOM | 2961 | CA | LYS | A | 445 | -26.005 | 46.864 | -17.942 | 1.00 | 23.04 | C |
| ATOM | 2962 | CB | LYS | A | 445 | -25.393 | 45.529 | -18.372 | 1.00 | 22.61 | C |
| ATOM | 2963 | CG | LYS | A | 445 | -24.041 | 45.209 | -17.777 | 1.00 | 22.42 | C |
| ATOM | 2964 | CD | LYS | A | 445 | -23.632 | 43.820 | -18.225 | 1.00 | 23.44 | C |
| ATOM | 2965 | CE | LYS | A | 445 | -22.464 | 43.296 | -17.420 | 1.00 | 24.14 | C |
| ATOM | 2966 | NZ | LYS | A | 445 | -21.680 | 42.300 | -18.201 | 1.00 | 25.15 | N |
| ATOM | 2967 | C | LYS | A | 445 | -27.209 | 47.128 | -18.835 | 1.00 | 23.63 | C |
| ATOM | 2968 | O | LYS | A | 445 | -27.040 | 47.310 | -20.041 | 1.00 | 24.95 | O |
| ATOM | 2969 | N | VAL | A | 446 | -28.396 | 47.106 | -18.250 | 1.00 | 23.29 | N |
| ATOM | 2970 | CA | VAL | A | 446 | -29.635 | 47.309 | -18.998 | 1.00 | 22.84 | C |
| ATOM | 2971 | CB | VAL | A | 446 | -30.839 | 47.268 | -18.032 | 1.00 | 22.92 | C |
| ATOM | 2972 | CG1 | VAL | A | 446 | -31.892 | 48.297 | -19.379 | 1.00 | 23.27 | C |
| ATOM | 2973 | CG2 | VAL | A | 446 | -31.425 | 45.864 | -18.002 | 1.00 | 23.41 | C |
| ATOM | 2974 | C | VAL | A | 446 | -29.556 | 48.603 | -19.819 | 1.00 | 22.23 | C |
| ATOM | 2975 | O | VAL | A | 446 | -29.989 | 48.668 | -20.966 | 1.00 | 22.00 | O |
| ATOM | 2976 | N | PHE | A | 447 | -29.927 | 49.612 | -19.242 | 1.00 | 21.95 | N |
| ATOM | 2977 | CA | PHE | A | 447 | -28.806 | 50.903 | -19.882 | 1.00 | 21.77 | C |
| ATOM | 2978 | CB | PHE | A | 447 | -28.184 | 51.895 | -18.897 | 1.00 | 20.11 | C |
| ATOM | 2979 | CG | PHE | A | 447 | -29.110 | 52.315 | -17.865 | 1.00 | 19.56 | C |
| ATOM | 2980 | CD1 | PHE | A | 447 | -28.817 | 52.024 | -16.476 | 1.00 | 20.04 | C |
| ATOM | 2981 | CE1 | PHE | A | 447 | 29.666 | 52.433 | 15.457 | 1.00 | 19.76 | C |
| ATOM | 2982 | CZ | PHE | A | 447 | -30.629 | 53.122 | -15.769 | 1.00 | 19.53 | C |
| ATOM | 2983 | CE2 | PHE | A | 447 | -31.134 | 53.405 | -17.092 | 1.00 | 18.88 | C |
| ATOM | 2984 | CD2 | PHE | A | 447 | -30.280 | 53.001 | -18.097 | 1.00 | 19.08 | C |
| ATOM | 2985 | C | PHE | A | 447 | -28.036 | 50.921 | -21.212 | 1.00 | 22.52 | C |
| ATOM | 2986 | O | PHE | A | 447 | -28.083 | 51.907 | -21.930 | 1.00 | 22.77 | O |
| ATOM | 2987 | N | GLN | A | 448 | -27.335 | 49.846 | -21.546 | 1.00 | 23.58 | N |
| ATOM | 2988 | CA | GLN | A | 448 | -26.452 | 49.870 | -22.712 | 1.00 | 25.90 | C |
| ATOM | 2989 | CB | GLN | A | 448 | -25.183 | 49.049 | -22.455 | 1.00 | 24.09 | C |
| ATOM | 2990 | CG | GLN | A | 448 | -24.266 | 49.664 | -21.399 | 1.00 | 23.54 | C |
| ATOM | 2991 | CD | GLN | A | 448 | -23.241 | 48.689 | -20.856 | 1.00 | 23.17 | C |
| ATOM | 2992 | OE1 | GLN | A | 448 | -22.702 | 47.880 | -21.595 | 1.00 | 23.52 | O |
| ATOM | 2993 | NE2 | GLN | A | 448 | -22.970 | 48.760 | -19.560 | 1.00 | 22.69 | N |
| ATOM | 2994 | C | GLN | A | 448 | 27.167 | 49.439 | 23.996 | 1.00 | 29.56 | C |
| ATOM | 2995 | O | GLN | A | 448 | -26.576 | 49.413 | -25.080 | 1.00 | 31.00 | O |
| ATOM | 2996 | N | GLU | A | 449 | -28.433 | 49.078 | -23.859 | 1.00 | 32.91 | N |
| ATOM | 2997 | CA | GLU | A | 449 | -29.288 | 49.813 | -25.001 | 1.00 | 34.52 | C |

FIG. 22MM

| | | | | | | | | |
|---|---|---|---|---|---|---|---|---|
| ATOM | 2998 | CB | GLU | A | 449 | -29.959 | 47.435 -24.869 | 1.00 36.00 | C |
| ATOM | 2999 | CG | GLU | A | 449 | -30.929 | 47.061 -25.993 | 1.00 41.43 | C |
| ATOM | 3000 | CD | GLU | A | 449 | -30.417 | 47.395 -27.399 | 1.00 43.93 | C |
| ATOM | 3001 | OE1 | GLU | A | 449 | -29.692 | 46.559 -27.979 | 1.00 45.18 | O |
| ATOM | 3002 | OE2 | GLU | A | 449 | -30.750 | 48.463 -27.935 | 1.00 42.81 | O |
| ATOM | 3003 | C | GLU | A | 449 | -30.280 | 49.973 -25.076 | 1.00 34.29 | C |
| ATOM | 3004 | O | GLU | A | 449 | -31.222 | 50.035 -24.274 | 1.00 34.25 | O |
| ATOM | 3005 | N | PRO | A | 450 | -30.070 | 50.925 -26.010 | 1.00 35.17 | N |
| ATOM | 3006 | CA | PRO | A | 450 | -31.001 | 52.059 -26.216 | 1.00 34.49 | C |
| ATOM | 3007 | CB | PRO | A | 450 | -30.382 | 52.846 -27.391 | 1.00 35.95 | C |
| ATOM | 3008 | CG | PRO | A | 450 | -29.298 | 51.976 -27.948 | 1.00 36.08 | C |
| ATOM | 3009 | CD | PRO | A | 450 | -28.869 | 51.038 -26.860 | 1.00 35.87 | C |
| ATOM | 3010 | C | PRO | A | 450 | -32.541 | 51.626 -26.544 | 1.00 33.31 | C |
| ATOM | 3011 | O | PRO | A | 450 | -33.386 | 52.376 -26.266 | 1.00 31.31 | O |
| ATOM | 3012 | N | LYS | A | 451 | -32.596 | 50.424 -27.108 | 1.00 32.08 | N |
| ATOM | 3013 | CA | LYS | A | 451 | -33.911 | 49.815 -27.305 | 1.00 30.47 | C |
| ATOM | 3014 | CB | LYS | A | 451 | -33.815 | 49.546 -28.161 | 1.00 33.87 | C |
| ATOM | 3015 | CG | LYS | A | 451 | -33.719 | 48.823 -29.667 | 1.00 38.53 | C |
| ATOM | 3016 | CD | LYS | A | 451 | -34.770 | 46.019 -30.450 | 1.00 43.33 | C |
| ATOM | 3017 | CE | LYS | A | 451 | -35.493 | 46.840 -31.533 | 1.00 41.69 | C |
| ATOM | 3018 | NZ | LYS | A | 451 | -36.971 | 48.598 -31.523 | 1.00 38.62 | N |
| ATOM | 3019 | C | LYS | A | 451 | -34.662 | 49.545 -25.996 | 1.00 27.77 | C |
| ATOM | 3020 | O | LYS | A | 451 | -35.885 | 49.512 -25.986 | 1.00 28.15 | O |
| ATOM | 3021 | N | ALA | A | 452 | -33.935 | 49.373 -24.894 | 1.00 25.39 | N |
| ATOM | 3022 | CA | ALA | A | 452 | -34.557 | 49.219 -23.575 | 1.00 23.76 | C |
| ATOM | 3023 | CB | ALA | A | 452 | -33.583 | 48.587 -22.587 | 1.00 23.40 | C |
| ATOM | 3024 | C | ALA | A | 452 | -35.142 | 50.523 -22.999 | 1.00 22.98 | C |
| ATOM | 3025 | O | ALA | A | 452 | -35.936 | 50.472 -22.050 | 1.00 23.12 | O |
| ATOM | 3026 | N | VAL | A | 453 | -34.740 | 51.678 -23.543 | 1.00 21.03 | N |
| ATOM | 3027 | CA | VAL | A | 453 | -35.353 | 52.954 -23.169 | 1.00 19.10 | C |
| ATOM | 3028 | CB | VAL | A | 453 | -34.349 | 54.122 -23.190 | 1.00 19.89 | C |
| ATOM | 3029 | CG1 | VAL | A | 453 | -35.016 | 55.412 -22.717 | 1.00 19.46 | C |
| ATOM | 3030 | CG2 | VAL | A | 453 | -33.112 | 53.810 -22.344 | 1.00 19.89 | C |
| ATOM | 3031 | C | VAL | A | 453 | -36.508 | 53.242 -24.124 | 1.00 18.41 | C |
| ATOM | 3032 | O | VAL | A | 453 | -36.291 | 53.540 -25.300 | 1.00 18.36 | O |
| ATOM | 3033 | N | THR | A | 454 | -37.738 | 53.160 -23.629 | 1.00 17.28 | N |
| ATOM | 3034 | CA | THR | A | 454 | -38.918 | 53.228 -24.494 | 1.00 16.19 | C |
| ATOM | 3035 | CB | THR | A | 454 | -40.033 | 52.308 -23.977 | 1.00 15.93 | C |
| ATOM | 3036 | OG1 | THR | A | 454 | -40.311 | 52.637 -22.605 | 1.00 15.89 | O |
| ATOM | 3037 | CG2 | THR | A | 454 | -39.614 | 50.857 -24.071 | 1.00 15.65 | C |
| ATOM | 3038 | C | THR | A | 454 | -39.498 | 54.624 -24.614 | 1.00 15.64 | C |
| ATOM | 3039 | O | THR | A | 454 | -40.016 | 54.965 -25.654 | 1.00 15.81 | O |
| ATOM | 3040 | N | HIS | A | 455 | -39.460 | 55.402 -23.531 | 1.00 15.47 | N |
| ATOM | 3041 | CA | HIS | A | 455 | -39.994 | 56.782 -23.520 | 1.00 15.39 | C |
| ATOM | 3042 | CB | HIS | A | 455 | -41.281 | 56.918 -22.693 | 1.00 14.50 | C |
| ATOM | 3043 | CG | HIS | A | 455 | -42.397 | 55.968 -23.080 | 1.00 14.07 | C |
| ATOM | 3044 | ND1 | HIS | A | 455 | -42.292 | 54.616 -22.985 | 1.00 13.83 | N |
| ATOM | 3045 | CE1 | HIS | A | 455 | -43.445 | 54.039 -23.362 | 1.00 13.47 | C |
| ATOM | 3046 | NE2 | HIS | A | 455 | -44.303 | 55.015 -23.707 | 1.00 13.92 | N |
| ATOM | 3047 | CD2 | HIS | A | 455 | -43.688 | 56.220 -23.539 | 1.00 13.96 | C |
| ATOM | 3048 | C | HIS | A | 455 | -39.976 | 57.747 -22.958 | 1.00 16.08 | C |
| ATOM | 3049 | O | HIS | A | 455 | -38.329 | 57.455 -21.924 | 1.00 16.21 | O |
| ATOM | 3050 | N | VAL | A | 456 | -38.822 | 58.895 -23.636 | 1.00 16.14 | N |
| ATOM | 3051 | CA | VAL | A | 456 | -38.006 | 60.003 -23.148 | 1.00 16.10 | C |
| ATOM | 3052 | CB | VAL | A | 456 | -36.694 | 60.164 -23.996 | 1.00 16.18 | C |
| ATOM | 3053 | CG1 | VAL | A | 456 | -35.847 | 61.335 -23.432 | 1.00 15.91 | C |
| ATOM | 3054 | CG2 | VAL | A | 456 | -35.897 | 58.868 -23.945 | 1.00 16.48 | C |
| ATOM | 3055 | C | VAL | A | 456 | -38.764 | 61.320 -23.155 | 1.00 16.33 | C |
| ATOM | 3056 | O | VAL | A | 456 | -39.228 | 61.782 -24.196 | 1.00 16.44 | O |
| ATOM | 3057 | N | TRP | A | 457 | -38.896 | 61.912 -21.973 | 1.00 17.27 | N |
| ATOM | 3058 | CA | TRP | A | 457 | -39.413 | 63.274 -21.825 | 1.00 17.62 | C |
| ATOM | 3059 | CB | TRP | A | 457 | -40.448 | 63.318 -20.727 | 1.00 17.22 | C |
| ATOM | 3060 | CG | TRP | A | 457 | -41.801 | 62.726 -21.051 | 1.00 17.34 | C |
| ATOM | 3061 | CD1 | TRP | A | 457 | -42.922 | 63.387 -21.553 | 1.00 17.08 | C |
| ATOM | 3062 | NE1 | TRP | A | 457 | -43.982 | 62.524 -21.678 | 1.00 17.05 | N |
| ATOM | 3063 | CE2 | TRP | A | 457 | -43.644 | 61.281 -21.263 | 1.00 17.22 | C |
| ATOM | 3064 | CD2 | TRP | A | 457 | -42.244 | 61.338 -20.833 | 1.00 17.08 | C |
| ATOM | 3065 | CE3 | TRP | A | 457 | -41.636 | 60.179 -20.355 | 1.00 17.03 | C |
| ATOM | 3066 | CZ3 | TRP | A | 457 | -42.396 | 59.997 -20.299 | 1.00 16.95 | C |
| ATOM | 3067 | CH2 | TRP | A | 457 | -43.738 | 58.962 -20.710 | 1.00 16.64 | C |
| ATOM | 3068 | CZ2 | TRP | A | 457 | -44.389 | 60.100 -21.204 | 1.00 17.23 | C |
| ATOM | 3069 | C | TRP | A | 457 | -38.301 | 64.206 -21.433 | 1.00 18.46 | C |
| ATOM | 3070 | O | TRP | A | 457 | -37.658 | 64.004 -20.395 | 1.00 19.58 | O |
| ATOM | 3071 | N | LYS | A | 458 | -38.045 | 65.232 -22.241 | 1.00 19.66 | N |
| ATOM | 3072 | CA | LYS | A | 458 | -37.191 | 66.330 -21.804 | 1.00 18.22 | C |
| ATOM | 3073 | CB | LYS | A | 458 | -36.691 | 66.609 -22.811 | 1.00 19.38 | C |
| ATOM | 3074 | CG | LYS | A | 458 | -35.108 | 67.657 -22.329 | 1.00 19.16 | C |

FIG. 22NN

```
ATOM   3075  CD   LYS A 458     -34.097  68.056 -23.402  1.00 19.97           C
ATOM   3076  CE   LYS A 458     -34.546  69.242 -24.244  1.00 19.71           C
ATOM   3077  NZ   LYS A 458     -33.367  69.735 -24.995  1.00 19.78           N
ATOM   3078  C    LYS A 458     -39.062  67.550 -21.629  1.00 18.66           C
ATOM   3079  O    LYS A 458     -38.737  67.980 -22.970  1.00 19.98           O
ATOM   3080  N    GLY A 459     -38.075  68.120 -20.421  1.00 18.32           N
ATOM   3081  CA   GLY A 459     -38.834  69.324 -20.155  1.00 19.02           C
ATOM   3082  C    GLY A 459     -40.309  69.113 -20.406  1.00 19.17           C
ATOM   3083  O    GLY A 459     -41.034  70.062 -20.731  1.00 20.13           O
ATOM   3084  N    GLY A 460     -40.765  67.869 -20.266  1.00 19.13           N
ATOM   3085  CA   GLY A 460     -42.197  67.576 -20.340  1.00 19.51           C
ATOM   3086  C    GLY A 460     -42.654  67.256 -21.742  1.00 20.61           C
ATOM   3087  O    GLY A 460     -43.836  67.007  21.974  1.00 20.67           O
ATOM   3088  N    LYS A 461     -41.709  67.256 -22.683  1.00 20.85           N
ATOM   3089  CA   LYS A 461     -42.010  66.966 -24.073  1.00 20.43           C
ATOM   3090  CB   LYS A 461     -41.433  68.113 -24.930  1.00 21.34           C
ATOM   3091  CG   LYS A 461     -41.653  67.971 -26.422  1.00 23.68           C
ATOM   3092  CD   LYS A 461     -41.131  69.199 -27.139  1.00 26.04           C
ATOM   3093  CE   LYS A 461     -41.473  69.155 -28.621  1.00 28.80           C
ATOM   3094  NZ   LYS A 461     -40.676  70.150 -29.397  1.00 28.93           N
ATOM   3095  C    LYS A 461     -41.466  65.608 -24.461  1.00 19.82           C
ATOM   3096  O    LYS A 461     -40.362  65.245 -24.065  1.00 19.40           O
ATOM   3097  N    LEU A 462     -42.255  64.830 -25.204  1.00 19.91           N
ATOM   3098  CA   LEU A 462     -41.805  63.513 -25.685  1.00 20.16           C
ATOM   3099  CB   LEU A 462     -42.978  62.593 -26.031  1.00 20.16           C
ATOM   3100  CG   LEU A 462     -43.536  61.714 -24.910  1.00 20.55           C
ATOM   3101  CD1  LEU A 462     -44.838  61.066 -25.353  1.00 19.48           C
ATOM   3102  CD2  LEU A 462     -42.532  60.666 -24.411  1.00 19.82           C
ATOM   3103  C    LEU A 462     -40.890  63.604 -26.890  1.00 19.78           C
ATOM   3104  O    LEU A 462     -41.286  64.119 -27.934  1.00 20.13           O
ATOM   3105  N    PHE A 463     -39.674  63.086 -26.723  1.00 19.69           N
ATOM   3106  CA   PHE A 463     -38.679  63.013 -27.791  1.00 19.33           C
ATOM   3107  CB   PHE A 463     -37.359  63.644 -27.348  1.00 19.03           C
ATOM   3108  CG   PHE A 463     -37.410  65.125 -27.311  1.00 18.43           C
ATOM   3109  CD1  PHE A 463      37.201  65.864  28.480  1.00 18.29           C
ATOM   3110  CE1  PHE A 463     -37.281  67.252 -28.454  1.00 19.26           C
ATOM   3111  CZ   PHE A 463     -37.587  67.908 -27.255  1.00 19.65           C
ATOM   3112  CE2  PHE A 463     -37.803  67.173 -26.983  1.00 18.13           C
ATOM   3113  CD2  PHE A 463      37.728  65.788  26.123  1.00 17.94           C
ATOM   3114  C    PHE A 463     -38.451  61.594 -28.261  1.00 19.04           C
ATOM   3115  O    PHE A 463     -37.838  61.390 -29.335  1.00 18.80           O
ATOM   3116  N    LYS A 464     -38.934  60.621 -27.509  1.00 18.17           N
ATOM   3117  CA   LYS A 464     -38.901  59.234 -27.928  1.00 17.61           C
ATOM   3118  CB   LYS A 464     -37.582  58.580 -27.526  1.00 17.44           C
ATOM   3119  CG   LYS A 464     -37.489  57.124 -27.922  1.00 17.44           C
ATOM   3120  CD   LYS A 464     -36.210  56.502 -27.423  1.00 17.69           C
ATOM   3121  CE   LYS A 464     -36.013  55.136 -28.039  1.00 17.52           C
ATOM   3122  NZ   LYS A 464     -34.842  54.512 -27.305  1.00 18.26           N
ATOM   3123  C    LYS A 464     -40.042  58.512 -27.254  1.00 18.40           C
ATOM   3124  O    LYS A 464     -40.282  58.718 -26.045  1.00 19.21           O
ATOM   3125  N    GLY A 465     -40.729  57.666 -28.030  1.00 18.14           N
ATOM   3126  CA   GLY A 465     -41.852  56.871 -27.544  1.00 18.95           C
ATOM   3127  C    GLY A 465     -42.694  56.290 -28.652  1.00 19.82           C
ATOM   3128  O    GLY A 465     -42.464  56.491 -29.832  1.00 19.51           O
ATOM   3129  N    PRO A 466     -43.689  55.439 -28.275  1.00 20.96           N
ATOM   3130  CA   PRO A 466     -44.556  54.840 -29.285  1.00 21.49           C
ATOM   3131  CB   PRO A 466     -45.650  54.166 -28.446  1.00 20.99           C
ATOM   3132  CG   PRO A 466     -44.997  53.862 -27.121  1.00 20.36           C
ATOM   3133  CD   PRO A 466     -43.980  54.928 -26.910  1.00 20.70           C
ATOM   3134  C    PRO A 466     -45.160  55.880 -30.246  1.00 22.44           C
ATOM   3135  O    PRO A 466      45.790  56.846  29.801  1.00 21.74           O
ATOM   3136  N    GLY A 467     -44.942  55.678 -31.550  1.00 22.57           N
ATOM   3137  CA   GLY A 467     -45.531  56.530 -32.576  1.00 22.91           C
ATOM   3138  C    GLY A 467     -44.943  57.922 -32.693  1.00 26.10           C
ATOM   3139  O    GLY A 467     -45.432  58.735 -33.465  1.00 25.07           O
ATOM   3140  N    ILE A 468     -43.892  58.201 -31.925  1.00 24.06           N
ATOM   3141  CA   ILE A 468     -43.214  59.491 -31.971  1.00 22.85           C
ATOM   3142  CB   ILE A 468     -42.778  59.919 -30.577  1.00 22.64           C
ATOM   3143  CG1  ILE A 468     -44.023  60.252 -29.757  1.00 23.05           C
ATOM   3144  CD1  ILE A 468     -43.829  59.996 -29.289  1.00 23.95           C
ATOM   3145  CG2  ILE A 468     -41.864  61.130 -30.663  1.00 22.31           C
ATOM   3146  C    ILE A 468     -42.014  59.493 -32.918  1.00 22.35           C
ATOM   3147  O    ILE A 468     -41.109  58.656 -32.812  1.00 21.71           O
ATOM   3148  N    GLY A 469      42.021  60.452  33.840  1.00 21.30           N
ATOM   3149  CA   GLY A 469     -41.007  60.546 -34.976  1.00 20.22           C
ATOM   3150  C    GLY A 469     -39.595  60.892 -34.418  1.00 19.54           C
ATOM   3151  O    GLY A 469     -39.360  61.242 -33.253  1.00 19.39           O
```

FIG. 22OO

| | | | | | | | | | |
|---|---|---|---|---|---|---|---|---|---|
| ATOM | 3152 | N | PRO | A 470 | -38.645 | 60.834 | -35.356 | 1.00 18.56 | N |
| ATOM | 3153 | CA | PRO | A 470 | -37.233 | 61.014 | -35.096 | 1.00 19.58 | C |
| ATOM | 3154 | CB | PRO | A 470 | -36.619 | 61.033 | -36.501 | 1.00 19.00 | C |
| ATOM | 3155 | CG | PRO | A 470 | 37.585 | 60.291 | 37.342 | 1.00 19.26 | C |
| ATOM | 3156 | CD | PRO | A 470 | -38.928 | 60.678 | -36.791 | 1.00 18.88 | C |
| ATOM | 3157 | C | PRO | A 470 | -36.924 | 62.321 | -34.392 | 1.00 18.25 | C |
| ATOM | 3158 | O | PRO | A 470 | -35.981 | 62.375 | -33.627 | 1.00 19.47 | O |
| ATOM | 3159 | N | TRP | A 471 | -37.698 | 63.368 | -34.654 | 1.00 17.98 | N |
| ATOM | 3160 | CA | TRP | A 471 | -37.404 | 64.673 | -34.066 | 1.00 19.10 | C |
| ATOM | 3161 | CB | TRP | A 471 | -37.365 | 65.747 | -35.156 | 1.00 16.79 | C |
| ATOM | 3162 | CG | TRP | A 471 | -36.333 | 65.404 | -36.196 | 1.00 15.64 | C |
| ATOM | 3163 | CD1 | TRP | A 471 | -36.565 | 64.858 | -37.454 | 1.00 15.33 | C |
| ATOM | 3164 | NE1 | TRP | A 471 | 35.356 | 64.626 | 38.093 | 1.00 14.98 | N |
| ATOM | 3165 | CE2 | TRP | A 471 | -34.314 | 64.996 | -37.312 | 1.00 15.22 | C |
| ATOM | 3166 | CD2 | TRP | A 471 | -34.871 | 65.480 | -36.056 | 1.00 15.25 | C |
| ATOM | 3167 | CE3 | TRP | A 471 | -34.002 | 65.917 | -35.061 | 1.00 14.57 | C |
| ATOM | 3168 | CZ3 | TRP | A 471 | -32.631 | 65.859 | -35.300 | 1.00 14.28 | C |
| ATOM | 3169 | CH2 | TRP | A 471 | -32.115 | 65.384 | -36.511 | 1.00 14.43 | C |
| ATOM | 3170 | CZ2 | TRP | A 471 | -32.940 | 64.950 | -37.543 | 1.00 14.99 | C |
| ATOM | 3171 | C | TRP | A 471 | -38.296 | 65.059 | -32.906 | 1.00 19.22 | C |
| ATOM | 3172 | O | TRP | A 471 | -38.276 | 66.204 | -32.478 | 1.00 20.12 | O |
| ATOM | 3173 | N | GLY | A 472 | -39.061 | 64.108 | -32.371 | 1.00 19.73 | N |
| ATOM | 3174 | CA | GLY | A 472 | -39.866 | 64.355 | -31.179 | 1.00 21.71 | C |
| ATOM | 3175 | C | GLY | A 472 | -41.279 | 64.741 | -31.559 | 1.00 23.22 | C |
| ATOM | 3176 | O | GLY | A 472 | -41.563 | 64.968 | -32.739 | 1.00 22.16 | O |
| ATOM | 3177 | N | GLU | A 473 | -42.164 | 64.832 | -30.569 | 1.00 25.09 | N |
| ATOM | 3178 | CA | GLU | A 473 | -43.588 | 65.055 | -30.867 | 1.00 29.31 | C |
| ATOM | 3179 | CB | GLU | A 473 | -44.490 | 64.848 | -29.646 | 1.00 29.86 | C |
| ATOM | 3180 | CG | GLU | A 473 | -44.379 | 65.921 | -28.577 | 1.00 31.63 | C |
| ATOM | 3181 | CD | GLU | A 473 | -45.120 | 65.541 | -27.313 | 1.00 33.39 | C |
| ATOM | 3182 | OE1 | GLU | A 473 | -46.275 | 65.044 | -27.415 | 1.00 32.86 | O |
| ATOM | 3183 | OE2 | GLU | A 473 | -44.533 | 65.730 | -26.221 | 1.00 32.23 | O |
| ATOM | 3184 | C | GLU | A 473 | -43.836 | 66.419 | -31.485 | 1.00 28.78 | C |
| ATOM | 3185 | O | GLU | A 473 | -43.126 | 67.398 | -31.172 | 1.00 28.80 | O |
| ATOM | 3186 | N | ASP | A 474 | -44.829 | 66.449 | 32.376 | 1.00 28.72 | N |
| ATOM | 3187 | CA | ASP | A 474 | -45.229 | 67.644 | -33.103 | 1.00 28.83 | C |
| ATOM | 3188 | CB | ASP | A 474 | -45.911 | 68.650 | -32.159 | 1.00 29.74 | C |
| ATOM | 3189 | CG | ASP | A 474 | -47.092 | 68.055 | -31.424 | 1.00 30.13 | C |
| ATOM | 3190 | OD1 | ASP | A 474 | 47.924 | 67.362 | 32.062 | 1.00 30.20 | O |
| ATOM | 3191 | OD2 | ASP | A 474 | -47.186 | 68.290 | -30.204 | 1.00 30.45 | O |
| ATOM | 3192 | C | ASP | A 474 | -44.041 | 68.308 | -33.766 | 1.00 28.71 | C |
| ATOM | 3193 | O | ASP | A 474 | -44.025 | 69.526 | -33.900 | 1.00 30.73 | O |
| ATOM | 3194 | N | ALA | A 475 | -43.036 | 67.518 | -34.144 | 1.00 28.11 | N |
| ATOM | 3195 | CA | ALA | A 475 | -41.872 | 68.030 | -34.852 | 1.00 26.55 | C |
| ATOM | 3196 | CB | ALA | A 475 | -40.845 | 66.937 | -35.030 | 1.00 24.82 | C |
| ATOM | 3197 | C | ALA | A 475 | -42.314 | 68.569 | -36.208 | 1.00 27.46 | C |
| ATOM | 3198 | O | ALA | A 475 | -43.092 | 67.929 | -36.904 | 1.00 26.63 | O |
| ATOM | 3199 | N | ARG | A 476 | -41.854 | 69.769 | -36.549 | 1.00 29.30 | N |
| ATOM | 3200 | CA | ARG | A 476 | -42.083 | 70.357 | -37.851 | 1.00 30.46 | C |
| ATOM | 3201 | CB | ARG | A 476 | -42.818 | 71.685 | -37.732 | 1.00 35.30 | C |
| ATOM | 3202 | CG | ARG | A 476 | -44.283 | 71.635 | -37.318 | 1.00 42.04 | C |
| ATOM | 3203 | CD | ARG | A 476 | -44.849 | 73.053 | -37.200 | 1.00 49.57 | C |
| ATOM | 3204 | NE | ARG | A 476 | -44.794 | 73.800 | -38.475 | 1.00 59.41 | N |
| ATOM | 3205 | CZ | ARG | A 476 | -43.857 | 74.695 | -38.826 | 1.00 60.23 | C |
| ATOM | 3206 | NH1 | ARG | A 476 | -42.852 | 75.035 | -38.063 | 1.00 59.83 | N |
| ATOM | 3207 | NH2 | ARG | A 476 | -43.926 | 75.291 | -40.016 | 1.00 59.16 | N |
| ATOM | 3208 | C | ARG | A 476 | -40.728 | 70.631 | -38.489 | 1.00 29.48 | C |
| ATOM | 3209 | O | ARG | A 476 | -39.754 | 70.884 | -37.784 | 1.00 28.50 | O |
| ATOM | 3210 | N | ASN | A 477 | -40.657 | 70.569 | -39.811 | 1.00 26.31 | N |
| ATOM | 3211 | CA | ASN | A 477 | -39.431 | 70.915 | -40.512 | 1.00 24.62 | C |
| ATOM | 3212 | CB | ASN | A 477 | 39.532 | 70.524 | 41.991 | 1.00 23.25 | C |
| ATOM | 3213 | CG | ASN | A 477 | -38.400 | 71.097 | -42.839 | 1.00 23.51 | C |
| ATOM | 3214 | OD1 | ASN | A 477 | -37.382 | 71.591 | -42.324 | 1.00 23.12 | O |
| ATOM | 3215 | ND2 | ASN | A 477 | -38.563 | 71.019 | -44.156 | 1.00 23.19 | N |
| ATOM | 3216 | C | ASN | A 477 | -39.171 | 72.411 | -40.362 | 1.00 24.00 | C |
| ATOM | 3217 | O | ASN | A 477 | -39.846 | 73.215 | -41.021 | 1.00 24.94 | O |
| ATOM | 3218 | N | PRO | A 478 | -38.182 | 72.796 | -39.521 | 1.00 26.24 | N |
| ATOM | 3219 | CA | PRO | A 478 | -37.962 | 74.212 | -39.211 | 1.00 23.91 | C |
| ATOM | 3220 | CB | PRO | A 478 | -36.894 | 74.167 | -38.125 | 1.00 23.47 | C |
| ATOM | 3221 | CG | PRO | A 478 | -36.120 | 72.936 | -38.439 | 1.00 23.59 | C |
| ATOM | 3222 | CD | PRO | A 478 | -37.151 | 71.943 | -38.901 | 1.00 23.82 | C |
| ATOM | 3223 | C | PRO | A 478 | -37.456 | 75.052 | -40.385 | 1.00 24.32 | C |
| ATOM | 3224 | O | PRO | A 478 | -37.280 | 76.249 | -40.231 | 1.00 24.82 | O |
| ATOM | 3225 | N | PHE | A 479 | 37.232 | 74.450 | 41.544 | 1.00 24.70 | N |
| ATOM | 3226 | CA | PHE | A 479 | -36.716 | 75.207 | -42.682 | 1.00 26.14 | C |
| ATOM | 3227 | CB | PHE | A 479 | -35.544 | 74.460 | -43.331 | 1.00 23.69 | C |
| ATOM | 3228 | CG | PHE | A 479 | -34.401 | 75.236 | -42.386 | 1.00 22.26 | C |

FIG. 22PP

| ATOM | 3229 | CD1 | PHE | A | 479 | -33.566 | 75.300 | -42.013 | 1.00 | 21.48 | C |
| ATOM | 3230 | CE1 | PHE | A | 479 | -32.519 | 75.103 | -41.124 | 1.00 | 20.91 | C |
| ATOM | 3231 | CZ | PHE | A | 479 | -32.306 | 73.636 | -40.989 | 1.00 | 29.51 | C |
| ATOM | 3232 | CE2 | PHE | A | 479 | -33.136 | 72.777 | -40.942 | 1.00 | 20.71 | C |
| ATOM | 3233 | CD2 | PHE | A | 479 | -34.178 | 72.981 | -41.829 | 1.00 | 21.12 | C |
| ATOM | 3234 | C | PHE | A | 479 | -37.771 | 75.651 | -43.697 | 1.00 | 29.86 | C |
| ATOM | 3235 | O | PHE | A | 479 | -37.439 | 76.237 | -44.726 | 1.00 | 29.37 | O |
| ATOM | 3236 | N | LEU | A | 480 | -39.038 | 75.355 | -43.400 | 1.00 | 37.76 | N |
| ATOM | 3237 | CA | LEU | A | 480 | -40.198 | 75.906 | -44.145 | 1.00 | 43.79 | C |
| ATOM | 3238 | CB | LEU | A | 480 | -41.154 | 74.802 | -44.562 | 1.00 | 40.84 | C |
| ATOM | 3239 | CG | LEU | A | 480 | -40.561 | 73.434 | -44.879 | 1.00 | 42.11 | C |
| ATOM | 3240 | CD1 | LEU | A | 480 | -41.541 | 72.347 | -44.458 | 1.00 | 41.30 | C |
| ATOM | 3241 | CD2 | LEU | A | 480 | -40.177 | 73.298 | -46.350 | 1.00 | 40.48 | C |
| ATOM | 3242 | C | LEU | A | 480 | -40.932 | 76.917 | -43.267 | 1.00 | 51.30 | C |
| ATOM | 3243 | O | LEU | A | 480 | -41.863 | 77.612 | -43.719 | 1.00 | 56.65 | O |
| ATOM | 3244 | OXT | LEU | A | 480 | -40.613 | 77.044 | -42.068 | 1.00 | 54.04 | O |

SEQUENCE LISTING

<160> NUMBER OF SEQ ID NOS: 42

<210> SEQ ID NO 1

<211> LENGTH: 480
<212> TYPE: PRT
<213> ORGANISM: Aspergillus niger

<400> SEQUENCE: 1

Met Val Arg Arg Ile Ala Ser Ala Thr Pro Met Val Gln Ser Pro Met
1               5                   10                  15

Ser Pro Leu Gly Thr Thr Tyr Cys Val Arg Pro Asn Pro Val Ser Leu
            20                  25                  30

Asn Leu Gln Arg Arg Pro Leu Val Ile Ala Ser Thr Asp Glu Ala Lys
        35                  40                  45

Val Thr Ile Ile Tyr Ala Gly Leu Leu Ile Pro Gly Asp Gly Glu Pro
    50                  55                  60

Leu Arg Asn Ala Ala Leu Val Ile Ser Asp Lys Ile Ile Ala Phe Val
65                  70                  75                  80

Gly Ser Glu Ala Asp Ile Pro Lys Lys Tyr Leu Arg Ser Thr Gln Ser
                85                  90                  95

Thr His Arg Val Pro Val Leu Met Pro Gly Leu Trp Asp Cys His Met
            100                 105                 110

His Phe Gly Gly Asp Asp Asp Tyr Tyr Asn Asp Tyr Thr Ser Gly Leu
        115                 120                 125

Ala Thr His Pro Ala Ser Ser Gly Ala Arg Leu Ala Arg Gly Cys Trp
    130                 135                 140

Glu Ala Leu Gln Asn Gly Tyr Thr Ser Tyr Arg Asp Leu Ala Gly Tyr
145                 150                 155                 160

Gly Cys Glu Val Ala Lys Ala Ile Asn Asp Gly Thr Ile Val Gly Pro
                165                 170                 175

Asn Val Tyr Ser Ser Gly Ala Ala Leu Ser Gln Thr Ala Gly His Gly
            180                 185                 190

Asp Ile Phe Ala Leu Pro Ala Gly Glu Val Leu Gly Ser Tyr Gly Val
        195                 200                 205

Met Asn Pro Arg Pro Gly Tyr Trp Gly Ala Gly Pro Leu Cys Ile Ala
    210                 215                 220

Asp Gly Val Glu Glu Val Arg Arg Ala Val Arg Leu Gln Ile Arg Arg
225                 230                 235                 240

Gly Ala Lys Val Ile Lys Val Met Ala Ser Gly Gly Val Met Ser Arg
                245                 250                 255

Asp Asp Asn Pro Asn Phe Ala Gln Phe Ser Pro Glu Glu Leu Lys Val
            260                 265                 270

Ile Val Glu Glu Ala Ala Arg Gln Asn Arg Ile Val Ser Ala His Val
        275                 280                 285

His Gly Lys Ala Gly Ile Met Ala Ala Ile Lys Ala Gly Cys Lys Ser
    290                 295                 300

Leu Glu His Val Ser Tyr Ala Asp Glu Glu Val Trp Glu Leu Met Lys
305                 310                 315                 320

Glu Lys Gly Ile Leu Tyr Val Ala Thr Arg Ser Val Ile Glu Ile Phe
                325                 330                 335

Leu Ala Ser Asn Gly Glu Gly Leu Val Lys Glu Ser Trp Ala Lys Leu
            340                 345                 350

Gln Ala Leu Ala Asp Ser His Leu Lys Ala Tyr Gln Gly Ala Ile Lys
        355                 360                 365

Ala Gly Val Thr Ile Ala Leu Gly Thr Asp Thr Ala Pro Gly Gly Pro
    370                 375                 380

Thr Ala Leu Glu Leu Gln Phe Ala Val Glu Arg Gly Gly Met Thr Pro

```
                385                 390                 395                 400
Leu Glu Ala Ile Lys Ala Ala Thr Ala Asn Ala Pro Leu Ser Val Gly
                    405                 410                 415

Pro Gln Ala Pro Leu Thr Gly Gln Leu Arg Glu Gly Tyr Glu Ala Asp
                420                 425                 430

Val Ile Ala Leu Glu Glu Asn Pro Leu Glu Asp Ile Lys Val Phe Gln
            435                 440                 445

Glu Pro Lys Ala Val Thr His Val Trp Lys Gly Lys Leu Phe Lys
        450                 455                 460

Gly Pro Gly Ile Gly Pro Trp Gly Glu Asp Ala Arg Asn Pro Phe Leu
465                 470                 475                 480

<210> SEQ ID NO 2
<211> LENGTH: 1443
<212> TYPE: DNA
<213> ORGANISM: Aspergillus niger

<400> SEQUENCE: 2
atggtccgcc gaattgcttc agctacacct atggtgcaat cgcccatgtc gccattgggc      60
acaacatact gcgtccgtcc taatcctgtt tcactgaatc ttcaaagaag acctctcgtg     120
atcgcatcaa cagacgaggc caaggtcact ataatatatg ccggactatt aatccctggc     180
gacggagaac ctctgcgcaa tgctgcccta gtcatcagcg ataagatcat cgcgttcgtt     240
ggatccgaag ccgacatccc taagaaatac ctccggtcca cgcagtctac tcatcgtgtc     300
cccgtgctca tgcctggttt gtgggattgc cacatgcatt ttggcgggga tgacgattat     360
tacaacgatt atacatctgg tctggccact catccagcat catcaggtgc tcgactagcc     420
cgtggttgct gggaagcatt gcagaatggg tatacatcct accgcgacct agccggatac     480
gggtgcgagg tcgcaaaggc gatcaatgat ggcactatcg ttggtccaaa cgtgtactcg     540
tctggcgctg cactcagtca gacagctgga cacggcgata tcttcgctct tccagcaggc     600
gaagtactgg ggagttatgg agtaatgaac ccacgccctg gtactggggg gcagggccg      660 ctatgtatcg ccgatggcgt agaggaggtc cgacgagcag tgaggttgca gatccgtcgc     720
ggtgcaaagg ttatcaaagt gatggcctct gggggtgtca tgtcgcgaga cgataatccc     780
aactttgcac agttctctcc agaagaactg aaggtgatag tggaagaggc ggctcgacag     840
aaccggatcg tttctgcaca tgtgcatggc aaggcgggga ttatggctgc atcaaagca      900 ggctgcaaga gtctggagca tgtgtcttat gctgacgagg aggtctggga gctcatgaaa     960
gagaagggaa ttttgtatgt ggccacacgc tcggttattg aaatctttct ggctagtaat    1020
ggagaggggt tggtgaaaga gtcgtgggcc aagttgcagg cccttgccga ttcgcatttg    1080
aaagcttatc agggagctat taggcgggt gttaccattg cgttgggaac ggataccgcc    1140
cccggtggtc ctaccgcact tgagttgcag tttgccgtcg agagaggagg tatgacgccg    1200
ttggaggcca tcaaagccgc aactgcgaac gctcccctgt cagttggtcc acaagcaccg    1260
ttgacgggtc agcttcgcga ggggtatgag gcagatgtga ttgcgttgga ggagaatcca    1320
ttggaggaca tcaaagtctt tcaggagccg aaggcagtta cccacgtctg gaaggggggg    1380
aaactgttca aggtccaggt attggtccg tggggagaag atgcacgtaa tcctttctg     1440 tag                                                                  1443

<210> SEQ ID NO 3
<211> LENGTH: 438
<212> TYPE: PRT
```

<213> ORGANISM: Aspergillus niger

<400> SEQUENCE: 3

```
Ser Thr Asp Glu Ala Lys Val Thr Ile Ile Tyr Ala Gly Leu Leu Ile
1               5                   10                  15

Pro Gly Asp Gly Glu Pro Leu Arg Asn Ala Ala Leu Val Ile Ser Asp
            20                  25                  30

Lys Ile Ile Ala Phe Val Gly Ser Glu Ala Asp Ile Pro Lys Lys Tyr
        35                  40                  45

Leu Arg Ser Thr Gln Ser Thr His Arg Val Pro Val Leu Met Pro Gly
    50                  55                  60

Leu Trp Asp Cys His Met His Phe Gly Asp Asp Tyr Tyr Asn
65                  70                  75                  80

Asp Tyr Thr Ser Gly Leu Ala Thr His Pro Ala Ser Ser Gly Ala Arg
                85                  90                  95

Leu Ala Arg Gly Cys Trp Glu Ala Leu Gln Asn Gly Tyr Thr Ser Tyr
            100                 105                 110

Arg Asp Leu Ala Gly Tyr Gly Cys Glu Val Ala Lys Ala Ile Asn Asp
        115                 120                 125

Gly Thr Ile Val Gly Pro Asn Val Tyr Ser Ser Gly Ala Ala Leu Ser
130                 135                 140

Gln Thr Ala Gly His Gly Asp Ile Phe Ala Leu Pro Ala Gly Glu Val
145                 150                 155                 160

Leu Gly Ser Tyr Gly Val Met Asn Pro Arg Pro Gly Tyr Trp Gly Ala
                165                 170                 175

Gly Pro Leu Cys Ile Ala Asp Gly Val Glu Glu Val Arg Ala Val
            180                 185                 190

Arg Leu Gln Ile Arg Arg Gly Ala Lys Val Ile Lys Val Met Ala Ser
        195                 200                 205

Gly Gly Val Met Ser Arg Asp Asp Asn Pro Asn Phe Ala Gln Phe Ser
210                 215                 220

Pro Glu Glu Leu Lys Val Ile Val Glu Glu Ala Ala Arg Gln Asn Arg
225                 230                 235                 240

Ile Val Ser Ala His Val His Gly Lys Ala Gly Ile Met Ala Ala Ile
                245                 250                 255

Lys Ala Gly Cys Lys Ser Leu Glu His Val Ser Tyr Ala Asp Glu Glu
            260                 265                 270

Val Trp Glu Leu Met Lys Glu Lys Gly Ile Leu Tyr Val Ala Thr Arg
        275                 280                 285

Ser Val Ile Glu Ile Phe Leu Ala Ser Asn Gly Glu Gly Leu Val Lys
290                 295                 300

Glu Ser Trp Ala Lys Leu Gln Ala Leu Ala Asp Ser His Leu Lys Ala
305                 310                 315                 320

Tyr Gln Gly Ala Ile Lys Ala Gly Val Thr Ile Ala Leu Gly Thr Asp
                325                 330                 335

Thr Ala Pro Gly Gly Pro Thr Ala Leu Glu Leu Gln Phe Ala Val Glu
            340                 345                 350

Arg Gly Gly Met Thr Pro Leu Glu Ala Ile Lys Ala Ala Thr Ala Asn
        355                 360                 365

Ala Pro Leu Ser Val Gly Pro Gln Ala Pro Leu Thr Gly Gln Leu Arg
370                 375                 380

Glu Gly Tyr Glu Ala Asp Val Ile Ala Leu Glu Glu Asn Pro Leu Glu
385                 390                 395                 400
```

```
Asp Ile Lys Val Phe Gln Glu Pro Lys Ala Val Thr His Val Trp Lys
                405                 410                 415
Gly Gly Lys Leu Phe Lys Gly Pro Gly Ile Gly Pro Trp Gly Glu Asp
            420                 425                 430
Ala Arg Asn Pro Phe Leu
        435

<210> SEQ ID NO 4
<211> LENGTH: 486
<212> TYPE: PRT
<213> ORGANISM: Aspergillus niger

<400> SEQUENCE: 4

Met Val Arg Arg Ile Ala Ser Ala Thr Pro Met Val Gln Ser Pro Met
1               5                   10                  15
Ser Pro Leu Gly Thr Thr Tyr Cys Val Arg Pro Asn Pro Val Ser Leu
            20                  25                  30
Asn Leu Gln Arg Arg Pro Leu Val Ile Ala Ser Thr Asp Glu Ala Lys
        35                  40                  45
Val Thr Ile Ile Tyr Ala Gly Leu Leu Ile Pro Gly Asp Gly Glu Pro
    50                  55                  60
Leu Arg Asn Ala Ala Leu Val Ile Ser Asp Lys Ile Ile Ala Phe Val
65                  70                  75                  80
Gly Ser Glu Ala Asp Ile Pro Lys Lys Tyr Leu Arg Ser Thr Gln Ser
                85                  90                  95
Thr His Arg Val Pro Val Leu Met Pro Gly Leu Trp Asp Cys His Met
            100                 105                 110
His Phe Gly Gly Asp Asp Asp Tyr Tyr Asn Asp Tyr Thr Ser Gly Leu
        115                 120                 125
Ala Thr His Pro Ala Ser Ser Gly Ala Arg Leu Ala Arg Gly Cys Trp
    130                 135                 140
Glu Ala Leu Gln Asn Gly Tyr Thr Ser Tyr Arg Asp Leu Ala Gly Tyr
145                 150                 155                 160
Gly Cys Glu Val Ala Lys Ala Ile Asn Asp Gly Thr Ile Val Gly Pro
                165                 170                 175
Asn Val Tyr Ser Ser Gly Ala Ala Leu Ser Gln Thr Ala Gly His Gly
            180                 185                 190
Asp Ile Phe Ala Leu Pro Ala Gly Glu Val Leu Gly Ser Tyr Gly Val
        195                 200                 205
Met Asn Pro Arg Pro Gly Tyr Trp Gly Ala Gly Pro Leu Cys Ile Ala
    210                 215                 220
Asp Gly Val Glu Glu Val Arg Arg Ala Val Arg Leu Gln Ile Arg Arg
225                 230                 235                 240
Gly Ala Lys Val Ile Lys Val Met Ala Ser Gly Val Met Ser Arg
                245                 250                 255
Asp Asp Asn Pro Asn Phe Ala Gln Phe Ser Pro Glu Glu Leu Lys Val
            260                 265                 270
Ile Val Glu Glu Ala Ala Arg Gln Asn Arg Ile Val Ser Ala His Val
        275                 280                 285
His Gly Lys Ala Gly Ile Met Ala Ala Ile Lys Ala Gly Cys Lys Ser
    290                 295                 300
Leu Glu His Val Ser Tyr Ala Asp Glu Glu Val Trp Glu Leu Met Lys
305                 310                 315                 320
Glu Lys Gly Ile Leu Tyr Val Ala Thr Arg Ser Val Ile Glu Ile Phe
                325                 330                 335
```

```
Leu Ala Ser Asn Gly Glu Gly Leu Val Lys Glu Ser Trp Ala Lys Leu
                340                 345                 350

Gln Ala Leu Ala Asp Ser His Leu Lys Ala Tyr Gln Gly Ala Ile Lys
            355                 360                 365

Ala Gly Val Thr Ile Ala Leu Gly Thr Asp Thr Ala Pro Gly Gly Pro
    370                 375                 380

Thr Ala Leu Glu Leu Gln Phe Ala Val Glu Arg Gly Gly Met Thr Pro
385                 390                 395                 400

Leu Glu Ala Ile Lys Ala Ala Thr Ala Asn Ala Pro Leu Ser Val Gly
                405                 410                 415

Pro Gln Ala Pro Leu Thr Gly Gln Leu Arg Glu Gly Tyr Glu Ala Asp
            420                 425                 430

Val Ile Ala Leu Glu Glu Asn Pro Leu Glu Asp Ile Lys Val Phe Gln
    435                 440                 445

Glu Pro Lys Ala Val Thr His Val Trp Lys Gly Gly Lys Leu Phe Lys
450                 455                 460

Gly Pro Gly Ile Gly Pro Trp Gly Glu Asp Ala Arg Asn Pro Phe Leu
465                 470                 475                 480

His His His His His His
            485

<210> SEQ ID NO 5
<211> LENGTH: 420
<212> TYPE: PRT
<213> ORGANISM: Aspergillus niger

<400> SEQUENCE: 5

Met His Arg Pro Leu Thr Asp Ser Thr Phe Tyr Arg Ile Asn Ala Asp
1               5                   10                  15

Ile Leu Ile Pro Gly Arg Gly Ala Pro Ile Ala Arg Gly Ala Val Val
            20                  25                  30

Trp Lys Ser Lys Thr Ile Leu Tyr Ser Gly Pro Gln His Glu Val Pro
        35                  40                  45

Val Glu Tyr Gln Asp Ala Val Thr Thr His Val Pro Val Ala Met Pro
50                  55                  60

Gly Met Trp Asp Cys His Ile His Phe Leu Gly Ala Thr Ala Ala Thr
65                  70                  75                  80

Met Asp Ser Ile Val Asn Thr Pro Gln Ala Leu Ala Gly Ala Arg Ser
                85                  90                  95

Val Pro Tyr Leu Tyr Ala Thr Ile Ile Ala Gly Phe Thr Ser Val Arg
            100                 105                 110

Glu Val Gly Gly Tyr Gly Cys Glu Leu Ala Lys Val Ile Asp Glu Gly
        115                 120                 125

Arg Ile Pro Gly Pro Thr Ile Tyr Gly Ala His Ser Ala Ile Ser Met
    130                 135                 140

Thr Ala Gly His Gly Asp Val His Gly Val Asn Pro Glu Gly Leu Arg
145                 150                 155                 160

Asp Leu Cys Thr His Gly Leu Pro Leu Thr Ile Ala Asp Gly Val Pro
                165                 170                 175

Glu Cys Leu Gln Ala Val Arg Lys Gln Leu Arg His Gly Ala Arg Ile
            180                 185                 190

Ile Lys Val Cys Ala Ser Gly Gly Val Val Ser Ala Ile Asp Asp Pro
        195                 200                 205

Gln His Gln Glu Phe Ser Phe Glu Glu Leu Lys Ala Ile Val Asp Glu
```

```
                210                 215                 220
Ala Ala Arg Ala Arg Arg Val Ala Ala His Cys His Gly Lys Ala
225                 230                 235                 240

Gly Ile Met Asn Ala Leu Arg Ala Gly Cys Arg Thr Ile Glu His Gly
                245                 250                 255

Ser Tyr Leu Asp Glu Glu Ala Ile Asp Leu Met Leu Glu Lys Gly Ala
                260                 265                 270

Met Leu Val Ala Thr Arg Ser Val Ile Glu Ser Gly Leu Ala Met Arg
                275                 280                 285

Asp Leu Phe Thr Pro Gly Ser Tyr Gln Lys Leu Leu Glu Val Ala Asp
                290                 295                 300

Thr His Lys Arg Ala Tyr Glu Leu Ala Val Arg Arg Gly Val Pro Ile
305                 310                 315                 320

Ala Leu Gly Thr Asp Gln Phe Ile Ser Ser Asp Asn Pro Ala Leu Gly
                325                 330                 335

Tyr Gly Arg Asn Gly Lys Glu Leu Val Tyr Ala Val Ala Ala Gly Met
                340                 345                 350

Thr Pro Leu Ala Ala Ile Glu Ala Ala Thr Ala Asn Gly Pro Leu Thr
                355                 360                 365

Leu Gly Asp Gln Ala Pro Lys Ser Gly Gln Leu Arg Glu Gly Phe Asp
                370                 375                 380

Ala Asp Ile Ile Ala Leu Thr Ala Asn Pro Leu Glu Asn Ile Ile Val
385                 390                 395                 400

Val Ser Asp Pro Lys Asn Val Thr His Val Trp Arg Tyr Gly Lys Leu
                405                 410                 415

Val Lys Ser Asn
            420

<210> SEQ ID NO 6
<211> LENGTH: 419
<212> TYPE: PRT
<213> ORGANISM: Aspergillus flavus

<400> SEQUENCE: 6

Met His Arg Met Leu Thr Asp Asp Arg Leu Tyr Arg Val Asp Ala Asp
1               5                   10                  15

Leu Leu Ile Pro Gly Lys Gly Asp Pro Ile Pro His Gly Ala Val Val
                20                  25                  30

Trp Gln Cys Lys Thr Ile Arg Tyr Ala Gly Pro Arg Ser Glu Val Pro
            35                  40                  45

Ala Glu Phe Gln Gly Ala Thr Thr His Val Pro Val Val Met Pro
        50                  55                  60

Gly Met Trp Asp Cys His Ile His Phe Leu Gly Ala Thr Ala Ala Thr
65                  70                  75                  80

Met Asn Ala Ile Val Asp Thr Pro Gln Ala Leu Ala Gly Ala Arg Ser
                85                  90                  95

Val Pro Asp Leu His Ala Thr Val Met Ala Gly Phe Thr Ser Val Arg
                100                 105                 110

Glu Val Gly Gly Tyr Gly Cys Asp Leu Ala Lys Ala Val Gly Glu Gly
            115                 120                 125

Arg Ile Pro Gly Pro Asn Ile Tyr Ser Ser His Ser Ala Ile Ser Met
        130                 135                 140

Thr Ala Gly His Gly Asp Val His Gly Val His Arg Asp Ser Leu Leu
145                 150                 155                 160
```

Asp Leu Cys Ala His Gly Leu Pro Leu Thr Ile Ala Asp Gly Val Pro
            165                 170                 175

Glu Cys Leu Leu Ala Val Arg Lys Gln Leu Arg Arg Gly Ala Thr Val
        180                 185                 190

Ile Lys Val Cys Ala Ser Gly Val Val Ser Ala Ile Asp Asp Pro
        195                 200                 205

Gln His Gln Glu Phe Ser Phe Glu Glu Leu Lys Ala Ile Val Asp Glu
    210                 215                 220

Ala Ala Arg Ala Arg Arg Val Val Ala Ala His Cys His Gly Lys Ala
225                 230                 235                 240

Gly Ile Met Asn Ala Leu Arg Ala Gly Cys Arg Thr Ile Glu His Gly
                245                 250                 255

Ser Phe Leu Asp Glu Glu Ala Val Glu Leu Met Lys Glu Lys Gly Ala
            260                 265                 270

Ile Leu Val Ala Thr Arg Ser Val Ile Glu Ser Gly Leu Ala Met Lys
        275                 280                 285

Asp Leu Phe Thr Pro Ser Ser Tyr Gln Lys Leu Leu Glu Val Ala Asp
    290                 295                 300

Ala His Arg Lys Ala Tyr Gln Leu Ala Ile Ser Arg Gly Val Thr Ile
305                 310                 315                 320

Ala Leu Gly Thr Asp Gln Phe Ile Ser Ser Asp Asn Pro Met Ile Gly
                325                 330                 335

Tyr Gly Arg Asn Gly His Glu Val Arg Tyr Ala Val Asp Ala Gly Leu
            340                 345                 350

Thr Pro Leu Ala Ala Ile Glu Ala Ala Thr Ala Asn Gly Pro Leu Thr
        355                 360                 365

Leu Gly Tyr Gln Ala Pro Gln Ser Gly Gln Leu Lys Glu Gly Tyr Asp
    370                 375                 380

Ala Asp Ile Ile Ala Val Arg Glu Asn Pro Leu Glu Asn Val Ala Val
385                 390                 395                 400

Leu Ser Asn Ser Lys Asn Val Thr His Val Trp Arg Gly Gly Met Leu
                405                 410                 415

Ile Lys Ser

<210> SEQ ID NO 7
<211> LENGTH: 405
<212> TYPE: PRT
<213> ORGANISM: Talaromyces stipitatus

<400> SEQUENCE: 7

Met Arg Val Arg Leu Lys Ala Ser Ile Leu Ile Pro Gly Arg Gly Glu
1               5                   10                  15

Pro Ile Glu Asn Gly Ala Leu Ile Ile Asp Gly Pro Lys Ile Ala Trp
            20                  25                  30

Val Gly Gln Gln Ser Ala Ile Pro Thr Lys Tyr Gln Asp Val Asp Phe
        35                  40                  45

Glu Tyr Leu Pro Val Leu Met Pro Gly Leu Trp Asp Cys His Thr His
    50                  55                  60

Phe Met Gly Leu Ser Asp Glu Ser Asp Thr Met Gln Ala Val Phe Gly
65                  70                  75                  80

Ser Ala Ala Leu Ala Gly Ala Ile Ala Ala Lys Glu Leu Glu Thr Ala
                85                  90                  95

Leu Met Ala Gly Phe Thr Thr Ile Arg Glu Val Gly Gly Val Ala Gly
            100                 105                 110

```
Glu Ile Tyr Pro Ala Ile Lys Asn Gly Thr Ile Val Gly Pro Asn Val
            115                 120                 125

Tyr Ser Ser Ile Gly Val Leu Gly Ile Thr Gly Gly His Ser Asp Val
130                 135                 140

His Asn Val Pro Ile Glu Ala Val Ile Ala Lys Arg Asn Glu Gly Thr
145                 150                 155                 160

Phe Val Val Cys Asp Gly Val Ser Asp Cys Ile Lys Thr Val Arg Met
            165                 170                 175

Met Val Arg Arg Gly Ala Thr Leu Ile Lys Ile Cys Ala Thr Gly Gly
            180                 185                 190

Val Gly Ser Leu Leu Asp Asp Pro Glu Asp Ala Gln Phe Ser Pro Glu
        195                 200                 205

Glu Ile Lys Ala Ile Val Asp Glu Ala Ala Arg Ser Lys Arg Ile Val
        210                 215                 220

Ala Ala His Cys His Gly Lys Glu Gly Ile Met Asn Ala Leu His Ala
225                 230                 235                 240

Gly Val His Thr Ile Glu His Gly Ser Tyr Leu Asp Glu Glu Val Ala
            245                 250                 255

Ala Leu Met Lys Glu Lys Lys Ala Leu Phe Val Ser Thr Arg Leu Ile
            260                 265                 270

Ile Glu Glu Gly Leu Lys Asn Pro Lys Leu Trp Pro Pro Ser Ser Tyr
        275                 280                 285

Arg Lys Leu Thr Lys Ile Ser Glu Ala His Lys Lys Ala Tyr Ala Leu
        290                 295                 300

Ala Val Lys Ser Gly Val Lys Ile Val Leu Gly Thr Asp Trp Thr Ala
305                 310                 315                 320

Gly Glu Asn Gly Lys Glu Leu Ala Tyr Ala Val Glu Ala Gly Met Ser
            325                 330                 335

Pro Leu Glu Ala Ile Glu Ala Ser Thr Ala Arg Cys Pro Glu Thr Leu
            340                 345                 350

Gly Ser His Phe Ala Pro Leu Ser Gly Gln Leu Lys Glu Gly Tyr Gly
        355                 360                 365

Ala Asp Val Ile Ala Val Ala Ser Asn Pro Leu Asp Asp Ile Lys Val
        370                 375                 380

Leu Gly Glu Pro Lys Asn Ile Thr His Val Trp Lys Gly Gly Lys Leu
385                 390                 395                 400

Tyr Lys Gly Thr Leu
            405

<210> SEQ ID NO 8
<211> LENGTH: 440
<212> TYPE: PRT
<213> ORGANISM: Neurospora crassa

<400> SEQUENCE: 8

Met Gln Ile Lys Val Thr Leu Pro Asn Asp Thr Ile Asn Arg Asp Ser
1               5                   10                  15

Val Asp Asp Arg Ala Ser Tyr His Gly Ile Leu Ala Asp Val Leu Ile
            20                  25                  30

Pro Gly Arg Gly Glu Pro Leu Lys Asn Gly Ala Leu Val Val Lys Asp
        35                  40                  45

Ser Val Ile Glu Trp Val Gly Pro Ser Asp Glu Ile Pro Ser Glu Tyr
    50                  55                  60

Ser Ser Ile Arg Val Ser Arg Val Pro Val Leu Met Pro Gly Met Trp
65                  70                  75                  80
```

```
Asp Val His Thr His Tyr Glu Gly Val Gly Val Ala Gln Gly Ile Arg
                85                  90                  95

Glu Ser Met Lys Pro Phe Leu Pro Gly Thr Ala Thr Leu Ile Gly Ala
            100                 105                 110

Val Ile Val Asp Asp Met Arg Arg Thr Leu Met Ala Gly Phe Thr Ser
        115                 120                 125

Ile Arg Glu Leu Gly Gly Tyr Ala Gly Asp Val Ala Pro Ala Ile Asp
    130                 135                 140

Met Gly Ala Ile Val Gly Pro His Val Tyr Ala Ala Met Ser Leu Leu
145                 150                 155                 160

Ser Ile Thr Gly Gly His Gly Asp Leu His Asp Val Pro Leu Arg Thr
                165                 170                 175

Val Leu Asp Ala Cys Ala Asn Gly Ser Ser Ser Cys Phe Leu Cys Asp
            180                 185                 190

Gly Val Asp Gly Cys Ile Asn Ala Val Arg Gln Gln Ile Arg Arg Gly
        195                 200                 205

Ala Lys Val Ile Lys Val Cys Ser Thr Gly Gly Val Leu Ser Leu Asn
    210                 215                 220

Asp Gln Pro Glu Asp Thr Gln Phe Ser Ala Glu Glu Leu Arg Ala Ile
225                 230                 235                 240

Val Gln Glu Ala Lys Arg Ser Ser Arg Val Val Ala Ala His Ala His
                245                 250                 255

Gly Lys Pro Gly Ile Met Ala Ala Leu Asp Ala Gly Val Lys Ser Ile
            260                 265                 270

Glu His Gly Ser Phe Leu Asp Glu Val Ala Ala Lys Met Lys Glu
        275                 280                 285

Lys Asp Ala Ile Leu Val Pro Thr Arg His Val Glu Gly Met Ala
290                 295                 300

Ala Asn Asn Asp Asp Leu Asp Pro Arg Gln Arg Ala Lys Leu Glu Arg
305                 310                 315                 320

Thr Met Gln Leu Ser Arg Asp Ser Ile Lys Leu Ala His Arg Met Gly
                325                 330                 335

Val Lys Ile Ala Leu Gly Thr Asp Thr Phe Arg Ser Asp Lys Asn His
            340                 345                 350

Ala Val Ala His Gly Lys Asn Ala Met Glu Leu Arg Tyr Ala Ile Glu
        355                 360                 365

Ala Gly Met Thr Pro Leu Gln Ala Ile Glu Met Ala Thr Ala Thr Pro
    370                 375                 380

Pro Glu Thr Leu Gly Pro Gln Ala Arg Lys Ser Gly Gln Leu Lys Ala
385                 390                 395                 400

Gly Tyr Asp Ala Asp Leu Ile Ala Ile Ser Ser Asn Pro Leu Glu Asp
                405                 410                 415

Ile Glu Ile Leu Ile Asp Pro Asp Asn Ile Thr His Val Trp Lys Gly
            420                 425                 430

Gly Val Leu Phe Lys Cys Pro Gln
        435                 440

<210> SEQ ID NO 9
<211> LENGTH: 413
<212> TYPE: PRT
<213> ORGANISM: Streptomyces roseosporus

<400> SEQUENCE: 9

Met Glu His Arg Ile Asp Ala Asp Leu Leu Ile Pro Gly Ala Gly Glu
```

```
1               5                   10                  15
Pro Thr Val Asn Gly Ser Val Val His Ala Asp Gly Arg Ile Arg Phe
                20                  25                  30

Ala Gly Pro Thr Ala Glu Leu Pro Arg Glu His Arg Ala Leu Glu Pro
                35                  40                  45

Thr Arg Val Ala Thr Leu Leu Pro Gly Leu Trp Asp Cys His Val His
            50                  55                  60

Phe Ala Gly Ile Arg Gly Arg Val Ser Thr Glu Glu Leu Met Leu Thr
65                  70                  75                  80

Pro Glu Thr Leu Ala Val Val Arg Ser Val Lys Asp Ala Glu Thr Ala
                85                  90                  95

Leu Arg Ala Gly Phe Thr Ser Val Arg Asp Met Gly Gly His Gly Cys
                100                 105                 110

Val Leu Ala Glu Ala Val Arg Glu Gly Thr Phe Thr Gly Pro Asn Ile
                115                 120                 125

Tyr Ser Ala Asn Gln Val Ile Gly Gln Thr Gly Gly His Ser Asp Ala
            130                 135                 140

His Arg Leu Pro Tyr Arg Trp Val Thr Asp Pro Cys Arg Ser Gly Gly
145                 150                 155                 160

Thr Leu Arg Ile Ala Asp Gly Val Asp Glu Cys Val Arg Ala Val Arg
                165                 170                 175

Leu Gln Leu Arg Ala Gly Ala Glu Leu Ile Lys Ile Cys Thr Ser Gly
                180                 185                 190

Gly Val Leu Ser Glu Val Asp Asn Pro Val His Gln Gln Tyr Arg Ser
            195                 200                 205

Glu Glu Leu Asn Ala Ile Val Thr Glu Ala Ala Arg Ala Asp Arg Val
210                 215                 220

Val Ala Ala His Cys His Gly Arg Ala Gly Ile Leu Ala Ala Ile Asp
225                 230                 235                 240

Ala Gly Cys His Thr Val Glu His Gly Thr Glu Ile Asp Glu Arg Thr
                245                 250                 255

Ala Asp Leu Met Ala Glu Arg Gly Met Thr Leu Val Pro Thr Arg Thr
                260                 265                 270

Ile Tyr Glu Ala Phe Arg Gln Asp Val Ala Ala Leu Pro Pro Ala Trp
            275                 280                 285

Arg Asp Arg Phe Ala Leu Met Ala Glu Arg His Leu Thr Ala Ile Gly
290                 295                 300

Ile Ala His Arg Ala Gly Val Thr Ile Ala Leu Gly Thr Asp Leu Gly
305                 310                 315                 320

Thr Ser Asp Arg Gly Gly Pro Leu Ser Trp Gly His Gly Ser Glu
                325                 330                 335

Phe Ala His Leu Val Ser Ala Gly Leu Ser Pro Leu Glu Ala Ile Lys
                340                 345                 350

Ala Ala Thr Ala His Gly Pro Gly Thr Leu Gly Pro Arg Ala Pro Arg
            355                 360                 365

Ser Gly Arg Leu Glu Ala Gly Tyr Asp Ala Asp Leu Leu Ala Val Asp
370                 375                 380

Gly Asn Pro Leu Ala Asp Ile Thr Val Leu Ala Asp Pro Asp Arg Ile
385                 390                 395                 400

Thr Arg Val Trp Lys Ser Gly Glu Pro Val Pro Ser Gly
                405                 410

<210> SEQ ID NO 10
```

```
<211> LENGTH: 407
<212> TYPE: PRT
<213> ORGANISM: Thermotoga lettingae

<400> SEQUENCE: 10
```

| | | | | | | | | | | | | | | |
|---|---|---|---|---|---|---|---|---|---|---|---|---|---|---|
|Glu|Ser|Ala|Val|Phe|Ile|Glu|Gly|Ala|Arg|Ile|Leu|Ala|Val|Glu|Lys|
|1| | | |5| | | | |10| | | | |15|
|Ile|Lys|Arg|Ser|Gln|Ile|Pro|Ser|Gly|Phe|Thr|Gln|Ile|Asp|Leu|Gln|
| | | |20| | | | |25| | | | |30| | |
|Gly|Arg|Tyr|Leu|Met|Pro|Gly|Leu|Ile|Asp|Ala|His|Leu|His|Leu|Ala|
| | | |35| | | | |40| | | | |45| | |
|Gly|Met|Arg|Ser|Gly|Asp|Met|Val|Lys|Glu|His|Leu|Leu|Thr|Pro|Tyr|
| |50| | | | |55| | | | |60| | | | |
|Glu|Thr|Leu|Val|Ala|Arg|Thr|Val|Thr|Asp|Leu|Lys|Ser|Leu|Ile|Glu|
|65| | | | |70| | | | |75| | | | |80|
|Ala|Gly|Phe|Thr|Thr|Val|Val|Asp|Ala|Gly|Gly|Ser|Ile|Ala|Ile|Asn|
| | | | |85| | | | |90| | | | |95| |
|Leu|Lys|Lys|Ala|Ile|Gln|Glu|Gly|Thr|Ile|Ala|Gly|Pro|Arg|Ile|Val|
| | | |100| | | | |105| | | | |110| | |
|Ala|Ala|Gly|His|Ser|Leu|Ser|Gln|Thr|Phe|Gly|His|Gly|Asp|Glu|His|
| | | |115| | | | |120| | | | |125| | |
|Phe|Leu|Pro|Ile|Asp|Tyr|Val|Asp|Pro|Arg|Thr|Ser|Lys|Phe|Lys|Gly|
| |130| | | | |135| | | | |140| | | | |
|Gly|Phe|Gly|Ser|Leu|Ile|Cys|Asp|Gly|Val|Ala|Glu|Cys|Ile|Lys|Ala|
|145| | | | |150| | | | |155| | | | |160|
|Ala|Arg|Tyr|Ala|Leu|Arg|Cys|Gly|Ala|Asp|Phe|Ile|Lys|Ile|Met|Ala|
| | | | |165| | | | |170| | | | |175| |
|Thr|Gly|Gly|Val|Leu|Ser|Glu|Arg|Asp|Arg|Pro|Glu|Tyr|Thr|Gln|Phe|
| | | |180| | | | |185| | | | |190| | |
|Thr|Val|Glu|Glu|Ile|Lys|Ala|Ile|Val|Glu|Glu|Ala|Asn|His|Ala|Arg|
| | |195| | | | |200| | | | |205| | | |
|Lys|Phe|Val|His|Ala|His|Ala|Gln|Gly|Lys|Asp|Gly|Ile|Met|Asn|Ala|
| |210| | | | |215| | | | |220| | | | |
|Leu|Leu|Gly|Gly|Val|Lys|Val|Ile|Ala|His|Ala|Ile|Tyr|Ile|Asp|Asp|
|225| | | | |230| | | | |235| | | | |240|
|Glu|Ser|Cys|Lys|Leu|Ala|Lys|Glu|Lys|Asn|Ala|Ile|Ile|Val|Pro|Thr|
| | | |245| | | | |250| | | | |255| | |
|Leu|Ser|Ile|Val|Glu|His|Leu|Ile|Ile|His|Gly|Lys|Gln|Ile|Gly|Ala|
| | |260| | | | |265| | | | |270| | | |
|Pro|Glu|Trp|Gly|Leu|Arg|Lys|Ser|Glu|Glu|Val|Tyr|Lys|Ile|His|Val|
| | |275| | | | |280| | | | |285| | | |
|Glu|Asn|Ile|Lys|Lys|Ala|Tyr|Glu|His|Gly|Val|Lys|Ile|Ala|Ala|Gly|
| |290| | | | |295| | | | |300| | | | |
|Thr|Asp|Phe|Ile|Gly|Gly|Thr|Lys|Ala|Phe|Lys|His|Gly|Glu|Asn|Ala|
|305| | | | |310| | | | |315| | | | |320|
|Leu|Glu|Ile|Leu|Leu|Leu|Val|Asp|Lys|Ile|Gly|Met|Lys|Pro|Glu|Gln|
| | | | |325| | | | |330| | | | |335| |
|Ala|Leu|Leu|Ser|Ala|Thr|Lys|Val|Ala|Ala|Glu|Ala|Ala|Gly|Leu|Ser|
| | | |340| | | | |345| | | | |350| | |
|Gln|Leu|Val|Gly|Ser|Ile|Asp|Lys|Gly|Lys|Leu|Ala|Asp|Leu|Leu|Ile|
| | |355| | | | |360| | | | |365| | | |
|Val|Glu|Asp|Asn|Pro|Leu|Ser|Asn|Val|Lys|Ile|Leu|Met|Asp|His|Ser|
| |370| | | | |375| | | | |380| | | | |
|Lys|Ile|Ser|Ala|Val|Phe|Lys|Glu|Gly|Ile|Leu|Phe|Lys|Asp|Lys|Ile|

```
                385                 390                 395                 400
Gly Leu Glu Lys Tyr Phe Asn
                            405

<210> SEQ ID NO 11
<211> LENGTH: 408
<212> TYPE: PRT
<213> ORGANISM: Salinispora arenicola

<400> SEQUENCE: 11

Met Ile Glu Cys Ile Glu Ala Asp Gln Leu Ile Pro Gly Arg Gly Glu
1               5                   10                  15

Pro Val Ala Asn Ala Val Val Leu Glu Asp Ala Thr Ile Arg Tyr
            20                  25                  30

Ala Gly Pro Ala Glu His Ala Pro Lys Val Ala Glu Ala Arg Arg Ser
        35                  40                  45

Arg Ala His Thr Val Leu Pro Gly Leu Trp Asp Ser His Val His Phe
    50                  55                  60

Met Gly Leu Arg Ser Ala Asp Val Gly Ile Leu Pro Gln Glu Pro Val
65                  70                  75                  80

Ala Leu Arg Ala Ala Arg Thr Val Ala Asp Leu Arg Ala Ala Leu Asp
                85                  90                  95

Ala Gly Phe Thr Ser Val Arg Glu Val Gly Gly Leu Gly Leu Asp Leu
            100                 105                 110

Ala Arg Ala Val Glu Glu Gly Thr Ala Val Gly Pro Ser Val Tyr Ala
        115                 120                 125

Ala Gly Cys Ala Leu Ser Thr Thr Gly Gly His Gly Asp Leu His Ser
    130                 135                 140

Tyr Pro Leu Ala Trp Met Glu Glu Phe Ala Arg His Gly Gly Glu Leu
145                 150                 155                 160

Arg Leu Ala Asp Gly Glu Ala Glu Cys Val Arg Ala Val Arg Glu Gln
                165                 170                 175

Leu Arg Arg Asn Ala Lys Val Ile Lys Val Tyr Ala Ser Gly Gly Val
            180                 185                 190

Leu Ser Glu Val Asp His Pro Ile His Arg Gln Phe Thr Asp Arg Glu
        195                 200                 205

Leu Arg Ala Ile Val Glu Val Ala Gly Leu Ala Asp Arg Val Val Ala
    210                 215                 220

Ala His Cys His Gly Lys Pro Gly Met Met Ala Ala Ile Glu Ala Gly
225                 230                 235                 240

Val Arg Thr Ile Glu His Gly Thr Tyr Leu Asp Glu Glu Val Ala Ala
                245                 250                 255

Ala Met Arg Glu Thr Gly Ala Ile Leu Val Thr Thr Arg Thr Ile Met
            260                 265                 270

Gln Glu Leu Ile Asp Ser Arg Ala Leu Pro Pro Tyr Ala Leu Arg Lys
        275                 280                 285

Leu Glu Ser Ile Val Asp Arg His Ala Glu Ala Ile Val Ile Ala Arg
    290                 295                 300

Glu Ser Gly Val Arg Ile Ala Ala Gly Thr Asp Val Ala Leu Thr Gly
305                 310                 315                 320

Ala Glu Leu Pro Asp Ser Trp Gly Arg Asn Gly Arg Glu Leu Pro Leu
                325                 330                 335

Leu Ala Glu Ile Gly Phe Ser Pro Leu Glu Val Ile Glu Ala Ala Thr
            340                 345                 350
```

```
Ala Ala Ala Pro Ala Thr Leu Gly Pro Gln Ala Pro Arg Ser Gly Gln
            355                 360                 365

Leu Val Glu Gly Tyr Asp Ala Asp Val Ile Thr Leu Asp Ala Asp Pro
370                 375                 380

Leu Ala Asp Ile Gly Val Leu Ala Lys Pro Ala His Ile Thr Gly Val
385                 390                 395                 400

Trp Lys Ala Gly Cys Arg Val Ala
                405

<210> SEQ ID NO 12
<211> LENGTH: 480
<212> TYPE: PRT
<213> ORGANISM: Aspergillus niger

<400> SEQUENCE: 12

Met His Leu Pro Gln Arg Leu Val Thr Ala Ala Cys Leu Cys Ala Ser
1               5                   10                  15

Ala Thr Ala Phe Ile Pro Tyr Thr Ile Lys Leu Asp Thr Ser Asp Asp
            20                  25                  30

Ile Ser Ala Arg Asp Ser Leu Ala Arg Arg Phe Leu Pro Val Pro Asn
        35                  40                  45

Pro Ser Asp Ala Leu Ala Asp Asp Ser Thr Ser Ser Ala Ser Asp Glu
    50                  55                  60

Ser Leu Ser Leu Asn Ile Lys Arg Ile Pro Val Arg Arg Asp Asn Asp
65                  70                  75                  80

Phe Lys Ile Val Val Ala Glu Thr Pro Ser Trp Ser Asn Thr Ala Ala
                85                  90                  95

Leu Asp Gln Asp Gly Ser Asp Ile Ser Tyr Ile Ser Val Val Asn Ile
            100                 105                 110

Gly Ser Asp Glu Lys Ser Met Tyr Met Leu Leu Asp Thr Gly Gly Ser
        115                 120                 125

Asp Thr Trp Val Phe Gly Ser Asn Cys Thr Ser Thr Pro Cys Thr Met
    130                 135                 140

His Asn Thr Phe Gly Ser Asp Ser Ser Thr Leu Glu Met Thr Ser
145                 150                 155                 160

Glu Glu Trp Ser Val Gly Tyr Gly Thr Gly Ser Val Ser Gly Leu Leu
                165                 170                 175

Gly Lys Asp Lys Leu Thr Ile Ala Asn Val Thr Val Arg Met Thr Phe
            180                 185                 190

Gly Leu Ala Ser Asn Ala Ser Asp Asn Phe Glu Ser Tyr Pro Met Asp
        195                 200                 205

Gly Ile Leu Gly Leu Gly Arg Thr Asn Asp Ser Ser Tyr Asp Asn Pro
    210                 215                 220

Thr Phe Met Asp Ala Val Ala Glu Ser Asn Val Phe Lys Ser Asn Ile
225                 230                 235                 240

Val Gly Phe Ala Leu Ser Arg Ser Pro Ala Lys Asp Gly Thr Val Ser
                245                 250                 255

Phe Gly Thr Thr Asp Lys Asp Lys Tyr Thr Gly Asp Ile Thr Tyr Thr
            260                 265                 270

Asp Thr Val Gly Ser Asp Ser Tyr Trp Arg Ile Pro Val Asp Asp Val
        275                 280                 285

Tyr Val Gly Gly Thr Ser Cys Asp Phe Ser Asn Lys Ser Ala Ile Ile
    290                 295                 300

Asp Thr Gly Thr Ser Tyr Ala Met Leu Pro Ser Ser Asp Ser Lys Thr
305                 310                 315                 320
```

Leu His Ser Leu Ile Pro Gly Ala Lys Ser Gly Ser Tyr His Ile
                325                 330                 335

Ile Pro Cys Asn Thr Thr Thr Lys Leu Gln Val Ala Phe Ser Gly Val
            340                 345                 350

Asn Tyr Thr Ile Ser Pro Lys Asp Tyr Val Gly Ala Thr Ser Gly Ser
        355                 360                 365

Gly Cys Val Ser Asn Ile Ile Ser Tyr Asp Leu Phe Gly Asp Asp Ile
    370                 375                 380

Trp Leu Leu Gly Asp Thr Phe Leu Lys Asn Val Tyr Ala Val Phe Asp
385                 390                 395                 400

Tyr Asp Glu Leu Arg Val Gly Phe Ala Glu Arg Ser Ser Asn Thr Thr
                405                 410                 415

Ser Ala Ser Asn Ser Thr Ser Ser Gly Thr Ser Ser Thr Ser Gly Ser
            420                 425                 430

Thr Thr Thr Gly Ser Ser Thr Thr Thr Ser Ser Ala Ser Ser Ser
        435                 440                 445

Ser Ser Ser Asp Ala Glu Ser Gly Ser Ser Met Thr Ile Pro Ala Pro
    450                 455                 460

Gln Tyr Phe Phe Ser Ala Leu Ala Ile Ala Ser Phe Met Leu Trp Leu
465                 470                 475                 480

<210> SEQ ID NO 13
<211> LENGTH: 472
<212> TYPE: PRT
<213> ORGANISM: Glomerella graminicola

<400> SEQUENCE: 13

Met Gly Gly Ser Phe Arg Pro Asn Tyr Ala Asp Gly Pro Glu Pro Pro
1               5                   10                  15

Phe Ser Pro Thr Lys Lys Thr Thr Leu Val Ile Ile Lys Thr Ser Leu
            20                  25                  30

Leu Ile Pro Gly Asp Gly Glu Pro Leu Lys Asp Gly Ala Leu Val Ile
        35                  40                  45

Ser Ser Lys Val Ile Ala Trp Val Gly Pro Gln Ser Ser Leu Pro Ser
    50                  55                  60

Glu Tyr Ala Asp Ser Pro His Arg Ser Tyr Thr Val Pro Tyr Leu Met
65                  70                  75                  80

Pro Gly Leu Trp Asp Cys His Ala His Phe Gly Gly Glu Ser Pro Asn
                85                  90                  95

Asp Asp Gly Gly Asn Asp Pro Tyr Gln Val Phe Ile Thr Glu His Pro
            100                 105                 110

Ala Ala Ser Gly Ala Arg Leu Thr Arg Gly Cys Trp Leu Ala Leu Gln
        115                 120                 125

Arg Gly Tyr Thr Ser Leu Arg Asp Val Ala Gly Leu Gly Cys Glu Val
    130                 135                 140

Ser Arg Ala Ile Glu Asp Gly Ser Ile Val Gly Pro Asn Val Tyr Ser
145                 150                 155                 160

Ser Gly Ser Gly Leu Ser Gln Leu Ala Gly His Gly Asp Ile Phe Ser
                165                 170                 175

Leu Pro Ala Gly Asp Val Leu Asn Leu Gly Val Ser Gln Ile Thr
            180                 185                 190

Pro Gly His Phe Gly Thr His Ala Thr Met Ile Val Asp Gly Val Asp
        195                 200                 205

Glu Cys Arg Arg Ala Val Arg Leu Gln Ile Arg Arg Gly Ala Lys Cys

```
            210                 215                 220
Ile Lys Val Met Ala Ser Gly Val Met Ser Arg Asp Asp Asn Pro
225                 230                 235                 240

Asn Tyr Ala Gln Phe Ser Ala Ala Glu Leu Glu Thr Ile Val Glu Glu
                245                 250                 255

Ala Thr Arg Gln Asn Arg Val Val Ala His Val His Gly Lys Ala
                260                 265                 270

Gly Ile Leu Ala Ala Ile Asn Ala Gly Val Thr Thr Leu Glu His Ala
                275                 280                 285

Ser Phe Ala Asp Arg Glu Cys Ile Asp Leu Ile Lys Glu Lys Gly Ile
290                 295                 300

Val Tyr Ile Ala Thr Arg Ile Val Val His Leu Leu Leu Ser Thr Gly
305                 310                 315                 320

Gly Lys Gly Leu Pro Pro Thr Val Trp Glu Lys Ala Lys Leu Val Ala
                325                 330                 335

Lys Asn His Met Thr Ala Tyr Lys Met Ala Ile Glu Ser Gly Val Gln
                340                 345                 350

Ile Ala Leu Gly Thr Asp Thr Gly Pro Gly Tyr Asn Met Ala Thr Glu
                355                 360                 365

Leu Glu Cys Ala Val Glu Ala Gly Met Ser Asn Leu Glu Ala Ile Lys
370                 375                 380

Ala Ala Thr Ala Asn Gly Pro Leu Ser Val Gly Gln Ala Pro Lys
385                 390                 395                 400

Thr Gly Gln Leu Lys Val Gly Tyr Glu Ala Asp Val Ile Gly Leu Leu
                405                 410                 415

Gln Asn Pro Val Glu Asp Val Lys Val Leu Gln Lys Val Asp Asn Val
                420                 425                 430

Gly Trp Val Trp Lys Gly Lys Leu Phe Lys Gly Pro Gly Val Gly
                435                 440                 445

Pro Trp Gly Glu Glu Pro Gly Val Trp Glu Asp Ile Thr Gly Val Ser
450                 455                 460

Arg Leu Arg Cys Thr Thr Gly Tyr
465                 470

<210> SEQ ID NO 14
<211> LENGTH: 485
<212> TYPE: PRT
<213> ORGANISM: Metarhizium anisopliae

<400> SEQUENCE: 14

Met Thr Arg Arg Val Ile Pro His Ser Glu Ser Ala Glu Ser Val Asp
1               5                   10                  15

Asp Ala Gln His Val Ser Gly Arg Ile Tyr Ser Thr Gly Phe Gly Ile
                20                  25                  30

Ala Val Arg Thr Gly Gln Pro Gln Ser Gln Asp Asp Ala Glu Thr
                35                  40                  45

Gly Val Lys Lys Val Phe Tyr Thr Ile Val Met Thr Lys Leu Leu Ile
50                  55                  60

Pro Gly Asp Gly Glu Pro Ile Lys Asp Ala Ala Leu Val Val Lys Asn
65                  70                  75                  80

Lys Ile Ile Asp Trp Val Gly Arg Gln Ala Asp Leu Pro Asn Glu Tyr
                85                  90                  95

Thr Glu Lys Pro His Lys Leu His Asn Val Pro Tyr Leu Met Pro Gly
                100                 105                 110
```

Leu Trp Asp Cys His Val His Phe Ala Gly Ser Asn Gly Glu Arg Glu
            115                 120                 125

Ala Glu Glu Gly Ser Thr Gly Leu Ser Phe Leu Ala Asp His Pro Thr
        130                 135                 140

Thr Ala Gly Ala Arg Leu Ala Arg Gly Cys Trp Asp Ala Ile Gln Arg
145                 150                 155                 160

Gly Tyr Thr Ser Met Arg Asp Leu Ala Gly Phe Gly Cys Glu Ile Ser
                165                 170                 175

Lys Ala Ile Glu Asp Gly Val Ile Ile Gly Pro Asn Ile Tyr Ser Ala
            180                 185                 190

Gly Ala Cys Leu Ser Gln Leu Ala Gly His Gly Asp Val Phe Ala Leu
        195                 200                 205

Pro Ala Gly Asp Ala Leu Leu Asn Leu Gly Leu Ala Ser Val Lys Ala
    210                 215                 220

Gly Gln Phe Gly Ala Gly Met Ser Cys Leu Val Asp Gly Val Asp Glu
225                 230                 235                 240

Cys Arg Arg Gly Val Arg Leu Gln Ile Arg Arg Gly Ala Lys Cys Ile
                245                 250                 255

Lys Val Met Ala Ser Gly Gly Val Leu Ser Arg Asp Asp Asn Pro Leu
            260                 265                 270

Tyr Ala Gln Phe Ser Arg Glu Glu Leu Asp Thr Ile Val Ser Glu Ala
        275                 280                 285

Lys Arg Met Glu Arg Thr Val Ala Ala His Val His Gly Lys Pro Gly
    290                 295                 300

Ile Leu Gln Ala Val Glu Ala Gly Val Thr Ser Val Glu His Val Ser
305                 310                 315                 320

Phe Ala Asp Gln Glu Cys Ile Asp Leu Ile Lys Asp Arg Gly Thr Ile
                325                 330                 335

Phe Val Gly Thr Arg Thr Ile Val Asn Leu Leu Leu Asp Ser Lys Gly
            340                 345                 350

Glu Gly Met Pro Lys Lys Met Trp Glu Lys Ala Lys Leu Val Gly Thr
        355                 360                 365

His Ser Leu Glu Gly Tyr Lys Lys Ala Ile Lys Ala Gly Cys Thr Ile
    370                 375                 380

Ala Leu Gly Thr Asp Thr Glu Pro Gly Phe Asn Met Ala Ile Glu Leu
385                 390                 395                 400

Gln Tyr Ala Val Glu Ala Gly Met Ser Ser Leu Glu Ala Ile Lys Ala
                405                 410                 415

Ala Thr Ala Asn Gly Pro Leu Thr Val Ala Gly Gln Ala Pro Leu Thr
            420                 425                 430

Gly Gln Leu Lys Ala Gly Tyr Glu Ala Asp Met Ile Gly Val Cys Asp
        435                 440                 445

Asn Pro Val Glu Asp Val Lys Val Leu Gln Lys Lys Ser Asn Ile Gly
    450                 455                 460

Trp Val Trp Lys Gly Gly Lys Leu Phe Lys Gly Pro Gly Ile Gly Pro
465                 470                 475                 480

Trp Gly Glu Glu Leu
            485

<210> SEQ ID NO 15
<211> LENGTH: 419
<212> TYPE: PRT
<213> ORGANISM: Aspergillus oryzae

<400> SEQUENCE: 15

-continued

```
Met His Arg Met Leu Thr Asp Asp Arg Leu Tyr Arg Val Asp Ala Asp
1               5                   10                  15

Leu Leu Ile Pro Gly Lys Gly Asp Pro Ile Pro His Gly Ala Val Val
            20                  25                  30

Trp Gln Cys Lys Thr Ile Arg Tyr Ala Gly Pro Arg Ser Gly Val Pro
        35                  40                  45

Thr Glu Phe Gln Gly Ala Thr Thr His Val Pro Val Met Pro
    50                  55                  60

Gly Met Trp Asp Cys His Ile His Phe Leu Gly Ala Thr Ala Ala Thr
65                  70                  75                  80

Met Asn Ala Ile Val Asp Thr Pro Gln Ala Leu Ala Gly Ala Arg Ser
                85                  90                  95

Val Pro Asp Leu His Ala Thr Val Met Ala Gly Phe Thr Ser Val Arg
            100                 105                 110

Glu Val Gly Gly Tyr Gly Cys Asp Leu Ala Lys Ala Val Gly Glu Gly
            115                 120                 125

Arg Ile Pro Gly Pro Asn Ile Tyr Ser Ser His Ser Ala Ile Ser Met
        130                 135                 140

Thr Ala Gly His Gly Asp Val His Gly Val His Arg Asp Ser Leu Leu
145                 150                 155                 160

Asp Leu Cys Ala His Gly Leu Pro Leu Thr Ile Ala Asp Gly Val Pro
                165                 170                 175

Glu Cys Leu Leu Ala Val Arg Lys Gln Leu Arg Arg Gly Ala Lys Val
            180                 185                 190

Ile Lys Val Cys Ala Ser Gly Gly Val Val Ser Ala Ile Asp Asp Pro
        195                 200                 205

Gln His Gln Glu Phe Ser Phe Glu Leu Lys Ala Ile Val Asp Glu
    210                 215                 220

Ala Ala Arg Ala Arg Arg Val Val Ala Ala His Cys His Gly Lys Ala
225                 230                 235                 240

Gly Ile Met Asn Ala Leu Arg Ala Gly Cys Arg Thr Ile Glu His Gly
                245                 250                 255

Ser Phe Leu Asp Glu Glu Ala Val Gly Leu Met Lys Glu Lys Gly Ala
            260                 265                 270

Ile Leu Val Ala Thr Arg Ser Val Ile Glu Ser Gly Leu Ala Met Lys
        275                 280                 285

Asp Leu Phe Thr Pro Ser Ser Tyr Gln Lys Leu Leu Ala Val Ala Asp
    290                 295                 300

Ala His Arg Lys Ala Tyr Gln Leu Ala Ile Ser Arg Gly Val Thr Ile
305                 310                 315                 320

Ala Leu Gly Thr Asp Gln Phe Ile Ser Ser Asp Asn Pro Met Ile Gly
                325                 330                 335

Tyr Gly Arg Asn Gly His Glu Val Arg Tyr Ala Val Asp Ala Gly Leu
            340                 345                 350

Thr Pro Leu Ala Ala Ile Glu Ala Thr Ala Asn Gly Pro Leu Thr
        355                 360                 365

Leu Gly Tyr Gln Ala Pro Gln Ser Gly Gln Leu Lys Glu Gly Tyr Asp
    370                 375                 380

Ala Asp Ile Ile Ala Val Arg Glu Asn Pro Leu Glu Asn Val Ala Val
385                 390                 395                 400

Leu Ser Asn Ser Lys Asn Val Thr His Val Trp Arg Gly Gly Met Leu
                405                 410                 415
```

Ile Lys Ser

<210> SEQ ID NO 16
<211> LENGTH: 419
<212> TYPE: PRT
<213> ORGANISM: Bos taurus

<400> SEQUENCE: 16

Met Gln Gly Leu Leu Ile Leu Ser Val Leu Leu Gly Ala Ala Leu Gly
1               5                   10                  15

Lys Glu Asp Phe Val Gly His Gln Val Leu Arg Ile Thr Ala Ala Asp
                20                  25                  30

Glu Ala Glu Val Gln Thr Val Lys Glu Leu Glu Asp Leu Glu His Leu
            35                  40                  45

Gln Leu Asp Phe Trp Arg Gly Pro Gln Pro Gly Ser Pro Ile Asp
        50                  55                  60

Val Arg Val Pro Phe Pro Ser Leu Gln Ala Val Lys Val Phe Leu Glu
65                  70                  75                  80

Ala His Gly Ile Arg Tyr Arg Ile Met Ile Glu Asp Val Gln Ser Leu
                85                  90                  95

Leu Asp Glu Glu Gln Glu Gln Met Phe Ala Ser Gln Ser Arg Ala Arg
            100                 105                 110

Ser Thr Asn Thr Phe Asn Tyr Ala Thr Tyr His Thr Leu Asp Glu Ile
        115                 120                 125

Tyr Asp Phe Met Asp Leu Leu Val Ala Glu His Pro Gln Leu Val Ser
130                 135                 140

Lys Leu Gln Ile Gly Arg Ser Tyr Glu Gly Arg Pro Ile Tyr Val Leu
145                 150                 155                 160

Lys Phe Ser Thr Gly Gly Ser Asn Arg Pro Ala Ile Trp Ile Asp Leu
                165                 170                 175

Gly Ile His Ser Arg Glu Trp Ile Thr Gln Ala Thr Gly Val Trp Phe
            180                 185                 190

Ala Lys Lys Phe Thr Glu Asp Tyr Gly Gln Asp Pro Ser Phe Thr Ala
        195                 200                 205

Ile Leu Asp Ser Met Asp Ile Phe Leu Glu Ile Val Thr Asn Pro Asp
        210                 215                 220

Gly Phe Ala Phe Thr His Ser Gln Asn Arg Leu Trp Arg Lys Thr Arg
225                 230                 235                 240

Ser Val Thr Ser Ser Ser Leu Cys Val Gly Val Asp Ala Asn Arg Asn
                245                 250                 255

Trp Asp Ala Gly Phe Gly Lys Ala Gly Ala Ser Ser Ser Pro Cys Ser
            260                 265                 270

Glu Thr Tyr His Gly Lys Tyr Ala Asn Ser Glu Val Glu Val Lys Ser
        275                 280                 285

Ile Val Asp Phe Val Lys Asp His Gly Asn Phe Lys Ala Phe Leu Ser
        290                 295                 300

Ile His Ser Tyr Ser Gln Leu Leu Leu Tyr Pro Tyr Gly Tyr Thr Thr
305                 310                 315                 320

Gln Ser Ile Pro Asp Lys Thr Glu Leu Asn Gln Val Ala Lys Ser Ala
                325                 330                 335

Val Glu Ala Leu Lys Ser Leu Tyr Gly Thr Ser Tyr Lys Tyr Gly Ser
            340                 345                 350

Ile Ile Thr Thr Ile Tyr Gln Ala Ser Gly Gly Ser Ile Asp Trp Ser
        355                 360                 365

```
Tyr Asn Gln Gly Ile Lys Tyr Ser Phe Thr Phe Glu Leu Arg Asp Thr
            370                 375                 380

Gly Arg Tyr Gly Phe Leu Leu Pro Ala Ser Gln Ile Ile Pro Thr Ala
385                 390                 395                 400

Gln Glu Thr Trp Leu Gly Val Leu Thr Ile Met Glu His Thr Leu Asn
                405                 410                 415

Asn Leu Tyr

<210> SEQ ID NO 17
<211> LENGTH: 532
<212> TYPE: PRT
<213> ORGANISM: Saccharomyces cerevisiae

<400> SEQUENCE: 17

Met Lys Ala Phe Thr Ser Leu Leu Cys Gly Leu Gly Leu Ser Thr Thr
1               5                   10                  15

Leu Ala Lys Ala Ile Ser Leu Gln Arg Pro Leu Gly Leu Asp Lys Asp
            20                  25                  30

Val Leu Leu Gln Ala Ala Glu Lys Phe Gly Leu Asn Leu Asp Leu Asp
        35                  40                  45

His Leu Leu Lys Glu Leu Asp Ser Asn Val Leu Asp Ala Trp Ala Gln
50                  55                  60

Ile Glu His Leu Tyr Pro Asn Gln Val Met Ser Leu Glu Thr Ser Thr
65                  70                  75                  80

Lys Pro Lys Phe Pro Glu Ala Ile Lys Thr Lys Lys Asp Trp Asp Phe
                85                  90                  95

Val Val Lys Asn Asp Ala Ile Glu Asn Tyr Gln Leu Arg Val Asn Lys
            100                 105                 110

Ile Lys Asp Pro Lys Ile Leu Gly Ile Asp Pro Asn Val Thr Gln Tyr
        115                 120                 125

Thr Gly Tyr Leu Asp Val Glu Asp Glu Asp Lys His Phe Phe Phe Trp
130                 135                 140

Thr Phe Glu Ser Arg Asn Asp Pro Ala Lys Asp Pro Val Ile Leu Trp
145                 150                 155                 160

Leu Asn Gly Gly Pro Gly Cys Ser Ser Leu Thr Gly Leu Phe Phe Glu
                165                 170                 175

Leu Gly Pro Ser Ser Ile Gly Pro Asp Leu Lys Pro Ile Gly Asn Pro
            180                 185                 190

Tyr Ser Trp Asn Ser Asn Ala Thr Val Ile Phe Leu Asp Gln Pro Val
        195                 200                 205

Asn Val Gly Phe Ser Tyr Ser Gly Ser Ser Gly Val Ser Asn Thr Val
210                 215                 220

Ala Ala Gly Lys Asp Val Tyr Asn Phe Leu Glu Leu Phe Phe Asp Gln
225                 230                 235                 240

Phe Pro Glu Tyr Val Asn Lys Gly Gln Asp Phe His Ile Ala Gly Glu
                245                 250                 255

Ser Tyr Ala Gly His Tyr Ile Pro Val Phe Ala Ser Glu Ile Leu Ser
            260                 265                 270

His Lys Asp Arg Asn Phe Asn Leu Thr Ser Val Leu Ile Gly Asn Gly
        275                 280                 285

Leu Thr Asp Pro Leu Thr Gln Tyr Asn Tyr Tyr Glu Pro Met Ala Cys
290                 295                 300

Gly Glu Gly Gly Glu Pro Ser Val Leu Pro Ser Glu Glu Cys Ser Ala
305                 310                 315                 320
```

```
Met Glu Asp Ser Leu Glu Arg Cys Leu Gly Leu Ile Glu Ser Cys Tyr
            325                 330                 335

Asp Ser Gln Ser Val Trp Ser Cys Val Pro Ala Thr Ile Tyr Cys Asn
        340                 345                 350

Asn Ala Gln Leu Ala Pro Tyr Gln Arg Thr Gly Arg Asn Val Tyr Asp
    355                 360                 365

Ile Arg Lys Asp Cys Glu Gly Gly Asn Leu Cys Tyr Pro Thr Leu Gln
370                 375                 380

Asp Ile Asp Asp Tyr Leu Asn Gln Asp Tyr Val Lys Glu Ala Val Gly
385                 390                 395                 400

Ala Glu Val Asp His Tyr Glu Ser Cys Asn Phe Asp Ile Asn Arg Asn
                405                 410                 415

Phe Leu Phe Ala Gly Asp Trp Met Lys Pro Tyr His Thr Ala Val Thr
            420                 425                 430

Asp Leu Leu Asn Gln Asp Leu Pro Ile Leu Val Tyr Ala Gly Asp Lys
        435                 440                 445

Asp Phe Ile Cys Asn Trp Leu Gly Asn Lys Ala Trp Thr Asp Val Leu
    450                 455                 460

Pro Trp Lys Tyr Asp Glu Glu Phe Ala Ser Gln Lys Val Arg Asn Trp
465                 470                 475                 480

Thr Ala Ser Ile Thr Asp Glu Val Ala Gly Glu Val Lys Ser Tyr Lys
                485                 490                 495

His Phe Thr Tyr Leu Arg Val Phe Asn Gly Gly His Met Val Pro Phe
            500                 505                 510

Asp Val Pro Glu Asn Ala Leu Ser Met Val Asn Glu Trp Ile His Gly
        515                 520                 525

Gly Phe Ser Leu
    530

<210> SEQ ID NO 18
<211> LENGTH: 13
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 18

Xaa Pro Gly Xaa Xaa Asp Xaa His Xaa His Xaa Xaa Gly
1               5                   10

<210> SEQ ID NO 19
<211> LENGTH: 6
<212> TYPE: PRT
```

```
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 19

Gly Xaa Xaa Xaa Gly Pro
1               5

<210> SEQ ID NO 20
<211> LENGTH: 4
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Gly His Xaa Asp
1

<210> SEQ ID NO 21
<211> LENGTH: 22
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 21

Asp Gly Xaa Xaa Xaa Cys Xaa Xaa Xaa Xaa Arg Xaa Xaa Xaa Arg Xaa
1               5                   10                  15

Xaa Ala Xaa Xaa Ile Lys
            20

<210> SEQ ID NO 22
<211> LENGTH: 10
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
```

```
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 22

Gly Gly Val Xaa Ser Xaa Xaa Asp Xaa Pro
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 23

Val Xaa Ala His Xaa Xaa Gly Xaa Xaa Gly
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 24

His Xaa Xaa Xaa Xaa Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 25

Gly Val Xaa Ile Xaa Xaa Gly Thr Asp
1               5

<210> SEQ ID NO 26
<211> LENGTH: 13
<212> TYPE: PRT
```

```
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (1)..(1)
<223> OTHER INFORMATION: Xaa can be Leu or Met
<220> FEATURE:
<221> NAME/KEY: MISC_FEATURE
<222> LOCATION: (4)..(4)
<223> OTHER INFORMATION: Xaa can be Leu or Met
<220> FEATURE:
<221> NAME/KEY: MISC_FEATURE
<222> LOCATION: (5)..(5)
<223> OTHER INFORMATION: Xaa can be Trp or Ile
<220> FEATURE:
<221> NAME/KEY: MISC_FEATURE
<222> LOCATION: (7)..(7)
<223> OTHER INFORMATION: Xaa can be Cys, Val, Ser or Ala
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be Phe, Tyr or Leu
<220> FEATURE:
<221> NAME/KEY: misc_feature
<222> LOCATION: (12)..(12)
<223> OTHER INFORMATION: Xaa can be any naturally occurring amino acid

<400> SEQUENCE: 26

Xaa Pro Gly Xaa Xaa Asp Xaa His Xaa His Xaa Xaa Gly
1               5                   10

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
ggagatctat catggtccgc cgaattg                                          27

<210> SEQ ID NO 28
<211> LENGTH: 46
<212> TYPE: DNA
<213> ORGANISM: Artificial Sequence
<220> FEATURE:
<223> OTHER INFORMATION: Primer

<400> SEQUENCE: 28
aatctagact agtgatggtg atggtgatgc agaaaggat tacgtg                      46

<210> SEQ ID NO 29
<211> LENGTH: 7
<212> TYPE: PRT
<213> ORGANISM: Aspergillus niger

<400> SEQUENCE: 29

Glu Ala Leu Gln Asn Gly Tyr
1               5

<210> SEQ ID NO 30
<211> LENGTH: 11
<212> TYPE: PRT
<213> ORGANISM: Aspergillus niger

<400> SEQUENCE: 30
```

```
Ala Leu Pro Ala Gly Glu Val Leu Gly Ser Tyr
1               5                   10

<210> SEQ ID NO 31
<211> LENGTH: 5
<212> TYPE: PRT
<213> ORGANISM: Aspergillus niger

<400> SEQUENCE: 31

Gly Ala Gly Pro Leu
1               5

<210> SEQ ID NO 32
<211> LENGTH: 8
<212> TYPE: PRT
<213> ORGANISM: Aspergillus niger

<400> SEQUENCE: 32

Ser Val Gly Pro Gln Ala Pro Leu
1               5

<210> SEQ ID NO 33
<211> LENGTH: 9
<212> TYPE: PRT
<213> ORGANISM: Aspergillus niger

<400> SEQUENCE: 33

Ser Thr Asp Glu Ala Lys Val Thr Ile
1               5

<210> SEQ ID NO 34
<211> LENGTH: 60
<212> TYPE: DNA
<213> ORGANISM: Artificial Sequence
<220> FEATURE:
<223> OTHER INFORMATION: Primer

<400> SEQUENCE: 34
gggacaagtt tgtacaaaaa agcaggctca ccatgcaccg gatgctcaca gacgacagac        60

<210> SEQ ID NO 35
<211> LENGTH: 71
<212> TYPE: DNA
<213> ORGANISM: Artificial Sequence
<220> FEATURE:
<223> OTHER INFORMATION: Primer

<400> SEQUENCE: 35
accactttgt acaagaaagc tgggtctagt ggtggtggtg gtggtgtgat ttaatcagca        60
tgccgccacg c                                                            71

<210> SEQ ID NO 36
<211> LENGTH: 6
<212> TYPE: PRT
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (2)..(2)
<223> OTHER INFORMATION: Xaa can be Thr, Ala, Ser, Val or Arg
<220> FEATURE:
<221> NAME/KEY: MISC_FEATURE
<222> LOCATION: (3)..(3)
<223> OTHER INFORMATION: Xaa can be Ile, Phe or Ala
<220> FEATURE:
```

```
<221> NAME/KEY: misc_feature
<222> LOCATION: (4)..(4)
<223> OTHER INFORMATION: Xaa can be any naturally occurring amino acid

<400> SEQUENCE: 36

Gly Xaa Xaa Xaa Gly Pro
1               5

<210> SEQ ID NO 37
<211> LENGTH: 4
<212> TYPE: PRT
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (3)..(3)
<223> OTHER INFORMATION: Xaa can be Gly or Ser

<400> SEQUENCE: 37

Gly His Xaa Asp
1

<210> SEQ ID NO 38
<211> LENGTH: 22
<212> TYPE: PRT
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (3)..(3)
<223> OTHER INFORMATION: Xaa can be Val or Glu
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Glu, Asp or Gly
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be Ala, Gly or Thr
<220> FEATURE:
<221> NAME/KEY: MISC_FEATURE
<222> LOCATION: (10)..(10)
<223> OTHER INFORMATION: Xaa can be Val or Ala
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be Gln, Met or Ala
<220> FEATURE:
<221> NAME/KEY: MISC_FEATURE
<222> LOCATION: (14)..(14)
<223> OTHER INFORMATION: Xaa can be Leu, Ile, or Val
<220> FEATURE:
<221> NAME/KEY: MISC_FEATURE
<222> LOCATION: (16)..(16)
<223> OTHER INFORMATION: Xaa can be Arg, His or Cys
<220> FEATURE:
<221> NAME/KEY: MISC_FEATURE
<222> LOCATION: (17)..(17)
<223> OTHER INFORMATION: Xaa can be Gly or Asn
<220> FEATURE:
<221> NAME/KEY: MISC_FEATURE
```

```
<222> LOCATION: (19)..(19)
<223> OTHER INFORMATION: Xaa can be Lys, Arg, Thr, Glu or Asp
<220> FEATURE:
<221> NAME/KEY: misc_feature
<222> LOCATION: (20)..(20)
<223> OTHER INFORMATION: Xaa can be any naturally occurring amino acid

<400> SEQUENCE: 38

Asp Gly Xaa Xaa Xaa Cys Xaa Xaa Xaa Arg Xaa Xaa Xaa Arg Xaa
1               5                   10                  15

Xaa Ala Xaa Xaa Ile Lys
            20

<210> SEQ ID NO 39
<211> LENGTH: 10
<212> TYPE: PRT
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (4)..(4)
<223> OTHER INFORMATION: Xaa can be Leu, Met, Val or Gly
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 39

Gly Gly Val Xaa Ser Xaa Xaa Asp Xaa Pro
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Amino acid sequence motif
<220> FEATURE:
<221> NAME/KEY: MISC_FEATURE
<222> LOCATION: (2)..(2)
<223> OTHER INFORMATION: Xaa can be Ala, Ser or His
<220> FEATURE:
<221> NAME/KEY: MISC_FEATURE
<222> LOCATION: (5)..(5)
<223> OTHER INFORMATION: Xaa can be Cys, Val or Ala
<220> FEATURE:
<221> NAME/KEY: MISC_FEATURE
<222> LOCATION: (6)..(6)
<223> OTHER INFORMATION: Xaa can be His or Gln
<220> FEATURE:
<221> NAME/KEY: MISC_FEATURE
<222> LOCATION: (8)..(8)
<223> OTHER INFORMATION: Xaa can be Lys or Arg
<220> FEATURE:
<221> NAME/KEY: misc_feature
<222> LOCATION: (9)..(9)
<223> OTHER INFORMATION: Xaa can be any naturally occurring amino acid

<400> SEQUENCE: 40

Val Xaa Ala His Xaa Xaa Gly Xaa Xaa Gly
1               5                   10

<210> SEQ ID NO 41
<211> LENGTH: 6
<212> TYPE: PRT
<213> ORGANISM: Artificial Sequence
<220> FEATURE:
```

```
<223> OTHER INFORMATION: Amino acid sequence motif
<220> FEATURE:
<221> NAME/KEY: MISC_FEATURE
<222> LOCATION: (2)..(2)
<223> OTHER INFORMATION: Xaa can be Gly, Val or Ala
<220> FEATURE:
<221> NAME/KEY: MISC_FEATURE
<222> LOCATION: (3)..(3)
<223> OTHER INFORMATION: Xaa can be Ser, Thr or Ile
<220> FEATURE:
<221> NAME/KEY: MISC_FEATURE
<222> LOCATION: (4)..(4)
<223> OTHER INFORMATION: Xaa can be Tyr, Phe or Glu
<220> FEATURE:
<221> NAME/KEY: MISC_FEATURE
<222> LOCATION: (5)..(5)
<223> OTHER INFORMATION: Xaa can be Leu, Ala or Ile

<400> SEQUENCE: 41

His Xaa Xaa Xaa Xaa Asp
1               5

<210> SEQ ID NO 42
<211> LENGTH: 9
<212> TYPE: PRT
<213> ORGANISM: Artificial Sequence
<220> FEATURE:
<223> OTHER INFORMATION: Amino acid sequence motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Ala or Val
<220> FEATURE:
<221> NAME/KEY: MISC_FEATURE
<222> LOCATION: (6)..(6)
<223> OTHER INFORMATION: Xaa can be Leu or Ala

<400> SEQUENCE: 42

Gly Val Xaa Ile Xaa Xaa Gly Thr Asp
1               5
```

FOOD ADDITIVE COMPRISING AN AMIDASE FOR DETOXIFYING OCHRATOXIN

CROSS-REFERENCE TO RELATED APPLICATIONS

This application claims priority to PCT Application No. PCT/IB2011/053901 entitled "Food Additive Comprising An Amidase For Detoxifying Ochratoxin," filed Sep. 6, 2011, which claims priority to EP No. 10177410.7, filed Sep. 17, 2010 and U.S. Provisional Application No. 61/380,280, filed Sep. 6, 2010, all of which are expressly incorporated by reference herein in their entirety.

SEQUENCE LISTING

A text file in compliance with ASCII and having a ".txt" extension has been electronically submitted via EFS-Web. The text file named "Sequence Listing" was created on Mar. 5, 2013, and is 74,537 bytes. The text file is expressly incorporated by reference herein in its entirety.

FIELD OF INVENTION

The present invention relates to methods of detoxifying mycotoxins. More specifically, the invention relates to amidase enzymes and feed and or food additives comprising at least one amidase for detoxifying ochratoxin, particularly ochratoxin A.

BACKGROUND

Mycotoxins are toxic secondary metabolites of fungi belonging, essentially, to the *Aspergillus, Penicillium* and *Fusarium* genera. They can be produced on a wide range of agricultural commodities and under a diverse range of agronomic, ecological and post harvest conditions worldwide.

Mycotoxins can enter the food chain in the field, during storage of a feed or food material, or at later points in the food chain. Their accumulation in foods and feeds represents a major threat to human and animal health since consumption of a mycotoxin-contaminated diet may result in teratogenic, carcinogenic and oestrogenic or immunosuppressive effects.

In 1985 the World Health Organization estimated that approximately 25% of the world's grains were contaminated by mycotoxins (Jelinek et al., 1989). This figure has likely grown since then due to an increase in global import and export of grains and cereals and the changing environmental and weather patterns.

Currently there are more than 400 mycotoxins documented but the mycotoxins of greatest concern and consequently the most studied include: aflatoxin, deoxynivalenol, zearalenone, fumonisin and ochratoxin.

Although there are many species of toxigenic moulds, only a few mycotoxins are considered to be significant for humans.

Three genera of fungi, *Aspergillus, Penicillium*, and *Fusarium* are most frequently involved with cases of mycotoxin contamination. Fungal colonization, growth and mycotoxin production are generally influenced by a variety of factors. The most important of which are temperature and water activity.

Generally, in warm regions aflatoxins are of major concern. This is because the *Aspergillus* species that produce these toxins find optimum conditions present in tropical regions. In contrast, *Fusarium* and *Penicillium* species have lower optimum temperatures and as a result are adapted to a more moderate climate. Ochratoxins, fumonisins and zearalenone are consequently produced in regions providing these conditions.

Ochratoxins are a group of mycotoxins produced as secondary metabolites by several fungi of the *Aspergillus* or *Penicillium* families and are weak organic acids consisting of a derivative of an isocoumarin. There are three generally recognized ochratoxins, designated A, B and C. Ochratoxin A is the most abundant member of the ochratoxin family and hence the most commonly detected, but is also the most toxic. Ochratoxin A (ochratoxin A) is a nephrotoxic, teratogenic, hepatotoxic, and carcinogenic mycotoxin present in cereals and other starch rich foods. Besides cereals and cereal products, ochratoxin A is also found in a range of other food commodities, including coffee, cocoa, wine, beer, pulses, spices, dried fruits, grape juice, pig kidney and other meat and meat products of non-ruminant animals exposed to feedstuffs contaminated with this mycotoxin. Many countries have set limits on ochratoxin A level in food, typically between 1 and 10 ppb (parts per billion) depending on the type and quality of the foodstuffs.

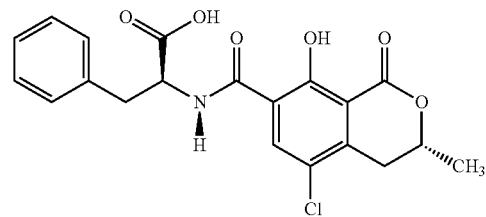

Molecular structure of ochratoxin A ochratoxin A production is due to a fungal infection in crops, in the field during growth, at harvest, in storage and in shipment under favourable environmental conditions, especially when they are not properly dried.

Ochratoxin A is a stable compound that can be hydrolysed into ochratoxin α (OTα) and L-phenylalanine by heating under reflux for 48 h in 6M hydrochloric acid (Van der Merwe et al., 1965) or with the carboxypeptidase A (Pitout, 1969). The conversion of OTA into ochratoxin α is considered to be a way to reduce its toxicity since OTα is commonly reported to be much less toxic than OTA. Moreover, ochratoxin α elimination half-time in the body (9.6 h) is shorter than that of OTA (103 h) (Li et al., 1997).

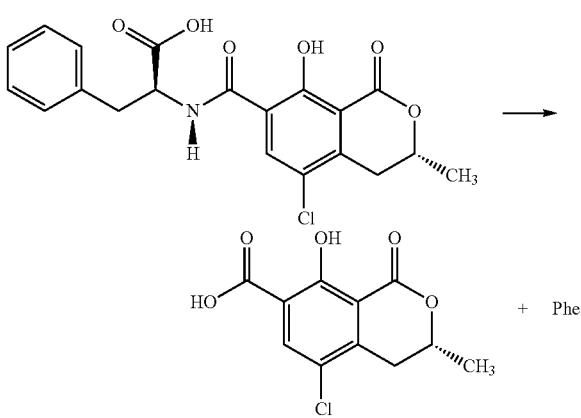

In order to ensure food safety, different approaches to prevent mycotoxin intake are developed at several stages along the food production chain.

It has been known since the 1970s that the mammalian digestive enzyme called carboxypeptidase A is cable of degrading OTA but that the efficiency of this enzyme is low. In fact in animals having carboxypeptidase A, such as pig, OTA toxicity due to its presence in feed is a problem. Furthermore, it has been found that OTA can to some extent inhibit carboxypeptidase A activity.

Prior to the present invention, there has been no disclosure of efficient enzyme solutions to degrade ochratoxins including ochratoxin A (OTA). Enzyme activities other than carboxypeptidase have been reported for OTA degradation, but until now no one has been able to identify a protein showing OTA degrading activity.

It is known that a commercial lipase product called "Amano™ lipase" which is a crude lipase produced from *A. niger* (Amano™ company, Japan) has ochratoxin degrading activity.

The OTA degrading activity in this lipase product has previously been attributed to a lipase or protease activity. For example, Maria A. Stander (*J. Agric. Food Chem*, 2000, 48, 5736-5739) concluded that the OTA degrading activity of Amano™ lipase resulted from a lipase.

Abrunhosa et al., (Biotechnology Lett., 2007, 29, 1909-1914) describe an enzyme preparation isolated from *A. niger* having OTA degrading activity. However, this enzyme preparation was not purified to an extent where the sequence of the active component could be determined at the amino acid or DNA level. Similar problems have been reported in other cases (Abrunhosa et al., TOXINS, [2010], 2, 1078-1099)

SUMMARY

The present invention is based on work undertaken by the inventors to identify and isolate an enzyme which is capable of efficiently degrading ochratoxin, more specifically ochratoxin A (OTA).

The inventors have discovered that contrary to their initial hypothesis formamidase from *A. niger* and *A. nidulans* and also the formamidase that exists in the Amano™ lipase product have no activity towards OTA but as expected do have activity towards formamide.

The inventors have surprisingly found that a 480 amino acid hypothetical protein, hereinafter referred to as amidase 2, which is encoded by an *A. niger* open reading frame has ochratoxin degrading activity, and particularly ochratoxin A degrading activity.

Furthermore, the inventors have also surprisingly found that the full length 480 amino acid amidase 2 comprising the N-terminal or signal sequence and having a MW of about 51 kDa (referred to as amidase 2 sig) has ochratoxin A degrading activity as well as the secreted mature 438 amino acid amidase 2 having a MW of about 47 kDa (referred to as amidase 2 mat).

It has been found that in amidase 2 mat, the N-terminal 42 amino acids are cleaved, that is, when amidase 2 is secreted into the culture medium its N-terminal 42 aa is cleaved to form the mature amidase 2 (i.e., amidase 2 mat) by an *A. niger* peptidase.

The inventors have isolated and cloned the *A. niger* gene encoding the amidase enzyme responsible for the degradation of ochratoxin A and have identified its crystal structure. They have identified that this gene encodes a polypeptide having the sequence of SEQ ID NO: 1 (amidase 2 sig). They have further identified that this enzyme is post translationally modified by cleavage of an N-terminal 42 amino acid sequence the mature amidase 2 shown as SEQ ID NO: 3

According to a first aspect of the present invention there is provided an isolated amidase enzyme capable of degrading ochratoxin. More particularly ochratoxin A According to a second aspect of the present invention there is provided a food or feed additive comprising an amidase enzyme capable of degrading ochratoxin. More particularly ochratoxin A According to a third aspect of the present invention there is provided a food or feed material comprising the feed additive of the present invention.

According to a Fourth aspect of the present invention there is provided a foodstuff or feedstuff comprising a feed material of the present invention.

According to a fifth aspect of the present invention there is provided a method for making a food or feed additive comprising admixing an amidase enzyme capable of degrading ochratoxin with at least one physiologically acceptable carrier.

According to a sixth aspect of the present invention there is provided a method of reducing ochratoxin contamination in a material comprising adding to said material an amidase enzyme capable of degrading ochratoxin.

According to a seventh aspect of the present invention there is provided a composition comprising an ochratoxin contaminated material and an amidase enzyme capable of degrading ochratoxin.

According to a eighth aspect of the present invention there is provided a method of making a foodstuff or feedstuff comprising adding to a food or feed material a food or feed additive according to the present invention.

According to a ninth aspect of the present invention there is provided a method of increasing the growth rate and/or health of an animal comprising feeding the animal an effective amount of a feedstuff according to the present invention.

According to an tenth aspect of the present invention there is provided the use of an amidase which degrades ochratoxin in the manufacture of a foodstuff or feedstuff.

According to a eleventh aspect of the present invention there is provided a foodstuff or feedstuff obtainable by the methods of the present invention.

According to a twelfth aspect of the present invention there is provided a recombinant cell comprising an amidase enzyme capable of degrading ochratoxin.

In a thirteenth aspect of the present invention there is provided an amidase enzyme comprising a polypeptide sequence having at least 30%, 35%, 40%, 50%, 60%, 70%, 80%, 90%, 95%, 98%, 99% identity to SEQ ID NO:1 or SEQ ID NO: 3, or a polypeptide which differs from SEQ ID NO: 1 or SEQ ID NO: 3 by one or several amino acid additions, deletions and/or substitutions; or a polypeptide encoded by a polynucleotide having at least 30%, 35%, 40%, 50%, 60%, 70%, 80%, 90%, 95%, 98%, 99% identity to SEQ ID NO:2, or a polynucleotide which differs from SEQ ID NO: 2 by one or several nucleotide additions, deletions and/or substitutions; and wherein said polypeptide is not SEQ ID NO:1.

According to a fourteenth aspect of the present invention there is provided a food or feed additive comprising the peptidase enzyme PEPAd (SEQ ID NO: 12) capable of degrading ochratoxin A.

According to a fifteenth aspect of the present invention there is provided a food or feed material comprising the feed additive of the thirteenth aspect.

According to a sixteenth aspect of the present invention there is provided a foodstuff or feedstuff comprising a feed material of the fourteenth aspect.

DETAILED DESCRIPTION OF THE INVENTION

In the description which follows, it will be understood that any of the preferred features described are applicable to any aspect of the present invention unless explicitly stated otherwise. It will be further understood that any of the preferred features are envisaged as being used in combination where appropriate.

It will be further understood that the terms ochratoxin or an amidase enzyme capable of degrading ochratoxin in preferred embodiments refers to ochratoxin A or an amidase enzyme capable of degrading ochratoxin A.

As used herein the term amidase (amidohydrolase) refers to an enzyme of the amidohydrolase superfamily which can hydrolyse an amide.

The inventors have isolated and cloned the amidase 2 enzyme from *A. niger* responsible for ochratoxin degradation. This enzyme is particularly effective at degrading ochratoxin A. They have shown that this enzyme is expressed by an ORF encoding a hypothetical 480 amino acid *A. niger* protein (An14g02080, Acc No. XP_001400834) which shows ~40% identity to certain bacterial amidases which are uncharacterised biochemically especially with respect to their substrate specificity.

Database searching indicates that this putative amidohydrolase (amidase 2) has 36% amino acid sequence identity with certain dipeptidases, such as the carboxypeptidase Sgx9355e encoded by an environmental DNA sequence isolated from the Sargasso Sea (Biochemistry 48 (2009): 4567-4576). The 3D structure of Sgx9355e is known and it is a member of the amidohydrolase superfamily (AHS). Sequence alignment of amidase 2 with Sgx9355e suggests that amidase 2 is as a member of the AHS.

This is a group of enzymes which have a remarkable substrate diversity with a $(\beta/\alpha)_8$-barrel (Tim barrel) structural fold. Most of the enzymes within this superfamily catalyse the hydrolysis of C—O, C—N, or P—O bonds. No members of the superfamily have been linked to the hydrolysis of OTA.

It will be understood that the terms amidase (i.e amidohydrolase) and amidase which can degrade ochratoxin are used interchangeably herein unless specifically stated otherwise or it is obvious from the context that a different enzyme is being discussed.

The terms amidase and amidase which can degrade ochratoxin A refer to an enzyme which can break down at least 5%, 10%, 15%, 20%, 25%, 30%, 40%, 50%, 60%, 70%, 75%, 80%, 90%, 95%, 97%, 98%, 99% or 100% of the ochratoxin A present in a sample to ochratoxin α.

It will be apparent to the skilled person that any amidase which can degrade ochratoxin will be suitable for use in the present invention. Preferably, the amidase for use in any aspect of the present invention is an amidase which degrades at least ochratoxin A.

Preferably, the amidase enzymes according to the present invention comprises at least one, preferably, at least two, at least three, at least four, at least five, at least six, at least seven, at least eight, more preferably nine of the amino acid sequence motifs:
1) x-P-G-x-x-D-x-H-x-H-x-xG, where the two H is residues are in the active site;
2) G-x-T;
3) G-x-x-x-G-P;
4) G-H-x-D where the H is residue is in the active site;
5) D-G-x-x-x-C-x-x-x-x-R-x-x-x-R-x-x-A-x-x-I—K, where the Lys residue is in the active site
6) G-G-V-x-S-x-x-D-x-P, where the Val residue is in the active site;
7) V-x-A-H-x-x-G-x-x-G, where the two H is residues are in the active site;
8) H-x-x-x-x-D, where the H is residue is in the active site;
9) G-V-x-I-x-x-G-T-D, where Asp residue is in the active site.

Preferably, the motifs are:
1) $x^1$-P-G-$x^2$-$x^3$-D-$x^4$-H-$x^5$-H-$x^6$-$x^7$-G, where the two H is residues are in the active site;
2) G-$x^8$-T;
3) G-$x^9$-$x^{10}$-$x^{11}$-G-P;
4) G-H-$x^{12}$-D where the H is residue is in the active site;
5)$_{D-G-x}$$^{13}$-$x^{14}$-$x^{15}$-C-$x^{16}$-$x^{17}$-$x^{18}$-$x^{19}$-R-$x^{20}$-$x^{21}$-$x^{22}$-R-$x^{23}$-$x^{24}$-A-$z^{25}$-$x^{26}$-I-K, where the Lys residue is in the active site
6) G-G-V-$x^{27}$-S-$x^{28}$-$x^{29}$-D-$x^{39}$-P, where the Val residue is in the active site;
7) V-$x^{31}$-A-H-$x^{32}$-$x^{33}$-G-$x^{34}$-$x^{35}$-G, where the two H is residues are in the active site;
8) H-$x^{36}$-$x^{37}$-$x^{38}$-$x^{39}$-D, where the H is residue is in the active site;
9) G-V-$x^{40}$-I-$x^{41}$-$x^{42}$-G-T-D, where Asp residue is in the active site;
wherein:
$x^1$=l/m; $x^2$=l/m; $x^3$=w/i; $x^4$=c/v/s/a; $x^5$=any amino acid; $x^6$=f/y/l; $x^7$=any amino acid; $x^8$=y/f; $x^9$=t/a/s/v/r; $x^{10}$=i/f/a; $x^{11}$=any amino acid; $x^{12}$=g/s; $x^{14}$=any amino acid; $x^{15}$=e/d/g; $x^{16}$=any amino acid; $x^{17}$=any amino acid; $x^{18}$=a/g/t; $x^{19}$=v/a; $x^{20}$=any amino acid; $x^{21}$=q/m/a; $x^{22}$=l/i/v; $x^{23}$=r/h/c; $x^{24}$=g/n; $x^{25}$=k/r/t/e/d; $x^{26}$=any amino acid; $x^{27}$=l/m/v/g; $x^{28}$=any amino acid; $x^{29}$=any amino acid; $x^{30}$=any amino acid; $x^{31}$=a/s/h; $x^{32}$=c/v/a; $x^{33}$=h/q; $x^{34}$=k/r; $x^{35}$=any amino acid; $x^{36}$=g/v/a; $x^{37}$=s/t/i; $x^{38}$=y/f/e; $x^{39}$=l/a/i; $x^{40}$=any amino acid; $x^{41}$=a/v; $x^{42}$=–l/a.

It will be understood that the term any amino acid refers to any one of amino acids G, A, V, L, I, M, F, W, P, S, T, C, Y, N, O, D, E, K, R or H, or an unnatural amino acid or amino acid derivative.

In a more preferred embodiment the motifs are:
1) l/m-P-G-l/m-w-D-c-H-x-H-f-x-G, where the two H is residues are in the active site;
2) G-y/f-T;
3) G-t-l-x-G-P;
4) G-H-g-D where the H is residue is in the active site;
5) D-G-v-x-e-C-x-x-a-v-R-x-q-l-R-r-g-A-k-x-l-K, where the Lys residue is in the active site
6) G-G-V-l/-S-x-x-D-x-P, where the Val residue is in the active site;
7) V-a-A-H-c-h-G-k-x-G, where the two H is residues are in the active site;
8) H-g-s-y-l-D, where the H is residue is in the active site;
9) G-V-x-l-a-l-G-T-D, where Asp residue is in the active site.

It will be readily apparent to the skilled person that the carboxypeptidase enzymes of the prior art which are capable of degrading ochratoxin do not comprise any of the recited motifs and show no sequence homology to amidases of the present invention.

In one preferred embodiment the amidase is an isolated amidase substantially free from other components in the culture media in which it is produced.

In a further preferred embodiment the amidase is at least 30%, 40%, 50%, 60%, 70%, 80%, 90%, 95%, 97%, 99% pure.

In a further preferred embodiment, the amidase is an amidase comprising a distorted Tim-like barrel structure including an active site comprising 6 histidine residues, 1 lysine residue and 1 aspartic acid residue, wherein the amino acids residues in the active site corresponding to positions H111, H113, H191, K246, H287, H289, H307 and D378 of SEQ ID NO:1 when the tertiary structure of the amidase and SEQ ID NO:1 are compared.

It will be understood by the skilled person that a Tim barrel is a conserved protein fold consisting of eight α-helices and eight parallel β-strands that alternate along the peptide backbone. Tim barrels are considered α/β protein folds because they include an alternating pattern of α-helices and β-strands in a single domain. In a Tim barrel the helices and strands (usually 8 of each) form a solenoid that curves around to close on itself in a doughnut shape, topologically known as a toroid. The parallel β-strands form the inner wall of the doughnut, whereas the α-helices form the outer wall of the doughnut. Each β-strand connects to the next adjacent strand in the barrel through a long right-handed loop that includes one of the helices.

The structure of amidase 2 can be divided into two domains, a core catalytic domain and a smaller β-sandwich domain. The catalytic domain comprises residues 107-425, which form a rather distorted TIM-like barrel of eight parallel β-strands (β5-7, 9-13) flanked on the outer face by α-helices. A kink in the middle of strand β7 occurring at residue 182 divides it into two separate strands, β7a and β7b. This kink represents the features that cause the barrel distortion. While β7a has only one neighbouring barrel strand, β6, strand β7b has two neighbours to which it is hydrogen-bonded, β8 and β9. The former represents a secondary structure element that is attached to the barrel core without formally being a part of it. The second cause for the barrel distortion is the absence of a canonical hydrogen-bonding interaction of residues 375-378 directly downstream of β13 with the first barrel strand β5 that would close the circle. Thus, the overall appearance of the domain core rather resembles a sandwich of parallel β-sheets, one consisting of three and the other of seven strands. Of them in total 13 helices (12 α and 1 g) of the catalytic domain those directly following the barrels strands and β8 can be assigned as barrel helices, while the remaining four helices represent additional secondary structure elements lining the top and bottom of the barrel.

The β-sandwich domain comprises residues of both the N- and the C-terminus (43-106, 426-480). The three strands formed by C-terminal residues (β14-16) are part of the larger of the two sheets. From the four strands formed by N-terminal residues β3 belongs to the smaller sheet, while the long and sharply bent strands β1, β2 and β4 contribute to the formation of both sheets. Only β1 and β4 are parallel to each other. Helical turns γ16 and γ17 are inserted between β14 and β15 and pack against the catalytic domain. Helices γ1 and α2 inserted between β3 and β4 are pointing in the opposite direction and are solvent exposed.

It will be understood by the skilled person that the tertiary structure of a given amidase can be readily compared to the tertiary structure of SEQ ID NO:1 having the co-ordinates shown in FIG. 25 using standard software packages with their default parameters, for example, PyMOL (www.Pymol.org).

It will be further readily apparent to the skilled person that the carboxypeptidase enzymes of the prior art which are capable of degrading ochratoxin do not comprise a Tim barrel-like structure including the specified residues in the active site.

In one embodiment, the amidase is an enzyme of EC 3.5.1.X, according to the Recommendations of the Nomenclature Committee of the International Union of Biochemistry and Molecular Biology (IUBMB) where X is a designation number provided by the committee.

It will be understood by the skilled person that carboxypeptidase A and carboxypeptidase Y of the prior art are designated in EC 3.4.17.1 and 3.4.16.5 respectively.

In one preferred embodiment, the amidase is one which degrades ochratoxin A when incubated at pH3-9 and 21-40° C.

It will be apparent that the ability of an amidase enzyme to degrade ochratoxin A can be determined using the OTA degradation assay described in the method section below.

Suitable amidases comprise those from *Aspergillus niger*, *Aspergillus flavus*, *Talaromyces stipitatus*, *Neurospora crassa*, *Streptomyces*, for example, *S. roseosporus*, *Thermotoga lettingae*, *Salinispora arenicola*, *Glomerella graminicola*, *Metarhizium anisopliae* and *Aspergillus oryzae* shown as SEQ ID NO: 1, 3, 5, 6, 7, 8, 9, 10, 11, 13, 14 and 15 respectively or a sequence having at least 10%, 20%, 30%, 40%, 50%, 60%, 70%, 75%, 80%, 90%, 95%, 98%, 99% identity to any one of SEQ ID NOs:1, 3, 5 to 11, 13, 14 or 15.

In preferred embodiments of the present invention the amidase enzyme for use in the additives, foods, feeds, uses and methods of the present invention comprises a polypeptide having the sequence of SEQ ID NO: 1 or SEQ ID NO: 3, or a sequence having at least 10%, 20%, 30%, 40%, 50%, 60%, 70%, 75%, 80%, 90%, 95%, 98%, 99% identity to SEQ ID NO: 1 or SEQ ID NO: 3, or a polypeptide which differs from SEQ ID NO: 1 or SEQ ID NO 3 by one or several amino acid additions, deletions and/or substitutions; or a polypeptide produced by expression of a polynucleotide comprising SEQ ID NO: 2 or a polynucleotide having at least 10%, 20%, 30%, 40%, 50%, 60%, 70%, 75%, 80%, 90%, 95%, 98%, 99% identity to SEQ ID NO:2, or a polynucleotide which differs from SEQ ID NO: 2 by one or several nucleotide additions, deletions and/or substitutions; or a sequence which hybridises under stringent conditions to the complement of SEQ ID NO:2, or a sequence having at least 10%, 20%, 30%, 40%, 50%, 60%, 70%, 75%, 80%, 90%, 95%, 97%, 98% or 99% identity thereto.

In further preferred embodiments, the enzyme according to the present invention catalyzes the chemical bond breakage of C—N, C—O or P—O, more preferably C—N.

It will be apparent to the skilled person that full length amidase 2 variants can be made using any well known technique in the art. More stable variants resistant to cleavage of the N-terminal or signal sequence can be produced by mutating the protease liable peptide bonds in the peptide sequence.

For example, mutations can be made at one or more of the following 71 sites of the 480aa amidase 2 sequence shown in SEC) ID NO: 1 these may alter the sensitivity to hydrolysis by signal peptidases, peptidases secreted by the host organism into its medium and pepsin:

18 31 33 34 42 55 56 56 64 69 70 78 79 107 114 127 128 139 146 147 156 184 185 194 195 197 202 203 220 236 262 264 269 270 304 317 318 325 335 336 336 337 343 344 351 352 354 355 359 360 374 375 386 387 388 389 390 391 400 412 420 424 425 435 436 440 446 461 462 462 480;

mutations at the following 44 sites may alter trypsin resistance:

3 4 36 48 66 75 88 89 92 99 138 141 155 166 231 232 235 239 240 243 246 256 271 279 282 291 299 303 320 322 330 346 351 361 368 395 405 426 445 451 458 461 464 476;

mutations at the following 90 sites may alter chymotrypsin resistance: 1 11 16 19 23 32 34 39 53 56 57 65 70 79 90 91 98 103 107 108 112 113 114 120 121 124 128 139 144 147 151 154 157 160 179 185 191 195 203 206 209 215 216 221 236 248 254 262 265 270 287 289 295 305 307 310 316 318 319

325 326 336 337 344 349 352 355 359 360 363 375 387 389 391 398 401 413 421 425 429 436 441 447 455 457 462 463 471 479 480.

It will be further understood that the 480 aa amidase 2 polypeptide or its variants may be N- and/or O-glycosylated at any of its asparagine (Asn), serine (Ser) and threonine (Thr) residues in order to improve solubility and heat-stability.

It will be understood that as defined herein, the term stringent conditions refers to washing at. 50° C. and 0.2×SSC {1×SSC=0.15 M NaCl, 0.015 M Na₃citrate pH 7.0}.

It will be understood that these conditions may also be high stringent conditions which are defined herein as washing at 65° C. and 0.1×SSC {1×SSC=0.15 M NaCl, 0.015 M Na₃citrate pH 7.0}.

In another preferred embodiment, the amidase enzyme is produced by expression of a polynucleotide encoding a polypeptide having an amino acid sequence comprising SEQ ID NO: 1, 3, 5-11, 13, 14 or 15, or a sequence having at least 10%, 20%, 30%, 40%, 50%, 60%, 70%, 75%, 80%, 90%, 95%, 97%, 98%, 99% identity thereto, or a polypeptide which differs from SEQ ID NO: 1, 3, 5-11, 13, 14 or 15 by one or several amino acid additions, deletions and/or substitutions.

More preferably, the amidase is encoded by a polynucleotide selected from:—
a) a polynucleotide comprising SEQ ID NO: 2 or a sequence having at least 10%, 20%, 30%, 40%, 50%, 60%, 70%, 80%, 90%, 95%, 98%, 99% identity thereto, or a polynucleotide which differs from SEQ ID NO: 2 by one or several nucleotide additions, deletions and/or substitutions;
b) a polynucleotide which differs from SEQ ID NO: 2 due to the degeneracy of the genetic code;
c) a polynucleotide which hybridises under stringent conditions to the complement of SEQ ID NO: 2 or a sequence having at least 10%, 20%, 30%, 40%, 50%, 60%, 70%, 80%, 90%, 95%, 98%, 99% identity thereto, or a polynucleotide which differs from the complement of SEQ ID NO: 2 by one or several nucleotide additions, deletions and/or substitutions.

In another preferred embodiment, there is provided a vector comprising a polynucleotide encoding the amidase enzyme which degrades ochratoxin A for use in the present invention.

It will be apparent to the skilled person that the vector can be any suitable expression vector and that the choice of vector may vary depending upon the type of cell into which the vector is to be inserted. Suitable vectors include pGAPT-PG, pRAX1, pGAMD and pGPT-pyrG1.

In a further preferred embodiment, the vector is comprised in a cell. In a further embodiment, the cell is a spore.

It will be understood that as used herein the term spore refers to a fungal or bacterial spore, endospore or exospore.

The cell according to the present invention may be any suitable cell. More preferably, any suitable bacterial, fungal or plant cell. Even more preferably the cell is selected from *E. coli*, *Streptomyces*, *Hansenula*, *Trichoderma* (particularly *T. reesei*), *Bacillus*, *Lactobacillus*, *Aspergillus* (particularly *A. niger*), a plant cell and/or spores of *Bacillus*, *Trichoderma*, or *Aspergillus*.

In a more preferred embodiment there is provided a recombinant cell or spore comprising a polynucleotide encoding an amidase enzyme which degrades ochratoxin, preferably ochratoxin A for use in the present invention.

In further preferred embodiments, the amidase enzyme for use in the present invention is recombinant.

In a preferred aspect of the present invention there is provided a food or feed additive comprising an amidase enzyme which is capable of degrading ochratoxin.

Preferably, the amidase enzyme will degrade at least ochratoxin A.

More preferably, the amidase enzyme will also degrade at least one other ochratoxin, more preferably, at, least ochratoxin B.

In a further embodiment, the enzyme will also degrade at least one ochratoxin derivatives beside ochratoxin B and ochratoxin C, and/or at least one ergot alkaloid.

It will be understood that ergot alkaloids are compounds containing amide bonds and include, for example, ergocornine, ergocorninine, ergocristine, ergocristinine, ergocryptine, ergocryptinine, ergometrine, ergosine, ergotamine and ergotaminine. These compounds are toxic to living organisms including humans and farm animals.

It will be apparent to the skilled person that this food or feed additive may be added to a food or feed material contaminated with ochratoxin in order to reduce the level of the toxin present in the food or feedstuff consumed by an animal. Ochratoxin A is known to be an important contaminant of cereals and other starch rich foods as well as, for example, coffee, cocoa, wine, beer, pulses, spices, dried fruit, grape juice, milk and meat products from non ruminant animals. Ochratoxin A is a nephrotoxic, teratogenic, hepatotoxic and carcinogenic compound which if present even at low levels can be harmful.

In a more preferred embodiment the additive is a feed additive.

In preferred embodiments the food or feed additive comprises the amidase at a level of at least 0.001 g/kg, at least 0.01 g/kg, at least 0.1 g/kg, at least 1 g/kg, at least 5 g/kg, at least 7.5 g/kg, at least 10.0 g/kg, at least 15.0 g/kg, at least 20.0 g/kg, at least 25.0 g/kg. Preferably, the food or feed additive comprises the amidase at a level such that when added to a food or feed material, the feed material comprises the amidase in a range of 1-500 mg/kg, 1-100 mg/kg, more preferably 2-50 mg/kg or 2-10 mg/kg.

In preferred embodiments of the present invention the amidase can hydrolyse at least 10, 20, 50, 100, 200, 300, 500, 700, 900, 1000 nanomoles OTA per min per mg protein at pH 7.0 and 40° C. when the OTA is present at a concentration of 1 µg/ml.

More preferably, the food or feed additive of the present invention comprises a recombinant cell capable of expressing an amidase enzyme capable of degrading ochratoxin. More preferably, the amidase enzyme is capable of degrading at least ochratoxin A.

Even more preferably, the amidase enzyme is also capable of degrading at least one further ochratoxin or ochratoxin derivative and/or at least one ergot alkaloid, more preferably, ochratoxin B.

Most preferably, the amidase comprises SEQ ID NO: 1, SEQ ID NO: 3 or any one of SEQ ID NO: 5-11, 13, 14 or 15 or a sequence having at least 10%, 20%, 30%, 40%, 50%, 60%, 70%, 75%, 80%, 90%, 95%, 98%, 99% identity to any one of SEQ ID NOs: 1, 3, 5 to 11, 13, 14 or 15.

In another preferred embodiment the cell is an *Aspergillus* cell or spore. It will be apparent to the skilled person that *Aspergillus* cell may be a living cell, a dead cell or a disrupted cell.

In preferred embodiments, the recombinant cell is an *A. niger* cell. More preferably, the cell has increased OTA degrading activity when compared to a non recombinant cell of the same species.

It will be understood by the skilled person that the amidase enzyme capable of degrading ochratoxin A for use in the present invention can be provided independently as either liquid or solid/granulated compositions.

Preferably, when said enzyme is in liquid form, said enzyme is secreted into the medium following culturing of a cell comprising said enzyme. Preferably said medium is cell-free (i.e. the cell(s) have been separated from the medium). Preferably said medium is concentrated. It will be understood that the medium can be granulated to provide a solid enzyme composition.

It will be further understood that the food or feed additive according to the present invention may be provided in the form of a solution or as a solid—depending on the use and/or the mode of application and/or the mode of administration.

In a further embodiment, the additive may be used to pre-treat a material which will be used as a food or feed.

For example, the amidase may be used for treating liquids such as those produced as by-products from ethanol plants. In this case, the additive will be added to a liquid fermentation broth in order to degrade ochratoxin A contaminants found in the medium used to grow yeast or microbes for ethanol production.

It will be understood that the broth may be subsequently dried and fed to animals.

In an alternativel embodiment, the additive may be added to milk, for example, cows milk, contaminated with OTA.

In one embodiment the food or feed additive according to the present invention is in a liquid formulation suitable for consumption, preferably such liquid composition further comprises at least one of a buffer, a salt, sorbitol and/or glycerol.

Preferably, the food or feed additive further comprises at least one physiologically acceptable carrier.

The physiologically acceptable carrier is preferably selected from at least one of maltodextrin, limestone (calcium carbonate), cyclodextrin, wheat or a wheat component, sucrose, starch, $Na_2SO_4$, Talc, PVA and mixtures thereof.

In a further embodiment, the food or feed additive may further comprise a metal ion chelator. The metal ion chelator may be selected from EDTA or citric acid.

In one embodiment the amidase enzyme is dried on the physiologically acceptable carrier.

In one embodiment the food or feed additive is granulated or co-granulated with other enzymes.

In preferred embodiments, the amidase for use in the present invention may be used is combination with one or more further enzyme. In preferred embodiments, the one or more further enzyme is selected from the group consisting of those involved in protein degradation including carboxypeptidases preferably carboxypeptidase A, carboxypeptidase Y, *A. niger* aspartic acid proteases of PEPAa, PEPAb, PEPAc and PEPAd, elastase, amino peptidases, pepsin or pepsin-like, trypsin or trypsin—like proteases and bacterial proteases including subtilisin and its variants, and of those involved in starch metabolism, fibre degradation, lipid metabolism, proteins or enzymes involved in glycogen metabolism, enzymes which degrade other contaminants, acetyl esterases, amylases, arabinases, arabinofuranosidases, exo- and endo-peptidases, catalases, cellulases, chitinases, chymosin, cutinase, deoxyribonucleases, epimerases, esterases, formamidase, -galactosidases, for example $\alpha$ or $\beta$-galactosidases, exo-glucanases, glucan lysases, endo-glucanases, glucoamylases, glucose oxidases, -glucosidases, for example $\alpha$ or $\beta$-glucosidases, glucuronidases, hemicellulases, hydrolases, invertases, isomerases, laccases, phenol oxidases, lipase, lyases, mannosidases, oxidases, oxidoreductases, pectinase, pectate lyases, pectin acetyl esterases, pectin depolymerases, peptidase, pectin methyl esterases, pectinolytic enzymes, peroxidases, phenoloxidases, phytase, polygalacturonases, rhamno-galacturonases, ribonucleases, thaumatin, transferases, transport proteins, transglutaminases, xylanases, hexose oxidase (D-hexose: $O_2$-oxidoreductase, EC 1.1.3.5), acid phosphatases and/or others or combinations thereof. These include enzymes that, for example, modulate the viscosity of the composition or feed.

In a particularly preferred embodiment, the enzyme is used in combination with carboxypeptidase A.

In a further preferred embodiment, the enzyme is used in combination with PEPAd protease.

In a further embodiment the amidase may be used in combination with at least one of a detoxifying enzyme selected from the group consisting of a mycotoxin degrading enzyme, for example, aflatoxin detoxizyme, zearalenone esterases, zearalenone lactonases, fumonisin carboxylesterases, fumonisin aminotransferases, aminopolyol amine oxidases, deoxynivalenol expoxide hydrolases, a mycotoxin degrading microorganism, for example, *Bacillus subtilis, B. licheniformis, Lactobacillus* or an absorbent (i.e., myctoxin binders) including at least one polymer, for example, microbial cell walls or an inorganic material such as bentonite.

It will be understood that the feed additive may be for any suitable animal. In one preferred embodiment the animal is a monogastric animal, for example, poultry, swine, fish, shellfish and crustacea, for example, shrimps, pet animals such as, for example, cats or dogs. In an alternative preferred example the animal is a ruminant selected from, for example, cows or other bovines, sheep, goats, camels, deer, llama, antelope, alpacas or wildebeest.

It will be obvious to the skilled person that the food or feed additive according to the present invention may also comprise other components such as stabilising agents and/or bulking agents and/or other enzymes.

Preferably, the food or feed additive according to the present invention will be thermally stable to heat treatment up to about 70° C.; up to about 80° C.; or up to about 95° C. The heat treatment may be performed for up to about 0.5 minute; up to about 5 minutes; up to about 10 minutes; up to about 30 minutes; up to about 60 minutes. The term thermally stable means that at least about 75% of the enzyme components that were present/active in the additive before heating to the specified temperature are still present/active after it cools to room temperature. Preferably, at least about 80% of the enzyme components that were present and active in the additive before heating to the specified temperature are still present and active after it cools to room temperature.

The food or feed additive according to the present invention may have a shelf-life of greater than about 30 weeks; greater than about 40 weeks; greater than about 50 weeks; greater than about 1 year; greater than about 1.5 years. The shelf-life means that at least about 80% of the enzyme components that were present and active in the additive when it was prepared are still present and active.

Preferably, the method of preparing a food or feed additive according to the present invention comprises a mixing step that comprises admixing the amidase enzyme which degrades ochratoxin, preferably ochratoxin A, optionally with at least one physiologically acceptable carrier.

More preferably, the amidase enzyme is also capable of degrading at least one further ochratoxin or ochratoxin derivative and/or at least one ergot alkaloid, more preferably, ochratoxin B.

In a particularly preferred embodiment the food or feed additive is homogenized to produce a powder In an alternative preferred embodiment, the food or feed additive is formulated in to granules as described in WO20071044968 (referred to as TPT granules) incorporated herein by reference.

In another preferred embodiment when the food or feed additive is formulated into granules the granules comprises a hydrated barrier salt coated over the protein core. The advantage of such salt coating is improved thermo-tolerance, improved storage stability and protection against other food or feed additives otherwise having adverse effect on the enzyme.

Preferably, the salt used for the salt coating has a water activity less than 0.25 or constant humidity greater than 60% at 20° C.

Preferably, the salt coating comprises a $Na_2SO_4$.

The method of preparing a food or feed additive may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 85° C., 90° C. or 95° C. The residence time can be variable from seconds to minutes and even hours. Such as 5 seconds, 10 seconds, 15 seconds, 30 seconds, 1 minutes 2 minutes., 5 minutes, 10 minutes, 15 minutes, 30 minutes and 1 hour.

In a further aspect there is provided a food or feed material comprising the food or feed additive of the present invention. It will be understood that the food or feed additive of the present invention is suitable for addition to any appropriate food or feed material.

It will be obvious to the skilled person that the food or feed additive can be added to any food or feed material as a precautionary step. Alternatively, the food or feed additive can be added to food or feed materials which are known to be prone to ochratoxin, preferably ochratoxin A, contamination or to food or feed materials which have been shown to be contaminated with ochratoxin, preferably ochratoxin A. It will be further apparent to the skilled person that the presence of ochratoxin, preferably ochratoxin A can be identified by any suitable means, for example, HPLC, ELISA or through the use of commercially available ochratoxin detection strips (Helica Biosystems, Inc., Fullerton Calif.).

As used herein, the term feed material refers to the basic feed material to be consumed by an animal. It will be further understood that this may comprise, for example, at least one or more unprocessed grains, and/or processed plant and/or animal material such as soybean meal or bone meal.

In some embodiments, the feed material will comprise one or more of the following components: a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) silage such as maize silage; d) protein obtained from sources such as soya, sunflower, peanut, lupin, peas, fava beans, cotton, canola, fish meal, dried plasma protein, meat and bone meal, potato protein, whey, copra, sesame; e) oils and fats obtained from vegetable and animal sources; f) minerals and vitamins.

As used herein, the term feedstuff refers to a feed material to which one or more feed additives have been added. According to another aspect there is provided a feedstuff comprising the feed material of the present invention.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

As used herein, the term food material refers to a basic food to be consumed by a human. It will be understood that this may comprise grain, plant or animal material.

In some embodiments, the food material may comprise one or more of a cereal or cereal product, coffee, cocoa, wine, beer, pulses, spices, dried fruits, grape juice, milk, meat or meat products.

As used herein, the term foodstuff refers to a food material to which one or more food additives have been added. According to another aspect there is provided a foodstuff comprising the food material of the present invention.

In preferred embodiments, the foodstuff or feedstuff comprises amidase at a level of about 0.001 mg-10 g/kg, 0.01 mg-10 g/kg, 0.1 mg-10 g/kg, 0.1 mg-5 g/kg, 1 mg-5 g/kg, 0.5 g-1 g/kg food/feedstuff.

It will be readily apparent to the skilled person that in order for the food or feed additive of the present invention to provide the claimed advantages the food/feedstuff must be a food/feedstuff contaminated with ochratoxin, preferably ochratoxin A.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for any suitable animal. Preferably, the feedstuff is for domestic or farm animals.

In one embodiment the animal is a monogastric animal, such as poultry (for example, broiler, layer, broiler breeders, turkey, duck, geese, water fowl), swine (all age categories), fish, shell fish including crustaceans such as shrimps, a pet (for example dogs, cats).

In a further embodiment the animal is a ruminant, such as a bovine (for example, cow water buffalo, bison, yak), sheep, goats, camels, deer, llamas, antelope, alpacas or wildebeest.

The feedstuff may comprise at least 0.0001% by weight of the feed additive. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the feed additive.

In a further aspect there is provided the use of at least one amidase enzyme capable of degrading ochratoxin, preferably ochratoxin A, in the manufacture of a foodstuff or feedstuff for reducing the level of mycotoxin contamination in the foodstuff or feedstuff.

Preferably, the amidase enzyme is also capable of degrading at least one further ochratoxin or ochratoxin derivative and/or at least one ergot alkaloid, more preferably, ochratoxin B.

Preferably, the at least one amidase enzyme is formulated as a food or feed additive. More preferably, the food or feed additive is the food or feed additive according to the present invention.

In a further aspect of the present invention there is provided a composition comprising an ochratoxin, preferably ochratoxin A, contaminated material and an amidase which degrades ochratoxin, preferably ochratoxin A as described herein.

In a preferred embodiment of the present invention, the composition comprises a recombinant cell capable of expressing the ochratoxin A degrading amidase.

It will be understood that said composition can comprise any suitable ochratoxin A contaminated material. In preferred embodiments the composition comprises a food or feed material, a fermentation broth or waste product of the fermentation process such as DDGS, waste water or contaminated soil.

The skilled person will understand that ochratoxin A contamination of compositions other than food and feed materials can be problematical. For example, waste water containing ochratoxin A from industrial processes can result in contamination of water ways.

Also provided by the present invention, is a method of reducing ochratoxin contamination in a material, comprising adding to the contaminated material an amidase enzyme capable of degrading ochratoxin, preferably ochratoxin A.

Also provided by the present invention is a food or feed material obtainable by the methods of the present invention.

In a further aspect of the present invention there is provided a method of increasing the growth rate and/or health of an animal comprising feeding the animal an effective amount of a feedstuff according to the present invention.

As used in the present context, the term health refers to a reduction in the detrimental effects on an animal caused by ochratoxin toxicity resulting from levels of ochratoxin present in the feedstuff.

EXAMPLES

The invention will be further described with reference to the examples and figures in which:—

Figure 4:
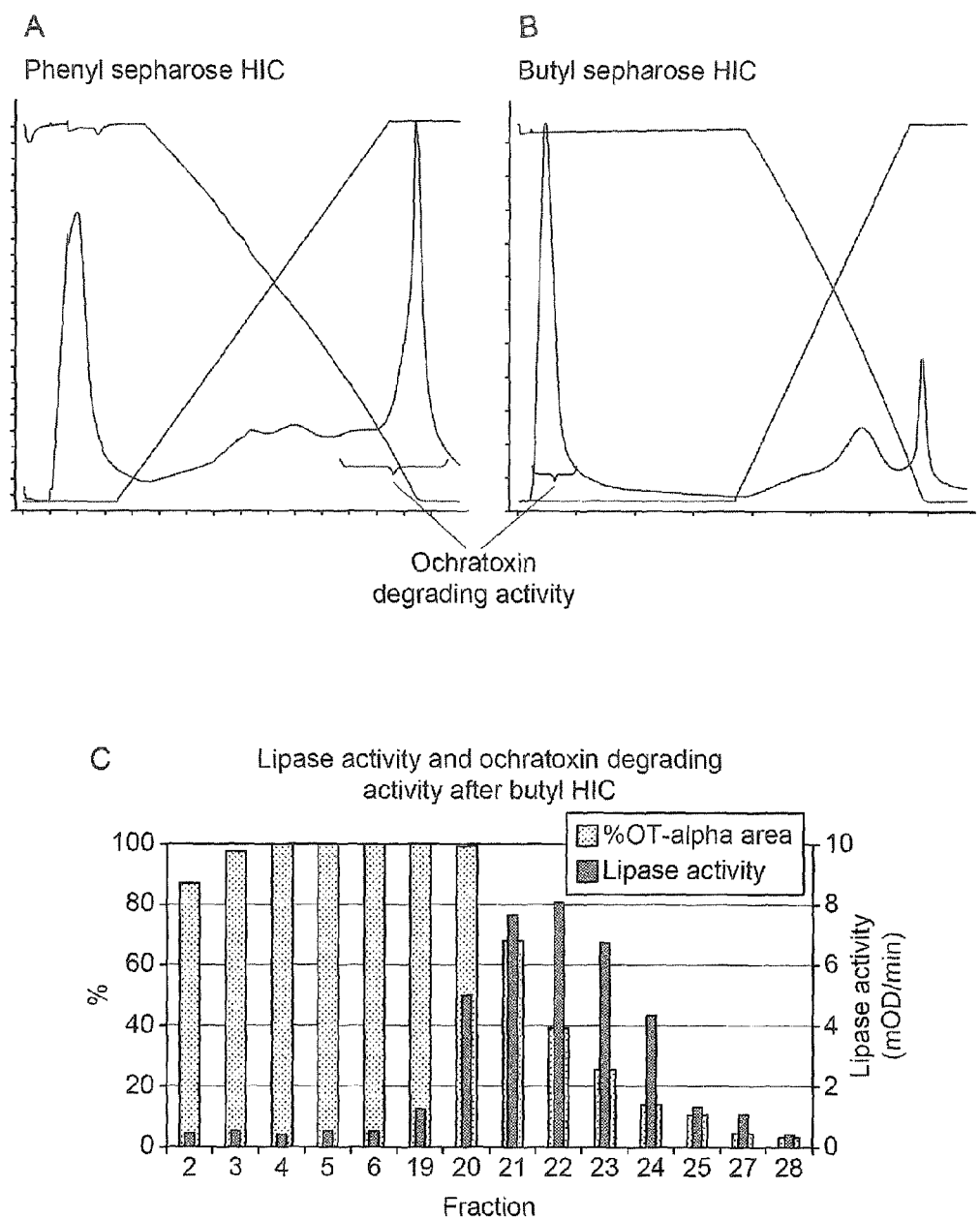

FIG. 4 shows graphically the separation of OTA active fractions by HIC/affinity chromatography after ammonium sulfate fractionation. FIG. 4A shows HIC or affinity chromatography on Phenyl Sepharose column; FIG. 4B shows HIC on Butyl Sepharose column. FIG. 4C shows the lipase and OTA activity distribution in the collected fractions 2-28 from the Butyl Sepharose column.

Figure 5:
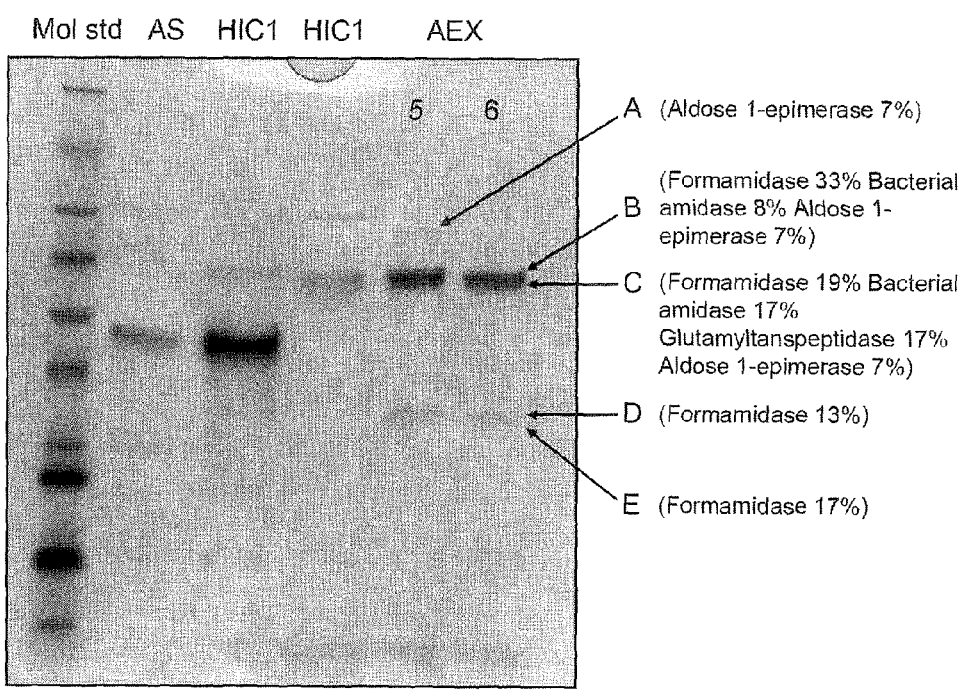

FIG. 5 shows SDS-PAGE analysis of concentrated OTA active fractions after the purification steps of ammonium fractionation, HIC/affinity on Phenyl Sepharose, HIC on Butyl Sepharose, AEX on Source Q30 and membrane separation/concentration on Amicon centriprep 10 concentrator (molecular cutoff of 10 kDa).

Figure 6:
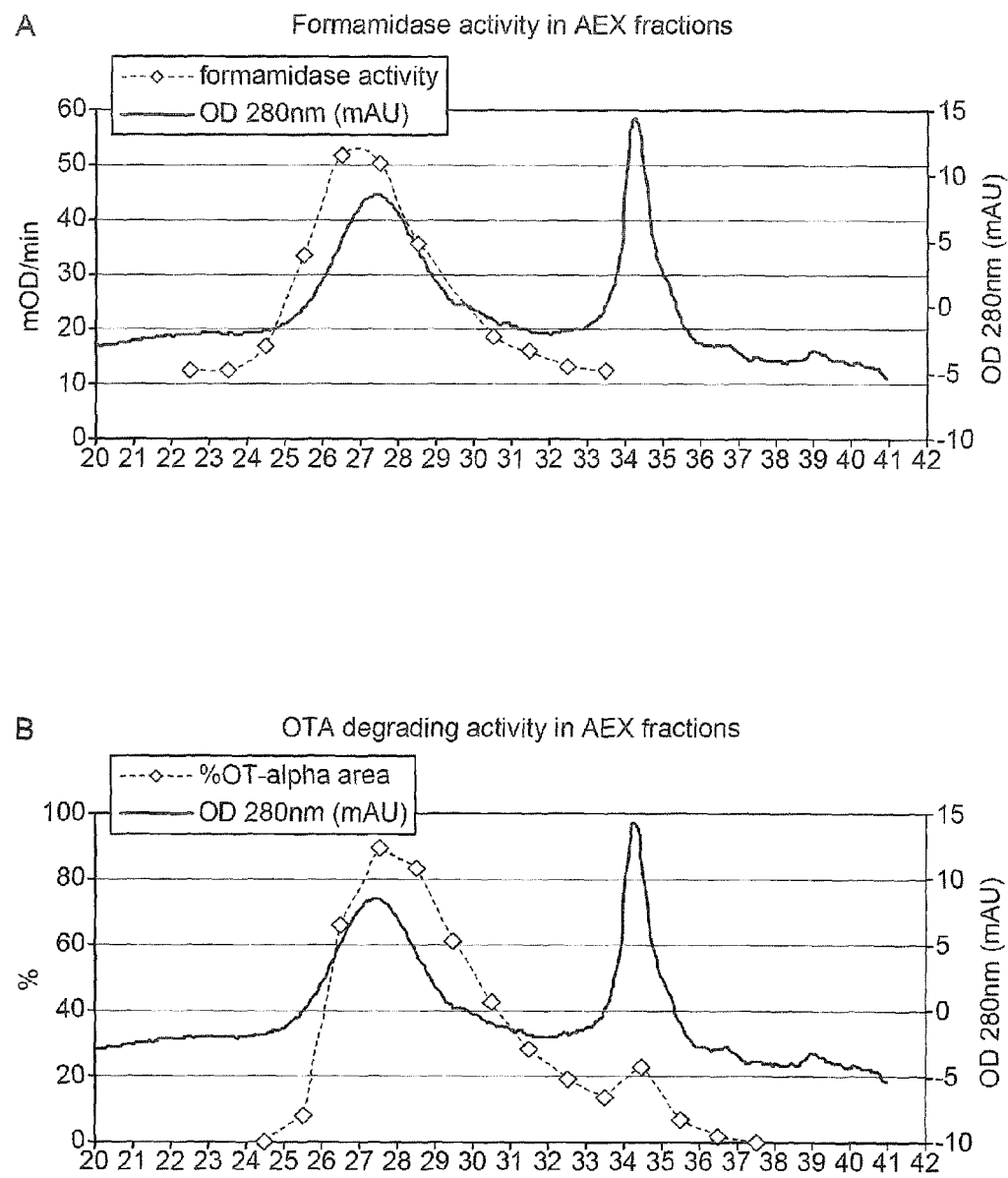

FIG. 6 shows the activities present in the membrane separated and concentrated AEX fractions of FIG. 5 on formamide (FIG. 6A) and OTA (FIG. 6B), protein peaks assayed at 280 nm.

Figure 7:
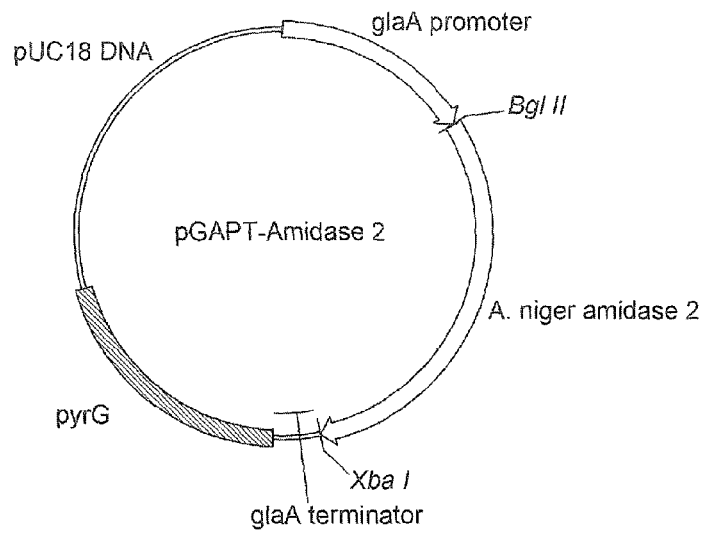

FIG. 7 shows the construction of the amidase 2 expression cassette.

Figure 8:
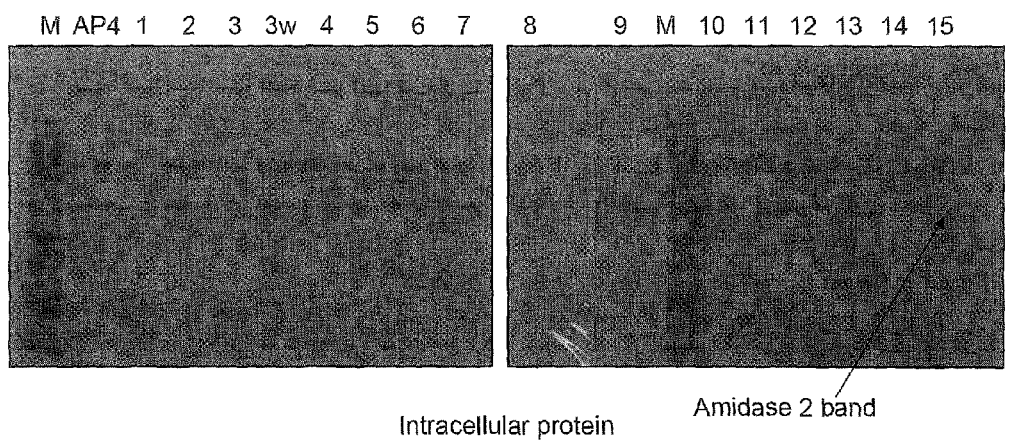

FIG. 8 shows SOS-PAGE analysis of intracellular proteins of *A. niger* transformants harboring the Amidase 2 gene. The protein band of amidase 2 is indicated by an arrow bar.

Figure 9:
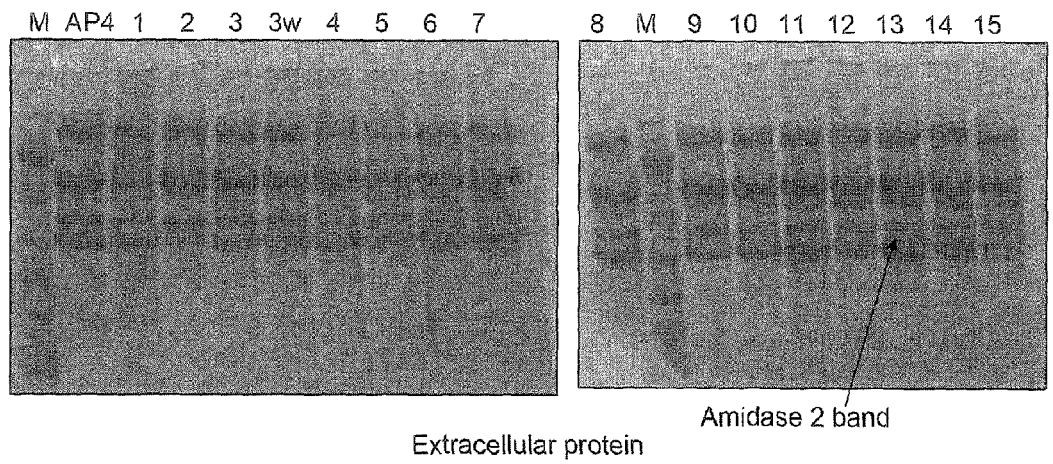

FIG. 9 shows SDS-PAGE analysis of extracellular proteins of *A. niger* transformants harboring the Amidase 2 gene. The protein band of amidase 2 is indicated by an arrow bar.

Figure 10:
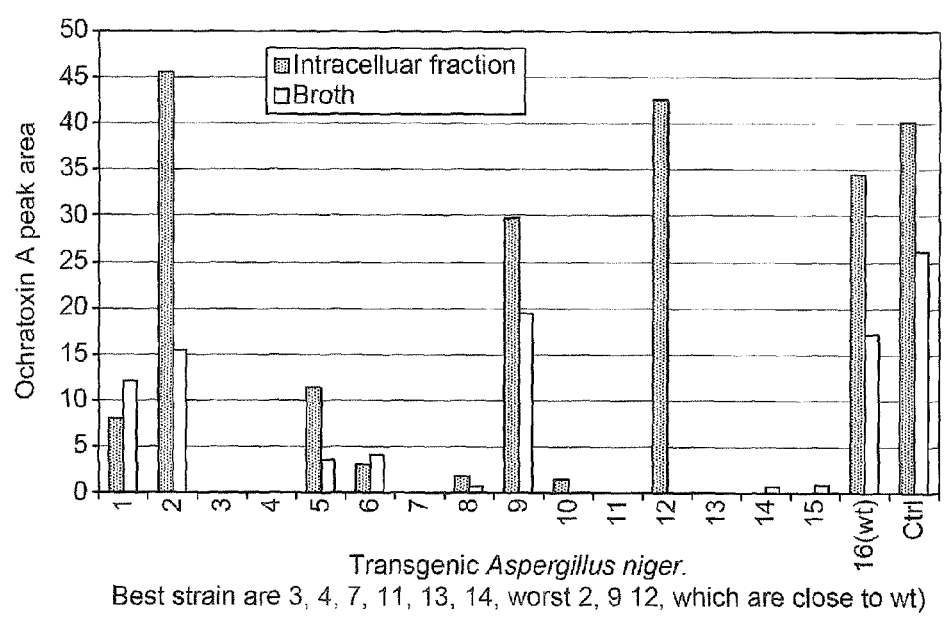

FIG. 10 shows the screening of intracellular and extracellular (fermentation broth) fractions of *Aspergillus niger* transformants (1-15) harboring the amidase 2 gene for their ability to break down OTA. 10 μl of the intracellular fractions or the broth was mixed with 25 μL 1 μg/ml OTA, 100 μl sodium phosphate (67 mM, pH7.0) and incubated at 40° C. for 35 min. At the end of the reaction 130 μl acetonitrile containing 0.2% acetic acid was added to stop the reaction. The reaction mixture was filtered and 5 μl analysed by RP-HPLC analysis of remaining OTA. wt refers to the parent strain used for the transformation; ctrl, refers to the reaction in the absence of *A. niger* transformants.

Figure 11:
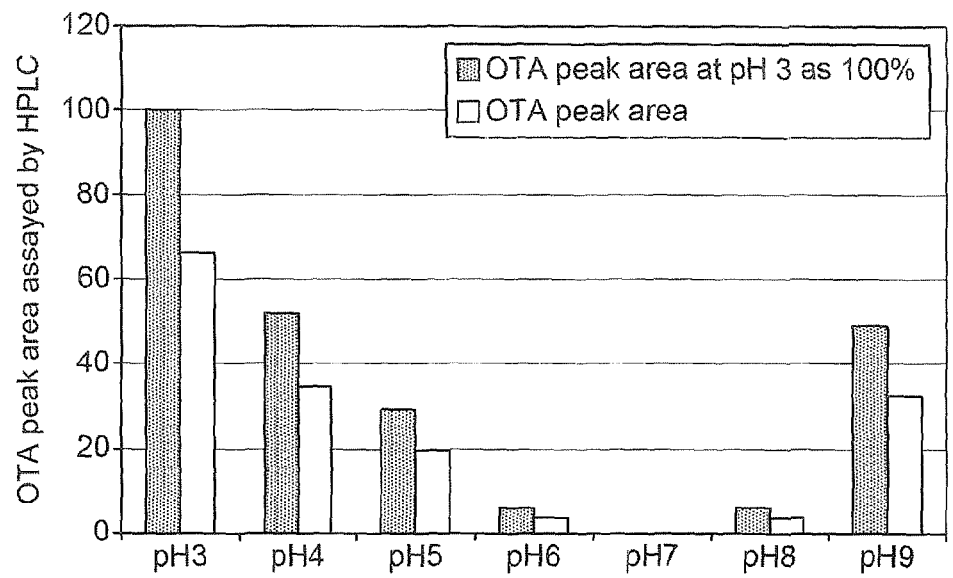

FIG. 11 shows the pH optimum of the amidase 2 from transgenic *A. niger* intracellular preparation in degrading OTA. The reaction mixture contained 5 μl amidase 2 mixture (a mixture of the intracellular fractions of transformant 3, 4, 7-8, 10-11 and 13-15) with a protein concentration of 155 μg protein/ml), 0.1 ml 67 mM phosphate buffer (pH3, 4, 5, 6, 7, 8 and 9), 25 μl OTA (1 μg/ml). The reaction was performed at 30° C. for 60 min and stopped by the addition of 0.13 ml acetonitrile containing 0.2% HAC. An injection volume of 10 μl was used for RP-HPLC analysis of remaining OTA after filtering.

Figure 12:
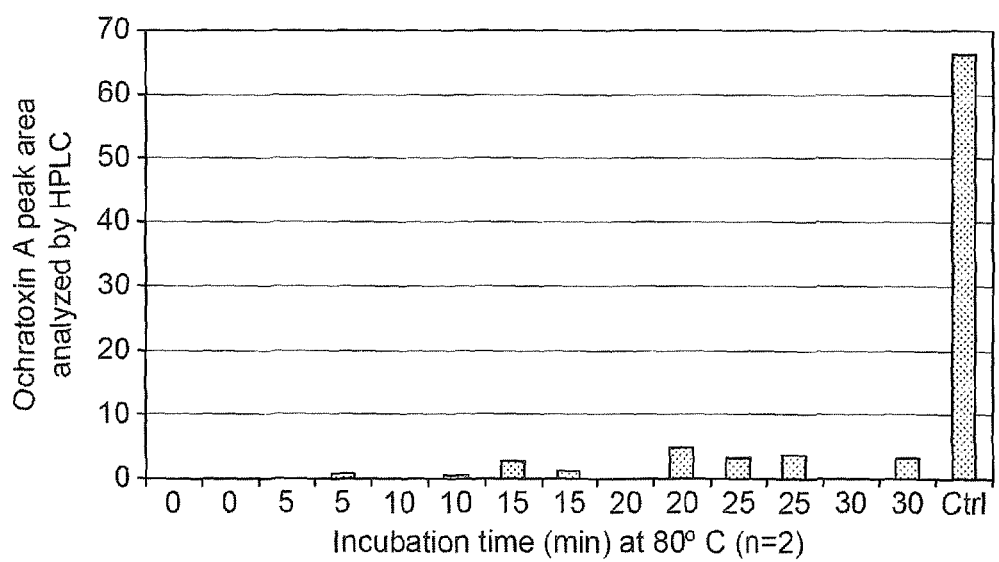

FIG. 12 shows the heat stability of amidase 2 from transgenic *A. niger* intracellular preparation. The pre-incubation mixture in a 1.5 ml ependorpf tube contained 5 μl of the amidase 2 mixture (155 μg protein/ml), and 45 μl 67 mM phosphate buffer pH7.0. The samples were pre-incubated at 80° C. for 0, 5, 10, 15, 20, 25 and 30 min. After cooling to 15° C., 50 μl 67 mM phosphate buffer and 25 μl OTA (1 μg/ml) were added to start the reaction this was incubated at 30° C. for 60 min, the reaction was stopped by the addition of 130 μl acetonitrile containing 0.2% HAC. An injection volume of 10 μl was used for RP-HPLC analysis of remaining OTA after filtering.

Figure 13:
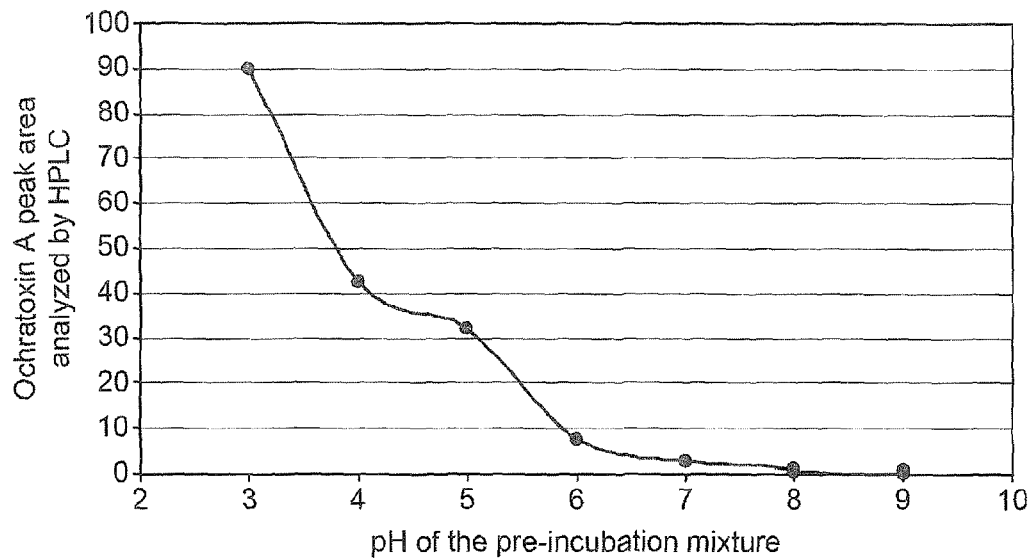

FIG. 13 shows pH and temperature stability of amidase 2 from transgenic *A. niger* inrtracellular preparation at incubated at 70° C. at pH 3-9 in 67 mM sodium phosphate. The reaction mixture contained 5 μl amidase 2 mixture (155 μg protein/ml), 45 μl 67 mM phosphate buffer at either pH3, 4, 5, 6, 7, 8 or 9. The reaction mixes were incubated at 70° C. for 30 min, before 2 μl 0.5 mg/ml OTA in ethanol and 80 μl 0.2M Mops pH 7.0 were added and the samples incubated at 30° C. for 60 min. The reaction was stopped by adding 130 μl acetonitrile containing 0.2% HAC, filtered and analysed by RP-HPLC.

Figure 14:
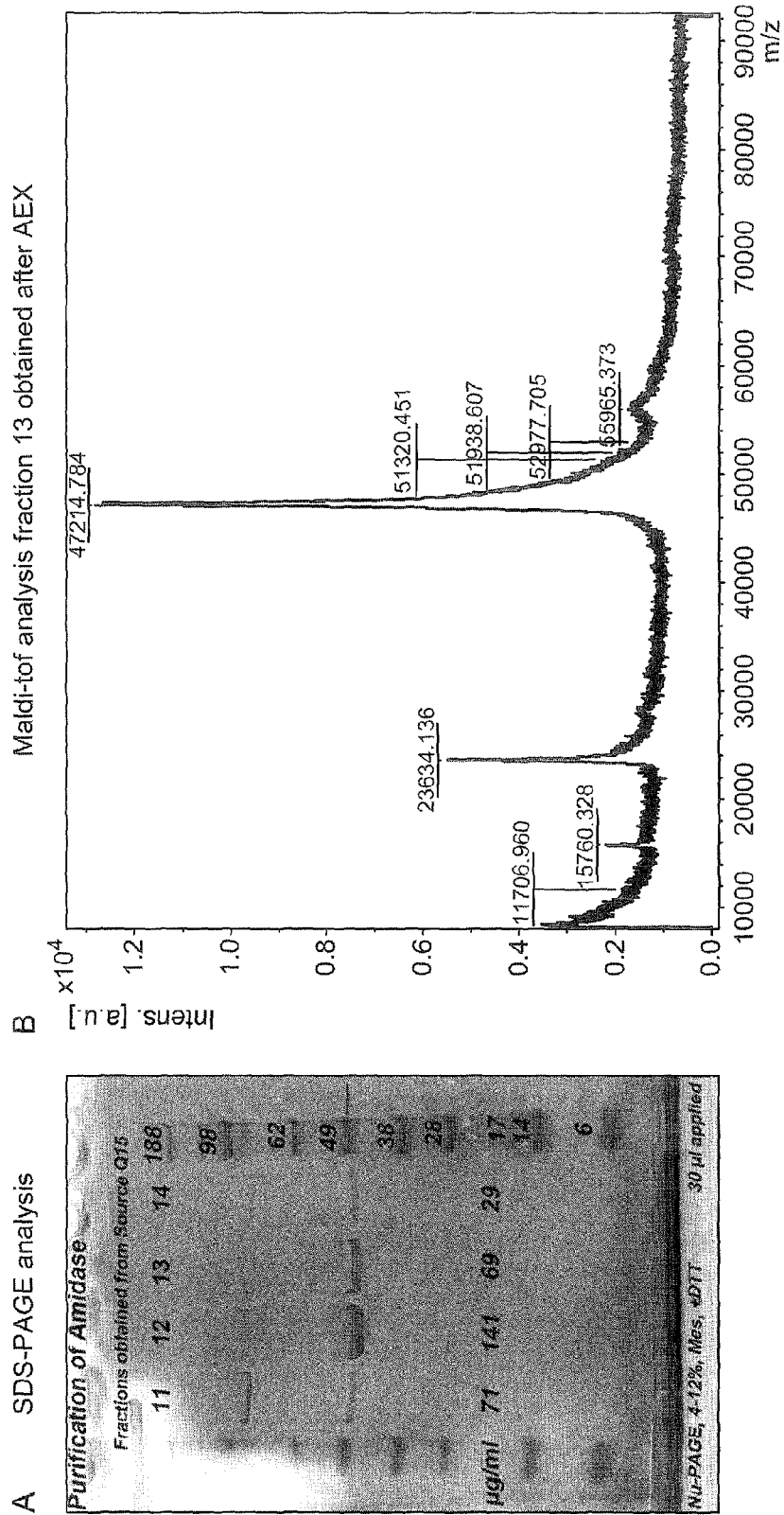

FIG. 14 shows analysis of recombinant amidase 2 purified from the broth of *A. niger* transformant 13 by SDS-PAGE on AEX fractions (A) and by mass-spectrometry (B) on fraction 13 after AEX.

Figure 15:
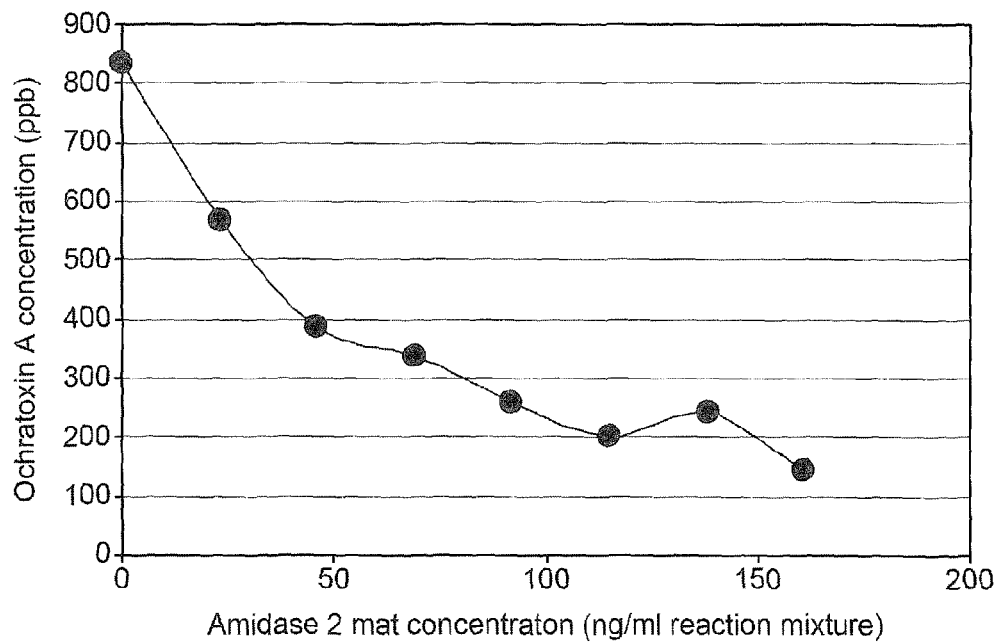

FIG. 15 shows OTA degradation as a function of amidase protein concentration. The amidase used was purified from the broth of transformant 13 (438aa protein referred to as amidase 2 mat).

Figure 16:
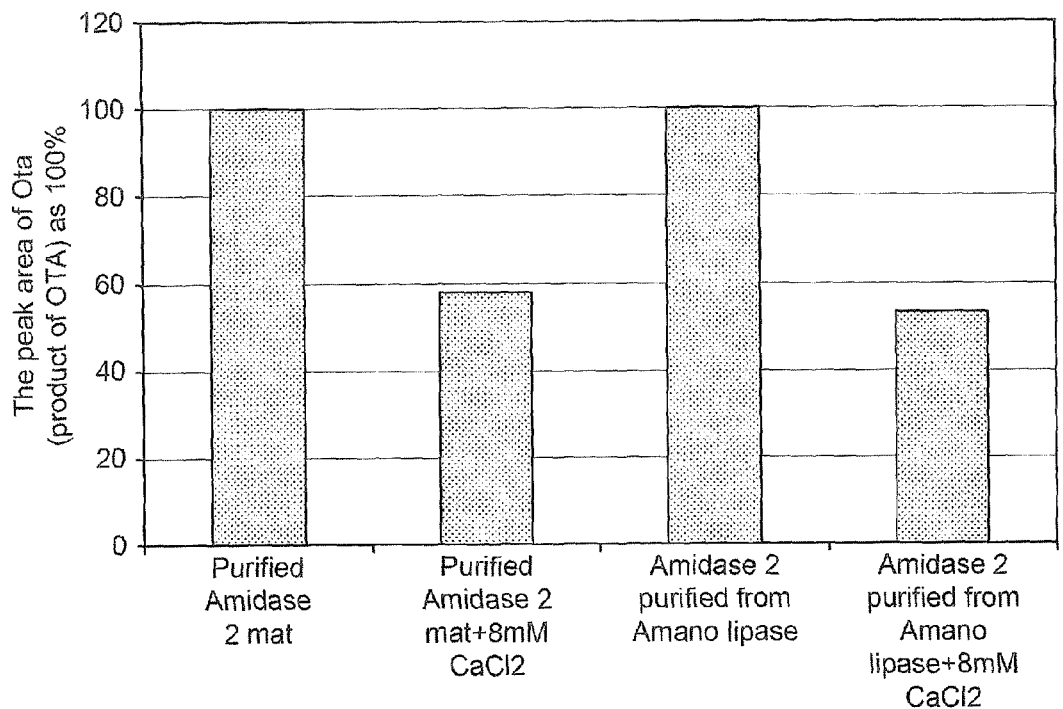

FIG. 16 shows the effect of calcium ion concentration on the activity of amidase 2 mat purified from the transgenic *A. niger* and the Amano™ lipase product.

Figure 17:
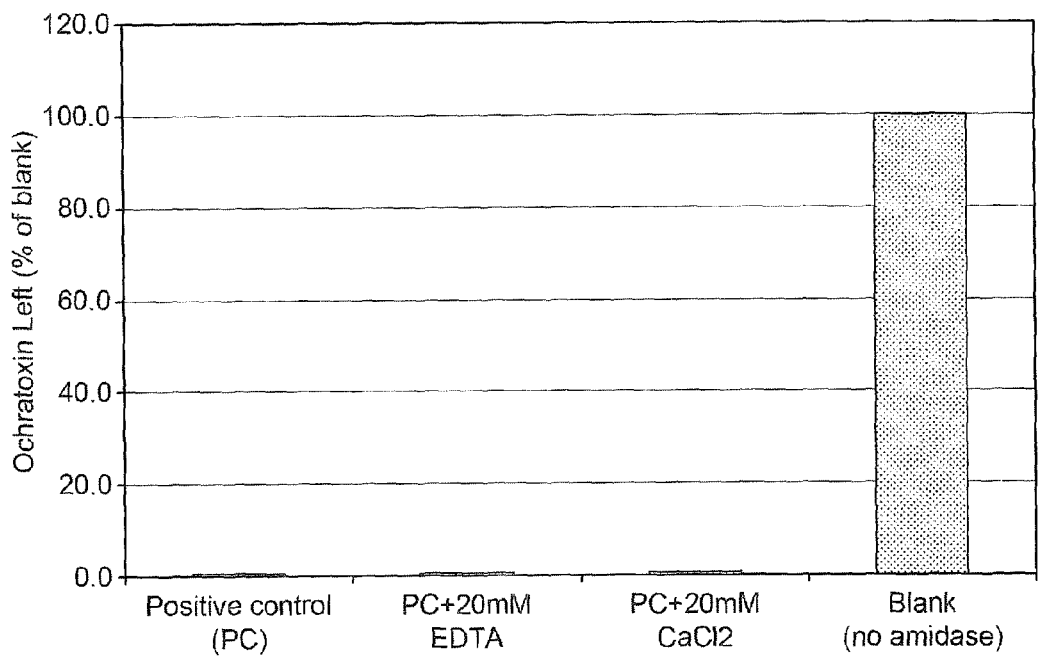

FIG. 17. Degradation of OTA by the amidase 2 extracted from the intracellular fraction (Amidase 2 sig) of *A. niger*. No inhibition by $CaCl_2$ or EDTA to amidase 2 sig is seen.

FIG. 18A shows the amidase 2 amino acid sequence (480aa) (SEQ ID NO: 1) from *Aspergillus niger* in one letter format. Single underlined sequences are those obtained from FIG. 5; double underlined are those obtained from FIG. 8.

FIG. 18B shows the amidase 2 amino acid sequence (480aa) plus 6 histidine residues at its C-terminal from *Aspergillus niger* in one letter format (SEQ ID NO. 4).

FIG. 19 shows the amidase 2 amino acid sequence (480aa) (SEQ ID NO: 1) from *Aspergillus niger* in three letter format. Features characteristic of OTA-degrading amidases are indicated as bold and underlined amino acid residues: conserved residues (bold) and nine sequence motifs.

FIG. 20a shows the structure of the amidase 2 (SEQ ID NO:1) protein tetramer forming the distorted TIM-like barrel structure; b shows the structure of 1 of the 8 subunits.

Figure 21:
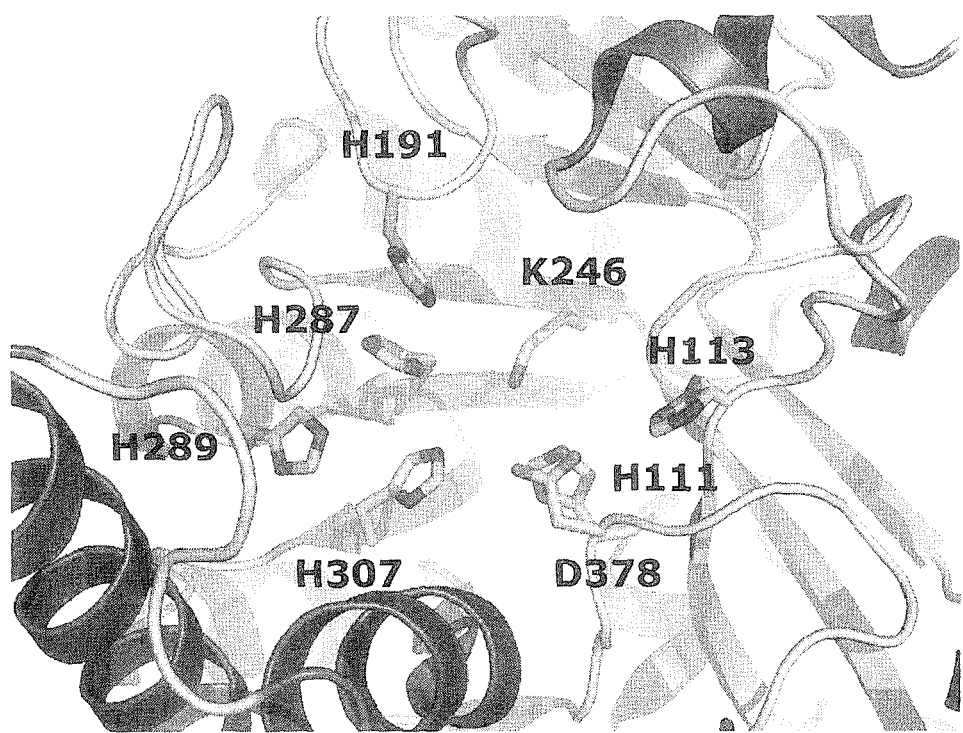

FIG. 21 shows the structure of the amidase 2 active site environment.

FIG. 22 shows the crystal co-ordinates of a monomer of amidase 2 (SEQ ID NO: 1).

Figure 23:
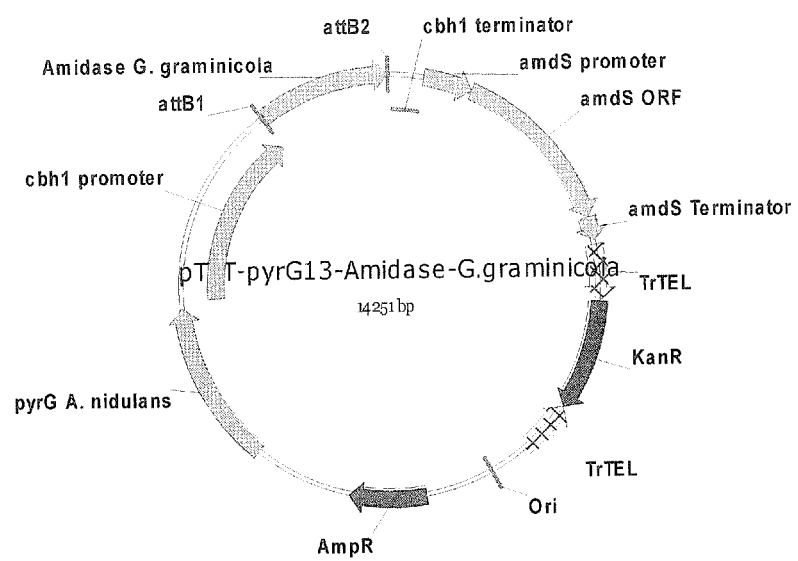

FIG. 23 shows a schematic representation of the expression plasmid pTTT-pyrG13-Amidase *G. graminicola*.

Figure 24:
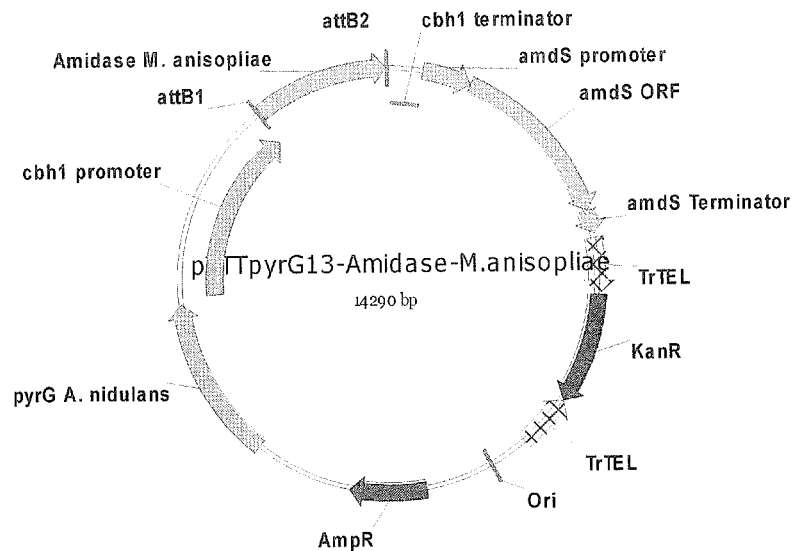

FIG. 24 shows a schematic representation of the expression plasmid pTTT-pyrG13-Amidase *M. anisopliae*.

Figure 25:
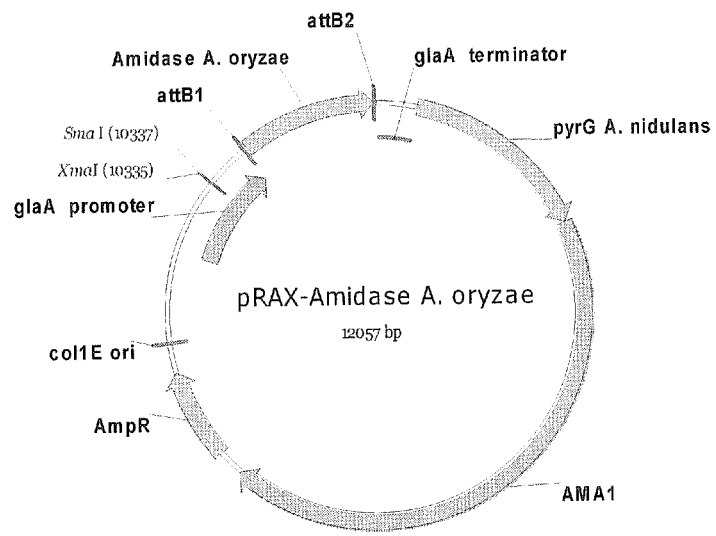

FIG. 25 shows a map of the expression plasmid pRAX-Amidase *A. oryzae*.

Figure 26:
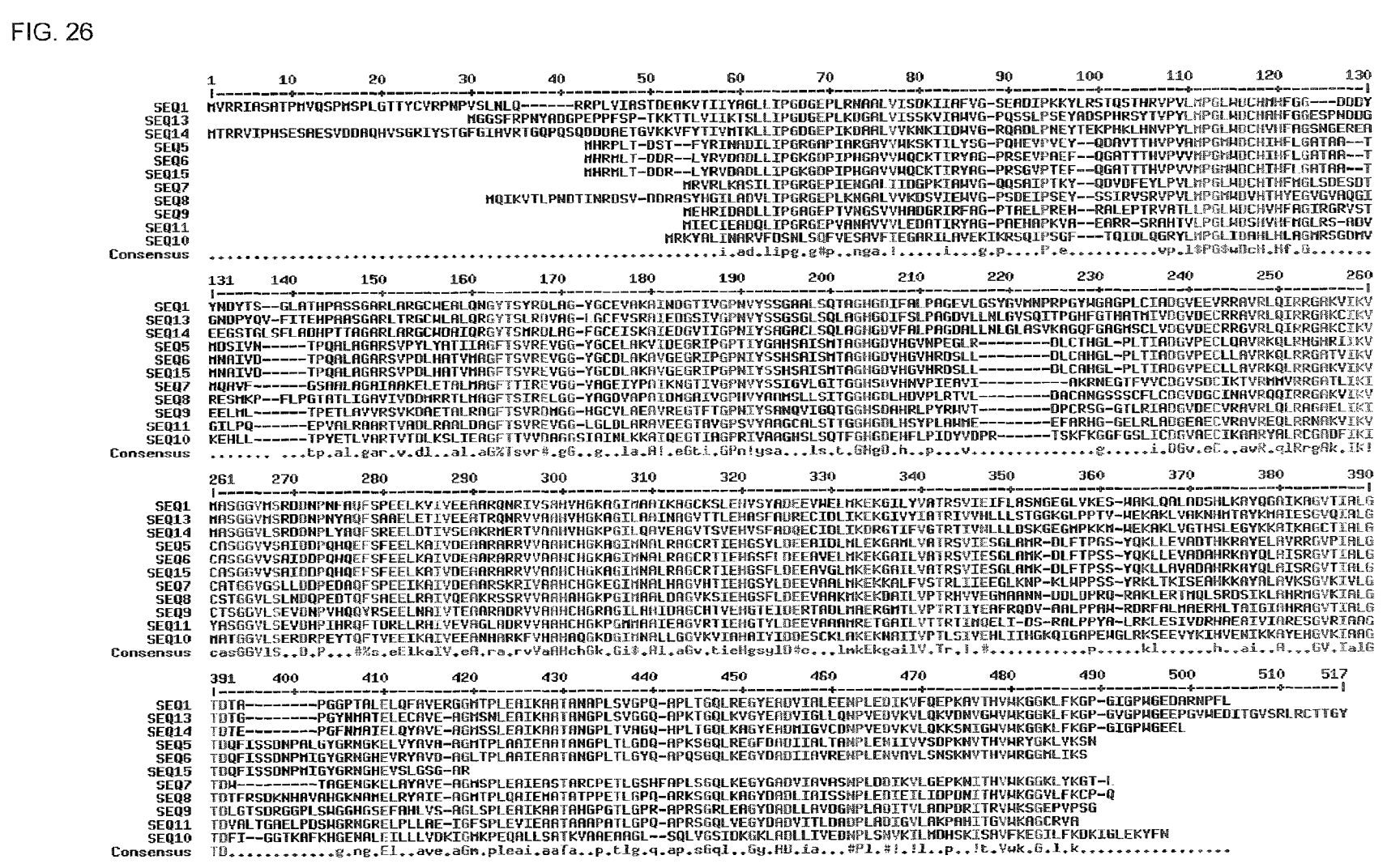

FIG. 26 shows an alignment of 11 amidase sequences (SEQ ID NO: 1, SEQ ID NO: 5-11, and SEQ ID NO: 13-15) showing the 9 sequence motifs that are essential for amidase activity degrading ochratoxin.

Figure 27:
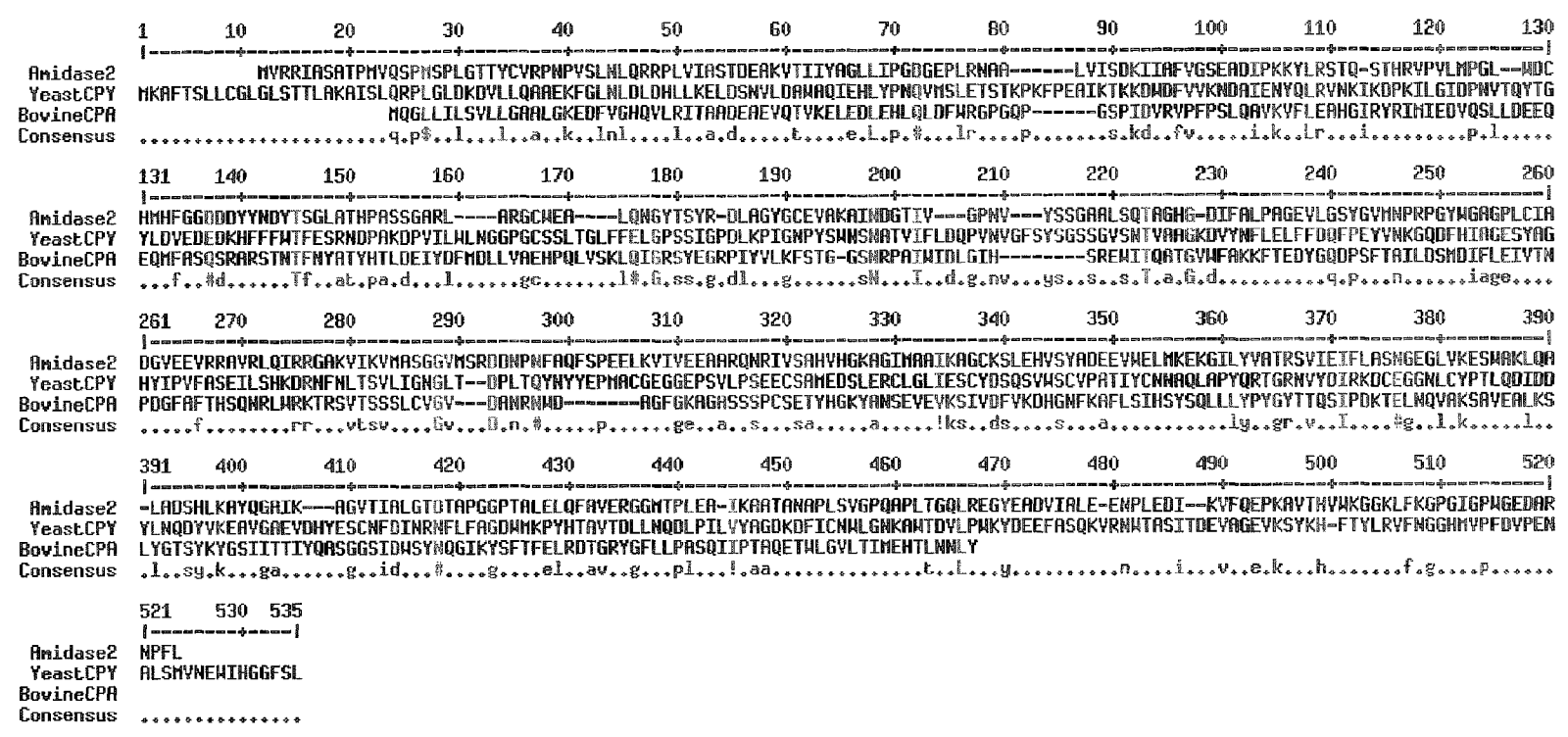

FIG. 27 shows an alignment of SEQ ID NO:1 and carboxypeptidases A (SEQ ID NO: 16) and Y (SEQ ID NO: 17) which are known to have low ochratoxin degrading activity.

Unless defined otherwise, all technical and scientific terms used herein have the same meaning as commonly understood by one of ordinary skill in the art to which this disclosure belongs. Singleton, at al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

As used herein, the term "identity" means an entity having a certain homology with the amino acid sequences and the nucleotide sequences. The term "identity" in this context refers to the percentage of sequence identity between two enzymes after aligning their sequences using alignment algorithms as described in more detail below.

In the present context, a homologous amino acid sequence is taken to include an amino acid sequence which may be at least 30, 40, 50, 60, 70, 75, 80, 85 or 90% identical, preferably at least 95, 96, 97, 98 or 99% identical to the sequence. Typically, the homologues will comprise the same active sites etc.—e.g. as the subject amino acid sequence. Although homology can also be considered in terms of similarity (i.e. amino acid residues having similar chemical properties/functions A), in the context of the present invention it is preferred to express homology in terms of sequence identity.

For amino acid sequences and nucleotide sequences, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et a/1984 Nuc. Acids Research 12 p 387). Examples of other software than can perform sequence comparisons include, but are not limited to, the BLAST package (see Ausubel et al., 1999 *Short Protocols in Molecular Biology*, 4th Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

In a preferable aspect of the present invention the following software and settings for calculating percentage sequence homology/identity are used. For amino acid sequences percentage of identities (homology) or "positives" are calculated by the AlignX Vector NTI (Vector NTI Advance 9.1 from Invitrogen Corporation, Carlsbad, Calif., USA.) for each possible pair of amino acid sequences. Settings are default parameters (Gap opening penalty—10, Gap extension penalty 0.1).

For nucleic acid sequences percentage of identities (homology) or "positives" are calculated by the AlignX Vector NTI programme from informax Inc. (USA) for each possible pair of nucleic acid sequences. Settings are default settings for DNA are: Gap opening penalty: 15 and Gap extension penalty: 6.66 (same settings for multiple alignments).

Preferably the amino acid identity (homology) is calculated across the full-length amino acid sequence or for nucleic acid to a corresponding polynucleotide which encodes the respective the full-length amino acid sequence.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756)(Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| SET | | SUB-SET | |
| --- | --- | --- | --- |
| Hydrophobic | F W Y H K M I L V A G | C Aromatic | F W Y H |
| | | Aliphatic | I L V |
| Polar | W Y H K R E D C S T N | Q Charged | H K R E D |
| | | Positively charged | H K R |
| | | Negatively charged | E D |
| Small | V C A G S P T N D | Tiny | A G S |

The present invention also encompasses homologous substitution (substitution and replacement are both used herein to mean the interchange of an existing amino acid residue, with an alternative residue) that may occur i.e. like-for-like substitution such as basic for
basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

The term "protein", as used herein, includes proteins, polypeptides, and peptides.

The terms "amino acid residue equivalent to", "amino acid corresponding to" and grammatical equivalents thereof are used herein to refer to an amino acid residue of a protein having the similar position and effect as that indicated in a particular amino acid sequence of a particular protein. The person of skill in the art will recognize the equivalence of specified residues in comparable proteins.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, temperature and/or pH activity profile, feed processing stability, and ability to be secreted.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The terms "protein" and "polypeptide" are used interchangeably herein. In the present disclosure and claims, the conventional one-letter and three-letter codes for amino acid residues are used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein.

By "functional fragment" is meant a fragment of the polypeptide that retains that characteristic properties of that polypeptide. In the context of the present invention, a functional fragment of an amidase enzyme is a fragment that retains the amidase enzyme cleavage capability of the whole protein.

The term "isolated", "recovered" or "purified" refers to a material that is removed from its original environment. The term "substantially purified" means that the material has been purified to at least a substantial degree.

In one aspect, preferably the nucleotide or amino acid sequence is in an isolated form. The term "isolated" means that the sequence is at least substantially free from at least one other component with which the sequence is naturally associated in nature and as found in nature.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulphur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, ~volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Aspergillus niger* or *Trichoderma reesei* the temperature generally will be within the range of about 20° C. to 40° C., generally preferably in the range of about 25° C. to 34° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Aspergillius niger* or *Trichoderma reesei*, the pH normally is within the range of about 3.0 to 7.0. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 24 to 500 hours, preferably presently about 24 to 400 hours. Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps. As described above, the time to reach this level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is much to be preferred for ease of control, production of uniform quantities of products, and most economical uses of all equipment. If desired, part or all of the carbon and energy source material and/or part of the assimilable nitrogen source such as ammonia can be added to the aqueous mineral medium prior to feeding the aqueous mineral medium to the fermentor. Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15 L Biolafitte (Saint-Germain-en-Laye, France).

The collection and purification of the enzymes of the present invention from the fermentation broth can also be done by procedures known per se in the art. The fermentation broth will generally contain cellular debris, including cells, various suspended solids and other biomass contaminants, as well as the desired enzyme product of the present invention, which are preferably removed from the fermentation broth by means known in the art. Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate using techniques such as ultrafiltration, evaporation or precipitation. Precipitating the proteinaceous components of the supernatant or filtrate may be accomplished by means of a salt, e.g., ammonium sulfate. Further purification may optionally be achieved by crystallization or by a variety of chromatographic procedures, e.g., ion exchange chromatography, affinity chromatography or similar art recognized procedures.

Variants/Derivatives

The present invention also encompasses the use of variants, homologues and derivatives of any amino acid sequence of an enzyme or of any nucleotide sequence encoding such an enzyme.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J at al., *PNAS* (1992) 89(20), 9367-9371 and Norwell D C, *Trends Biotechnol.* (1995) 13(4), 132-134.

Other Components

The feed additives or compositions of the present invention may be used in combination with other components or carriers.

Suitable carriers for feed enzymes include maltodextrin, limestone (calcium carbonate), cyclodextrin, wheat, wheat bran or a wheat component, rice or rice bran, sucrose, starch, $Na_2SO_4$, Talc, PVA and mixtures thereof. In addition there are a number of encapsulation techniques including those based on fat/wax coverage, adding plant gums etc.

Examples of other components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions.

As used herein the term "binder" refers to an ingredient (e.g. a food ingredient) that binds the product together through a physical or chemical reaction.

The term "crystal modifier" as used herein refers to an ingredient (e.g. a food ingredient) that affects the crystallisation of either fat or water.

"Carriers" or "vehicles" mean materials suitable for compound administration and include any such material known in the art such as, for example, any liquid, gel, solvent, liquid diluent, solubiliser, or the like, which is non-toxic and which does not interact with any components of the composition in a deleterious manner.

Examples of nutritionally acceptable carriers include, for example, grain, water, salt solutions, alcohol, silicone, waxes, petroleum jelly, vegetable oils, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

As used herein the term "component suitable for animal or human consumption" means a compound which is or can be added to the composition of the present invention as a additive which may be of nutritional benefit, a fibre substitute or have a generally beneficial effect to the consumer.

By way of example, the components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Isolated

In one aspect, preferably the amidase enzyme for use in the present invention is in an isolated form. The term "isolated" means that the amidase enzyme is at least substantially free from at least one other component with which the amidase enzyme is naturally associated in nature and as found in nature. The term "isolated" may mean that the amidase enzyme is at least substantially free from at least one other component in the culture media in which it is produced. The amidase enzyme of the present invention may be provided in a form that is substantially free of one or more contaminants with which the substance might otherwise be associated or with which the enzyme may be produced.

Thus, for example it may be substantially free of the cell(s) or one or more potentially contaminating polypeptides and/or nucleic acid molecules. The amidase enzyme may be isolated by separating the cell(s) from the broth during or after fermentation so that the amidase enzyme remains in the broth. The amidase enzyme may be isolated by subjecting the fermentation broth to cell separation by vacuum filtration.

In one embodiment the term isolated means that the amidase is isolated from the broth such that it substantially free from other components in the culture media in which it is produced.

Purified

In one aspect, preferably the amidase enzyme for use in the present invention is in a purified form. The term "purified" means that the given component is present at a high level. The component is desirably the predominant component present in a composition. Preferably, it is present at a level of at least about 30%, 40%, 50%, 60%, or at least about 65%, or at least about 70%, or at least about 75%, or at least about 80%, or at least about 85%, or at least about 90%, or at least about 95%, or at least about 97%, or at least about 99% said level being determined on a dry weight/dry weight basis with respect to the total composition under consideration. For some embodiments the amount is at least about 85% said level being determined on a dry weight/dry weight basis with respect to the total composition under consideration.

Concentrate

In one aspect, preferably the amidase enzyme for use in the present invention is used as a concentrate. The concentrate may be a concentrated form of the medium into which the enzyme has been excreted. Preferably, the concentrate may be a concentrated form of the medium into which the enzyme has been secreted and wherein the cell(s) have been removed.

Materials and Methods

Ochratoxin A was from Fluka (cat. no. 32937-5MG). Carboxypeptidase A from bovine pancreas (Sigma, cat. No. 09268). All other enzymes including commercial available amidases and reagents were from Sigma, Roche, Merck and Danisco. Amano™ lipase was from Amano Enzyme Inc. (Nagoya, Japan). All chromatgraphy medium 1.0 including Phenyl-, Octyl-Butyl-Sepharose, anion Exchange, gel filtration (PD10 column) and protein purification apparatus Äkta explorer were from GE Healthcare. Microplates were from Nunc A/S (Denmark) and Corning (USA). Microplate reader was from Biotek (USA). Corn flour was obtained from local market while soy-corn based feed was obtained from The Danish Technological Institute at Kolding (Denmark).

Mycotoxin Degradation Assays:

Method for Measuring Formamidase Activity

Solutions used: Megazyme formic acid assay kit (K-form 05/06) Bottle 1, add 4 ml milliQ water to produce potassium phosphate buffer pH7.6. Keep at 5° C.; Bottle 2, add 5.2 ml water to obtain the right NAD concentration (Kept at −20° C.); Bottle 3, is FDH shake before use (Kept it at 5° C.). Formamide is a liquid product at 99.80% from Sigma (F9037) (kept at 5° C.) and was used as it was without further dilution.

Assay procedure: to 96 well half area uv transparent microplate add:

10 µl potassium phosphate buffer (pH 7.6) (Solution 1 from the kit),
10 µl NAD (Solution 2 from the kit),
2.5 µl formic acid dehydrogenase (FDH)(Solution 3 from the kit),
1.6 µl 100% (v/v) formamide solution (from Sigma, F9037),
100 µl milliQ water.

At 37° C. in a microplate reader, read OD increase at 340 nm every min and shake before each reading for 15-60 min. Reading interval: 1 min.

After 5 min reading, add 5 µl-20 µl *A. niger* preparation (depending on the activity). Get the reaction rate (maximum linear slope).

Control: no formamidase was added but add buffer or water or cell-extract having no formamidase activity instead.

Determination of Enzymatic Degradation of OTA.

The buffers employed in the assay were: 50 mM sodium acetate buffer (pH 4, 4.5, 5 and 5.5); 50 mM MES buffer (pH 6, 6.5 and 7); 0.2M Mops-NaOH) pH7.0), 50 mM Tris-HCl buffer (pH 7.5, 8 and 8.5). Ochratoxin A (OTA) solution (1 mg/mL) was made of 5 mg ochratoxin A (Sigma, ref. 32937) dissolved in ethanol/water (60/40) and stored at −20° C. Screening assays were performed with 154 OTA solution and different enzyme concentrations (for example, 0.1-5 mg/ml) in a final volume of 300 µL. Enzymatic reactions were done at 37° C. for 20 h±1 h under constant agitation. Samples were filtered using syringe filter 0.20 µm for HPLC analysis. The HPLC apparatus consisted of a Dionex P580 pump and Dionex ASI-100 autosampler connected to a Dionex RF-2000 fluorescence detector ($\lambda_{ex}$=333 nm; $\lambda_{em}$=460 nm) and a Dionex UVD340 U UV detector at 257 nm. Elution was through a nucleosil 100-5 C18 column (250×4.6 mm, 5 µm particle size; Chrompack) with water/acetonitrile/acetic acid (100:100:1, v/v/v) at a 0.6 mL/min flow-rate. The column was kept at 30° C. and was connected to guard column (C18, 1 mm, Optimize technologies). The OTA and its degradation products were monitored both by uv at 235 nm and fluorescence (excitation at 278 nm emission at 440 nm).

Assay of *A. niger* Preparations for OTA Activity.

The reactions mixture consisted of 245 µL OTA (1 µg/mL) diluted in buffer pH7.0 of 50 mM Mes-NaOH and 54. of sample (*A. niger* broth, cell-free extract, fractions after ammonium fractionation and chromatography or product from *A. niger*). The reaction was performed at 40° C. for 30 min to 2 hours. Heating at 95° C. for 5 min was used to stop the reaction. Samples were filtered using syringe filter 0.20 µm and 54 injected in the HPLC apparatus.

Lipase and Esterase Assay.

Lipase and esterase activity were assayed using p-nitrophenyl butyrate (pNPB) purchased from Sigma as the substrate. Five microliters pNPB 40 mM dissolved in acetonitrile was added to 165 µL of 50 mM Tris-HCl buffer pH 7.5 and 5 µL of enzyme solution and used to test OTA degradation. Optical density was followed at 410 nm for 60 min.

Protease Activity Assay (Petri Dish Method).

Protease activity was confirmed using plates containing 1% casein, 1% agarose in 100 mM di-sodium hydrogen phosphate buffer pH 6. The plate was incubated overnight at 37° C. and the protease activity was revealed by the development of a whitish ring around the well containing enzyme.

Protein Concentration Assay.

Protein concentration was determined with Bio-rad protein assay reagent based on the method of Bradford according to the procedure provided by the manufacturer. Using BSA as standard, the OD was measured in microplate at 595 nm, each samples dosed in duplicate.

Purification of OTA Degrading Activity from *A. niger*
Sample Preparation: Ammonium Sulfate Fractionation.

Five grams of Amano lipase enzyme were dissolved in 100 mL of 50 mM Tris/HCl buffer pH 7.5. The amount of ammonium sulfate corresponding to 40% saturation was added and crystals dissolved. After 10 min centrifugation at 3500 rpm, the supernatant was collected and ammonium sulfate added to reach 60% saturation. Crystals were dissolved by stirring and the solution centrifuged again. The pellet corresponding to the precipitate from 40% to 60% ammonium sulfate saturation was dissolved in 4×40 mL of 50 mM tricine, 1M ammonium sulfate pH7 and filtered with 0.22 µm filter.

Hydrophobic Interaction Chromatography (HIC).

The sample from ammonium sulfate fractionation was injected and applied to either Phenyl Sepharose FF, Butyl- or Octyl-Sepharose CL4B column equilibrated with 50 mM tricine containing 1M ammonium sulfate pH 7 (buffer A). The column, connected to Akta purifier system, was washed with buffer A (10 mL/min) and the bound proteins were eluted with a linear gradient of 50 mM tricine (Buffer B). Fractions of 10 mL were collected and used for OTA activity assay or formamidase assay.

Anion Exchange Chromatography (AEX).

Fractions with high conversion of OTA were pooled and desalted on a PD10 column equilibrated in 20 mM Tris-HCl, pH 7.5 (buffer A). The desalted sample was applied to a Source Q30 column equilibrated in buffer A (10 ml/min). The column was washed with buffer A and the bound proteins were eluted with a linear gradient of 0-1 M NaCl in buffer A (Buffer B is the same as Buffer A containing 1M NaCl). During the gradient, fractions of 5 ml were collected.

Concentration of Protein.

Fractions with OTA degrading activity obtained by anion exchange chromatography were concentrated using Amicon Centriprep™ concentrators with regenerated cellulose membrane (molecular cutoff 10 kDa).

Optimum pH Determination.

Five microliters of enzyme solution were combined with 2454 OTA 1 µg/mL diluted in different buffers: 50 mM sodium acetate buffer (pH 4, 4.5, 5 and 5.5); 50 mM MES-NaOH buffer (pH 6, 6.5 and 7); 50 mM Tris-HCl buffer (pH 7.5, 8 and 8.5). Reactions were performed at 37° C. for 30 min and stopped by heating at 95° C. for 5 min.

Optimum Temperature.

Five microliters of enzyme solution were mixed with 245 µL OTA 1 µg/mL at optimum pH and incubated at 20, 30, 40, 60, 70° C. for 30 min. Reactions were stopped by heating at 95° C. for 5 min.

Temperature Stability.

The enzyme solution was incubated at different temperature (30, 40, 60, 70, 80 and 90° C.) for 1 h and 5 µL were mixed with 2454 OTA 1 µg/mL for ochratoxin degradation reaction under optimum conditions. Reactions were stopped by heating at 95° C. for 5 min. The control was not incubated.

SDS-PAGE.

To separate and analyze the proteins sodium dodecyl sulfate polyacrylamide gel eletrophoresis, (SDS-PAGE) was used. Forty microliter samples were mixed with 10 µL 5× loading buffer (containing DDT and SDS), and boiled for 5 min. 20 µL were loaded on a NuPAGE 4-12% Bis-Tris gel (Invitrogen, USA). The electrophoresis was run according to the procedure from the manufacturer. The gel was stained with Coomassie brilliant blue.

Mass Spectrometry.

The protein of interest was cut from the gel (as above) using a scalpel and transferred to an Eppendorf tube. The protein was digested with an enzyme (primarily trypsin). After digestion peptides were extracted and analyzed by HPLC-MS/MS.

The MS/MS spectra were automatically searched against protein databases for the purpose of idenity and characterisation.

Inhibition Assays for Formamidase and Amidase 2.

One protease inhibitor cocktail (PIC) tablet (Roche Applied Science, Mannhein, Germany) was dissolved in 1.5 mL. milliQ water to obtain a 7× stock solution. For formamidase inhibition assay, instead of 100 μL milliQ water normally employed, 20 μL of 7×PIC stock solution and 80 μL of milliQ water were mixed with other components listed in formamidase activity assay section. For OTA degrading activity, 35 μL 7×PIC solution were mixed with 210 μL OTA 1 μg/mL and 5 μL enzyme solution. A 125 mM EDTA stock solution was prepared and appropriate volumes to obtain 10 mM and 50 mM final concentration were mixed with OTA 1 μg/mL and 54 enzyme. For controls, inhibitor solution is replaced either by milliQ water for formamidase activity assay or MES-NaOH pH7 buffer for OTA degrading activity.

RESULTS

Example 1

Screening for OTA Activity

Figure 1:
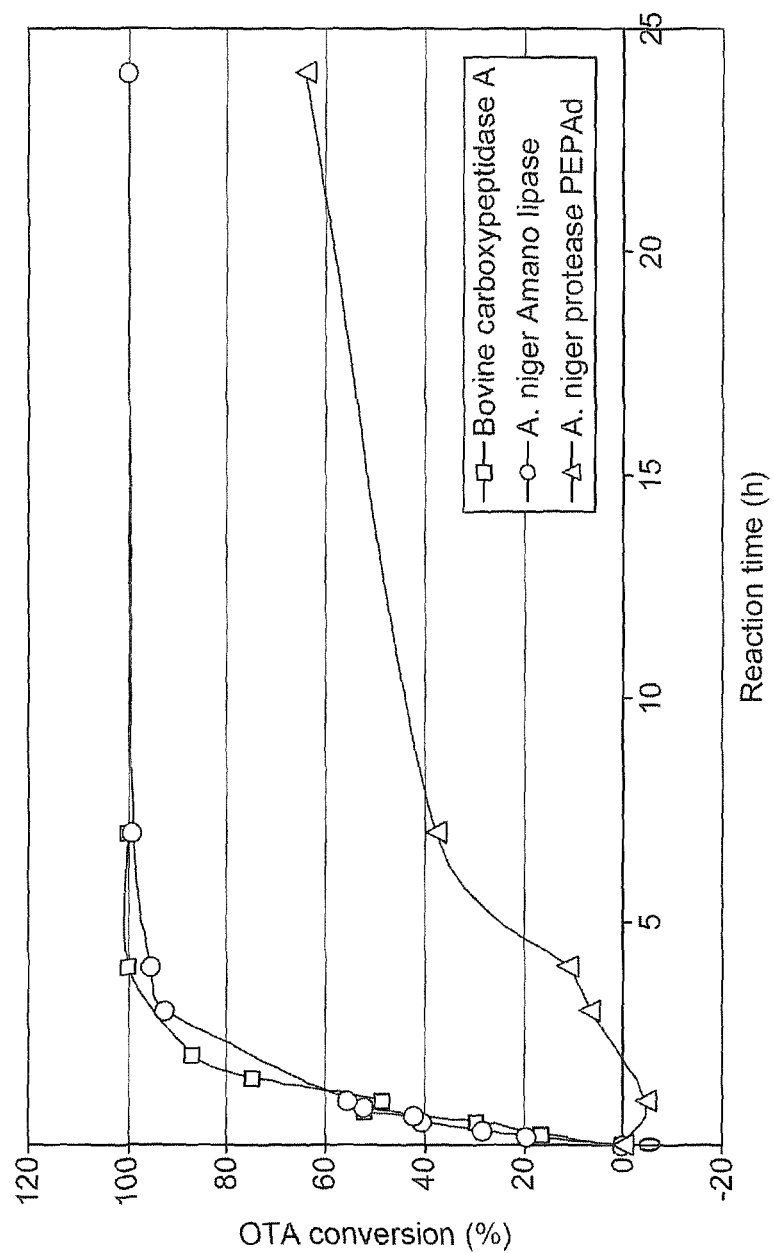
FIG. 1 shows the ability of PEPAd (a Danisco aspartic acid protease cloned from *A. niger*), Amano™ lipase and bovine Carboxypeptidase A at the same protein concentrations to breakdown OTA. Activity was expressed in % OT-α (product of OTA) area: the area corresponding to the product divided by the total area (peak area of OTA plus OT-α).

Thirty enzymes including various lipases, proteases and amdiases were investigated for their ability to degrade ochratoxin A (Table 1). Only carboxypeptidase A and lipase from *A. niger* (Amano™ A) were able to breakdown OTA as previously reported (Pitout, 1969; Stander et al., 2000). Moreover, aspartic acid protease pepAd2 (Danisco) from *A. niger* showed an OTA converting activity although this was less efficient. To facilitate the comparison of these three enzymes, the protein concentration of PEPAd was determined and enzyme solutions of carboxypeptidase A and Amano™ lipase A were prepared at the same concentration (1 mg/ml). A kinetic of the degradation was carried out (FIG. 1). FIG. 1 shows that the OTA degradation kinetics of Amano™ lipase A and carboxypeptidase A were similar. After 7 h reaction at 37° C., no OTA peak was visible, meaning that full conversion of OTA was obtained. For PEPAd, full conversion was not reached even after 1 day reaction. Amano™ lipase A product was a mixture of different enzymes with the dominant activity being lipase. Besides PEPAd, other *A. niger* aspartic acid proteases of PEPAa, PEPAb and PEPAc (Wang, 2010), porcine elastase, and yeast carboxypeptiase Y all showed certain activity with OTA. This is the first time aspartic proteases other than metallo-protease (i.e., carboxypeptidase A, a $Zn^{2+}$ dependent protease), serine protease elastase and carboxypeptidase Y have been shown to be able to break OTA down. Other proteases, lipases and amidases listed in Table 1 were not able to break OTA down (data not shown).

TABLE 1

Enzymes screened for ochratoxin A degradation

| Enzyme | Organism | Ref | pH | Manufacturer |
| --- | --- | --- | --- | --- |
| Carboxypeptidase A | Bovine pancreas | C9268 | 7.5 | Sigma |
| Carboxypeptidase Y | Yeast | 12758 | 7 | USB |
| Carboxypeptidase Y | Yeast | C3888 | 7 | Sigma |
| Chymotrypsin Chymostar | | | 8 | Christian Hansen |
| Elastase | Porcine prancreas | E0258 | 8.5 | Sigma |
| Endoproteinase Glu-C | *S. Aureus* | 791156 | 7.5 | Roche Diagnostics |
| LG12 | *Bacillus subtilis* | | 7.5 | Danisco |
| Lipase A Amano ™ | *Aspergillus niger* | 534781 | 7.5 | Amano ™ |
| PROACT #3617 | *Nocardiopsis prasina* | | 7.5/4 | Novozymes |
| Proline peptidase proC | | | 7 | |
| Protease thermolysin | *Bacillus thermoproteolyticus rokko* | P1512 | 8 | Sigma |
| Proteinase K | *Tritirachium album* | p0390 | 8 | Sigma |
| Protease P3000 | *Bacillus subtilis* | | 7.5 | |
| Trypsin | *Bovine pancreas* | 109819 | 8 | Roche Diagnostics |
| phospholipase KLM1 | | | 7 | Danisco |
| lipase 3 | | | 5.5 | Danisco |
| Lipase | *Rhizopus arrhizus* | 62305 | 8.5 | Sigma |
| Lipase | *Candida cylindracea* | 62316 | 6.5 | Sigma |
| Lipase | *Rhizopus niveus* | 62310 | 7.5 | Sigma |
| GAP3 | *Aspergillus Niger* | | 6 | Danisco |
| PEPAa | *Aspergillus Niger* | | 6 | Danisco |
| PEPAb | *Aspergillus Niger* | | 6 | Danisco |
| PEPAc | *Aspergillus Niger* | | 6 | Danisco |
| PEPAd1 (c-terminal deletion) | *Aspergillus Niger* | | 6 | Danisco |
| PEPAd2 (full length) | *Aspergillus Niger* | | 6 | Danisco |
| Grindamyl | *Aspergillus Niger* | | 7.5 | Danisco |
| Amidase | *Pseudomonas aeruginosa* | A6691 | 7 | Sigma |
| Peptide Amidase | *Citrus sinensis* | 17232 | 7 | Fluka |
| Amidase | | PLY511 | 7 | Profors |
| Penicillin amidase | *E. coli* | 76429 | 7 | Sigma |

Example 2

Purification of Ochratoxin A Degrading Activity from *A. niger* Fermentation Liquid or Filtered Broth (Cell Free)

Firstly ammonium sulfate precipitation was employed. Several ammonium sulfate concentrations were applied to an *A. niger* crude protein extract. The OTA degrading activity was determined in both supernatant and pellet. By increasing the ammonium sulfate concentration, the OTA degrading activity was transferred from the supernatant to the pellet. At 60% ammonium sulfate, all the degrading activity was found in the pellet. This demonstrated that the enzyme was able to hydrolyze the mycotoxin precipitates from 40% to 60% ammonium sulfate. At the same salt concentration (60%), a slight lipase activity remained in the pellet (data not shown).

The ammonium sulfate fraction from 40% to 60% was employed as the starting material for further ochratoxin degrading enzyme purification. Hydrophobic interaction chromatography (HIC) followed by anion exchange chromatography (AEX) as described above were used to separate lipase activity from OTA degrading activity. The active fraction was suspended in 50 mM tricine-HCl (pH7.0) containing 1M $(NH_4)_2SO_4$ (Buffer A).

Figure 2:
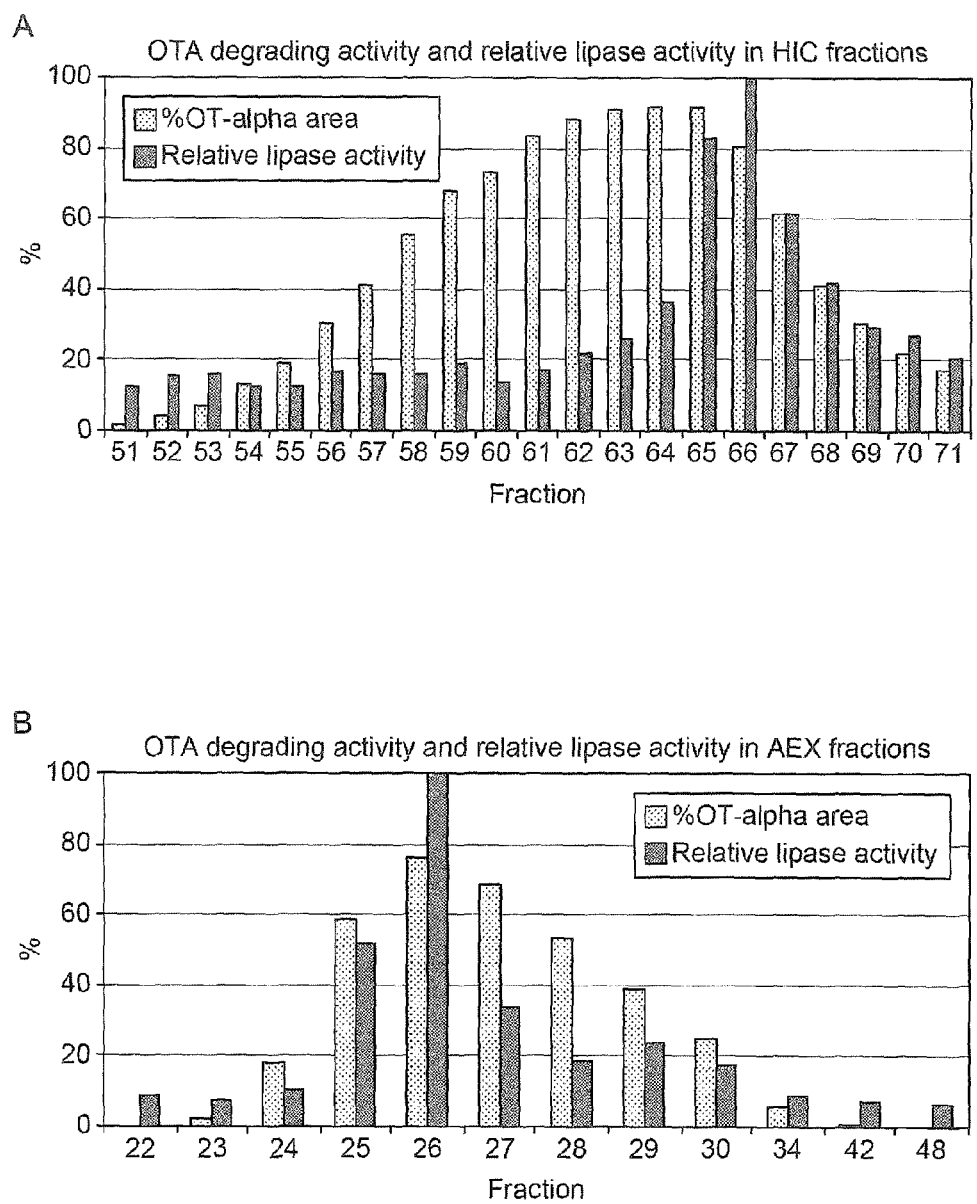
FIG. 2 shows the percentage of OT-α area and relative lipase activity (%) in fractions from (A): hydrophobic interaction chromatography (HIC)/affinity chromatography with a Phenyl Sepharose packed column (2.6 cm×10 cm) and gradient from 1M ammonium sulfate to 0. (B): Anion exchange chromatography (AEX) Q30 column with gradient from 0 to 1M NaCl after HIC.

FIG. 2A shows the percentage of OT-alpha area obtained after 1 h reaction of the fractions obtained from Phenyl Sepharose with OTA. This figure shows an increase in OTA degrading activity from fraction no. 51 to no. 64, while the highest lipase/esterase activity was found in fraction no. 65-68. This observation indicates that the ochratoxin degrading activity had apparently nothing to with the lipase/esterase activity in the Amano™ lipase product (it has previously been indicated that OTA degrading activity was due to lipase activity, Stander at al., 2000). The protein that degrades OTA was eluted between 90% and 100% buffer B (50 mM tricine-HCl (pH 7.0), indicating that Phenyl Sepharose chromatography medium apparently functioned as an affinity medium. OTA also contains a phenyl group and the OTA degrading enzyme must be able to bind the phenyl group from either OTA or the separation medium used here. Concerning the lipase/esterase activity, which was present in all fractions obtained from this step, it was eluted at 100% buffer B. This is not unexpected because lipases/esterases perform hydrolysis of lipids and triglycerides, which are very hydrophobic substrates and therefore bind tightly with hydrophobic matrices like Phenyl-Sepharose.

FIG. 2B shows the percentage of OT-alpha area obtained after 30 min reaction of the AEX fractions with OTA. The maximum OTA activity was found in fraction no. 26. However, it was also in these fractions that the relative lipase activity was the highest. This indicates that the AEX step was not able to separate lipase/esterase from OTA degrading activity, this was used by earlier investigators as the sole chromatography step in their attempt to purify OTA degrading activity (Abrunhosa at al., 2007).

In summary FIGS. 2A and 2B indicate that lipase/esterase is not the enzyme that is responsible for the degradation of OTA (FIG. 2A) as it has been assumed earlier (Stander et al. (2000) and the separation of lipase/esterase activity from OTA degrading activity was not achieved by AEX, which was practiced by earlier investigators in an effort to purify the enzyme degrading OTA from Amano™ lipase (Abrunhosa at al., 2007). The earlier investigators did not show that Phenyl Sepharose chromatography medium usually regarded as an hydrophobic interaction chromatography medium separating proteins based on their difference in hydrophobicity could be used here as an affinity separation medium for OTA degrading activity.

After the purification by ammonium sulfate fractionation followed by HIC/affinity chromatography on Phenyl Sepharose and AEX, the fractions which contained the OTA degrading activity still had some lipase/esterase activity. FIG. 4 shows the results of analysis of the active fractions on OTA obtained in the AEX purification procedure of FIG. 2B by SDS-PAGE. It can be seen that on the gel there are two major bands: A and B. The partial sequencing of those bands by mass spectrometry followed by homology searching in the protein database suggests that Band A comprises at least 3 proteins corresponding respectively to:

1—Predicted acetamidase/formamidase from *Aspergillus oryzae* 45,012Da (27% coverage)
   2—Formamidase from *Aspergillus fumigatus* 45,277Da (24% coverage)
   3—Formamidase from *Aspergillus nidulans* 44,907Da (20% coverage)

And that Band B comprises at least 3 proteins corresponding to:

1—Glyoxylate/hydroxypyruvate reductase from *Aspergillus oryzae* 39,603 Da (34% coverage)
   2—Acetylesterase from *Aspergillus awamori* 32,640 Da (9% coverage)
   3—Endo-1,4-beta-xylanase A precursor from *Aspergillus niger* 35,486 Da (17% coverage).

From the results indicated in FIG. 4, it appeared likely that the enzyme which breaks down OTA was *A. niger* formamidase. The other identified enzymes have theoretically nothing to do with OTA degradation. Further purification of *A. niger* formamidase was undertaken.

Example 3

Improved Purification of Ochratoxin A Degrading Enzyme

Further improvement for the purification by HIC and AEX was not achieved by using different buffers and different gradient programs. Purification using Phenyl Sepharose can be regarded as an affinity step because the OTA molecule has the phenyl group however, the impurities have high hydrophobicity and bind tightly to the phenyl Sepharose medium and therefore elute very late (FIG. 4A). When Octyl- and Butyl Sepharose were employed, the OTA degrading activity fraction was found in the unadsorbed flow-through fractions. This indicates that it has low hydrophobicity and that its tight biding to Phenyl Sepahrose is of affinity in nature (FIG. 4A) whilst the impurities having high hydrophobicity bound tightly and eluted later (FIG. 4B) as in the case with Phenyl-Sepharose.

The procedure was further improved using ammonium sulfate fractionation (AS), HIC/affinity on Phenyl-Sepharose (HIC1), HIC on Butyl-Sepharose (HIC2) and AEX, the active fraction was concentrated and desalted with a molecular sieve with cutoff of 10 kDa. The concentrated and desalted fractions 5 and 6 shown on FIG. 4 were analyzed on SDS-PAGE (FIG. 5). The protein bands were isolated from the gel and digested with trypsin. The digest was separated on RP-HPLC and analyzed by MS to identify the identity of the protein bands.

Figure 3:
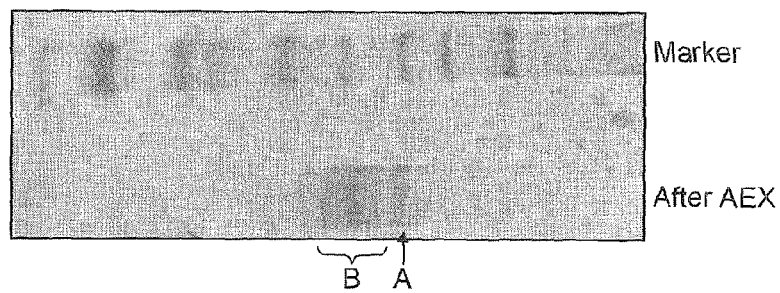
FIG. 3 shows SDS-PAGE analysis of the concentrated AEX fraction having highest OTA degrading activity. The indicated bands A and B were in-gel digested with trypsin and the digested peptides were separated on reverse phase HPLC and analyzed with MS for peptide identification.

The MS results indicate that after 4 steps of purification the OTA degrading activity was not confined to one single band, instead the following enzymes were identified (order of intensity): Formamidase (51% sequence coverage), formamidase degradation product (caused by protease) (30%), unannotated *A. niger* protein sequence (An14g02080, XP_001400834) having similarity to bacterial amidase (25%), glutamyltranspeptidase (17%), and aldose 1-epimerase (14%). From these results the identified enzyme that most likely breaks down OTA was considered to be *Aspergillus niger* formamidase as indicated by the results in FIGS. 3 and 5, followed by an unannotated *A. niger* protein sequence having similarity to bacterial amidase and glutamyltranspeptidase, all of the three having activities toward C—N bond, which exists in OTA molecule.

Example 4

Characterization of the Enzymes Identified that May have the Potential to Break OTA Down Based on the results from FIGS. 3, 4, 5 and 6, further studies were undertaken on the two putative *Aspergillus* enzymes formamidase and glutamyltranspeptidase, and the hypothetical protein An14g02080 (XP_001400834).

The putative formamidase of *Aspergillus* origin has not previously been characterized with respect to its biochemical properties including substrate specificity though it had been cloned from *A. nidulans* and expressed as indicated indirectly by the activity of beta-galactosidase activity (Fraser et al., 2001). Formamidase is known to be involved in glyoxylate and dicarboxylate metabolism and also nitrogen metabolism. It converts formamide in the presence of water to formic acid (formate) and ammonium (formamide+$H_2O$→formate+$NH_3$). The presence of formamidase activity was assayed using Megazyme formic acid kit as indicated in the Material and method section above.

When this assay was carried out with fractions obtained in the AEX step, formamidase was observed in fractions of 25 to 30 (FIG. 6A). This was the first indication that fungi and fungal preparations including the Amano™ lipase product prepared from *A. niger* had an active formamidase breaking down formamide to formic acid and ammonium. Equally important the formamidase activity was purified using the purification steps designed to purify OTA activity, suggesting that fungal formamidase breaks down OTA. When the same fractions tested for formamidase activity were assayed for degradation of OTA, the conversion increased from fraction 26 to 32 (FIG. 6B). As can be seen from FIG. 6A and FIG. 6B the two activities were present in the same fractions. From the data it was further hypothesised that the *A. niger* formamidase or *Aspergillus* formamidase that had not been characterized before had OTA degradation activities.

Example 5

Analysis of Formamidase and OTA Degradation Activity in *A. niger* Transformants Harboring the *A. nidulans* Formamidase Gene

*A. niger* formamidase transformants were analyzed for formamidase activity and OTA degrading activity. As can be seen from Table 2 formamidase activity was detected in 12 out of 15 transformants. Surprisingly the formamidase *A. niger* was apparently not able to break down OTA as can be seen in the transformants that had high formamidase activity but low or no OTA degrading activity. This indicates that fungal formamidase may not have OTA degradation activity but had been co-purified with the OTA activity through the 4 purification steps.

Interestingly by integrating the foreign DNA as in the case of *A. nidulans* formamidase gene into the *A. niger* genome the inventors have succeeded by unknown mechanism in creating transformants having higher OTA degrading activities compared to the parent strain used for the transformation *A. niger* see for example transformants 7#, 2#, 8#, 11#, 15#. Note that 16# was wild type (parent strain). Control was the reaction without the addition of broth. Fermentation broth was used for all these assays. The reaction mixture contained 10 µl broth, 50 µl OTA (1 µg/ml), 100 µl sodium phosphate (67 mM, pH7 or pH9). For control, 10 µl broth from 5-day old culture in a shake flask fermentation was replaced with 10 µl water. At the end of the reaction 160 µl acetonitrile was added to stop the reaction, and filtered and 10 µl injected for HPLC analysis.

Based on the surprising discovery that formamidase of *Aspergilli* was not able to breakdown OTA the inventors undertook further research to identify if a second candidate for OTA degradation, i.e. the hypothetical *A. niger* protein (An14g02080, XP_001400834) designated amidase 2 herein had OTA degrading activity.

Example 6

Construction of a Putative Amidase 2 Gene Expression Plasmid

The putative amidase 2 gene from *Aspergillus niger* encodes the amidase protein of 480 amino acids (SEQ ID NO: 1). To construct the recombinant expression plasmid for *A. niger* amidase 2 gene, two primers GGAGATCTATCATGGTCCGCCGAATTG and AATCTAGACTAGTGATGGTGATGGTGATGCAGAAAAGGATTACGTG were used in a Pfu Ultra II PCR reaction with genomic DNA template obtained from *A. niger* UVK143 strain (Ward et al., *Appl. Microbial. Biotechnol.*, 39: 738-743, 1993). The PCR reaction was performed for 30 cycles of 95° C. for 30 seconds, 50° C. for 30 seconds and 72° C. for 1 minute with the two primers. The final extension at 72° C. was done for 5 minutes and the reaction was chilled to 4° C. The nucleotide sequence of the coding region of the resulting PCR amplicon, without the His tag, is listed as SEQ ID NO: 2. The PCR fragment was purified with a Qiagen spin column. It was digested with restriction enzyme BgIII and XbaI and cloned into the pGAPT plasmid vector (see e.g., U.S. Pat. No. 6,426,410) that had been digested with BgIII and XbaI. The resulting plasmid, pGAPT-amidase 2 (shown in FIG. 7) was confirmed by DNA sequencing to have a recombinant gene comprising *A. niger* amidase 2 inserted between the *A. niger* glucoamylase promoter and an *A. tubingensis* glucoamylase terminator. The corresponding encoded protein sequence is shown in SEQ ID No. 4 which is identical to SEQ ID No. 1 except that six histidine residues were added at the c-terminal end of the protein to aid protein purification.

Example 7

Construction of a Recombinant Amidase 2 Production Strain

The AP4 strain of *A. niger* (Berka et al, *Gene* 86: 153-162, 1990) was transformed with the pGAPT-amidase 2 plasmid using a PEG-mediated protoplasts fusion transformation protocol. The transformation protocol utilized a modification of the Campbell method (see, Campbell et at., *Curr. Genet.* 16:53-56 (1989)) with Lysing Enzyme from *Trichoderma harzianum* (Sigma, L1412). More than one hundred transformants were obtained and thirty transformants were selected on MM plate. The control AP4 parental strain and fifteen transformants were chosen to be grown in CMA plates first and the mycellium agar plugs containing both mycellium and spores from CMA plates were transferred to the shake flasks containing 30 ml of culture medium. The transformants were grown for 6 days at 28° C. The mycellium pellets from control AP4 strain and all fifteen transformants were washed with water at least twice. The mycellium pellets were suspended in CelLytic Y Cell Lysis Reagent (Sigma, C4482). The intracellular proteins were extracted at room temperature for 2 hours. The suspensions were spun down and 15 µl of the supernatants containing extracted intracellular proteins were analyzed using SDS-PAGE gels (FIG. 8). The culture broths were spun down in a microfuge for 10 minutes and 15 µl of the supernatant (extracellular proteins) were analyzed using SDS-PAGE gels (FIG. 8).

amidase 2 was indicated by an arrow bar. M. molecular markers, AP4, the parent strain of *A. niger*. The transformants were numbered from 1 to 15.

FIG. 9 shows SDS-PAGE of extracellular proteins of *A. niger* harboring the Amidase 2 gene. The protein band of amidase 2 is indicated by an arrow bar. The other major bands above the amidase 2 band were α-amylase and glucoamylase secreted by *A. niger*. The samples loaded to the gels were the fermentation brothes of the different transformants.

In order to confirm the supposed amidase 2 band separated on SDS-PAGE was indeed the product of the amidase gene, the band was cut out, digested with trypsin by in-gel digestion. The digests were separated by RP-HPLC and analyzed by mass spectrometry. This revealed 4 amino acid sequences

TABLE 2

Analysis of formamidase and OTA degradation activity in *A. niger* transformants harboring the *A. nidulans* formamidase gene

| | *A. niger* Transformant No. # harboring the *A. nidulans* gene | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 Wt | Control |
| OTA Peak area, at pH 9, 19 hr, 37° C. | 30 | 7 | 23 | 13 | 27 | 20 | 0 | 7 | 10 | 115 | 7 | 37 | 70 | 108 | 8.2 | 36 | 168 |
| OTA Peak area, at pH 7, 19 hr at 37° C. | —* | — | — | — | — | — | — | — | — | 102 | — | 0 | 145 | 138 | 0 | 20 | 128 |
| OTA Peak area, at pH 9, 45° C. 4 hr | — | — | 70 | 55 | — | — | 93 | — | — | 105 | 52 | 86 | 129 | 116 | — | 117 | 116 |
| OTA Peak area of OTA, at pH 7, 45° C. 4 h | — | — | 17 | 17 | — | — | 4.3 | — | — | 104 | 16 | 14 | 118 | 122 | — | 76 | 126 |
| Formamidase activity at pH 7 at 37° C. | 216 | 23 | 0 | 0 | 325 | 160 | 195 | 104 | 129 | 108 | 4 | 431 | 232 | 0 | 171 | 0 | 0 |

*not analyzed

Table 3 shows the medium used (per liter) for growing *Aspergillus niger* and its transformants in 250 ml siliconized flasks with 30 ml of medium. The *A. niger* strains were first grown in CMA plates for 3-5 days and 2 cm² plus were transferred to flask and grown at 30° C. for 5 days. For the wild type (control strain or parental strain 620), 0.5 mg/ml of uridine was supplemented.

| | |
|---|---|
| Corn Streep Solids | 50 g |
| NaH$_2$PO$_4$•H$_2$O | 1 g |
| MgSO$_4$•7H$_2$O | 1.0238173 g |
| 50% (w/v) Staley 7350 Corn Syrup | 100 mL |
| Sodium Citrate Dihydrate (Na$_3$C$_6$H$_5$O$_7$2H$_2$O) | 8 g |
| pH to 5.8-6.0 | |
| Bring to volume with milliQ H$_2$O. | |

Strain can be grown in CMA plate (per liter):

| | |
|---|---|
| Dextrose (Glucose) | 20 g |
| BD Bacto Malt Extract | 20 g |
| BD Bacto Peptone | 1 g |
| BD Bacto Agar | 20 g |
| Autoclave and poor plates | |

FIG. 8. The SDS-PAGE analysis of intracellular proteins of *A. niger* harboring the Amidase 2 gene. The protein band of which are found in the putative amidase 2 sequence (SEQ ID NO: 1) (FIG. 18A). The four sequences identified were:

```
1. EALQNGY;

2. ALPAGEVLGSY;

3. GAGPL;

4. SVGPQAPL.
```

Example 8

Characterization of Recombinant Amidase 2 with Respect to its Degradation of OTA and Biochemical, Catalytical Parameters As shown in FIG. 10, both the intracellular and extracellular fractions (broth) of the transformants of *A. niger* harboring the putative protein coding gene (amidase 2) plus the parent strain (wt) were assayed for their capability to breakdown OTA. FIG. 10 surprisingly shows that the hypothetical protein encoding *A. niger* gene from Genbank (An14g02080, Acc No. XP_001400834) encodes an active enzyme having OTA degrading activity and this active enzyme was found both intracellularly and extracellularly. One can see the best transformants are transformant 3, 4, 7, 11, 13 and 14 as no detectable OTA was left (i.e. below the detectable level of 2pbb) after the incubation with the intracellular or the extracellular fractions (the broth). Compared to the parent strain (wt) *A. niger*, transformant 8, 10 and 15 also had much higher OTA degrading activity.

The recombinant amidase 2 was active at least between pH 3 to 9 in the degrading OTA. FIG. 11 shows that the enzyme activity was the highest at pH 7.0 followed by pH 6 and 8; pH 5 and 9.

The recombinant amidase 2 was apparently heat stable as seen from FIG. 12 as more than 80% activity remained after 5-30 min pre-incubation at 80° C. compared to control where no enzyme was added. The reaction mixture of 5 µl enzyme plus 45 µl 68 mM sodium phosphate (pH7.0) was incubated at 80° C. for 0-30 min before adding another 50 µl the phosphate buffer and 25 µl 1 µg/ml OTA, and incubated at 30° C. for 60 min. The reaction was stopped by adding 130 µl acetonitrile containing 0.2% acetic acid (v/v). The reaction mixture was filtered and injected (10 µl) for HPLC analysis. Ctrl was control where no amidase was added.

Further more the recombinant amidase 2 was quite stable at 70° C. between pH 6 and 9. The stability decreased with the decrease in pH (FIG. 13). Activity was assayed at pH 7.0 and 30° C. The pre-incubation mixture contained 5 µl amidase 2 mixture (155 µg protein/ml), 45 µl 67 mM phosphate buffer (pH3, 4, 5, 6, 7, 8 and 9). The samples were pre-incubated at 70° C. for 30 min. After cooling to 30° C., 2 µl 0.5 mg/ml OTA in ethanol and 80 µl 0.2M Mops-NaOH (pH 7.0) were added and the reaction incubated at 30° C. for 60 min. The reaction was stopped by adding 130 µl acetonitrile containing 0.2% HAC, filtered and injected on RP-HPLC with an injection of 5 µl to monitor the remaining OTA.

Example 9

Purification of the Recombinant Amidase 2 Mat from the Fermentation Broth of *A. niger* Harboring the Amidase 2 Gene The broth of transformant 13 which had high OTA activity (FIG. 10) was used to purify the recombinant amidase 2 mat by ammonium sulfate fractionation, affinity chromatography on Phenyl Sepharose, HIC on Butyl-Sepharose and AEX as described below.

1) $(NH_4)_2SO_4$ fractionation. To 40 ml of the *A. niger* broth harboring the *A. niger* amidase 2 gene was added $(NH_4)_2SO_4$ to 40% saturation by stirring. After 10 min centrifugation at 3500 rpm, the supernatant was collected and $(NH_4)_2SO_4$ added to 60% saturation by stirring and the solution centrifuged again. The pellet corresponding to the precipitate between 40 to 60% $(NH_4)_2SO_4$ saturation was dissolved in 40 ml of 50 mM tricine-HCl (pH7.0) containing 1M $(NH_4)_2SO_4$ and filtered with 0.22 µm filter.

2) Hydrophobic interaction/affinity chromatography. The filtered sample from the above step was loaded a Phenyl Sepharose FF column (2.6×10 cm). Following a wash with tricine-HCl (pH7.0) containing 1M $(NH_4)_2SO_4$, the active fractions were eluted in 10 ml per tube at a flow rate of 10 ml/min with a linear gradient of 50 mM tricine-HCl (pH 7.0) from 1 M to 0 M of $(NH_4)_2SO_4$. The purification was achieved on Akta purifier system.

3) Anion exchange chromatography. The active fractions were pooled and desalted on a PD10 column equilibrated in 20 mM Tris/HCl, pH 7.5 (buffer A). The desalted sample was applied to a Source Q15 column equilibrated in buffer A (10 ml/min). The column was washed with buffer A and the bound proteins were eluted with a linear gradient of 0-1 M NaCl in buffer A. During the gradient elution, fractions of 5 ml were collected. The active fractions were analyzed on SDS-PAGE (FIG. 14A), which indicates that the amidase 2 mat was purified basically to homogeneity. The activity was related to a protein band having a molecular mass just below 49 kDa on the SDS-PAGE (FIG. 14). Mass spectrometry by Maldi-tof measurement indicates that this protein band may have a mass of 47214 Da (±2%) (FIG. 14B). N-terminal sequencing of fraction 12 indicate that the N-terminal of the Amidase 2 mat started at STDEAKVTI (SEQ ID NO. 33). The full length of the 480aa amidase 2 with 6 histidine residues is estimated to have a molecular mass of 51,983 Da while the N-terminal 42aa truncated amidase 2 with 6 histidine residues at its C-terminal is supposed to have a mass of 47,338 Da. These indicate that the amidase 2 secreted into the *A. niger* broth, i.e., amidase 2 mat is the amidase 2 that has been processed by a signal peptidase or other peptidase in the culture broth cleaving between the peptide bond of Ala-Ser in Amidase 2 sig.

Example 10

Substrate Specificity of Amidase 2

Km/Vm Determination:
Using the fractions obtained in the AEX step of amidase 2 mat the kinetic constants of Km and Vm of the enzyme degrading OTA were 0.29 µM/min and 13 µM, respectively by using the Lineweaver-Burk calculation method.
Ochratoxin B Degradation:
The enzyme solution of Amidase 2 mat obtained after AEX was tested on ochratoxin B at the same concentration under optimum conditions for one hour. The degrading rate with ochratoxin B was 8% compared to OTA.

Example 11

The Activity of Pure Amidase 2 mat in Breaking Down OTA

Ochratoxin A (OTA) degrading activity of amidase 2 mat purified from the fermentation broth of *A. niger* harboring the amidase 2 gene as a function of its concentration is shown in FIG. 15. It can be seen from FIG. 15 that the degradation of OTA was amidase 2 mat concentration dependent. One can also see that after 30 min with an amidase 2 mat concentration of 160 ng/ml the OTA decreased by 83%. From the linear region of FIG. 15 the calculated specific activity for amidase 2 mat was 900 nanomole OTA hydrolyzed per min per mg protein at pH7.0 and 40° C. at an OTA concentration of 1 µg/ml reaction mixture. The reaction for FIG. 15 was performed in 0.1 Mops-NaOH (pH 7.0) and 40° C. for 30 min before it was stopped by adding equal volume of acetonitrile containing 0.2% acetic acid and analyzed on RP-HPLC on a C18 column as described in the Material and Method section.

Example 12

Differences in Sensitivity to $Ca^{2+}$ Between the Intracellular and Extracellular Amidase 2 Found in *A. niger*

It was observed that the amidase 2 (i.e., amidase 2 mat) purified from the Amano™ lipase product or from the broth of transgenic *A. niger* harboring the amidase 2 gene were both inhibited by around 40% of its activity in the hydrolysis of OTA by 8 mM $CaCl_2$ (FIG. 16), while the intracellular fraction of amidase 2 (amidase 2 sig) of transgenic *A. niger* was not appreciably inhibited by $CaCl_2$ at 8 mM $CaCl_2$ (FIG. 17).

These results indicate that the loss of the N-terminal of amidase 2 resulted in sensitivity to $Ca^{2+}$ inhibition. The inhibition by $Ca^{2+}$ was overcome by the addition of divalent chelators including EDTA in an equal molar basis. Also it is known that the OTA degrading activity in the Amano™ lipase product is sensitive to EDTA. This example indicates that use of amidase 2 mat in systems containing divalent ions may be aided by the addition of a chelator such as EDTA. Citric acid and other organic acid such as propionic acid are widely used as feed additives and can chelate the divalent ion or trivalent ions, relieving their inhibition of amidase 2 mat. On the other hand extra EDTA also inhibited the recombinant Amidase 2 mat (data not shown). These results suggest that amidase 2 mat can be used for detoxification of OTA but has certain limitations due to its sensitivity to divalent or trivalent metal ions and to chelators like EDTA, while amidase 2 sig was discovered to be much less sensitive to divalent or trivalent metal ions and to chelators like EDTA (see below) indicating the importance of the full length of amidase 2 instead of the secreted or processed or mature amidase 2 (i.e., amidase 2 mat) found in the *A. niger* broth.

Example 13

Degradation of OTA by the Amidase 2 Extracted from the Intracellular Fraction (Amidase 2 Sig) of *A. niger*

This example shows the advantage of using the less sensitive form of amidase 2, i.e., amidase 2 sig. As can be seen from FIG. 17, 20 mM $CaCl_2$ or 20 mM EDTA had no inhibition to the amidase 2 sig compared to amidase 2 mat (FIG. 16). This provides a clear advantage for using amidase 2 sig in additives comprising a chelator in detoxifying OTA. The reaction contained 60 µl mops-NaOH (0.2M, pH7.0), 20 mM $CaCl_2$, 20 mM EDTA, amidase 2 sig (0.46 µg protein) extracted from *A. niger* cell harboring the amidase gene, 2 µl 25 µg/ml OTA and water to a final volume of 120 µl. The reaction was performed at 37° C. for 30 min and stopped by adding 150 µl acetonitrile containing 0.2% acetic acid. OTA and its product OT-alpha (=ODα) were analyzed on RP-HPLC on C18 column with an injection of 5 µl. Positive control (PC) contained no additives other than the buffer the amidase and OTA. Blank contained only buffer and OTA.

Example 14

Degradation of OTA in Corn flour and DDGS (Dried Distillers Grains With Solubles) by the Amidase 2 sig Extracted from the Intracellular Fraction (Amidase 2 sig) of *A. niger*

Corn is the major carrier for OTA and it can be further carried through to and concentrated in DDGS in bioethanol production. Corn and DDGS are widely used as feed ingredients. Mycotoxin level in DDGS is the usual factor that limits the amount of DDGS that can be added to feed. The examples here indicate that ability of amidase 2 sig in degrading OTA in corn flour and DDGS:

For corn flour, 50 mg corn flour was added 210 µl water, 8 µl OTA (25 µg/ml) and 20 µl amidase 2 sig (3.1 µg protein), mixed and incubated at 37° C. for 22 hr. The OTA concentration decreased from 800 ppb at the start to 14 ppb at the end. OTA analysis by HPLC is described in the materials and methods section above.

For DDGS, 1 g was suspended in 10 ml water, pH adjusted to 6.7 with NaOH. To 210 µl of this slurry was added 8 µl OTA (25 µg/ml) and 20 µl amidase 2 sig (3.1 µg protein), mixed and incubated at 37° C. for 22 hr. The OTA concentration decreased from 800 ppb at start to 5 ppb at the end. OTA analysis by HPLC was described in the materials and methods section above.

Example 15

Degradation of OTA in Milk by Amidase 2 mat

It is known that many food products including milk and cheese can be contaminated with OTA. This example tests OTA degradation in milk using amidase 2 mat.

Light milk (1.5% fat, protein 3.4 g, carbohydrate 4.7 g Calcium 120 mg, Phosphorus 95 mg in 100 ml) from Aria Foods Amba (Aarhus, Denmark) 0.15 ml, 3 µl OTA (2.5 µg/ml), 7.5 µl purified amidase 2 mat (from the broth of *A. niger* harboring the amidase 2 gene) containing 0.22 µg protein were mixed and reacted at 40° C. for 2.5 hr. The OTA decreased from 47 ppb at start to undetectable level (<2 ppb) after 2.5 hr incubation. OTA analysis by HPLC was described in the materials and methods section above.

Example 16

Amidase 2 mat in the Detoxification of OTA in Corn Flour

The reaction mixture in 1.5 ml eppendorf tubes (C1-3) comprised 60 mg corn flower, 200 µl Mops-NaOH (0.2 M pH7.0), 40 µl amidase 2 mixture (which was mixture of an equal volume of the broth of *A. niger* transformant having amdiase 2 gene 3, 4, 7, 8, 10, 11, 13, 14, and 15), 20 µl OTA (0.5 mg/ml). Total volume of the three components was 260 µl; final OTA was 38 µg/ml or 38 ppm (ppm, parts per million). Control: Tubes of Controls (C-4-6) were the same as C1-3 except that the amidase preparation (the broth) was replaced with water.

The reaction was performed at 30° C. with skaking for 20 hr before the addition of equal volume of acetonitrile 260 µl containing 0.2% acetic acid to stop the reaction and to extract the OTA. After centrifugation and filter, the filtrate was analyzed on HPLC. The HPLC results indicate that the remaining OTA was undetectable (less than 2 ppb), indicating that amidase 2 mat was able to reduce the OTA in corn flour from 38 ppm to less than 2 ppb.

Example 17

Amidase 2 Mat in the Detoxification of OTA in Corn-Soy Based Feed

The tests of amidase 2 mat with soy-corn based feed (whose composition is given in Table 3) contaminated with OTA was exactly as the test with corn flour, that is, tubes S1-3 (experimental) were with the broth while for tubes S 5-6 (controls) water replaced the broth. After 20 hr incubation, the OTA level was reduced from 38 ppm to 6.6 ppm, a reduction of 6 times or 82%.

TABLE 3

The composition of corn/soy based feed used

| Corn Diet Ingredients | Percent |
| --- | --- |
| Corn | 60.01% |
| Soybean meal 48 | 31.52% |

TABLE 3-continued

The composition of corn/soy based feed used

| Corn Diet Ingredients | Percent |
|---|---|
| Soy oil | 4.00% |
| Salt | 0.40% |
| DL Methionine | 0.20% |
| Limestone | 1.16% |
| Dicalcium Phos | 1.46% |
| VIT/MIN | 1.25% |
| Total | 100% |

Example 18

Solving the crystal structure of Amidase 2

15 crystals of amidase 2 were obtained as shown in Table 4.

Crystals AM7 and AM15 were x-ray diffracted and the structure of these two crystals of amidase 2 (aa 45-480) was solved at 2.5 Å resolution.

Amidase 2 was shown to have a structure similar to a Tim Barrel structure as shown in FIG. 20 and the active site as shown in FIG. 21. A summary of the data for the solved crystal structure for the AM7 crystal set is set out below.

Dataset: am7

|  | Overall | InnerShell | OuterShell |
|---|---|---|---|
| Low resolution limit | 80.00 | 80.00 | 2.64 |
| High resolution limit | 2.50 | 7.91 | 2.50 |
| Rmerge | 0.182 | 0.044 | 0.611 |
| Rmerge in top intensity bin | 0.057 | — | — |
| Total number of observations | 441395 | 14486 | 65195 |
| Total number unique | 46056 | 1566 | 6711 |
| Mean((I)/sd(I)) | 9.4 | 20.5 | 3.3 |
| Completeness | 96.5 | 93.3 | 97.6 |
| Multiplicity | 9.6 | 9.3 | 9.7 |

The structure was solved using Phaser and analyzing an ensemble of 5 most similar structures.

It was found that the active site of amidase 2 (SEQ ID NO:1) includes at least the following residues: His111, His113, His191, Lys246, His287, His289, His307, Asp378 and Val 253. It may accommodate at least two metal ions for catalysis and/structure purposes forming so-called a binuclear metal centre.

The coordinates for one monomer of the enzyme which is in the form of a tetramer are shown in FIG. 22.

TABLE 4

Crystal sets and related parameters

| Set | SG | cell | Resol./ after scal. | Rmerge | compl | mol/ ASU | Plate/ drop | Cryst. cond. | Beamline/ synchrotron |
|---|---|---|---|---|---|---|---|---|---|
| AM1 | P2$_1$2$_1$2$_1$? | 80 112 173 | 1.85/1.9 | 15.5/50.6 | 95.3/97.4 | 2-4 | AM3/C1 | PEG3K, NaAc4.6 | ID14-4 ESRF |
| AM2 | P42$_1$2 | 184 184 79 | 3.19/3.2 | 16.5/46.4 | 100/100 | 2 | AM8/B5 | PEG3K, K$_3$cit, Tris 8.5 | ID29 ESRF |
| AM3 | P42$_1$2 | 183.5 183.5 79.5 | 2.8/3.4 | 17.4/43.0 | 99.9/99.6 | 2 | AM8/B6 | PEG3K, K$_3$cit, Bicine 9 | ID29 ESRF |
| AM4 | ??? | ??? | 2.9/? | ?? | ?? | ?? | AM13/C2 | AS, Hepes 7 | ID29 ESRF |
| AM5 | P42$_1$2 | 184 184 79 | 2.9/3.2 | 17.4/56.5 | 99.8/99.4 | 2 | AM8/B6 | PEG3K, K$_3$cit, Bicine 9 | ID29 ESRF |
| AM6 | P42$_1$2 | 184 184 79 | 2.81/3.5 | 22.3/50.9 | 99.7/100 | 2 | AM8/A5 | PEG3K, K$_3$cit, Tris 8.5 | ID29 ESRF |
| AM7 | P42$_1$2 | 184 184 80 | 2.5/2.5 | 18.2/61.1 | 96.5/97.6 | 2 | AM8/A5 | PEG3K, K$_3$cit, Tris 8.5 | ID29 ESRF |
| AM8 | I2 | 213 80 218 | 2.7/~3 | 13.1/66.1 | 85.8/85.8 | 8 | AM5/A5 | PEG3K, K$_3$cit | ID29 ESRF |
| AM9 | P42$_1$2 | 183 183 94 | 2.57/3.1 | 30.3/84.6 | 86.7/86.7 | 2 | AM12/B5 | PEG3K, K$_3$cit, Tris 8.5 4MF | ID14-4 ESRF |
| AM10 | P42$_1$2 | 183 183 94 | 2.7/2.7 | 16.3/64.7 | 94.9/97.8 | 2 | AM8/A6 | PEG3K, K$_3$cit, Bicine 9 4MF | ID14-4 ESRF |
| AM11_Zn | P2$_1$2$_1$2$_1$? | 79 111 172.5 | ~2.5 | ?? | ?? | 2-4 | AM3/C5 | PEG3K, NaAc4.6 Zn | ID29 ESRF |
| AM12 | P42$_1$2 | 184 184 79 | 2.5/2.95 | 18.3/62.9 | 91.5/92.8 | 2 | AM15/C6 | PEG3K, K$_3$cit, Bicine 9 Zn + 4MF | ID29 ESRF |
| AM13 | P42$_1$2 | 184 184 79 | | | | | AM15/C6 | PEG3K, K$_3$cit, Bicine 9 Zn + 4MF | |
| AM14 | P42$_1$2 | 113.5 183.5 79 | 2.5/3.0 | 19.7/74.6 | 96.2/97.2 | 2 | AM15/C6 | PEG3K, K$_3$cit, Bicine 9 Zn + 4MF | ID29 ESRF |
| AM15 | I2 | 213 80 218 | 2.45/2.5 | 10.1/35.8 | 91.0/70.5 | 8 | AM15/B1 | PEG3K, K$_3$cit, Cit 5 | ID29 ESRF |

TABLE 5

The structural elements of amidase 2

| β-strand nr. | β-strand residues | α-helix nr. | α-helix residues | γ-helix nr. | γ-helix residue |
|---|---|---|---|---|---|
| 1 | 48–58 | | | | |
| 2 | 65–74 | | | | |
| 3 | 76–83 | | | | |
| | | | | 1 | 84–86 |
| | | 2 | 87–94 | | |
| 4 | 96–105 | | | | |
| 5 | 106–112 | | | | |
| | | 3 | 124–130 | | |
| | | 4 | 131–149 | | |
| 6 | 150–157 | | | | |
| | | 5 | 160–170 | | |
| 7a | 177–181 | | | | |
| 7b | 184–186 | | | | |
| | | 6 | 198–207 | | |
| 8 | 220–224 | | | | |
| | | 7 | 226–240 | | |
| 9 | 245–249 | | | | |
| | | 8 | 266–280 | | |
| 10 | 283–288 | | | | |
| | | 9 | 290–301 | | |
| 11 | 303–308 | | | | |
| | | 10 | 312–323 | | |
| 12 | 325–328 | | | | |
| | | 11 | 329–338 | | |
| | | 12 | 345–370 | | |
| 13 | 372–374 | | | | |
| | | 13 | 386–395 | | |
| | | 14 | 399–408 | | |
| | | | | 15 | 410–419 |
| 14 | 432–437 | | | | |
| | | | | 16 | 443–448 |
| | | | | 17 | 449–451 |
| 15 | 452–458 | | | | |
| 16 | 461–464 | | | | |

Color coding: white = small sandwich domain, Dark gray = catalytic barrel domain, light gray = barrel strands and barrel helices; helix α7 may also be considered a barrel helix Example 19

Expression of Amidases from Fungal Species *Glomerella qraminicola* M1.001 and *Metarhizium anisopliae* ARSEF 23 in *Trichoderma reesei*

To express amidases from *Glomerella graminicola* M1.001 and *Metarhizium anisopliae* ARSEF 23, both genes were synthesized as codon optimized sequences for expression in *T. reesei* and cloned in pDonor221 vector (Invitrogen, Carlsbad, Calif., USA) by Life technologies (Germany). 6×His codons were added at the 3' coding region of each gene for purification purposes. To enable the expression of the both amidases in *Trichoderma reesei*, their coding sequences were cloned into the Gateway compatible destination vector pTTT-pyrG13 (described in WO2010141779A1 and PCT/US10/57531) via the Gateway® LR recombination reaction. This vector contains the *T. reesei* cbhl-derived promoter and terminator regions allowing for a strong inducible expression of a gene of interest, the *Aspergillus nidulans* amdS and pyrG selective markers conferring growth of transformants on either acetamide as a sole nitrogen source or in the absence of uridine or both, and the *T. reesei* telomere regions allowing for non-chromosomal plasmid maintenance in a fungal cell. The cbhl promoter and terminator regions are separated by the chloramphenicol resistance gene, $Cm^R$, and the lethal *E. coli* gene, ccdB, flanked by the bacteriophage lambda-based specific recombination sites attR1, attR2. Such configuration allows for direct selection of recombinants containing a gene of interest under the control of the cbhl regulatory elements in the correct orientation via the Gateway® LR recombination reaction.

LR recombination reactions between the pEntry clones of each amidase gene and the destination vector pTTT-pyrG13 were done using the LR Clonase™ II enzyme mix according to the protocol from Invitrogen. Recombination products generated were transformed to E. coli Max Efficiency DH5α, as described by the supplier (Invitrogen), and clones containing the expression constructs pTTT-pyrG13-Amidase G. graminicola and pTTT-pyrG13-Amidase M. anisoplia were selected on 2xYT agar plates (16 g/L Bacto Tryptone (Difco, USA), 10 g/L Bacto Yeast Extract (Difco, USA), 5 g/L NaCl, 16 g/L Bacto Agar (Difco, USA)) with 100 µg/ml ampicillin. After growth of bacterial cultures in 2xYT medium with 100 µg/ml ampicillin, isolated plasmids were subjected to restriction analysis and clones with correct restriction pattern were used for transformation of the Trichoderma reeei 2830 pyrG negative strain deleted for 4 major cellulases cbhl, cbhll, egll, eglll (WO2010141779A1). The final expression plasmids pTTT-pyrG13-Amidase G. graminicola and pTTT-pyrG13-Amidase M. anisopliae are shown in FIG. 23-25.

0.5-2 µg of each expression plasmid was transformed in T. reesei using PEG-Protoplast method with slight modifications, as indicated. For protoplasts preparation, spores were grown for 16-24 hours at 24° C. in Trichoderma Minimal Medium MM (20 g/L glucose, 15 g/L $KH_2PO_4$, pH 4.5, 5 g/L $(NH_4)_2SO_4$, 0.6 g/L $MgSO_4 \times 7H_2O$, 0.6 g/L $CaCl_2 \times 2H_2O$, 1 ml of 1000×T. reesei Trace elements solution {5 g/L $FeSO_4 \times 7H_2O$, 1.4 g/L $ZnSO_4 \times 7H_2O$, 1.6 g/L $MnSO_4 \times H_2O$, 3.7 g/L $CoCl_2 \times 6H_2O$}) with shaking at 150 rpm. Germinating spores were harvested by centrifugation and treated with 50 mg/ml of Glucanex G200 (Novozymes AG, Switzerland) solution for lyses of the fungal cell walls. Further preparation of protoplasts was performed by a standard method, as described by Penttiläet al. [Gene 61 (1987) 155-164].

In general, transformation mixtures containing appx 1 µg of DNA and $1-5 \times 10^7$ protoplasts in a total volume of 200 µl were treated with 2 ml of 25% PEG solution, diluted with 2 volumes of 1.2M sorbitol/10 mM Tris, pH7.5/10 mM $CaCl_2$ solution, mixed with 3% selective top agarose MM containing 1 M sorbitol and 20 mM acetamide (the same Minimal medium as mentioned above but $(NH_4)_2SO_4$ was substituted with acetamide) and poured onto 2% selective agarose with acetamide. Plates were incubated for 5-7 days at 28° C. before transformants grew and started sporulation.

A spore mixture ($10^6$ spores/ml) harvested from a transformation plate was used to inoculate shake flasks with production medium (per 1 L): Glycine production medium (4.7 g/L $(NH_4)_2SO_4$, 33 g/L 1,4-Piperazinebis(propanesulfonic acid), pH 5.5, 6.0 g/L glycine, 5.0 g/L $KH_2PO_4$, 1.0 g/L $CaCl_2 \times 2H_2O$, 1.0 g/L $MgSO_4 \times 7H_2O$, 2.5 ml/L of 400×T. reesei trace elements, 20 g/L Glucose, 6.5 g/L Sophorose). As a control, T. reesei recipient 2830 strain was grown under the same conditions but in the presence of 10 mM uridine. After 5 days of fermentation at 30° C. and 200 rpm, cultures were harvested and subjected to enzymatic analysis from both extracellular and intracellular extracts.

Example 20

Expression of Aspergillus oryzae Amidase in Aspergillus niger GICC#2445 Strain

To express putative amidase gene from A. oryzae in Aspergillus niger, the amidase encoding sequence was amplified from the Aspergillus oryzae RIB40 genomic DNA (obtained from the Fungal Genetics Stock Collection, FGSC, USA) using the gene specific primers with attB1 and attB2 sites at the 5' and 3' termini for subsequent cloning via a Gateway approach. In addition the reverse primer contains 6×His encoding triplets to facilitate purification of the protein expressed.

The following set of primers was used:

```
Forward
5'
GGGACAAGTTTGTACAAAAAAGCAGGCTCACCATGCACCGGATGCTCAC
AGACGACAGAC3'

Reverse
5'
ACCACTTTGTACAAGAAAGCTGGGTCTAGTGGTGGTGGTGGTGGTGTGA
TTTAATCAGCATGCCGCCACGC 3'.
```

All PCR reactions were amplified with a high fidelity Phusion DNA polymerase (Finnzymes OY, Espoo, Finland) under standard conditions recommended by the supplier. After separation of the amplified DNA fragment on a 0.8% agarose gel, it was purified with a Nucleospin® Extract PCR clean-up kit (Macherey-Nagel GmbH & co. KG, Duren, Germany) and 150 ng were recombined with the pDonor221 vector (Invitrogen, Carlsbad, Calif., USA) according to recommendation of the supplier. E. coli DH5α colonies with pEntry clones containing the A. oryzae amidase were selected on 2xYT agar plates with 50 µg/ml kanamycin. Plasmids isolated from bacterial cells were analyzed by their restriction digestion pattern for the insert presence and checked by sequence analysis using a ABI3100 sequence analyzer (Applied Biosystems). The resulting pEntry-Amidase A. oryzae plasmid was used for cloning into a destination vector pRAXdest2, as described in U.S. Pat. No. 7,459,299, via subsequent Gateway LR reaction according to the protocol from Invitrogen (Carlsbad, Calif., USA). Recombination products formed were transformed to E. coli Max Efficiency DH5α, as described by the supplier (Invitrogen), and clones containing the expression construct pRAX-Amidase A. oryzae (FIG. 25) were selected on 2xYT agar plates (16 g/L Bacto Tryptone (Difco, USA), 10 g/L Bacto Yeast Extract (Difco, USA), 5 g/L NaCl, 16 g/L Bacto Agar (Difco, USA)) with 100 g/ml ampicillin. After growth of bacterial cultures in 2xYT medium with 100 µg/ml ampicillin, isolated plasmids were subjected to restriction analysis followed by sequencing using a ABI3100 sequence analyzer (Applied Biosystems). Besides a bacterial sequence, the final expression plasmid pRAX2-Amidase A. oryzae contains the A. oryzae amidase coding region under the control of the A. niger glucoamylase promoter and terminator, the Aspergillus nidulans pyrG gene as a selective marker and the A. nidulans AMA1 sequence for autonomous replication in fungal cells.

0.5-2 µg of this plasmid was transformed in A. niger var awamori GICC#2445 strain developed by Genencor using a common transformation procedure known in the art or described in U.S. Pat. No. 7,459,299. This strain is deleted for the endogenous glucoamylase glaA gene and carries a mutation in the pyrG gene allowing for selection of transformants for uridine prototrophy. A. niger transformants were grown on MM medium (the same minimal medium as was used for T. reesei transformation but 10 mM $NH_4Cl$ was used instead of acetamide as a Nitrogen source) for 4-5 days at 37° C. and a total population of spores ($10^6$ spores/ml) from different transformation plates was used to inoculate shake flasks with production medium (per 1 L): 12 g Trypton; 8 g Soyton; 15 g $(NH_4)_2SO_4$; 12.1 g $NaH_2PO_4xH_2O$; 2.19 g $Na_2HPO_4x2H_2O$; 1 g $MgSO_4x7H_2O$; 1 ml Tween 80; 150 g Maltose; pH 5.8. After 5 days of fermentation at 30° C. and 200 rpm, cultures were harvested and subjected to enzymatic analysis from both extracellular and intracellular extracts.

Example 21

Amidases from Three Additional Fungi for Ochratoxin Degradation

The putative amidase sequences from *Glomerella* graminicola (GMGM), *Metarhizium anisopliae* and *Aspergillus oryzae* all showed activity in degrading ochratoxin A.

Table 6 shows the activity of three fungal amidases from *Glomerella graminicola, Metarhizium anisopliae* and *Aspergillus oryzae* expressed intracellularly in *Trichoderma reesei* and *Aspergillus niger*. The reaction mixture using OTA as substrate consisted of 75 µl phosphate (67 mM, pH7), 5 µl OTA (2.4 µg/ml) and 20 µl intracellular cell-free fraction. The reaction was performed at 23° C. for 17 h and stopped by adding 0.15 ml acetonitrile and analyzed on HPLC with an injection volume of 5 µl.

TABLE 6

| Strains/and activities | *Trichoderma reesei* parent strain used for the transformation | *Trichoderma reesei* parent strain transformed with putative amidase gene from *Glomerella gramicola* | *Trichoderma reesei* parent strain transformed with putative amidase gene from *Metarhizium anisopliae* | *Aspergillus niger* strain transformed with putative amidase gene from *Aspergillus oryzae* |
|---|---|---|---|---|
| Activity on ochratoxin A expressed as ochratoxin A peak area | 12.26 | 0.68 | 0.96 | 8.57 |

The data in the table indicate that the amidase from *C. gramicola* has the highest activity against ochratoxin, whereas the amidase from *A. oryzae* has lower activity against this substrate.

Example 22

Sequence Comparison of Putative Amidase Sequences

Sequence comparisons were done over the full length of the polypeptide sequences using the AlignX Vector NTI program (InvitrogenCorporation) using the default parameters (Gap opening penalty−10, Gap extension penalty 0.1). As can be seen in Table 7 the putative amidases may have low overall homology. However, as can be seen from FIG. 26 all of the polypeptides of SEQ ID NOs: 5-11, 13, 14 and 15 have the same motifs as amidase 2 (SEQ ID NO:1 and 3).

The sequences are aligned with Multalin version 5.4.1 (F. CORPET, 1988, *Nucl. Acids Res.,* 16: 10881-10890). Parameters used: blosum62, Gap weight: 12, Gap length weight: 2, Consensus levels: high=90% low=50%, Consensus symbols: ! is anyone of IV, $ is anyone of LM, % is anyone of FY, # is anyone of NDQEBZ. Descriptions of the sequences and their web accession number (in parenthsis):

Furthermore, as shown in Example 21 (Table 6) SEQ ID NO:13-15 have ochratoxin degrading activity.

TABLE 7

| Sequence ID NO | % identity to SEQ ID NO: 1 (full length) |
|---|---|
| SEQ ID NO: 5 | 41.8% |
| SEQ ID NO: 6 | 42.4% |
| SEQ ID NO: 7 | 42.4% |
| SEQ ID NO: 8 | 40.7% |
| SEQ ID NO: 9 | 36.5% |
| SEQ ID NO: 10 | 28.2% |
| SEQ ID NO: 11 | 36.5% |
| SEQ ID NO: 13 | 56.1% |
| SEQ ID NO: 14 | 53.4% |
| SEQ ID NO: 15 | 34.6% |

The common sequence motifs of the 11 sequences have the Consensus:

1) l/m-P-G-l/m-w/l-D-c/v/s/a-H-x-H-f/y/l-xG, where the two His residues are in the active site;

2) G-y/f-T;

3) G-t/a/s/v/r-i/f/a-x-G-P;

4) G-H-g/s-D where the His residue is in the active site;

5) D-G-v/e-x-e/d/g-C-x-x-a/g/t-v/a-R-x-q/m/a-l/i/v-R-r/h/c-g/n-A-k/r/t/e/d-x-l-K, where the Lys residue is in the active site 6) G-G-V-l/m/v/g-S-x-x-D-x-P, where the Val residue is in the active site;

7) V-a/s/h-A-H-c/v/a-h/q-G-k/r-x-G, where the two His residues are in the active site;

8) H-g/v/a-s/t/l-y/f/e-l/a/l-D, where the His residue is in the active site;

9) G-V-x-l-a/v-I/a-G-T-D, where Asp residue is in the active site.

SEQ ID NO:1, is amidase 2 from *A. niger*, SEQ5, hypothetical protein from *A. niger* (XP_001400981), SEQ ID NO:6, hypothetical protein from *A. flavus* (XP_002385313), SEQ ID NO:7, hypothetical protein from *Talaromyces stipitatus* (XP_002477972), SEQ ID NO:8, hypothetical protein from *Neurospora crassa* (XP_962238), SEQ ID NO:9, putative amidohydrolase from *Streptomyces* roseosporus (ZP_04712156), SEQ ID NO:10, putative amidohydrolase from *Thermotoga lettingae* (YP_001470371), SEQ ID NO:11, putative amidohydrolase from *Salinispora arenicola* (YP_001536995), SEQ ID NO:13, putative amidohydrolase from *Glomerella* graminicola (EFQ25792), SEQ ID NO:14, putative amidohydrolase from *Metarhizium* anisopliae (EFZ00058), SEQ ID NO:15, hypothetical protein from *Aspergillus oryzae* (XP_001826758).

Example 23

Sequence Comparison of SEQ ID NO:1 to Carboxypeptidase Having Ochratoxin Degrading Activity Two carboxypeptidases are known which have low ochratoxin degradding activity, namely bovine carboxypeptidase A and yeast carboxypeptidase Y (Luis Abrunhosa, Robert R. M. Paterson and Armando Venancio, Biodegradation of Ochratoxin A for Food and Feed Decontamination, *Toxins* 2010, 2, 1078-1099).

The ochratoxin degrading activity of these enzymes has been confirmed. However, as can be seen from FIG. 27, these enzymes show no homology to SEQ ID NO:1 and do not contain any of the 9 motifs associated with ochratoxin degrading ability. Furthermore, these enzymes do not have the amidase typeTim Barrel structure.

```
SEQUENCE LISTING
                                                                   SEQ ID NO: 1
Amidase 2 sig from A. niger
   1 MVRRIASATP MVQSPMSPLG TTYCVRPNPV SLNLQRRPLV IASTDEAKVT

51 IIYAGLLIPG DGEPLRNAAL VISDKIIAFV GSEADIPKKY LRSTQSTHRV

101 PVLMPGLWDC HMHFGGDDDY YNDYTSGLAT HPASSGARLA RGCWEALQNG

151 YTSYRDLAGY GCEVAKAIND GTIVGPNVYS SGAALSQTAG HGDIFALPAG

201 EVLGSYGVMN PRPGYWGAGP LCIADGVEEV RRAVRLQIRR GAKVIKVMAS

251 GGVMSRDDNP NFAQFSPEEL KVIVEEAARQ NRIVSAHVHG KAGIMAAIKA

301 GCKSLEHVSY ADEEVWELMK EKGILYVATR SVIEIFLASN GEGLVKESWA

351 KLQALADSHL KAYQGAIKAG VTIALGTDTA PGGPTALELQ FAVERGGMTP

401 LEAIKAATAN APLSVGPQAP LTGQLREGYE ADVIALEENP LEDIKVFQEP

451 KAVTHVWKGG KLFKGPGIGP WGEDARNPFL

SEQ ID NO. 2
Sequence type: DNA; DNA name: DNA containing amidase 2 gene,
Length: 1443, Organism: Aspergillus niger

ATGGTCCGCC GAATTGCTTC AGCTACACCT ATGGTGCAAT CGCCCATGTC GCCATTGGGC

ACAACATACT GCGTCCGTCC TAATCCTGTT TCACTGAATC TTCAAAGAAG ACCTCTCGTG

ATCGCATCAA CAGACGAGGC CAAGGTCACT ATAATATATG CCGGACTATT AATCCCTGGC

GACGGAGAAC CTCTGCGCAA TGCTGCCCTA GTCATCAGCG ATAAGATCAT CGCGTTCGTT

GGATCCGAAG CCGACATCCC TAAGAAATAC CTCCGGTCCA CGCAGTCTAC TCATCGTGTC

CCCGTGCTCA TGCCTGGTTT GTGGGATTGC CACATGCATT TTGGCGGGGA TGACGATTAT

TACAACGATT ATACATCTGG TCTGGCCACT CATCCAGCAT CATCAGGTGC TCGACTAGCC

CGTGGTTGCT GGGAAGCATT GCAGAATGGG TATACATCCT ACCGCGACCT AGCCGGATAC

GGGTGCGAGG TCGCAAAGGC GATCAATGAT GGCACTATCG TTGGTCCAAA CGTGTACTCG

TCTGGCGCTG CACTCAGTCA GACAGCTGGA CACGGCGATA TCTTCGCTCT TCCAGCAGGC

GAAGTACTGG GGAGTTATGG AGTAATGAAC CCACGCCCTG GGTACTGGGG GGCAGGGCCG

CTATGTATCG CCGATGGCGT AGAGGAGGTC CGACGAGCAG TGAGGTTGCA GATCCGTCGC

GGTGCAAAGG TTATCAAAGT GATGGCCTCT GGGGGTGTCA TGTCGCGAGA CGATAATCCC

AACTTTGCAC AGTTCTCTCC AGAAGAACTG AAGGTGATAG TGGAAGAGGC GGCTCGACAG

AACCGGATCG TTTCTGCACA TGTGCATGGC AAGGCGGGGA TTATGGCTGC TATCAAAGCA

GGCTGCAAGA GTCTGGAGCA TGTGTCTTAT GCTGACGAGG AGGTCTGGGA GCTCATGAAA

GAGAAGGGAA TTTTGTATGT GGCCACACGC TCGGTTATTG AAATCTTTCT GGCTAGTAAT

GGAGAGGGGT TGGTGAAAGA GTCGTGGGCC AAGTTGCAGG CCCTTGCCGA TTCGCATTTG

AAAGCTTATC AGGGAGCTAT TAAGGCGGGT GTTACCATTG CGTTGGGAAC GGATACCGCC

CCCGGTGGTC CTACCGCACT TGAGTTGCAG TTTGCCGTCG AGAGAGGAGG TATGACGCCG

TTGGAGGCCA TCAAAGCCGC AACTGCGAAC GCTCCCCTGT CAGTTGGTCC ACAAGCACCG
```

```
TTGACGGGTC AGCTTCGCGA GGGGTATGAG GCAGATGTGA TTGCGTTGGA GGAGAATCCA

TTGGAGGACA TCAAAGTCTT TCAGGAGCCG AAGGCAGTTA CCCACGTCTG GAAGGGAGGG

AAACTGTTCA AAGTCCAGG TATTGGTCCG TGGGGAGAAG ATGCACGTAA TCCTTTTCTG

TAG
```

SEQ ID NO. 3

Sequence type: Protein; Protein name: amidase 2 mat, Length: 438, Organism: *Aspergillus niger*

SerThrAspGluAlaLysValThrIleIleTyrAlaGlyLeuLeuIleProGlyAspGly

GluProLeuArgAsnAlaAlaLeuValIleSerAspLysIleIleAlaPheValGlySer

GluAlaAspIleProLysLysTyrLeuArgSerThrGlnSerThrHisArgValProVal

LeuMetProGlyLeuTrpAspCysHisMetHisPheGlyGlyAspAspAspTyrTyrAsn

AspTyrThrSerGlyLeuAlaThrHisProAlaSerSerGlyAlaArgLeuAlaArgGly

CysTrpGluAlaLeuGlnAsnGlyTyrThrSerTyrArgAspLeuAlaGlyTyrGlyCys

GluValAlaLysAlaIleAsnAspGlyThrIleValGlyProAsnValTyrSerSerGly

AlaAlaLeuSerGlnThrAlaGlyHisGlyAspIlePheAlaLeuProAlaGlyGluVal

LeuGlySerTyrGlyValMetAsnProArgProGlyTyrTrpGlyAlaGlyProLeuCys

IleAlaAspGlyValGluGluValArgArgAlaValArgLeuGlnIleArgArgGlyAla

LysValIleLysValMetAlaSerGlyGlyValMetSerArgAspAspAsnProAsnPhe

AlaGlnPheSerProGluGluLeuLysValIleValGluGluAlaAlaArgGlnAsnArg

IleValSerAlaHisValHisGlyLysAlaGlyIleMetAlaAlaIleLysAlaGlyCys

LysSerLeuGluHisValSerTyrAlaAspGluGluValTrpGluLeuMetLysGluLys

GlyIleLeuTyrValAlaThrArgSerValIleGluIlePheLeuAlaSerAsnGlyGlu

GlyLeuValLysGluSerTrpAlaLysLeuGlnAlaLeuAlaAspSerHisLeuLysAla

TyrGlnGlyAlaIleLysAlaGlyValThrIleAlaLeuGlyThrAspThrAlaProGly

GlyProThrAlaLeuGluLeuGlnPheAlaValGluArgGlyGlyMetThrProLeuGlu

AlaIleLysAlaAlaThrAlaAsnAlaProLeuSerValGlyProGlnAlaProLeuThr

GlyGlnLeuArgGluGlyTyrGluAlaAspValIleAlaLeuGluGluAsnProLeuGlu

AspIleLysValPheGlnGluProLysAlaValThrHisValTrpLysGlyGlyLysLeu

PheLysGlyProGlyIleGlyProTrpGlyGluAspAlaArgAsnProPheLeu

SEQ ID NO. 4

Amidase 2 *A. niger* + c terminal 6H

MVRRIASATPMVQSPMSPLGTTYCVRPNPVSLNLQRRPLVIASTDEAKVTIIYAGLLIPGDGE

PLRNAALVISDKIIAFVGSEADIPKKYLRSTQSTHRVPVLMPGLWDCHMHFGGDDDYYNDYTS

GLATHPASSGARLARGCWEALQNGYTSYRDLAGYGCEVAKAINDGTIVGPNVYSSGAALSQTA

GHGDIFALPAGEVLGSYGVMNPRPGYWGAGPLCIADGVEEVRRAVRLQIRRGAKVIKVMASGG

VMSRDDNPNFAQFSPEELKVIVEEAARONRIVSAHVHGKAGIMAAIKAGCKSLEHVSYADEEV

WELMKEKGILYVATRSVIEIFLASNGEGLVKESWAKLQALADSHLKAYQGAIKAGVTIALGTD

TAPGGPTALELQFAVERGGMTPLEAIKAATANAPLSVGPQAPLTGQLREGYEADVIALEENPL

EDIKVFQEPKAVTHVWKGGKLFKGPGIGPWGEDARNPFLHHHHHH

SEQ ID NO. 5

Sequence type: Protein; Protein name: putative amidase 2 homologue, Length: 420, Organism: *Aspergillus niger*

MetHisArgProLeuThrAspSerThrPheTyrArgIleAsnAlaAspIleLeuIlePro

GlyArgGlyAlaProIleAlaArgGlyAlaValValTrpLysSerLysThrIleLeuTyr

SerGlyProGlnHisGluValProValGluTyrGlnAspAlaValThrThrHisValPro

-continued

ValAlaMetProGlyMetTrpAspCysHisIleHisPheLeuGlyAlaThrAlaAlaThr

MetAspSerIleValAsnThrProGlnAlaLeuAlaGlyAlaArgSerValProTyrLeu

TyrAlaThrIleIleAlaGlyPheThrSerValArgGluValGlyGlyTyrGlyCysGlu

LeuAlaLysValIleAspGluGlyArgIleProGlyProThrIleTyrGlyAlaHisSer

AlaIleSerMetThrAlaGlyHisGlyAspValHisGlyValAsnProGluGlyLeuArg

AspLeuCysThrHisGlyLeuProLeuThrIleAlaAspGlyValProGluCysLeuGln

AlaValArgLysGlnLeuArgHisGlyAlaArgIleIleLysValCysAlaSerGlyGly

ValValSerAlaIleAspAspProGlnHisGlnGluPheSerPheGluGluLeuLysAla

IleValAspGluAlaAlaArgAlaArgArgValValAlaAlaHisCysHisGlyLysAla

GlyIleMetAsnAlaLeuArgAlaGlyCysArgThrIleGluHisGlySerTyrLeuAsp

GluGluAlaIleAspLeuMetLeuGluLysGlyAlaMetLeuValAlaThrArgSerVal

IleGluSerGlyLeuAlaMetArgAspLeuPheThrProGlySerTyrGlnLysLeuLeu

GluValAlaAspThrHisLysArgAlaTyrGluLeuAlaValArgArgGlyValProIle

AlaLeuGlyThrAspGlnPheIleSerSerAspAsnProAlaLeuGlyTyrGlyArgAsn

GlyLysGluLeuValTyrAlaValAlaAlaGlyMetThrProLeuAlaAlaIleGluAla

AlaThrAlaAsnGlyProLeuThrLeuGlyAspGlnAlaProLysSerGlyGlnLeuArg

GluGlyPheAspAlaAspIleIleAlaLeuThrAlaAsnProLeuGluAsnIleIleVal

ValSerAspProLysAsnValThrHisValTrpArgTyrGlyLysLeuValLysSerAsn

SEQ ID NO. 6

Sequence type: Protein; Protein name: putative amidase 2
homologue, Length: 419, Organism: *Aspergillus flavus*
MetHisArgMetLeuThrAspAspArgLeuTyrArgValAspAlaAspLeuLeuIlePro GlyLysGlyAspProIleProHisGlyAlaValValTrpGlnCysLysThrIleArgTyr AlaGlyProArgSerGluValProAlaGluPheGlnGlyAlaThrThrThrHisValPro ValValMetProGlyMetTrpAspCysHisIleHisPheLeuGlyAlaThrAlaAlaThr MetAsnAlaIleValAspThrProGlnAlaLeuAlaGlyAlaArgSerValProAspLeu HisAlaThrValMetAlaGlyPheThrSerValArgGluValGlyGlyTyrGlyCysAsp LeuAlaLysAlaValGlyGluGlyArgIleProGlyProAsnIleTyrSerSerHisSer AlaIleSerMetThrAlaGlyHisGlyAspValHisGlyValHisArgAspSerLeuLeu AspLeuCysAlaHisGlyLeuProLeuThrIleAlaAspGlyValProGluCysLeuLeu AlaValArgLysGlnLeuArgArgGlyAlaThrValIleLysValCysAlaSerGlyGly ValValSerAlaIleAspAspProGlnHisGlnGluPheSerPheGluGluLeuLysAla IleValAspGluAlaAlaArgAlaArgArgValValAlaAlaHisCysHisGlyLysAla GlyIleMetAsnAlaLeuArgAlaGlyCysArgThrIleGluHisGlySerPheLeuAsp GluGluAlaValGluLeuMetLysGluLysGlyAlaIleLeuValAlaThrArgSerVal IleGluSerGlyLeuAlaMetLysAspLeuPheThrProSerSerTyrGlnLysLeuLeu GluValAlaAspAlaHisArgLysAlaTyrGlnLeuAlaIleSerArgGlyValThrIle AlaLeuGlyThrAspGlnPheIleSerSerAspAsnProMetIleGlyTyrGlyArgAsn GlyHisGluValArgTyrAlaValAspAlaGlyLeuThrProLeuAlaAlaIleGluAla AlaThrAlaAsnGlyProLeuThrLeuGlyTyrGlnAlaProGlnSerGlyGlnLeuLys GluGlyTyrAspAlaAspIleIleAlaValArgGluAsnProLeuGluAsnValAlaVal LeuSerAsnSerLysAsnValThrHisValTrpArgGlyGlyMetLeuIleLysSer

SEQ ID NO. 7

Sequence type: Protein; Protein name: putative amidase 2 homologue, Length: 405, Organism: *Talaromyces stipitatus*
MetArgValArgLeuLysAlaSerIleLeuIleProGlyArgGlyGluProIleGluAsn
GlyAlaLeuIleIleAspGlyProLysIleAlaTrpValGlyGlnGlnSerAlaIlePro
ThrLysTyrGlnAspValAspPheGluTyrLeuProValLeuMetProGlyLeuTrpAsp
CysHisThrHisPheMetGlyLeuSerAspGluSerAspThrMetGlnAlaValPheGly
SerAlaAlaLeuAlaGlyAlaIleAlaAlaLysGluLeuGluThrAlaLeuMetAlaGly
PheThrThrIleArgGluValGlyGlyValAlaGlyGluIleTyrProAlaIleLysAsn
GlyThrIleValGlyProAsnValTyrSerSerIleGlyValLeuGlyIleThrGlyGly
HisSerAspValHisAsnValProIleGluAlaValIleAlaLysArgAsnGluGlyThr
PheValValCysAspGlyValSerAspCysIleLysThrValArgMetMetValArgArg
GlyAlaThrLeuIleLysIleCysAlaThrGlyGlyValGlySerLeuLeuAspAspPro
GluAspAlaGlnPheSerProGluGluIleLysAlaIleValAspGluAlaAlaArgSer
LysArgIleValAlaAlaHisCysHisGlyLysGluGlyIleMetAsnAlaLeuHisAla
GlyValHisThrIleGluHisGlySerTyrLeuAspGluGluValAlaAlaLeuMetLys
GluLysLysAlaLeuPheValSerThrArgLeuIleIleGluGluGlyLeuLysAsnPro
LysLeuTrpProProSerSerTyrArgLysLeuThrLysIleSerGluAlaHisLysLys
AlaTyrAlaLeuAlaValLysSerGlyValLysIleValLeuGlyThrAspTrpThrAla
GlyGluAsnGlyLysGluLeuAlaTyrAlaValGluAlaGlyMetSerProLeuGluAla
IleGluAlaSerThrAlaArgCysProGluThrLeuGlySerHisPheAlaProLeuSer
GlyGlnLeuLysGluGlyTyrGlyAlaAspValIleAlaValAlaSerAsnProLeuAsp
AspIleLysValLeuGlyGluProLysAsnIleThrHisValTrpLysGlyGlyLysLeu
TyrLysGlyThrLeu

SEQ ID NO. 8

Sequence type: Protein; Protein name: putative amidase 2 homologue, Length: 440, Organism: *Neurospora crassa*
MetGlnIleLysValThrLeuProAsnAspThrIleAsnArgAspSerValAspAspArg
AlaSerTyrHisGlyIleLeuAlaAspValLeuIleProGlyArgGlyGluProLeuLys
AsnGlyAlaLeuValValLysAspSerValIleGluTrpValGlyProSerAspGluIle
ProSerGluTyrSerSerIleArgValSerArgValProValLeuMetProGlyMetTrp
AspValHisThrHisTyrGluGlyValGlyValAlaGlnGlyIleArgGluSerMetLys
ProPheLeuProGlyThrAlaThrLeuIleGlyAlaValIleValAspAspMetArgArg
ThrLeuMetAlaGlyPheThrSerIleArgGluLeuGlyGlyTyrAlaGlyAspValAla
ProAlaIleAspMetGlyAlaIleValGlyProHisValTyrAlaAlaMetSerLeuLeu
SerIleThrGlyGlyHisGlyAspLeuHisAspValProLeuArgThrValLeuAspAla
CysAlaAsnGlySerSerSerCysPheLeuCysAspGlyValAspGlyCysIleAsnAla
ValArgGlnGlnIleArgArgGlyAlaLysValIleLysValCysSerThrGlyGlyVal
LeuSerLeuAsnAspGlnProGluAspThrGlnPheSerAlaGluGluLeuArgAlaIle
ValGlnGluAlaLysArgSerSerArgValValAlaAlaHisAlaHisGlyLysProGly
IleMetAlaAlaLeuAspAlaGlyValLysSerIleGluHisGlySerPheLeuAspGlu
GluValAlaAlaLysMetLysGluLysAspAlaIleLeuValProThrArgHisValVal
GluGlyMetAlaAlaAsnAsnAspAspLeuAspProArgGlnArgAlaLysLeuGluArg -continued ThrMetGlnLeuSerArgAspSerIleLysLeuAlaHisArgMetGlyValLysIleAla LeuGlyThrAspThrPheArgSerAspLysAsnHisAlaValAlaHisGlyLysAsnAla MetGluLeuArgTyrAlaIleGluAlaGlyMetThrProLeuGlnAlaIleGluMetAla ThrAlaThrProProGluThrLeuGlyProGlnAlaArgLysSerGlyGlnLeuLysAla GlyTyrAspAlaAspLeuIleAlaIleSerSerAsnProLeuGluAspIleGluIleLeu IleAspProAspAsnIleThrHisValTrpLysGlyGlyValLeuPheLysCysProGln

SEQ ID NO. 9

Sequence type: Protein; Protein name: putative amidase 2
homologue, Length: 413, Organism: *Streptomyces roseosporus*
MetGluHisArgIleAspAlaAspLeuLeuIleProGlyAlaGlyGluProThrValAsn GlySerValValHisAlaAspGlyArgIleArgPheAlaGlyProThrAlaGluLeuPro ArgGluHisArgAlaLeuGluProThrArgValAlaThrLeuLeuProGlyLeuTrpAsp CysHisValHisPheAlaGlyIleArgGlyArgValSerThrGluGluLeuMetLeuThr ProGluThrLeuAlaValValArgSerValLysAspAlaGluThrAlaLeuArgAlaGly PheThrSerValArgAspMetGlyGlyHisGlyCysValLeuAlaGluAlaValArgGlu GlyThrPheThrGlyProAsnIleTyrSerAlaAsnGlnValIleGlyGlnThrGlyGly HisSerAspAlaHisArgLeuProTyrArgTrpValThrAspProCysArgSerGlyGly ThrLeuArgIleAlaAspGlyValAspGluCysValArgAlaValArgLeuGlnLeuArg AlaGlyAlaGluLeuIleLysIleCysThrSerGlyGlyValLeuSerGluValAspAsn ProValHisGlnGlnTyrArgSerGluGluLeuAsnAlaIleValThrGluAlaAlaArg AlaAspArgValValAlaAlaHisCysHisGlyArgAlaGlyIleLeuAlaAlaIleAsp AlaGlyCysHisThrValGluHisGlyThrGluIleAspGluArgThrAlaAspLeuMet AlaGluArgGlyMetThrLeuValProThrArgThrIleTyrGluAlaPheArgGlnAsp ValAlaAlaLeuProProAlaTrpArgAspArgPheAlaLeuMetAlaGluArgHisLeu ThrAlaIleGlyIleAlaHisArgAlaGlyValThrIleAlaLeuGlyThrAspLeuGly ThrSerAspArgGlyGlyProLeuSerTrpGlyGlyHisGlySerGluPheAlaHisLeu ValSerAlaGlyLeuSerProLeuGluAlaIleLysAlaAlaThrAlaHisGlyProGly ThrLeuGlyProArgAlaProArgSerGlyArgLeuGluAlaGlyTyrAspAlaAspLeu LeuAlaValAspGlyAsnProLeuAlaAspIleThrValLeuAlaAspProAspArgIle ThrArgValTrpLysSerGlyGluProValProSerGly

SEQ ID NO. 10

Sequence type: Protein; Protein name: putative amidase 2
homologue, Length: 407, Organism: *Thermotoga lettingae*
GluSerAlaValPheIleGluGlyAlaArgIleLeuAlaValGluLysIleLysArgSer GlnIleProSerGlyPheThrGlnIleAspLeuGlnGlyArgTyrLeuMetProGlyLeu IleAspAlaHisLeuHisLeuAlaGlyMetArgSerGlyAspMetValLysGluHisLeu LeuThrProTyrGluThrLeuValAlaArgThrValThrAspLeuLysSerLeuIleGlu AlaGlyPheThrThrValValAspAlaGlyGlySerIleAlaIleAsnLeuLysLysAla IleGlnGluGlyThrIleAlaGlyProArgIleValAlaAlaGlyHisSerLeuSerGln ThrPheGlyHisGlyAspGluHisPheLeuProIleAspTyrValAspProArgThrSer LysPheLysGlyGlyPheGlySerLeuIleCysAspGlyValAlaGluCysIleLysAla AlaArgTyrAlaLeuArgCysGlyAlaAspPheIleLysIleMetAlaThrGlyGlyVal LeuSerGluArgAspArgProGluTyrThrGlnPheThrValGluGluIleLysAlaIle ValGluGluAlaAsnHisAlaArgLysPheValHisAlaHisAlaGlnGlyLysAspGly -continued IleMetAsnAlaLeuLeuGlyGlyValLysValIleAlaHisAlaIleTyrIleAspAsp GluSerCysLysLeuAlaLysGluLysAsnAlaIleIleValProThrLeuSerIleVal GluHisLeuIleIleHisGlyLysGlnIleGlyAlaProGluTrpGlyLeuArgLysSer GluGluValTyrLysIleHisValGluAsnIleLysLysAlaTyrGluHisGlyValLys IleAlaAlaGlyThrAspPheIleGlyGlyThrLysAlaPheLysHisGlyGluAsnAla LeuGluIleLeuLeuLeuValAspLysIleGlyMetLysProGluGlnAlaLeuLeuSer AlaThrLysValAlaAlaGluAlaAlaGlyLeuSerGlnLeuValGlySerIleAspLys GlyLysLeuAlaAspLeuLeuIleValGluAspAsnProLeuSerAsnValLysIleLeu MetAspHisSerLysIleSerAlaValPheLysGluGlyIleLeuPheLysAspLysIle GlyLeuGluLysTyrPheAsn

SEQ ID NO. 11

Sequence type: Protein; Protein name: putative amidase 2
homologue, Length: 408, Organism: *Salinispora arenicola*
MetIleGluCysIleGluAlaAspGlnLeuIleProGlyArgGlyGluProValAlaAsn AlaValValValLeuGluAspAlaThrIleArgTyrAlaGlyProAlaGluHisAlaPro LysValAlaGluAlaArgArgSerArgAlaHisThrValLeuProGlyLeuTrpAspSer HisValHisPheMetGlyLeuArgSerAlaAspValGlyIleLeuProGlnGluProVal AlaLeuArgAlaAlaArgThrValAlaAspLeuArgAlaAlaLeuAspAlaGlyPheThr SerValArgGluValGlyGlyLeuGlyLeuAspLeuAlaArgAlaValGluGluGlyThr AlaValGlyProSerValTyrAlaAlaGlyCysAlaLeuSerThrThrGlyGlyHisGly AspLeuHisSerTyrProLeuAlaTrpMetGluGluPheAlaArgHisGlyGlyGluLeu ArgLeuAlaAspGlyGluAlaGluCysValArgAlaValArgGluGlnLeuArgArgAsn AlaLysValIleLysValTyrAlaSerGlyGlyValLeuSerGluValAspHisProIle HisArgGlnPheThrAspArgGluLeuArgAlaIleValGluValAlaGlyLeuAlaAsp ArgValValAlaAlaHisCysHisGlyLysProGlyMetMetAlaAlaIleGluAlaGly ValArgThrIleGluHisGlyThrTyrLeuAspGluGluValAlaAlaAlaMetArgGlu ThrGlyAlaIleLeuValThrThrArgThrIleMetGlnGluLeuIleAspSerArgAla LeuProProTyrAlaLeuArgLysLeuGluSerIleValAspArgHisAlaGluAlaIle ValIleAlaArgGluSerGlyValArgIleAlaAlaGlyThrAspValAlaLeuThrGly AlaGluLeuProAspSerTrpGlyArgAsnGlyArgGluLeuProLeuLeuAlaGluIle GlyPheSerProLeuGluValIleGluAlaAlaThrAlaAlaAlaProAlaThrLeuGly ProGlnAlaProArgSerGlyGlnLeuValGluGlyTyrAspAlaAspValIleThrLeu AspAlaAspProLeuAlaAspIleGlyValLeuAlaLysProAlaHisIleThrGlyVal TrpLysAlaGlyCysArgValAla

SEQ ID NO. 12.

Sequence type: Protein; Protein name: pepAd2 (protease),
Length: 480, Organism: *Aspergillus niger*
MetHisLeuProGlnArgLeuValThrAlaAlaCysLeuCysAlaSerAlaThrAlaPhe IleProTyrThrIleLysLeuAspThrSerAspAspIleSerAlaArgAspSerLeuAla ArgArgPheLeuProValProAsnProSerAspAlaLeuAlaAspAspSerThrSerSer AlaSerAspGluSerLeuSerLeuAsnIleLysArgIleProValArgArgAspAsnAsp PheLysIleValValAlaGluThrProSerTrpSerAsnThrAlaAlaLeuAspGlnAsp GlySerAspIleSerTyrIleSerValValAsnIleGlySerAspGluLysSerMetTyr -continued MetLeuLeuAspThrGlyGlySerAspThrTrpValPheGlySerAsnCysThrSerThr ProCysThrMetHisAsnThrPheGlySerAspAspSerSerThrLeuGluMetThrSer GluGluTrpSerValGlyTyrGlyThrGlySerValSerGlyLeuLeuGlyLysAspLys LeuThrIleAlaAsnValThrValArgMetThrPheGlyLeuAlaSerAsnAlaSerAsp AsnPheGluSerTyrProMetAspGlyIleLeuGlyLeuGlyArgThrAsnAspSerSer TyrAspAsnProThrPheMetAspAlaValAlaGluSerAsnValPheLysSerAsnIle ValGlyPheAlaLeuSerArgSerProAlaLysAspGlyThrValSerPheGlyThrThr AspLysAspLysTyrThrGlyAspIleThrTyrThrAspThrValGlySerAspSerTyr TrpArgIleProValAspAspValTyrValGlyGlyThrSerCysAspPheSerAsnLys SerAlaIleIleAspThrGlyThrSerTyrAlaMetLeuProSerSerAspSerLysThr LeuHisSerLeuIleProGlyAlaLysSerSerGlySerTyrHisIleIleProCysAsn ThrThrThrLysLeuGlnValAlaPheSerGlyValAsnTyrThrIleSerProLysAsp TyrValGlyAlaThrSerGlySerGlyCysValSerAsnIleIleSerTyrAspLeuPhe GlyAspAspIleTrpLeuLeuGlyAspThrPheLeuLysAsnValTyrAlaValPheAsp TyrAspGluLeuArgValGlyPheAlaGluArgSerSerAsnThrThrSerAlaSerAsn SerThrSerSerGlyThrSerSerThrSerGlySerThrThrThrGlySerSerThrThr ThrThrSerSerAlaSerSerSerSerSerSerAspAlaGluSerGlySerSerMetThr IleProAlaProGlnTyrPhePheSerAlaLeuAlaIleAlaSerPheMetLeuTrpLeu SEQ ID NO: 13
Organism *Glomerella graminicola* M1.001 (fungus), 472 aa
  1 mggsfrpnya dgpeppfspt kkttlviikt sllipgdgep lkdgalviss kviawvgpqs
 61 slpseyadsp hrsytvpylm pglwdchahf ggespnddgg ndpyqvfite hpaasgarlt
121 rgcwlalqrg ytslrdvagl gcevsraied gsivgpnvys sgsglsqlag hgdifslpag
181 dvllnlgvsq itpghfgtha tmivdgvdec rravrlqirr gakcikvmas ggvmsrddnp
241 nyaqfsaael etiveeatrq nrvvaahvhg kagilaaina gvttlehasf adrecidlik
301 ekgivyiatr ivvhllllstg gkglpptvwe kaklvaknhm taykmaiesg vqialgtdtg
361 pgynmatele caveagmsnl eaikaatang plsvggqapk tgqlkvgyea dvigllqnpv
421 edvkvlqkvd nvgwvwkggk lfkgpgvgpw geepgvwedi tgvsrlrctt gy SEQ ID NO: 14
Organism *Metarhizium anisopliae* ARSEF 23. 485 aa,
  1 mtrrviphse saesvddaqh vsgriystgf giavrtgqpq sqdddaetgv kkvfytivmt
 61 kllipgdgep ikdaalvvkn kiidwvgrqa dlpneytekp hklhnvpylm pglwdchvhf
121 agsngereae egstglsfla dhpttagarl argcwdaiqr gytsmrdlag fgceiskaie
181 dgviigpniy sagaclsqla ghgdvfalpa gdallnlgla svkagqfgag msclvdgvde
241 crrgvrlqir rgakcikvma sggvlsrddn plyaqfsree ldtivseakr mertvaahvh
301 gkpgilqave agvtsvehvs fadqecidli kdrgtifvgt rtivnlllds kgegmpkkmw
361 ekaklvgths legykkaika gctialgtdt epgfnmaiel qyaveagmss leaikaatan
421 gpltvagqap ltgqlkagye admigvcdnp vedvkvlqkk snigwvwkgg klfkgpgigp
481 wgeel SEQ ID NO: 15
*A. oryzae* amidohydrolase
Mhrmltddrlyrvdadllipgkgdpiphgavvwqcktiryagprsgvptefqgatthvpvvmpgmwdc hihflgataatmnaivdtpqalagarsvpdlhatvmagftsvrevggygcdlakavgegripgpniyss hsaismtaghgdvhgvhrdslldlcahglpltiadgvpecllavrkqlrrgakvikvcasggvvsaidd pqhqefsfeelkaivdeaararrvvaahchgkagimnalragcrtiehgsfldeeavglmkekgailva trsviesglamkdlftpssyqkllavadahrkayqlaisrgvtialgtdqfissdnpmigygrnghevr yavdagltplaaieaatangpltlgyqapqsgqlkegydadiiavrenplenvavlsnsknvthvwrgg mliks

SEQ ID NO: 16

Bovine carboxypeptidase A (419 aa). Accession: NP_777175.
Sigma product no. C0261.

```
  1 mqgllilsvl lgaalgkedf vghqvlrita adeaevqtvk eledlehlql dfwrgpgqpg
 61 spidvrvpfp slqavkvfle ahgiryrimi edvqslldee qeqmfasqsr arstntfnya
121 tyhtldeiyd fmdllvaehp qlvsklqigr syegrpiyvl kfstggsnrp aiwidlgihs
181 rewitqatgv wfakkftedy gqdpsftail dsmdifleiv tnpdgfafth sqnrlwrktr
241 svtssslcvg vdanrnwdag fgkagasssp csetyhgkya nsevevksiv dfvkdhgnfk
301 aflsihsysq lllypygytt qsipdkteln qvaksaveal kslygtsyky gsiittiyqa
361 sggsidwsyn qgikysftfe lrdtgrygfl lpasqiipta getwlgvlti mehtlnnly
```

SEQ ID NO: 17

Carboxypeptidase Y from baker's yeast (Saccharomyces cerevisiae), 532 aa, Accession: EDV11788. Sigma product no. C3888.

```
  1 mkaftsllcg lglsttlaka islqrplgld kdvllqaaek fglnldldhl lkeldsnvld
 61 awaqiehlyp nqvmsletst kpkfpeaikt kkdwdfvvkn daienyqlrv nkikdpkilg
121 idpnvtqytg yldvededkh fffwtfesrn dpakdpvilw lnggpgcssl tglffelgps
181 sigpdlkpig npyswnsnat vifldqpvnv gfsysgssgv sntvaagkdv ynflelffdq
241 fpeyvnkgqd fhiagesyag hyipvfasei lshkdrnfnl tsvlignglt dpltqynyye
301 pmacgeggep svlpseecsa medslerclg liescydsqs vwscvpatiy cnnaqlapyq
361 rtgrnvydir kdceggnlcy ptlqdiddyl nqdyvkeavg aevdhyescn fdinrnflfa
421 gdwmkpyhta vtdllnqdlp ilvyagdkdf icnwlgnkaw tdvlpwkyde efasqkvrnw
481 tasitdevag evksykhfty lrvfngghmv pfdvpenals mvnewihggf sl
```

REFERENCE LIST

1. Abrunhosa, L. and Venancio, A. (2007). Isolation and purification of an enzyme hydrolyzing ochratoxin A from Aspergillus niger. Biotechnol. Lett. 29: 1909-1914
2. Abrunhosa, L., Paterson, R. R. M. and Venancio, A. (2010). Biodegradation of Ochratoxin A for Food and Feed Decontamination. Toxins, 2: 1078-1099
3. Fraser, J. A., Davis, M. A., and Hynes, M. J. (2001). The Formamidase Gene of Aspergillus nidulans: Regulation by Nitrogen Metabolite Repression and Transcriptional Interference by an Overlapping Upstream Gene. Genetics 157: 19-131
4. Jelinek, C. F., Pohland, A. E., and Wood, G. E. (1989). Worldwide Occurrence of Mycotoxins in Foods and Feeds—An Update. Journal of the Association of Official Analytical Chemists 72: 223-230
5. Li, S., Marquardt, R. R., Frohlich, A. A., Vitti, T. G., and Crow, G. (1997). Pharmacokinetics of ochratoxin A and its metabolites in rats. Toxicol. Appl. Pharmacol. 145: 82-90
6. Pitout, M. J. (1969). The hydrolysis of ochratoxin A by some proteolytic enzymes. Biochem. Pharmacol. 18: 485-491
7. Stander, M. A., Bornscheuer, U. T., Henke, E., and Steyn, P. S. (2000). Screening of commercial hydrolases for the degradation of ochratoxin A. J. Agric. Food Chem. 48: 5736-5739
8. Van der Merwe, K. J., Steyn, P. S., and Fourie, L. (1965). Mycotoxins. II. The constitution of ochratoxins A, B, and C, metabolites of Aspergillus ochraceus Wilh. J. Chem. Soc. [Perkin 1] 7083-7088
9. WHO/FAO (1998). Food irradiation. A Technique for Preserving and Improving the Safety of Food. World Health Organization in collaboration with the Food and Agricultural Organization, Geneva
10. Wang, H (2010). Increased production of aspartic proteases in filamentous fungal cells. WO 2010014574 (A2)

The invention claimed is:

1. An isolated amidase enzyme capable of degrading ochratoxin, wherein the isolated amidase enzyme comprises a polypeptide sequence having a sequence of SEQ ID NO: 3 that has a cleavable tag, or a sequence having at least 70% sequence identity to SEQ ID NO: 3 that has the cleavable tag.

2. The amidase according to claim 1, wherein the ochratoxin is ochratoxin A.

3. The amidase according to claim 1, wherein the amidase comprises at least one of the amino acid sequence motifs:

1) x-P-G-x-x-D-x-H-x-H-x-xG;

2) G-x-T;

3) G-x-x-x-G-P;

4) G-H-x-D;

5) D-G-x-x-x-V-x-x-x-x-R-x-x-x-R-x-x-A-x-x-I-K;

6) G-G-V-x-S-x-x-D-x-P;

7) V-x-A-H-x-x-G-x-x-G;

8) H-x-x-x-x-D; or

9) G-V-x-I-x-x-G-T-D;

wherein x is defined as any amino acid.

4. The amidase according to claim 1, wherein the amidase has a Tim barrel structure including an active site comprising 6 histidine residues, 1 lysine residue and 1 aspartic acid residue, wherein the amino acid residues in the active site correspond to positions H111, H113, H191, K246, H287, H289, H307 and D378 of SEQ ID NO:1 when the tertiary structure of the amidase and SEQ ID NO:1 are compared.

5. The amidase according to claim 1, wherein the amidase enzyme comprises a polypeptide sequence having at least 75% identity to SEQ ID NO: 3 and which differs from SEQ ID NO: 3 by one or more amino acid additions, deletions or substitutions.

6. The amidase according to claim 1, wherein the amidase hydrolyzes about at least 100 to about 900 nanomoles ochratoxin A per min per mg protein at pH7.0 and 40° C.

7. The enzyme according to claim 3, wherein the motifs comprise:

1) $x^1$-P-G-$x^2$-$x^3$-D-$x^4$-H-$x^5$-H-$x^6$-$x^7$-G;

2) G-$x^8$-T;

3) G-$x^9$-$x^{10}$-$x^{11}$-G-P;

4) G-H-$x^{12}$-D;

5) D-G-$x^{13}$-$x^{14}$-$x^{15}$-C-$x^{16}$-$x^{17}$-$x^{18}$-$x^{19}$-R-$x^{20}$-$x^{21}$-$x^{22}$-R-$x^{23}$-$x^{24}$-A-$x^{25}$-$x^{26}$-I-K,

6) G-G-V-$x^{27}$-S-$x^{28}$-$x^{29}$-D-$x^{30}$-P;

7) V-$x^{31}$-A-H-$x^{32}$-$x^{33}$-G-$x^{34}$-$x^{35}$-G;

8) H-$x^{36}$-$x^{37}$-$x^{38}$-$x^{39}$-D; or

9) G-V-$x^{40}$-I-$x^{41}$-$x^{42}$-G-T-D;

wherein:
$X^1$=l/m; $x^2$=l/m; $x^3$=w/i; $x^4$=c/v/s/a; $x^5$=any amino acid; $x^6$=f/y/l; $x^7$=any amino acid; $x^8$=y/f; $x^9$=t/a/s/v/r; $x^{10}$=i/f/a; $x^{11}$=any amino acid; $x^{12}$=g/s; $x^{13}$=v/e; $x^{14}$=any amino acid; $x^{15}$=e/d/g; $x^{16}$=any amino acid; $x^{17}$=any amino acid; $x^{18}$=a/g/t; $x^{19}$=v/a; $x^{20}$=any amino acid; $x^{21}$=q/m/a; $x^{22}$=l/i/v; $x^{23}$=r/h/c; $x^{24}$=g/n; $x^{25}$=k/r/t/e/d; $x^{26}$=any amino acid; $x^{27}$=l/m/v/g; $x^{28}$=any amino acid; $x^{29}$=any amino acid; $x^{30}$=any amino acid; $x^{31}$=a/s/h; $x^{32}$=c/v/a; $x^{33}$=h/q; $x^{34}$=k/r; $x^{35}$=any amino acid; $x^{36}$=g/v/a; $x^{37}$=s/t/i; $x^{38}$=y/f/e; $x^{39}$=l/a/i; $x^{40}$=any amino acid; $x^{41}$=a/v; $x^{42}$=–l/a, wherein x is defined as any amino acid.

8. The enzyme according to claim 7, wherein the motifs comprise:

1) l/m-P-G-l/m-w-D-c-H-x-H-f-x-G;

2) G-y/f-T;

3) G-t-i-x-G-P;

4) G-H-g-D;

5) D-G-v-x-e-V-x-x-a-v-R-x-q-l-R-r-g-A-k-x-I-K;

6) G-G-V-l/-S-x-x-D-x-P;

7) V-a-A-H-c-h-G-k-x-G;

8) H-g-s-y-l-D; or

9) G-V-x-I-a-l-G-T-D;

wherein x is defined as any amino acid.

9. A feed or food composition comprising an amidase enzyme capable of degrading ochratoxin, wherein the amidase enzyme comprises a polypeptide sequence having a sequence of SEQ ID NO: 3 or a polypeptide sequence having at least 70% sequence identity to SEQ ID NO: 3, wherein said feed or food composition is selected from the group consisting of: grains, by products from cereals, silage, protein, oils and fats, and minerals and vitamins.

10. The feed or food composition according to claim 9, wherein the ochratoxin is ochratoxin A.

11. The feed or food composition according to claim 9, wherein the amidase comprises at least one of the amino acid sequence motifs:

1) x-P-G-x-x-D-x-H-x-H-x-xG;

2) G-x-T;

3) G-x-x-x-G-P;

4) G-H-x-D;

5) D-G-x-x-x-V-x-x-x-x-R-x-x-x-R-x-x-A-x-x-I-K;

6) G-G-V-x-S-x-x-D-x-P;

7) V-x-A-H-x-x-G-x-x-G;

8) H-x-x-x-x-D; or

9) G-V-x-I-x-x-G-T-D;

wherein x is defined as any amino acid.

12. The feed or food composition according to claim 9, wherein the amidase has a Tim barrel structure including an active site comprising 6 histidine residues, 1 lysine residue and 1 aspartic acid residue, wherein the amino acid residues in the active site correspond to positions H111, H113, H191, K246, H287, H289, H307 and D378 of SEQ ID NO:1 when the tertiary structure of the amidase and SEQ ID NO:1 are compared.

13. The feed or food composition according to claim 9, wherein the feed or food additive comprises a physiologically acceptable carrier selected from at least one of maltodextrin, limestone (calcium carbonate), cyclodextrin, wheat, wheat bran or a wheat component, rice or rice bran, sucrose, starch, $Na_2SO_4$, Talc, and PVA and mixtures thereof.

14. The feed or food additive according to claim 9, wherein the feed or food additive comprises one or more further feed enzyme(s) selected from the group consisting of those involved in protein degradation including carboxypeptidases carboxypeptidase A, carboxypeptidase Y, *A. niger* aspartic acid proteases of PEPAa, PEPAb, PEPAc and PEPAd, elastase, amino peptidases, pepsin or pepsin-like, trypsin or trypsin-like proteases and bacterial proteases including subtilisin and its variants, and of those involved in starch metabolism, fibre degradation, lipid metabolism, proteins or enzymes involved in glycogen metabolism, amylases, arabinases, arabinofuranosidases, catalases, cellulases, chitinases, chymosin, cutinase, deoxyribonucleases, epimerases, esterases, -galactosidases, glucanases, glucan lyases, endoglucanases, glucoamylases, glucose oxidases, -glucosidases, including β glucosidase, glucuronidases, hemicellulases, hexose oxidases, hydrolases, invertases, isomerases, lipolytic enzymes, laccases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: $O_2$-oxidoreductase, EC 1.1.3.5), or acid phosphatases and combinations thereof.

15. A feed or food material comprising the feed additive of claim 9.

16. A feedstuff or foodstuff comprising the food or feed material of claim 15.

17. The feedstuff according to claim 16, comprising one or more feed materials selected from the group consisting of a) cereals, small grains (wheat, barley, rye, oats and combinations thereof) and/or large grains, maize or sorghum; b) byproducts from cereals, corn gluten meal, Distillers Dried Grain Solubles (DDGS), wheat bran, wheat middlings, wheat shorts, rice bran, rice hulls, oat hulls, palm kernel, and citrus pulp; c) silage; d) protein obtained from soya, sunflower, peanut, lupin, peas, fava beans, cotton, canola, fish meal, dried plasma protein, meat and bone meal, potato protein, whey, copra, sesame; e) oils and fats obtained from vegetable and animal sources; f) minerals and vitamins.

18. The foodstuff according to claim 16, wherein said foodstuff comprises corn, wheat, barley, sorghum, a cereal product, porridges, noodles, bread or cakes, coffee, cocoa, wine, beer, pulses, spices, dried fruit, grape juice, milk, milk products, cheese, meat or meat products.

19. The enzyme according to claim 11, wherein the motifs comprise:

1) $x^1$-P-G-$x^2$-$x^3$-D-$x^4$-H-$x^5$-H-$x^6$-$x^7$-G;

2) G-$x^8$-T;

3) G-$x^9$-$x^{10}$-$x^{11}$-G-P;

4) G-H-$x^{12}$-D;

5) D-G-$x^{13}$-$x^{14}$-$x^{15}$-C-$x^{16}$-$x^{17}$-$x^{18}$-$x^{19}$-R-$x^{20}$-$x^{21}$-$x^{22}$-R-$x^{23}$-$x^{24}$-A-$x^{25}$-$x^{26}$-I-K,

6) G-G-V-$x^{27}$-S-$x^{28}$-$x^{29}$-D-$x^{30}$-P;

7) V-$x^{31}$-A-H-$x^{32}$-$x^{33}$-G-$x^{34}$-$x^{35}$-G;

8) H-$x^{36}$-$x^{37}$-$x^{38}$-$x^{39}$-D; or

9) G-V-$x^{40}$-I-$x^{41}$-$x^{42}$-G-T-D;

wherein:
$x^1$=l/m; $x^2$=l/m; $x^3$=w/i; $x^4$=c/v/s/a; $x^5$=any amino acid; $x^6$=f/y/l; $x^7$=any amino acid; $x^8$=y/f; $x^9$=t/a/s/v/r; $x^{10}$=i/f/a; $x^{11}$=any amino acid; $x^{12}$=g/s; $x^{13}$=v/e; $x^{14}$=any amino acid; $x^{15}$=e/d/g; $x^{16}$=any amino acid; $x^{17}$=any amino acid; $x^{18}$=a/g/t; $x^{19}$=v/a; $x^{20}$=any amino acid; $x^{21}$=q/m/a; $x^{22}$=l/i/v; $x^{23}$=r/h/c; $x^{24}$=g/n; $x^{25}$=k/r/t/e/d; $x^{26}$=any amino acid; $x^{27}$=l/m/v/g; $x^{28}$=any amino acid; $x^{29}$=any amino acid; $x^{30}$=any amino acid; $x^{31}$=a/s/h; $x^{32}$=c/v/a; $x^{33}$=h/q; $x^{34}$=k/r; $x^{35}$=any amino acid; $x^{36}$=g/v/a; $x^{37}$=s/t/i; $x^{38}$=y/f/e; $x^{39}$=l/a/i; $x^{40}$=any amino acid; $x^{41}$=a/v; $x^{42}$=–l/a.

20. A method of making a foodstuff or feedstuff according to claim 16 comprising adding to a food or feed material a food or feed additive that comprises an amidase enzyme capable of degrading ochratoxin.

21. A method of making a food or feed additive according to claim 16 comprising admixing the amidase with at least one physiologically acceptable carrier.

22. A method of reducing ochratoxin contamination of a feed or food composition comprising adding to said feed or food composition an ochratoxin degrading amidase enzyme, wherein the ochratoxin degrading amidase enzyme comprises a polypeptide sequence having a sequence of SEQ ID NO: 3 or a polypeptide sequence having at least 70% sequence identity to SEQ ID NO: 3, wherein said feed or food composition is selected from a group consisting of: grains, by products from cereals, silage, protein, oils and fats, and minerals and vitamins.

23. The method according to claim 22, wherein the amidase comprises at least one of the amino acid sequence motifs:

1) x-P-G-x-x-D-x-H-x-H-x-xG;

2) G-x-T;

3) G-x-x-x-G-P;

4) G-H-x-D;

5) D-G-x-x-x-V-x-x-x-x-R-x-x-x-R-x-x-A-x-x-I-K;

6) G-G-V-x-S-x-x-D-x-P;

7) V-x-A-H-x-x-G-x-x-G;

8) H-x-x-x-x-D; or

9) G-V-x-I-x-x-G-T-D.

24. A recombinant cell or spore encoding an amidase enzyme which degrades ochratoxin, wherein the amidase enzyme comprises a polypeptide sequence having a sequence of SEQ ID NO: 3 that has a cleavable tag, or a sequence having at least 70% sequence identity to SEQ ID NO: 3 that has the cleavable tag.

25. The cell or spore according to claim 24 wherein the amidase enzyme degrades ochratoxin A.

26. The cell or spore according to claim 24, wherein the amidase is isolated.

27. The cell or spore according to claim 24, wherein the amidase comprises at least one of the amino acid sequence motifs:

1) x-P-G-x-x-D-x-H-x-H-x-xG;

2) G-x-T;

3) G-x-x-x-G-P;

-continued

4) G-H-x-D;

5) D-G-x-x-x-V-x-x-x-x-R-x-x-x-R-x-x-A-x-x-I-K;

6) G-G-V-x-S-x-x-D-x-P;

7) V-x-A-H-x-x-G-x-x-G;

8) H-x-x-x-x-D; or

9) G-V-x-I-x-x-G-T-D.

28. The cell or spore according to claim 24, wherein the amidase has a Tim barrel structure including an active site comprising 6 histidine residues, 1 lysine residue and 1 aspartic acid residue, wherein the amino acid residues in the active site correspond to positions H111, H113, H191, K246, H287, H289, H307 and D378 of SEQ ID NO:1 when the tertiary structure of the amidase and SEQ ID NO:1 are compared.

29. The recombinant cell or spore according to claim 24, wherein the amidase is at least 30% pure.

* * * * *